(12) United States Patent
Tweardy et al.

(10) Patent No.: US 10,112,933 B2
(45) Date of Patent: Oct. 30, 2018

(54) METHODS AND COMPOSITIONS FOR TREATMENT OF FIBROSIS

(71) Applicant: Baylor College of Medicine, Houston, TX (US)

(72) Inventors: David J. Tweardy, Houston, TX (US); Moses M. Kasembeli, Houston, TX (US); Marvin X. Xu, Shanghai (CN); Sandeep K. Agarwal, Houston, TX (US); Mesias Pedroza, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 0 days.

(21) Appl. No.: 14/335,804

(22) Filed: Jul. 18, 2014

(65) Prior Publication Data

US 2015/0051233 A1    Feb. 19, 2015

Related U.S. Application Data

(60) Provisional application No. 61/847,744, filed on Jul. 18, 2013.

(51) Int. Cl.
| | |
|---|---|
| *C07D 417/12* | (2006.01) |
| *A61K 31/18* | (2006.01) |
| *C07C 317/28* | (2006.01) |
| *C07C 317/30* | (2006.01) |
| *C07C 317/32* | (2006.01) |
| *C07D 213/71* | (2006.01) |
| *C07D 215/06* | (2006.01) |
| *C07D 231/18* | (2006.01) |
| *C07D 239/60* | (2006.01) |
| *C07D 261/10* | (2006.01) |
| *C07D 333/34* | (2006.01) |
| *C07D 409/12* | (2006.01) |
| *C07D 413/12* | (2006.01) |
| *A61K 31/343* | (2006.01) |
| *A61K 31/39* | (2006.01) |
| *A61K 31/4196* | (2006.01) |
| *A61K 45/06* | (2006.01) |

(52) U.S. Cl.
CPC ............ *C07D 417/12* (2013.01); *A61K 31/18* (2013.01); *A61K 31/343* (2013.01); *A61K 31/39* (2013.01); *A61K 31/4196* (2013.01); *A61K 45/06* (2013.01); *C07C 317/28* (2013.01); *C07C 317/30* (2013.01); *C07C 317/32* (2013.01); *C07D 213/71* (2013.01); *C07D 215/06* (2013.01); *C07D 231/18* (2013.01); *C07D 239/60* (2013.01); *C07D 261/10* (2013.01); *C07D 333/34* (2013.01); *C07D 409/12* (2013.01); *C07D 413/12* (2013.01)

(58) Field of Classification Search
CPC .... C07D 417/12; A61K 31/18; C07C 317/28; C07C 317/30
See application file for complete search history.

(56) References Cited

U.S. PATENT DOCUMENTS

| | | | |
|---|---|---|---|
| 8,975,399 B2* | 3/2015 | Zagury | ............. C07D 295/215 544/248 |
| 2010/0035793 A1 | 2/2010 | Lim et al. | |
| 2010/0041685 A1 | 2/2010 | Tweardy et al. | |
| 2011/0312984 A1 | 12/2011 | Tweardy et al. | |
| 2013/0123266 A1 | 5/2013 | Zagury et al. | |
| 2015/0024032 A1 | 1/2015 | Tweardy et al. | |
| 2015/0031714 A1 | 1/2015 | Tweardy et al. | |

OTHER PUBLICATIONS

John Hopkins scleroderma ( Aug. 2010, Wayback Machine).*
Hakala (Rheumatoid Arthritis and Interstitial Lung Fibrosis (1988)) and.*
Lindsay et al. (Rheumatoilogy (2009); 48:569-572).*
Fan et al. (Fibrogenesis & Tissue Repair (2012), 5:15.*
Wynn, Thomas, A.; Common an dUniue Mechanisms Regulate Fibrosis in Various Fibroproliferative Diseases; The Journal of Clinical Investigation; vol. 117. No. 3; pp. 524-529; Mar. 2007.
Falke, Lucas L., et al; Diverse Organs of the Myofibroblast-Implications for Kidney Fibrosis; Nat. Rev. Nephrology; vol. 11, 233-244; Apr. 2015.
Iwaisako, Keiko, et al; Origins of Myofibroblasts in the Fibrotic Liver in Mice; PNAS, E3297-3305; Jul. 2014.
Rockey, Don C.; et al; Fibrosis—A Common Pathway to Organ Injury and Failure; The New England Journal of Medicine, pp. 1138-1149; Mar. 2015.
Bharadwaj et al., "Drug-repositioning screening identified piperlongumine as a direct STAT3 inhibitor with potent activity against breast cancer," Oncogene, 34(11):1341-1353, (2015).
Bharadwaj et al., "Small-molecule inhibition of STAT3 in radioresistant head and neck squamous cell carcinoma," Oncotarget, 7(18):26307-26330, (2016).
Debnath et al: "Small Molecule Inhibitors of Signal Transducer and Activator of Transcription 3 (Stat3) Protein", Journal of Medicinal Chemistry, vol. 55, No. 15, May 31, 2012, pp. 6645-6668.
Pedroza et al "The Role of Stat-3 in the Development of Pulmonary and Dermal Fibrosis", Oct. 1, 2013, p. 2573.
Topal et al: "Scleroderma therapy: clinical overview of current trends and future perspective", Rheumatology International; Clinical and Experimental Investigations, vol. 33, No. 1, Aug. 3, 2012, pp. 1-18, Springer, Berlin. DE.
Pedroza et al: "STAT-3 contributes to pulmonary fibrosis through epithelial injury and fibroblast-myofibroblast differentiation", The FASEB Journal, vol. 30, No. 1, Aug. 31, 2015, pp. 129-140.

* cited by examiner

*Primary Examiner* — Shirley V Gembeh
(74) *Attorney, Agent, or Firm* — Norton Rose Fulbright US LLP

(57) ABSTRACT

Embodiments of the invention include methods of treating, preventing, and/or reducing the risk of fibrosis in an individual in need thereof. In some embodiments, particular small molecules are employed for treatment, prevention, and/or reduction of the risk of fibrosis. In at least particular cases, the small molecules are inhibitors of STAT3.

23 Claims, 49 Drawing Sheets

B.

A. Cpd3

4-[3-(2,3-dihydro-1,4-benzodioxin-6-yl)-3-oxo-1-propen-1-yl] benzoic acid

B. Cpd30

4-{5-[(3-ethyl-4-oxo-2-thioxo-1,3-thiazolidin-5-ylidene)methyl]-2-furyl}benzoic acid D. Cpd3-2

3-({2-chloro-4-[(1,3-dioxo-1,3-dihydro-2H-inden-2-ylidene)methyl]-6-ethoxyphenoxy}methyl)benzoic acid E. Cpd3-7 methyl 4-({[3-(2-methoxy-2-oxoethyl)-4,8-dimethyl-2-oxo-2H-chromen-7-yl]oxy}methyl)benzoate F. Cpd30-12

4-chloro-3-{5-[(1,3-diethyl-4,6-dioxo-2-thioxotetrahydro-5(2H)-pyrimidinylidene)methyl]-2-furyl}benzoic acid

B.

4-[3-(2,3-dihydro-1,4-benzodioxin-6-yl)-3-oxo-1-propen-1-yl] benzoic acid

Cpd30

4-{5-[(3-ethyl-4-oxo-2-thioxo-1,3-thiazolidin-5-ylidene)methyl]-2-furyl} benzoic acid 4-[({3-[(carboxymethyl)thio]-4-hydroxy-1-naphthyl}amino)sulfonyl] benzoic acid

METHODS AND COMPOSITIONS FOR TREATMENT OF FIBROSIS

This application claims priority to U.S. Provisional Patent Application Ser. No. 61/847,744, filed Jul. 18, 2013, which is incorporated by reference herein in its entirety.

STATEMENT REGARDING FEDERALLY SPONSORED RESEARCH OR DEVELOPMENT

This invention was made with government support under P50 CA058183, K08 HL085018-01A2, P50 CA097007, R21CA149783, and R41CA153658 awarded by National Institutes of Health. The United States Government has certain rights in the invention.

TECHNICAL FIELD

The present invention generally concerns at least the fields of cell biology, molecular biology, and medicine.

BACKGROUND OF THE INVENTION

Fibrosis is a pathological process involving the accumulation of excessive extra-cellular matrix in tissues, leading to tissue damage and organ dysfunction, which can progress to organ failure and death. In systemic sclerosis, an idiopathic fibrosis disease, the trigger is postulated to be an autoimmune response that leads to tissue injury, production of growth factors, pro-inflammatory and pro-fibrotic cytokines, and accumulation of myofibroblasts. Two potential sources of myofibroblasts are the differentiation of local fibroblasts and the process of epithelial-to-mesenchymal transition (EMT). IL-6 is a proinflammatory and pro-fibrotic cytokine increasingly recognized as an important mediator of fibrosis that may contribute to the accumulation of myofibroblasts. After engaging its receptor, IL-6 signals through the STAT3. To be fully active, STAT3 becomes phosphorylated on Y705; levels of pY705-STAT3 are measured as an indicator of the level of activated STAT3.

The present disclosure satisfies a need in the art to provide novel compounds and methods for treating and/or preventing fibrosis in individuals.

SUMMARY OF THE INVENTION

Embodiments of the invention include methods and compositions for the treatment, prevention, or reduction in the risk of fibrosis. In specific embodiments, the fibrosis is not pulmonary fibrosis or myelofibrosis.

Embodiments of the invention include methods and/or compositions for the treatment of fibrosis in an individual known to have the fibrosis, suspected of having fibrosis, or at risk for having fibrosis. Patients at risk of fibrosis may be those that have autoimmune diseases such as schleroderma or systemic schlerosis, those exposed to certain drugs including chemotherapy, those exposed to environmental or other toxins or allergens, those who have suffered an ischemia/reperfusion injury such as myocardial infarction or hypotension, and/or those with idiopathic pulmonary fibrosis, idiopathic liver fibrosis, hepatitis induced by alcohol, toxins, drugs or infections, liver cirrhosis, primary biliary cirrhosis, viral infections involving the heart, liver, or lung, and idiopathic retroperiotoneal fibrosis. The compositions include small molecules and functional derivatives as described herein. In some embodiments, the individual is receiving an additional therapy for fibrosis. An individual in need thereof is an individual that has at least one symptom of fibrosis or is susceptible to or at risk of having fibrosis.

In embodiments of the invention, an individual is given more than one dose of one or more compositions described herein or functional derivatives thereof. The dosing regimen may include doses separated in time by hours, days, months or years. Delivery of the composition of the invention may occur by any suitable route, including systemic or local, although in specific embodiments, the delivery route is oral, intravenous, topical, subcutaneous, intraarterial, intraperitoneal, buccal, and so forth.

In some embodiments of the invention, the methods and/or compositions of the invention are useful for treating and/or preventing and/or reducing the risk or severity of fibrosis, and in specific cases such treatment occurs by inhibiting Stat3 and/or Stat1 activity, although in some aspects the composition(s) does not inhibit Stat3 or Stat1 or both. In certain embodiments, the compositions inhibit Stat3 but fail to inhibit Stat1. In some embodiments, compounds of the invention interact with the Stat3 SH2 domain, competitively inhibit recombinant Stat3 binding to its immobilized pY-peptide ligand, and/or inhibit IL-6-mediated tyrosine phosphorylation of Stat3, for example. In particular embodiments, the compositions of the invention fulfills the criteria of interaction analysis (CIA): 1) global minimum energy score≤−30; 2) formation of a salt-bridge and/or H-bond network within the pY-residue binding site of Stat3; and/or 3) formation of a H-bond with or blocking access to the amide hydrogen of E638 of Stat3, for example. In some embodiments, the composition(s) interacts with a hydrophobic binding pocket with the Stat3 SH2 domain.

In a specific embodiment of the invention, there is a method of treating, preventing, and/or reducing the risk of fibrosis in an individual comprising delivering to the individual a therapeutically effective amount of a compound selected from the group consisting of N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-ylsulfanyl)-naphthalen-1-yl]-benzenesulfonamide; a functionally active derivative thereof; and a mixture thereof.

In a specific embodiment of the invention, there is a method of treating, preventing, and/or reducing the risk of fibrosis in an individual comprising delivering to the individual a therapeutically effective amount of a compound selected from the group consisting of 4-[3-(2,3-dihydro-1,4-benzodioxin-6-yl)-3-oxo-1-propen-1-yl]benzoic acid; 4{5-[(3-ethyl-4-oxo-2-thioxo-1,3-thiazolidin-5-ylidene)methyl]-2-furyl}benzoic acid; 4-[({3-[(carboxymethyl)thio]-4-hydroxy-1-naphthyl}amino) sulfonyl]benzoic acid; 3-({2-chloro-4-[(1,3-dioxo-1,3-dihydro-2H-inden-2-ylidene)methyl]-6-ethoxyphenoxy}methyl)benzoic acid; methyl 4-({[3-(2-methyoxy-2-oxoethyl)-4,8-dimethyl-2-oxo-2H-chromen-7-yl]oxy}methyl)benzoate; 4-chloro-3-{5-[(1,3-diethyl-4,6-dioxo-2-thioxotetrahydro-5(2H)-pyrimidinylidene)methyl]-2-furyl}benzoic acid; a functionally active derivative thereof; and a mixture thereof. In a specific embodiment, any of the compounds disclosed herein are suitable to treat and/or prevent fibrosis, for example.

In another embodiment, the inhibitor comprises the general formula:

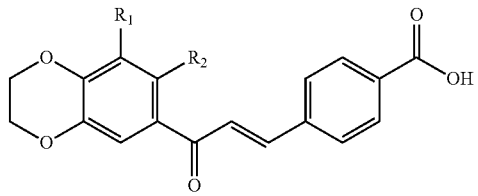

wherein $R_1$ and $R_2$ may be the same or different and are selected from the group consisting of hydrogen, carbon, sulfur, nitrogen, oxygen, flourine, chlorine, bromine, iodine, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

In another embodiment of the invention, the composition comprises the general formula:

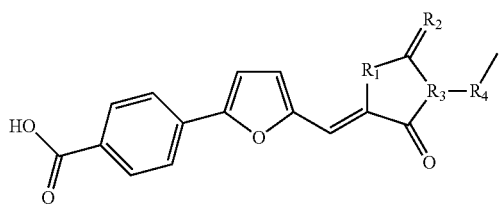

wherein $R_1$, and $R_3$ may be the same or different and are selected from the group consisting of hydrogen, carbon, nitrogen, sulfur, oxygen, flouring, chlorine, bromine, iodine, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives; and $R_2$ and $R_4$ may be the same or different and are selected from the group consisting of hydrogen, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

In another embodiment of the invention, the composition comprises the general formula:

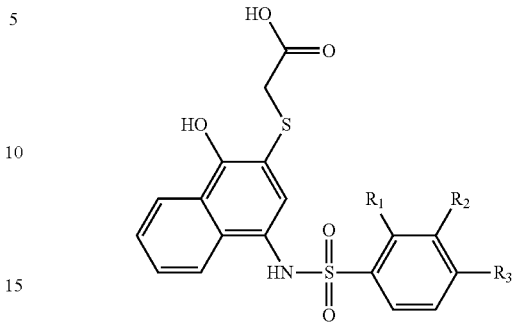

wherein $R_1$, $R_2$, and $R_3$ may be the same or different and are selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

In specific embodiments, the individual does not have cancer and/or is not suspected of having cancer nor has been diagnosed with cancer.

Mammals may be treated with the methods and/or compositions of the invention, including humans, dogs, cats, horses, cows, pigs, sheep, and goats, for example.

In other embodiments of the invention, there are methods of treating fibrosis in an individual wherein the composition(s) is an inhibitor of any members of the STAT protein family, including STAT1, STAT2, STAT3, STAT4, STAT5 (STAT5A and STAT5B), or STATE, for example.

Embodiments of the invention include methods for preventing or treating a fibrotic disease or complications thereof in a subject comprising providing to the subject an effective amount of a composition as described herein. The fibrosis may occur externally on the individual, such as on the skin, and/or the fibrosis may occur internally in the individual.

In some embodiments of the invention, the composition(s) are employed to treat or prevent scarring, such as of a wound or surgical incision, for example.

In one embodiment, there is a method of treating, preventing, or reducing the risk or severity of fibrosis in an individual that has fibrosis or that is at risk of having or susceptible to having fibrosis, comprising the step of providing to the individual an effective amount of one or more compositions of Table 6-11, FIG. 15, FIG. 16, or a functional derivative thereof. In specific embodiments, the fibrosis is not pulmonary fibrosis or myelofibrosis. The fibrosis may be of the lung, skin, heart, intestine, pancreas, joint, liver, or retroperionteum. The fibrosis may be of the skin, heart, intestine, pancreas, joint, liver, or retroperionteum. In some cases, the individual is provided the composition in multiple doses, such as multiple doses are separated by hours, days, or weeks. In specific embodiments, the individual is provided with an additional therapy for the fibrosis. In certain aspects, the composition is selected from the group consisting of N-(1',2-dihydroxy-1,2'-binaphthalen-4'-yl)-4-methoxybenzenesulfonamide, N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2'] binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2'] binaphthalenyl-4'-yl)-4-methoxy-benzenesulfonamide, 4-Bromo-N-(1,6'-dihydroxy-[2,2']binaphthalenyl-4-yl)-benzene sulfonamide, 4-Bromo-N-[4-hydroxy-3-(1H-[1,2,4]triazol-3-ylsulfanyl)-naphthalen-1-yl]-benzenesulfonamide, a functionally active derivative thereof, and a mixture thereof. The composition may inhibit Stat3, Stat1, or both, in specific embodiments. In particular aspects, a method further comprises the step of diagnosing the fibrosis.

Compositions may be provided intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion, via a catheter, via a lavage, in lipid compositions, in liposome compositions, or as an aerosol. The composition may be provided systemically or locally. In certain cases, the individual does not have cancer. In certain cases, the individual is not suspected of having cancer. In specific embodiments, the fibrosis is scleroderma.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DESCRIPTION OF THE DRAWINGS

In FIG. 6A the negatively charged benzoic acid moiety of Cpd3 has electrostatic interactions with the positively-charge pYresidue binding site consisting mainly of the guanidinium cation group of R609 and the basic ammonium group of K591. The benzoic acid group also forms a hydrogen-bond network consisting of double H-bonds between the carboxylic oxygen and the ammonium hydrogen of R609 and the amide hydrogen of E612. H-bond formation also occurs between the benzoic acid carbonyl oxygen and the side chain hydroxyl hydrogen of Serine 611. Within the +3 residue-binding site, the oxygen atom of 1,4-benzodioxin forms a hydrogen bond with the amide hydrogen of E638. In addition, the 2,3-dihydro-1,4-benzodioxin of Cpd3 interacts with the loops forming the hydrophobic binding site. In FIG. 6B the carboxylic terminus of the benzoic acid moiety of Cpd30, which is negatively charged under physiological conditions, forms a salt bridge with the guanidinium group of R609 within the pYresidue binding site. Within the +3 residue-binding site, the oxygen of the thiazolidin group forms a H-bond with the peptide backbone amide hydrogen of E638. In addition, the thiazolidin moiety plunges into the hydrophobic binding site. In FIG. 6C there is an electrostatic interaction between the (carboxymethyl)thio moiety of Cpd188 carrying a negative charge and the pY-residue binding site consisting of R609 and K591 carrying positive charge under physiological conditions. There are H-bonds between the hydroxyloxygen of the (carboxymethyl) thio group of Cpd188 and the guanidinium hydrogen of R609, between the hydroxyl-oxygen of the (carboxymethyl)thio group and the backbone amide hydrogen of E612, and between the carboxyl-oxygen of the (carboxymethyl)thio group of Cpd188 and the hydroxyl-hydrogen of 5611. Within the +3 residue-binding site, there is a H-bond between the hydroxyl-oxygen of benzoic acid group of Cpd188 and the amide-hydrogen of E638. In addition, the benzoic acid group extends and interacts with the hydrophobic binding site. In FIG. 6D the benzoic acid group of Cpd3-2 has significant electrostatic interactions with the pY-residue binding site pocket, mainly contributed by R609 and K591, and forms two H bonds; the carboxylic oxygen of the benzoic acid group binds the guanidinium hydrogen of R609, and the carbonyl oxygen of the benzoic acid group binds to the carbonyl hydrogen of S611. Within the +3 residue-binding site, oxygen within the 1,3-dihydro-2H-inden-2-ylidene group forms an H bond to the backbone amide-hydrogen of E638. In addition, the 1,3-dihydro-2H-inden-2-ylidene group plunges into the hydrophobic binding site. In FIG. 6E H-bonds are formed between the carbonyl-oxygen of the methyl 4-benzoate moiety of Cpd 3-7 and the side chain guanidinium of R609 and between the methoxy-oxygen and the hydrogen of the ammonium terminus of K591. The (2-methoxy-2-oxoethyl)-4,8-dimethyl-2-oxo-2H-chromen group of Cpd3-7 blocks access to the amide hydrogen of E638 within the +3 residue-binding site. In addition, this group plunges into the hydrophobic binding site. In FIG. 6F there are electrostatic interactions between the benzoic acid derivative group of Cpd30-12 and R609 and 591 within the pY-residue binding site. Also, H-bonds are formed between the hydroxyl-oxygen of Cpd30-12 and the guanidinium-hydrogen of R609, between the carboxyl-oxygen of Cpd30-12 and the hydroxyl-hydrogen of S611 and between the furyl group of Cpd30-12 and the hydrogen of ammonium of K591. The 1,3-diethyl-4,6-dioxo-2-thioxotetrahydro-5(2H)-pyrimidinylidene groups blocks access to the +3 residue binding site; however, it extends into the groove between the pY-residue binding site and Loop$\beta$C-$\beta$D, while sparing the hydrophobic binding site.

DETAILED DESCRIPTION OF THE INVENTION

Figure 1:
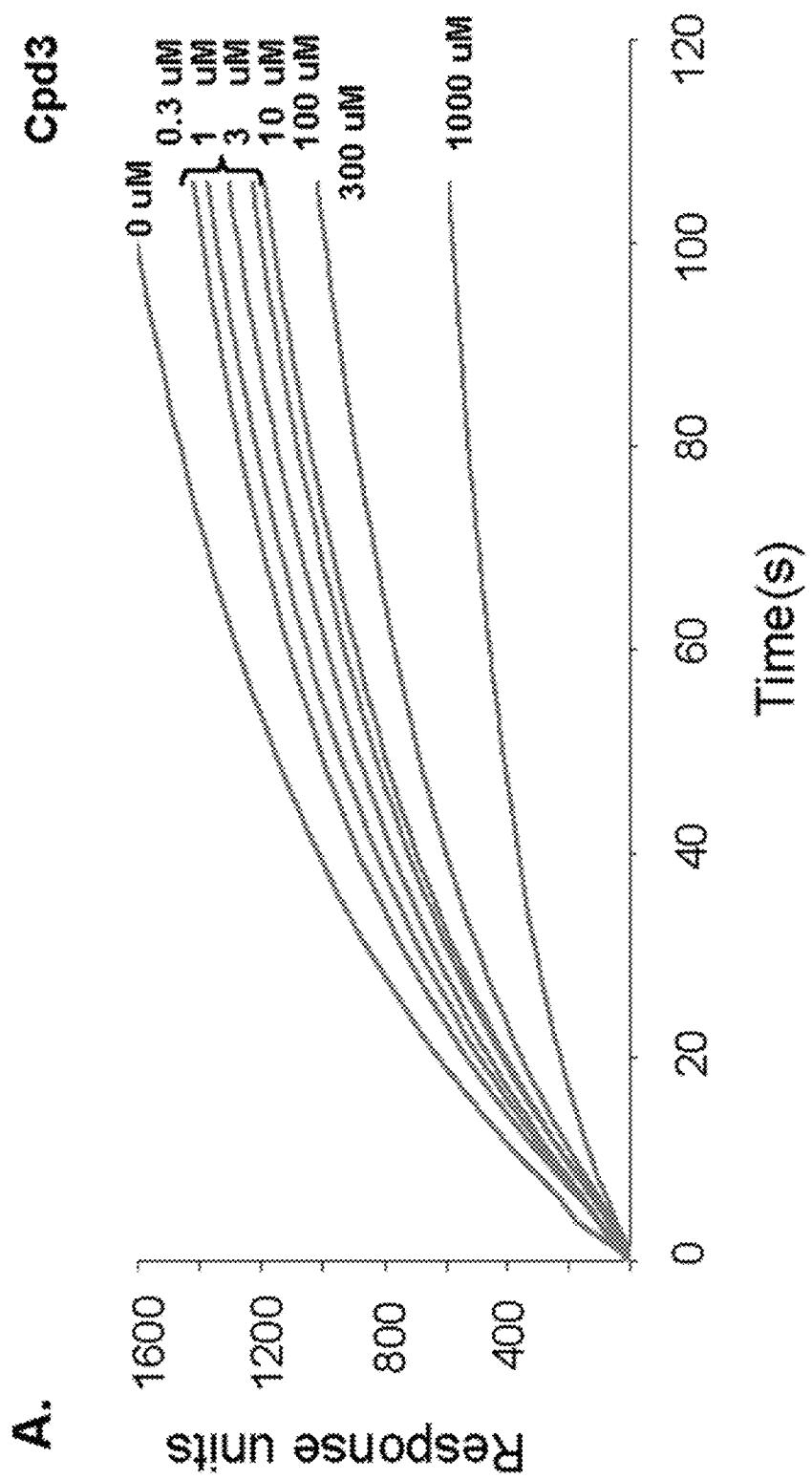
FIG. 1 demonstrates inhibition of Stat3 binding to immobilized phosphopeptide ligand by compounds. Binding of recombinant Stat3 (500 nM) to a BiaCore sensor chip coated with a phosphododecapeptide based on the amino acid sequence surrounding Y1068 within the EGFR was measured in real time by SPR (Response Units) in the absence (0 μM) or presence of increasing concentrations (0.1 to 1,000 μM) of Cpd3 (panel A), Cpd30 (panel B), Cpd188 (panel C), Cpd3-2 (panel D), Cpd3-7 (panel E) and Cpd30-12 (panel F). Data shown are representative of 2 or more experiments. The equilibrium binding levels obtained in the absence or presence of compounds were normalized (response obtained in the presence of compound÷the response obtained in the absence of compound×100), plotted against the log concentration (nM) of the compounds (panel G). The experimental points fit to a competitive binding curve that uses a four-parameter logistic equation (see exemplary methods for details). These curves were used to calculate $IC_{50}$ (Table 1).
Figure 1:
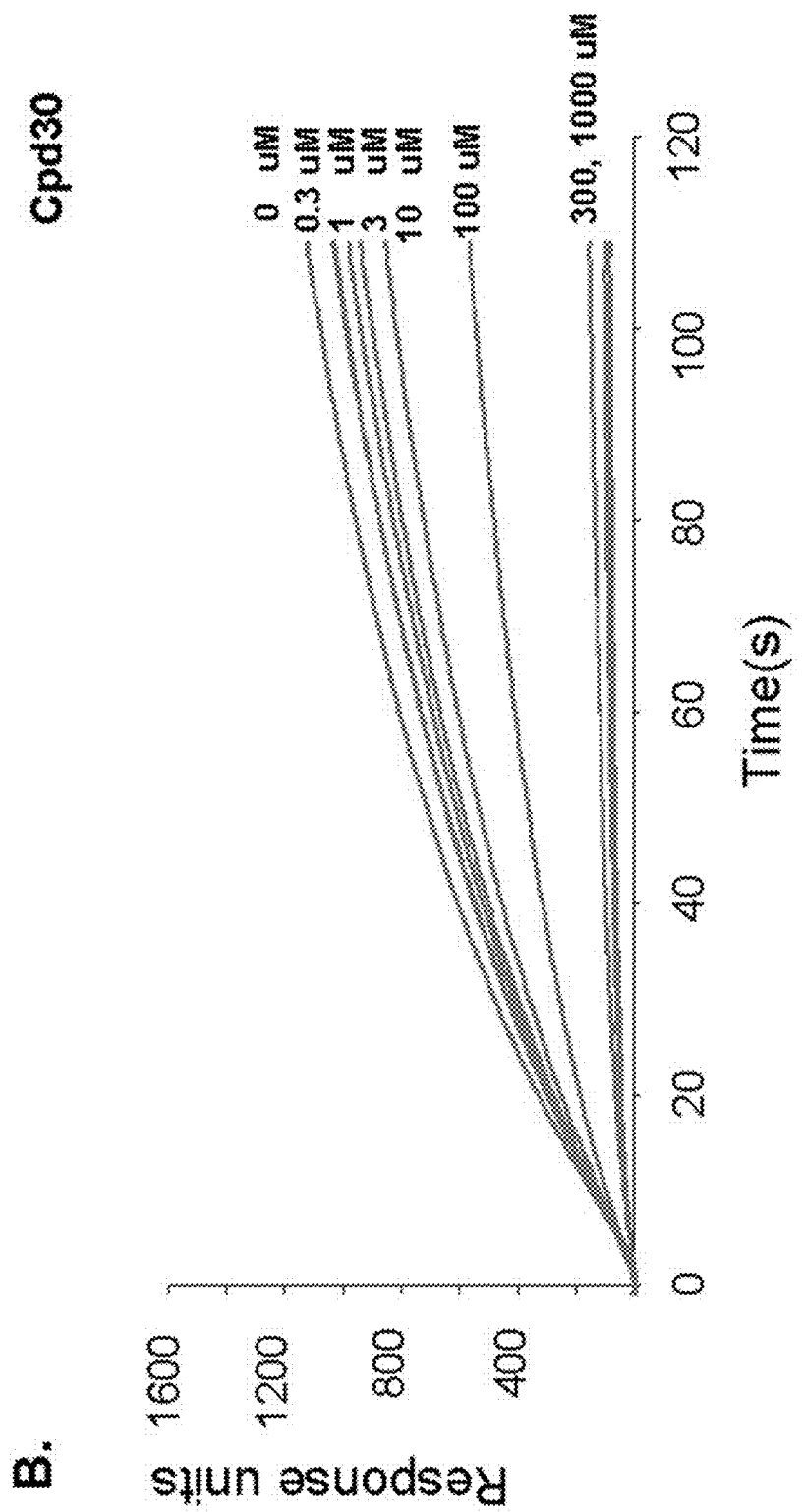
Figure 1:
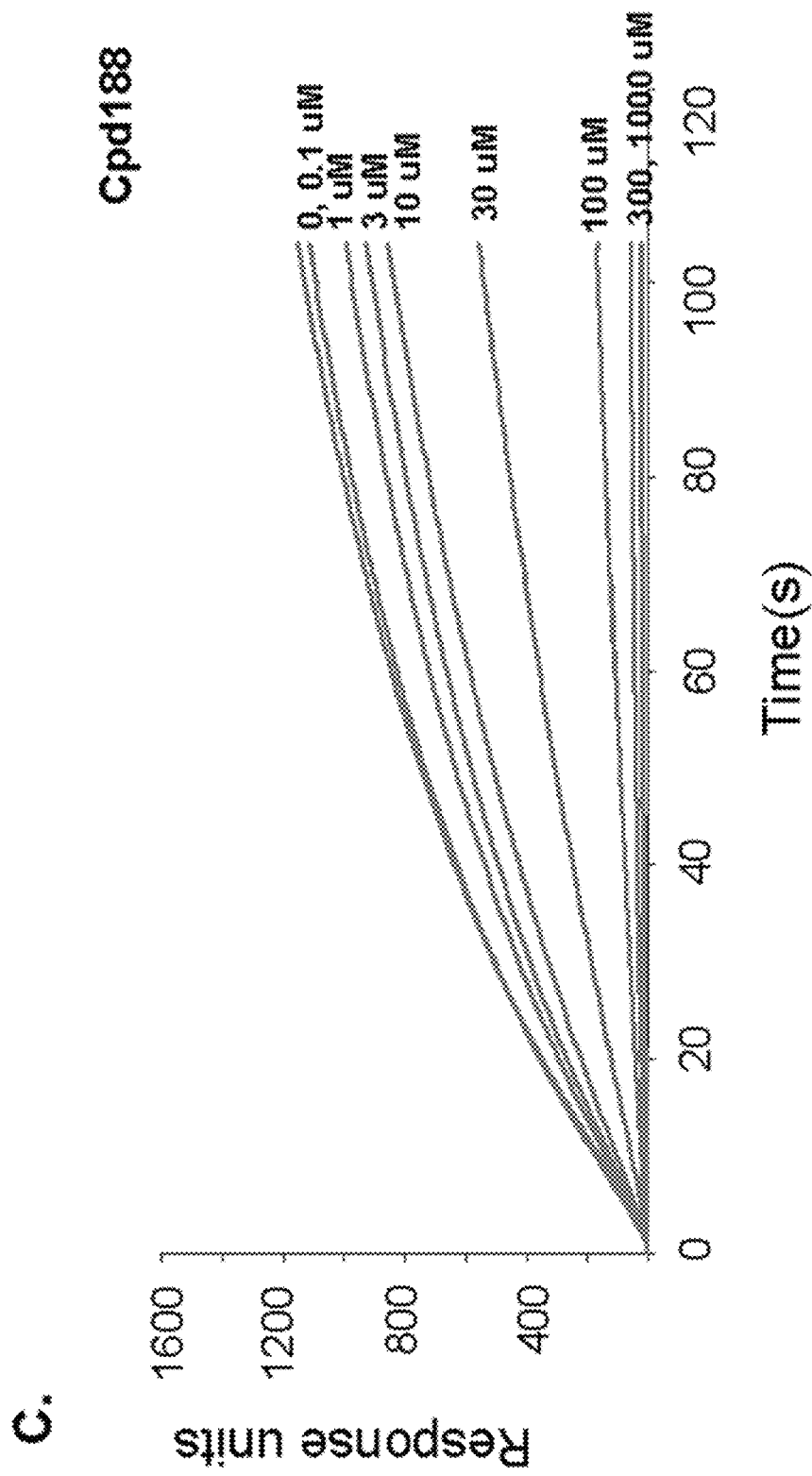
Figure 1:
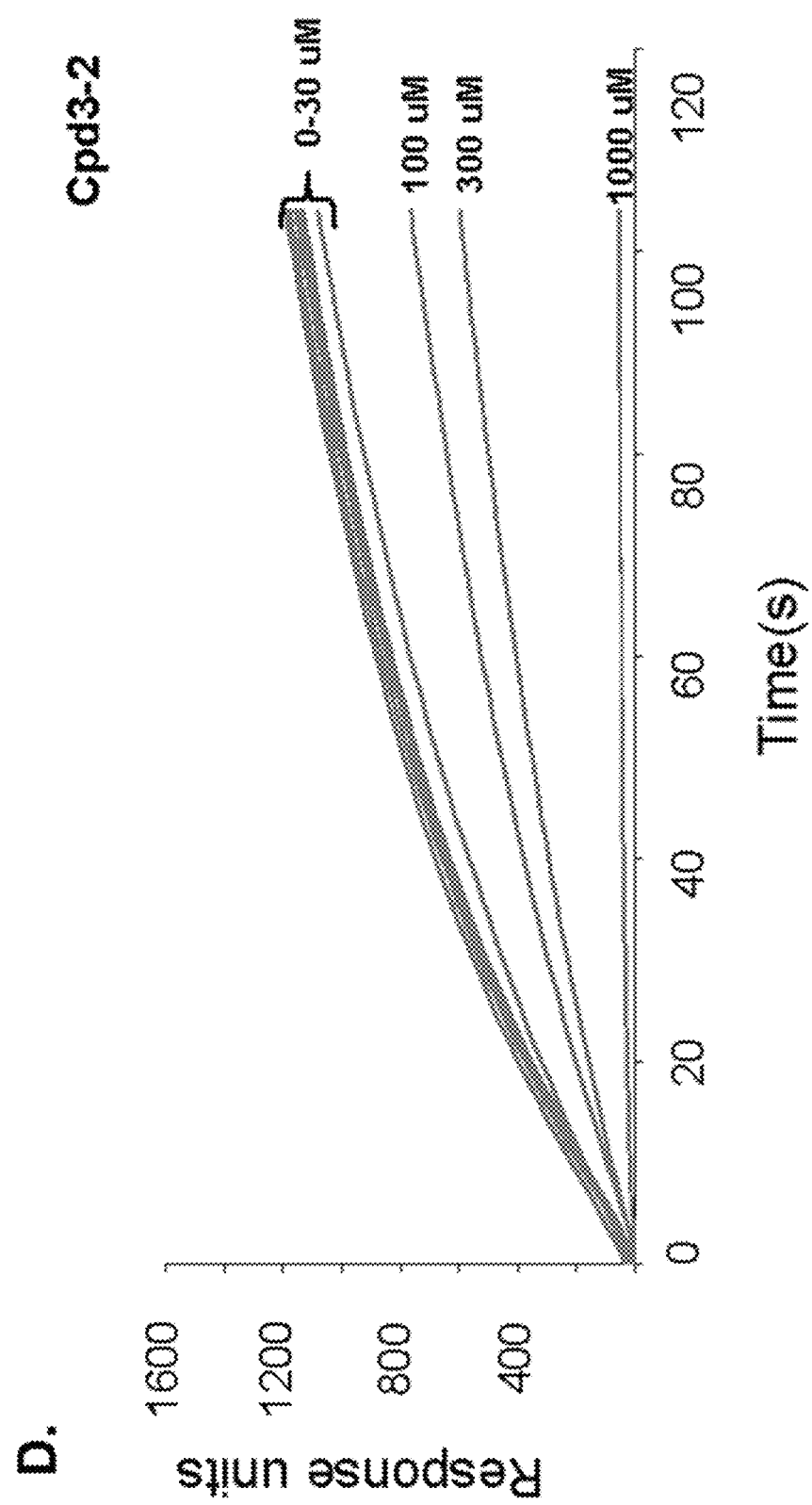
Figure 1:
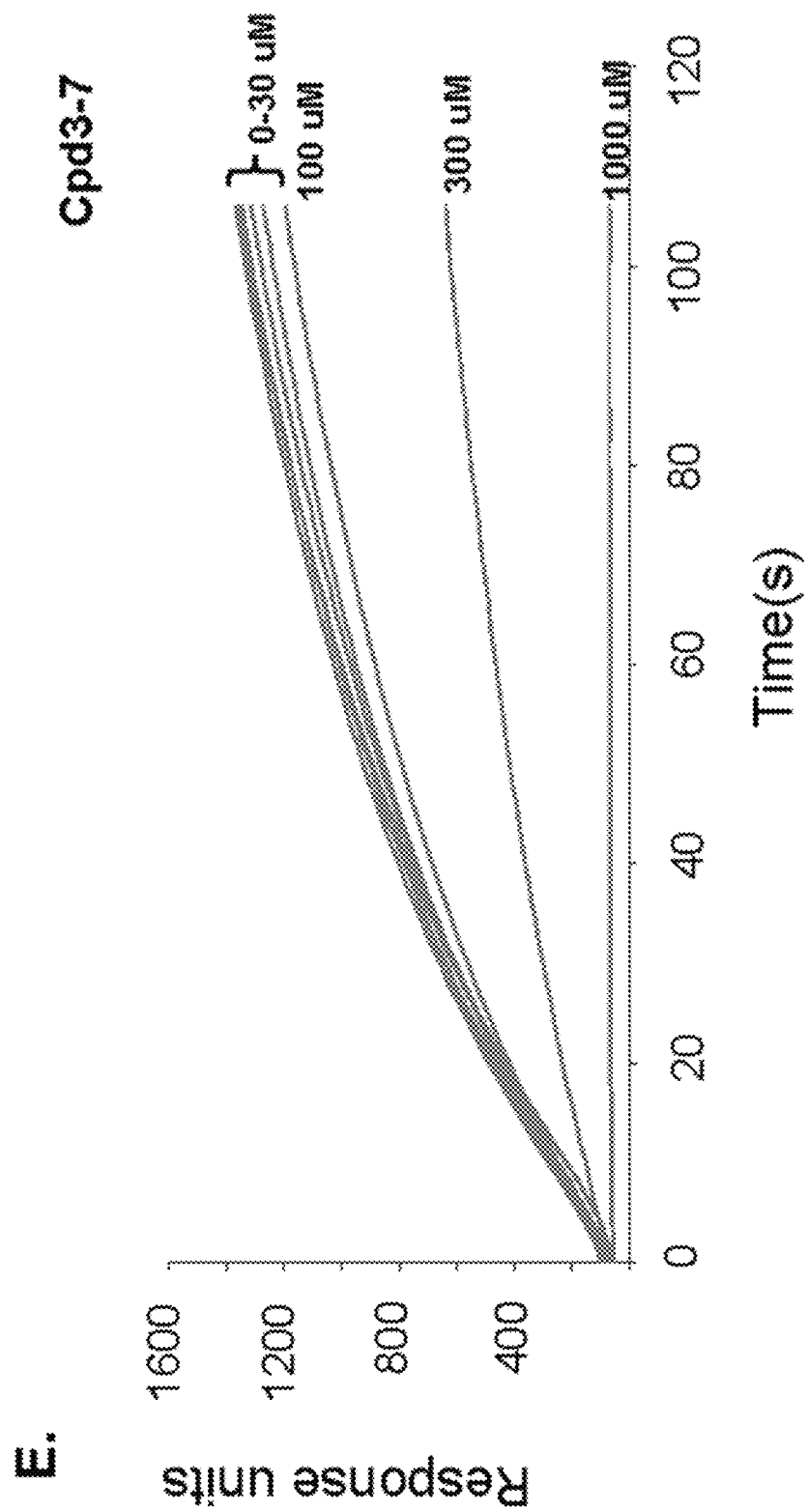
Figure 1:
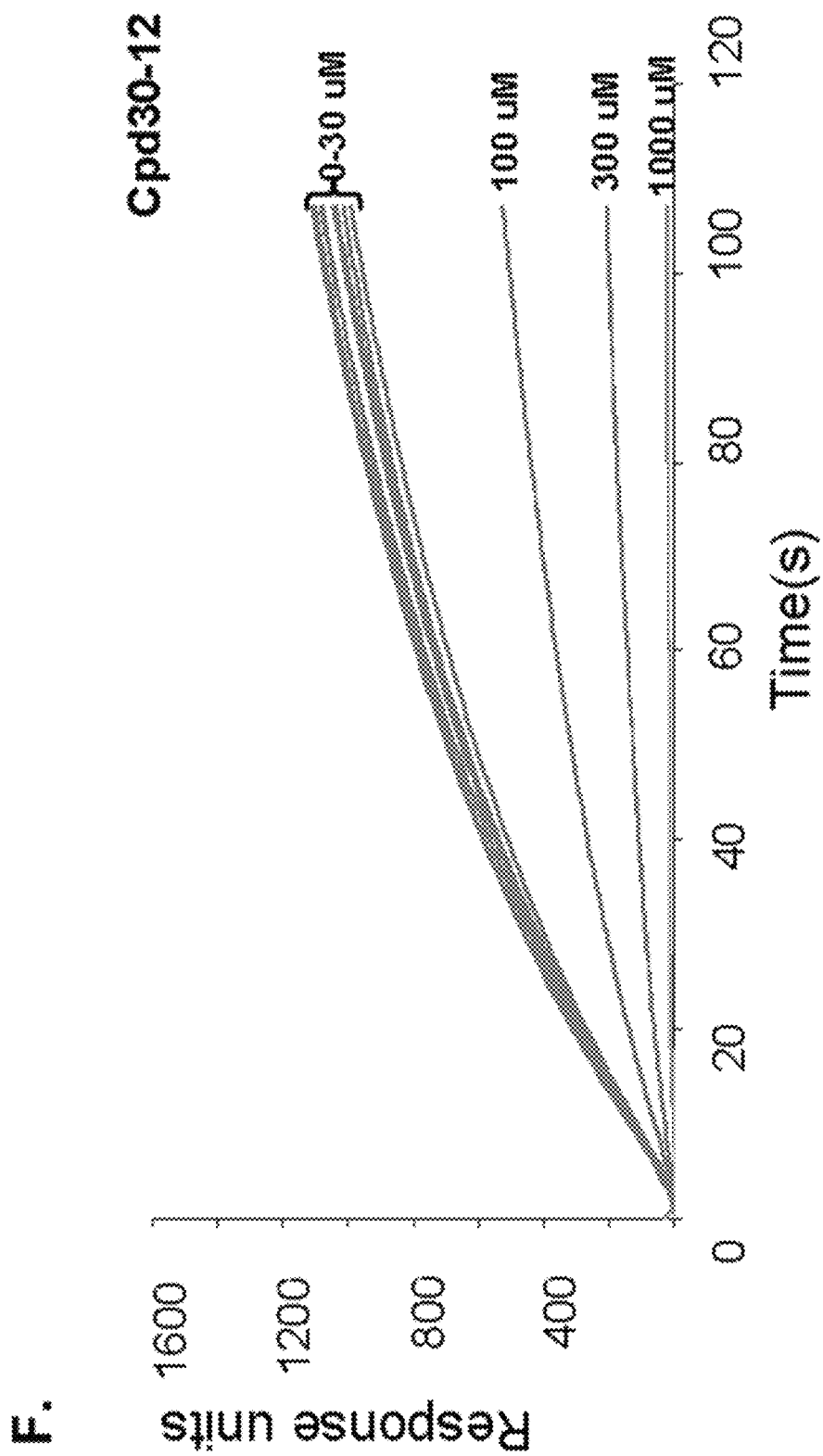
Figure 1:
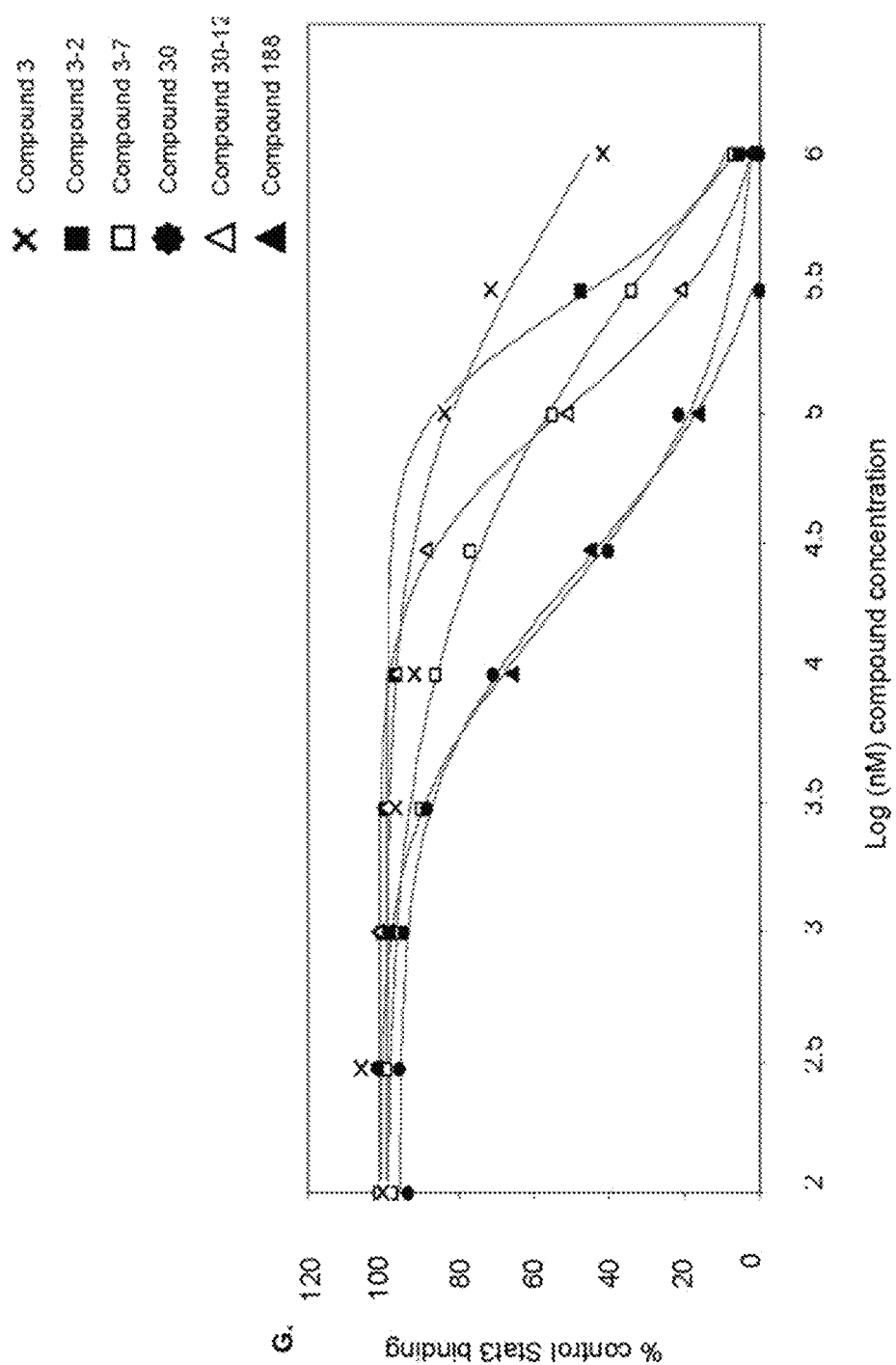

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

In some embodiments, there is a method of treating, preventing, and/or reducing the risk of fibrosis in an individual, comprising delivering to the individual one or more particular compounds. The fibrosis may be of any kind, although in some cases the fibrosis is not pulmonary fibrosis or myelofibrosis. In some embodiments, the compound(s) is a STAT3 inhibitor. In certain embodiments the compound(s) is not a STAT3 inhibitor. In particular cases, the compound(s) is a STAT1 inhibitor, but in particular cases it is not a STAT1 inhibitor. In certain aspects, there are some compounds that are both STAT3 and STAT1 inhibitors or is neither a STAT3 or STAT1 inhibitor.

In certain embodiments of the invention, there is a compound for use in the prevention, treatment, and/or reduction in risk for fibrosis, wherein the compound is selected from the group consisting of N-(1',2-dihydroxy-1,2'-binaphtha-len-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-yl sulfanyl)-naphthalen-1-yl]-benzenesulfonamide; a functionally active derivative and a mixture thereof.

In certain embodiments of the invention, there is a compound for use in the prevention, treatment, and/or reduction in risk for fibrosis, wherein the compound is selected from the group consisting of 4-[3-(2,3-dihydro-1,4-benzodioxin-6-yl)-3-oxo-1-propen-1-yl]benzoic acid; 4{5-[(3-ethyl-4-oxo-2-thioxo-1,3-thiazolidin-5-ylidene)methyl]-2-furyl}benzoic acid; 4-[({3-[(carboxymethyl)thio]-4-hydroxy-1-naphthyl}amino)sulfonyl]benzoic acid; 3-({2-chloro-4-[(1,3-dioxo-1,3-dihydro-2H-inden-2-ylidene) methyl]-6-ethoxyphenoxy}methyl)benzoic acid; methyl 4-({[3-(2-methyoxy-2-oxoethyl)-4,8-dimethyl-2-oxo-2H-chromen-7-yl]oxy}methyl)benzoate; 4-chloro-3-{5-[(1,3-diethyl-4,6-dioxo-2-thioxotetrahydro-5(2H)-pyrimidinylidene)methyl]-2-furyl}benzoic acid; a functionally active derivative and a mixture thereof. In a specific embodiment of the invention, the composition is a Stat3 inhibitor but does not inhibit Stat1.

In a specific embodiment of the invention, the composition is delivered in vivo in a mammal. In another embodiment the mammal is a human. In another specific embodiment the human is known to have fibrosis, is suspected of having fibrosis, or is at risk for developing fibrosis. In another embodiment, the human is known to have fibrosis and is receiving an additional therapy for the fibrosis and/or an underlying condition that is related to the fibrosis. Composition(s) of the disclosure treat, prevent, and/or reduce the risk or severity of fibrosis, in particular embodiments.

I. Definitions

As used herein the specification, "a" or "an" may mean one or more. As used herein in the claim(s), when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. Some embodiments of the invention may consist of or consist essentially of one or more elements, method steps, and/or methods of the invention. It is contemplated that any method or composition described herein can be implemented with respect to any other method or composition described herein.

The term "inhibitor" as used herein refers to one or more molecules that interfere at least in part with the activity of Stat3 to perform one or more activities, including the ability of Stat3 to bind to a molecule and/or the ability to be phosphorylated.

The phrase "therapeutically effective amount" as used herein means that amount of a compound, material, or composition comprising a compound of the present invention that is effective for producing some desired therapeutic effect, e.g., treating (i.e., preventing and/or ameliorating) cancer in a subject, or inhibiting protein-protein interactions mediated by an SH2 domain in a subject, at a reasonable benefit/risk ratio applicable to any medical treatment. In one embodiment, the therapeutically effective amount is enough to reduce or eliminate at least one symptom. One of skill in the art recognizes that an amount may be considered therapeutically effective even if the cancer is not totally eradicated but improved partially. For example, the spread of the cancer may be halted or reduced, a side effect from the cancer may be partially reduced or completed eliminated, life span of the subject may be increased, the subject may experience less pain, and so forth.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "at risk for having fibrosis" is used herein to refer to individuals that have a chance to have fibrosis because of past, present, or future factors.

As used herein, "binding affinity" refers to the strength of an interaction between two entities, such as a protein-protein interaction. Binding affinity is sometimes referred to as the $K_a$, or association constant, which describes the likelihood of the two separate entities to be in the bound state. Generally, the association constant is determined by a variety of methods in which two separate entities are mixed together, the unbound portion is separated from the bound portion, and concentrations of unbound and bound are measured. One of skill in the art realizes that there are a variety of methods for measuring association constants. For example, the unbound and bound portions may be separated from one another through adsorption, precipitation, gel filtration, dialysis, or centrifugation, for example. The measurement of the concentrations of bound and unbound portions may be accomplished, for example, by measuring radioactivity or fluorescence, for example. $K_a$ also can be inferred indirectly through determination of the $K_i$ or inhibitory constant. Determination of the $K_i$ can be made several ways for example by measuring the $K_a$ of STAT3 binding to its phosphopeptide ligand within the EGFR at position Y1068 and by measuring the concentration of a molecule that reduces binding of STAT3 by 50%. In certain embodiments of the invention, the binding affinity of a Stat3 inhibitor for the SH2 domain of Stat3 is similar to or greater than the affinity of the compounds listed herein.

The term "domain" as used herein refers to a subsection of a polypeptide that possesses a unique structural and/or functional characteristic; typically, this characteristic is similar across diverse polypeptides. The subsection typically comprises contiguous amino acids, although it may also comprise amino acids that act in concert or that are in close proximity due to folding or other configurations. An example of a protein domain is the Src homology 2 (SH2) domain of Stat3. The term "SH2 domain" is art-recognized, and, as used herein, refers to a protein domain involved in protein-protein interactions, such as a domain within the Src tyrosine kinase that regulates kinase activity. The invention contemplates modulation of activity, such as activity dependent upon protein-protein interactions, mediated by SH2 domains of proteins (e.g., tyrosine kinases such as Src) or proteins involved with transmission of a tyrosine kinase signal in organisms including mammals, such as humans.

As used herein, a "mammal" is an appropriate subject for the method of the present invention. A mammal may be any member of the higher vertebrate class Mammalia, including humans; characterized by live birth, body hair, and mammary glands in the female that secrete milk for feeding the young. Additionally, mammals are characterized by their ability to maintain a constant body temperature despite changing climatic conditions. Examples of mammals are humans, cats, dogs, cows, mice, rats, and chimpanzees. Mammals may be referred to as "patients" or "subjects" or "individuals".

II. General Embodiments

General embodiments include one or more compositions for the treatment and/or prevention of fibrosis and methods of use. The fibrosis may have an unknown cause or it may be associated with an underlying condition. The underlying condition may be a catabolic condition. The underlying condition may be autoimmune, chemical intoxication, a viral infection, and so forth.

In some cases an individual is suspected of having fibrosis; such suspicion may be because the individual has changes from normal in the characteristics and function of the skin, lung, heart, liver, and kidneys. In certain aspects, such suspicion may be because the individual has tight skin, shortness of breath with exertion, cough, yellowing of the sclera or skin and/or reduced urine production. In some cases, an individual may have at least one symptom of fibrosis but may have other symptoms as well.

In certain cases, an individual is at risk of having fibrosis. In such cases, the individual has a medical condition that can be associated with fibrosis and has not had enough progression of the medical condition to manifest fibrosis or has not yet had a detectable symptom of fibrosis.

In some embodiments, the individual is known to have an underlying condition that often has fibrosis as at least one symptom, and that individual may or may have not shown other symptoms or signs of having fibrosis. In cases wherein an individual has an underlying condition that often has fibrosis as at least one symptom, the individual may be provided with an effective amount of one or more compositions of the invention prior to and/or after the appearance of fibrosis. When the individual is provided one of more compositions prior to the appearance of fibrosis, the onset of fibrosis may be delayed or completely inhibited and/or the severity of the fibrosis may be reduced, compared to the condition of the individual without having received the composition(s), for example.

In particular embodiments, an individual has been diagnosed with an underlying condition known to have fibrosis as at least one symptom, and methods of the invention may include steps of diagnosing of the fibrosis and/or the underlying condition of the individual. An individual may be tested for fibrosis by standard means in the art.

Fibrosis can occur in response to or as part of autoimmune diseases such as systemic sclerosis, systemic lupus erythematosus or mixed connective tissue disease, for example. Fibrosis of the liver can occur in response to chronic liver disease from viral infections, parasitic infections, and toxins (such as alcohol), for example.

Embodiments concern STAT3 inhibitors as they related to biological mechanisms associated with fibrosis. To evaluate if STAT3 contributes to the development of tissue fibrosis in the lung and skin and whether it does so in part through the modulation of EMT, fibrotic tissue was examined from systemic sclerosis patients, idiopathic pulmonary fibrosis patients, and mouse models of lung and skin fibrosis. Tissues were assessed by immunohistology using a monoclonal antibody to the pY705 epitope within STAT3. The findings demonstrated that levels of pY705-STAT3 were increased in fibrotic tissue from systemic sclerosis patients, idiopathic pulmonary fibrosis patients, and mouse models of lung and skin fibrosis.

It was further determined that STAT3 signaling contributed to the development of fibrosis by using an example of a small molecule STAT-3 inhibitor. N-(1',2-dihydroxy-1,2'-binaphthalen-4'-yl)-4-methoxybenzenesulfonamide (herein also referred to as C188-9) was administered to mice in both the intraperitoneal (IP) bleomycin mouse model of lung fibrosis and the subcutaneous (SC) bleomycin mouse model of skin fibrosis. C-188-9 administration decreased fibrotic endpoints (collagen deposition by Sircol), expression of alpha-smooth muscle actin (SMA), and improved arterial oxygen saturation) in the IP bleomycin pulmonary fibrosis model. C-188-9 also decreased the development of dermal fibrosis in the SC bleomycin model as assessed by decreased dermal thickness, a reduction of alpha-SMA accumulation, and decreased collagen deposition.

The role of STAT3 in EMT and myofibroblast differentiation was determined by using C188-9 in tissue culture experiments with alveolar epithelial cells (AEC; MLE-12 and primary AEC) and murine lung fibroblasts. In vitro studies showed that TGF-beta or IL-6 trans-signaling (IL-6/sIL-6R-alpha) were able to induce EMT in primary AEC and MLE-12 cell line, as well as differentiation of fibroblasts into myofibroblast. C188-9 prevented TGF-beta and IL-6/sIL-6R-alpha induced EMT of AEC assessed by Col1a, alpha-SMA, Twist, and Snail mRNA levels and reduced myofibroblast differentiation as assessed by Col1a and alpha-SMA mRNA levels. Thus, the findings demonstrated that STAT3 contributes to the development of tissue fibrosis in the skin and the lung and plays a role in the development of myofibroblasts in vitro. Furthermore, the data indicate that STAT3 is a useful a therapeutic target in the treatment of dermal and pulmonary fibrosis, as well as fibrosis of any other tissue.

III. Fibrosis

Embodiments of the invention concern methods of treatment and/or prevention of any kind of fibrosis. Fibrosis includes the formation of excess fibrous connective tissue in a reparative or reactive process, such as in an organ or tissue. The establishment of fibrosis can be a reactive, benign, or pathological state. In injury cases, the fibrosis may be referred to as scarring. In particular embodiments, the fibrosis is related to overproduction of the protein collagen. The fibrosis may be related to excessive accumulation of extracellular matrix (ECM) proteins. The fibrosis may be related to accumulation of myofibroblasts.

In physiological embodiments, the fibrosis encompasses deposition of connective tissue that can severely impact the structure and/or function of the affected organ and/or tissue. In certain aspects, fibrosis is the pathological state of excess deposition of fibrous tissue and/or the state of undesirable connective tissue deposition in healing that is not necessarily pathological.

Although fibrosis can occur in many tissues and organs within the body, such as the result of inflammation or damage, for example, in some cases the fibrosis is not pulmonary fibrosis or myelofibrosis.

The fibrotic tissue may be present in the heart, lung, skin, intestine, joint, and/or liver, and so forth, in some cases, although in certain aspects the fibrotic tissue is not in the lung.

Specific types of fibrosis that may be treated and/or prevented in the present invention include at least liver cirrhosis, endomyocardial fibrosis, myocardial infarction, atrial fibrosis, mediastinal fibrosis, retroperitoneal fibrosis, progressive massive fibrosis, nephrogenic systemic fibrosis, Crohn's Disease, Keloid, scleroderma/systemic sclerosis, arthrofibrosis, adhesive capsulitis, fibrosis following exposure to certain drugs such as chemotherapy, fibrosis following exposure to environmental or other toxins or allergens, fibrosis occurring after an ischemia/reperfusion injury such as myocardial infarction or hypotension, fibrosis occurring after radiation, fibrosis following hepatitis induced by alcohol, toxins, drugs or infections, primary biliary cirrhosis, fibrosis following viral infections involving the heart, liver, or lung, and/or idiopathic retroperiotoneal fibrosis.

In embodiments of the invention, the fibrosis is skin fibrosis (that may also be referred to as dermal fibrosis), which may or may not be part of scleroderma. Diagnosis of skin fibrosis may include examination by a medical care provider and may include a biopsy. The skilled artisan recognizes that fibrosis may be evaluated, in certain settings (including research settings) in one or more of a variety of ways, including at least tissue staining (such as Hematoxylin and eosin (H& E) stain, Masson's trichrome stain (extracellular matrix (ECM, collagen)), or Sircol (for collagen); immunohistochemistry; western blot; and/or nucleic acid analysis, for example. Exemplary means of nucleic acid analysis includes expression analysis, such as using PCR (such as QRT-PCR); examples of genes for PCR analysis include at least (alpha smooth muscle actin) α-SMA and collagen, type 1, alpha 1 (Col1a).

In particular embodiments and in certain settings (such as research), one can analyze the fibrosis or suspicion of fibrosis by histology using H&E and Masson's trichrome and one can quantify certain measures by dermal thickness.

In particular embodiments and in certain settings (such as clinical), one can analyze the fibrosis or suspicion thereof. The analysis can include physical exam. For example, scleroderma patients have tight and fibrotic skin that starts in their fingers and creeps proximally (in some patients it totally encases them—diffuse systemic sclerosis/scleroderma; while in others it remains distal to the elbows—limited systemic sclerosis/scleroderma). The diagnosis can be confirmed by histology/skin biopsy.

In some embodiments, the skin fibrosis may be part of sclerodactyl), scleroderma, Amyloidosis, Dupytren's contracture, Peyronie's disease, Polymyositis, Carcinoid tumour, or Graft versus host disease, for example. Causes of skin fibrosis may be of any kind, such as unknown, Ainhum, Amyloidosis, Atrophoderma of Pasini and Pierini, Carcinoid tumours and carcinoid syndrome, Dupuytren's contracture, Eosinophilic fasciitis, Graft versus host disease, Hutchinson-Gilford progeria syndrome, Lichen myxedematosus, Mixed connective tissue disease, Morphoea, Nephrogenic systemic fibrosis, Peyronie's disease, Polymyositis, Porphyria cutanea tarda type 1 (sporadic), Scleredema adultorum, or systemic sclerosis.

An individual may be at risk for skin fibrosis because of family history or exposure to events or conditions that leaves them prone to fibrosis, such as radiation therapy or surgery.

Another type of fibrosis that may be treated, prevented, or have the risk reduced is cystic fibrosis (CF). CF includes scarring and cyst formation within the pancreas and can also affect the lungs, liver, and intestine. Symptoms include breathing difficulty, frequent lung infection, sinus infections, poor growth, infertility, accumulation of thick, sticky mucus, and salty skin. An individual may be at risk for CF if there is a family history, for example. Management of CF symptoms include intravenous, inhaled, and oral antibiotics; transplants; medications and/or mechanical techniques to dislodge and expectorate sputum, and so forth. Composition(s) of the invention may be utilized in conjuction with such management regimen(s).

Fibrosis of the liver can occur in reponse to chornic liver disease from viral infections, parasitic infections, and toxins (such as alcohol).

Renal fibrosis can occur from chronic kidney diseases, hypertension, diabetes, and autoimmune diseases, for example.

IV. Compositions

Embodiments of the invention encompass compositions that are useful for treating, preventing, and/or reducing the risk of fibrosis. Specific compositions are disclosed herein, but one of skill in the art recognizes that functional derivatives of such compositions are also encompassed by the invention. The term "derivative" as used herein is a compound that is formed from a similar compound or a compound that can be considered to arise from another compound, if one atom is replaced with another atom or group of atoms. Derivative can also refer to compounds that at least theoretically can be formed from the precursor compound.

In particular embodiments, compositions and functionally active derivatives as described herein are utilized in treatment and/or prevention of fibrosis. Specific but nonlimiting examples of different R groups for the compositions are provided in Tables 1, 2, and 3.

The term "functionally active derivative" or "functional derivative" is a derivative as previously defined that retains the function of the compound from which it is derived. In one embodiment of the invention, a derivative of N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2'] binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2'] binaphthalenyl-4'-yl)-4-methoxy-benzenesulfonamide, 4-Bromo-N-(1,6'-dihydroxy-[2,2']binaphthalenyl-4-yl)-benzene sulfonamide, 4-Bromo-N-[4-hydroxy-3-(1H-[1,2,4]triazol-3-yl sulfanyl)-naphthalen-1-yl]-benzene sulfonamide, 4-[3-(2,3-dihydro-1,4-benzodioxin-6-yl)-3-oxo-1-propen-1-yl]benzoic acid, 4{5-[(3-ethyl-4-oxo-2-thioxo-1,3-thiazolidin-5-ylidene)methyl]-2-furyl}benzoic acid, 4-[({3-[(carboxymethyl)thio]-4-hydroxy-1-naphthyl}amino)sulfonyl] benzoic acid, 3-({2-chloro-4-[1,3-dioxo-1,3-dihydro-2H-inden-2-ylidene)methyl]-6-ethoxyphenoxy}methyl)benzoic acid, methyl 4-({[3-(2-methyoxy-2-oxoethyl)-4,8-dimethyl-2-oxo-2H-chromen-7-yl]oxy}methyl)benzoate, or 4-chloro-3-{5-[(1,3-diethyl-4,6-dioxo-2-thioxotetrahydro-5(2H)-pyrimidinylidene)methyl]-2-furyl}benzoic acid retains Stat3 inhibitory activity. In another embodiment of the invention, a derivative of 4-[3-(2,3-dihydro-1,4-benzodioxin-6-yl)-3-oxo-1-propen-1-yl]benzoic acid, 4{5-[(3-ethyl-4-oxo-2-thioxo-1,3-thiazolidin-5-ylidene)methyl]-2-furyl}benzoic acid, 4-[({3-[(carboxymethyl)thio]-4-hydroxy-1-naphthyl}amino)sulfonyl]benzoic acid, 3-({2-chloro-4-[(1,3-dioxo-1,3-dihydro-2H-inden-2-ylidene)methyl]-6-ethoxyphenoxy}methyl)benzoic acid, methyl 4-({[3-(2- methoxy-2-oxoethyl)-4,8-dimethyl-2-oxo-2H-chromen-7-yl]oxy}methyl)benzoate, or 4-chloro-3-{5-[(1,3-diethyl-4,6-dioxo-2-thioxotetrahydro-5(2H)-pyrimidinylidene)methyl]-2-furyl}benzoic acid retains Stat3 inhibitory activity and, in specific embodiments, also retains non-inhibition of Stat1, although in some cases it may also inhibit Stat1.

In a specific embodiment of the invention, there is a method of treating and/or preventing fibrosis in an individual comprising delivering to the individual a compound selected from the group consisting of N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-ylsulfanyl)-naphthalen-1-yl]-benzenesulfonamide; 4-[3-(2,3-dihydro-1,4-benzodioxin-6-yl)-3-oxo-1-propen-1-yl]benzoic acid 4{5-[(3-ethyl-4-oxo-2-thioxo-1,3-thiazolidin-5-ylidene)methyl]-2-furyl}benzoic acid; 4-[({3-[(carboxymethyl)thio]-4-hydroxy-1-naphthyl}amino)sulfonyl]benzoic acid; 3-({2-chloro-4-[(1,3-dioxo-1,3-dihydro-2H-inden-2-ylidene)methyl]-6-ethoxyphenoxy}methyl)benzoic acid; methyl 4-({[3-(2-methyoxy-2-oxoethyl)-4,8-dimethyl-2-oxo-2H-chromen-7-yl]oxy}methyl)benzoate; 4-chloro-3-{5-[(1,3-diethyl-4,6-dioxo-2-thioxotetrahydro-5(2H)-pyrimidinylidene)methyl]-2-furyl}benzoic acid; and a mixture thereof.

In another embodiment, the composition comprises the general formula:

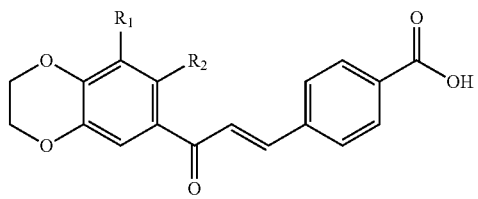

wherein $R_1$ and $R_2$ may be the same or different and are selected from the group consisting of hydrogen, carbon, sulfur, nitrogen, oxygen, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

In another embodiment of the invention, the composition comprises the general formula:

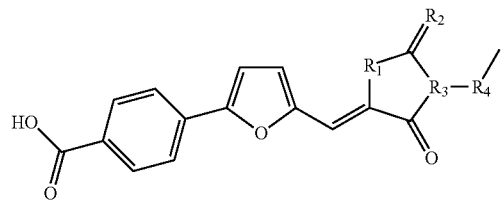

wherein $R_1$, and $R_3$ may be the same or different and are selected from the group consisting of hydrogen, carbon, nitrogen, sulfur, oxygen, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives, and $R_2$ and $R_4$ may be the same or different and are selected from the group consisting of hydrogen, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

In another embodiment of the invention, the composition comprises the general formula:

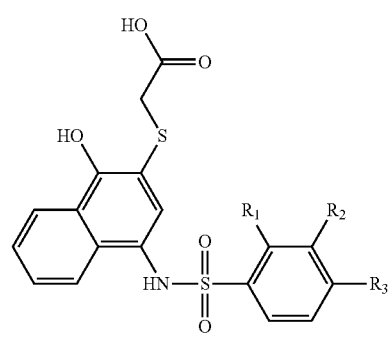

wherein $R_1$, $R_2$, and $R_3$ may be the same or different and are selected from the group consisting of hydrogen, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, and benzoic acid-based derivatives.

An exemplary and illustrative list of alkanes, cyclic alkanes, and alkane-based derivates are described herein. Non-limiting examples of ketones, ketone-based derivatives, aldehydes, aldehyde-based derivatives; carboxylic acids, carboxylic acid-based derivatives, ethers, ether-based derivatives, esters, ester-based derivatives, amines, amino-based derivatives, amides, and amide-based derivatives are listed herein. Exemplary monocyclic or polycyclic arene, heteroarenes, arene-based or heteroarene-based derivatives, phenols, phenol-based derivatives, benzoic acid and benzoic acid-based derivatives are described herein.

TABLE 1

| Chemical names | Formulas |
| --- | --- |
| Methyl | $CH_3$ |
| Ethyl | $C_2H_5$ |
| Vinyl (ethenyl) | $C_2H_3$ |
| Ethynyl | $C_2H$ |
| Cyclopropyl | $C_3H_5$ |
| Cyclobutyl | $C_4H_7$ |
| Cyclopentyl | $C_5H_9$ |
| Cyclohexyl | $C_6H_{11}$ |

TABLE 2

| Chemical names | Chemical formulas |
| --- | --- |
| Acetonyl | $C_3H_5O$ |
| Methanal (formaldehyde) | $CH_2O$ |
| Paraldehyde | $C_6H_{12}O_3$ |
| Ethanoic acid | $CH_3COOH$ |
| Diethyl ether | $C_4H_{10}O$ |
| Trimethylamine | $C_3H_9N$ |
| Acetamide | $C_2H_5NO$ |
| Ethanol | $C_2H_5OH$ |
| Methanol | $CH_3OH$ |

TABLE 3

| Chemical names | Chemical formulas |
| --- | --- |
| Benzol | $C_6H_6$ |
| Phenol | $C_6H_6O$ |
| Benzoic acid | $C_7H_6O_2$ |
| Aniline | $C_6H_7N$ |
| Toluene | $C_7H_8$ |
| Pyridazine | $C_4H_4N_2$ |
| Pyrimidine | $C_4H_4N_2$ |
| Pyrazine | $C_4H_4N_2$ |
| Biphenyl | $C_{12}H_{10}$ |

The compositions of the present invention and any functionally active derivatives thereof may be obtained by any suitable means. In specific embodiments, the derivatives of the invention are provided commercially, although in alternate embodiments the derivatives are synthesized. The chemical synthesis of the derivatives may employ well known techniques from readily available starting materials. Such synthetic transformations may include, but are not limited to protection, de-protection, oxidation, reduction, metal catalyzed C—C cross coupling, Heck coupling or Suzuki coupling steps (see for example, March's Advanced Organic Chemistry: Reactions, Mechanisms, and Structures, $5^{th}$ Edition John Wiley and Sons by Michael B. Smith and Jerry March, incorporated here in full by reference).

V. Embodiments for Targeting Stat3

STAT proteins, of which there are seven (1, 2, 3, 4, 5A, 5B and 6), transmit peptide hormone signals from the cell surface to the nucleus. Detailed structural information of STAT proteins currently is limited to Stat1 and Stat3. Stat1 was the first STAT to be discovered (Fu et al., 1992) and is required for signaling by the Type I and II IFNs (Meraz et al., 1996; Wiederkehr-Adam et al., 2003; Durbin et al., 1996; Haan et al., 1999). Studies in Stat1-deficient mice (Meraz et al., 1996; Durbin et al., 1996; Ryan et al., 1998) support an essential role for Stat1 in innate immunity, notably against viral pathogens. In addition, Stat1 is a potent inhibitor of growth and promoter of apoptosis (Bromberg and Darnell, 2000). Also, because tumors from carcinogen-treated wild-type animals grow more rapidly when transplanted into the Stat1-deficient animals than they do in a wild-type host, Stat1 contributes to tumor surveillance (Kaplan et al., 1998).

Stat3 was originally termed acute-phase response factor (APRF) because it was first identified as a transcription factor that bound to IL-6-response elements within the enhancer-promoter region of various acute-phase protein genes (Akira, 1997). In addition to receptors for the IL-6 cytokine family, other signaling pathways are linked to Stat3 activation include receptors for other type I and type II cytokine receptors, receptor tyrosine kinases, G-protein-coupled receptors and Src kinases (Schindler and Darnell, 1995; Turkson et al., 1998). Targeted disruption of the mouse Stat3 gene leads to embryonic lethality at 6.5 to 7.5 days (Takeda et al., 1997) indicating that Stat3 is essential for early embryonic development possibly gastrulation or visceral endoderm function (Akira, 2000). Tissue-specific deletion of Stat3 using Cre-lox technology has revealed decreased mammary epithelial cell apoptosis resulting in delayed breast involution during weaning (Chapman et al., 1999). Recent findings indicate that switching of the predominant STAT protein activated by a given receptor can occur when a STAT downstream of that receptor is genetically deleted (Costa-Pereira et al., 2002; Qing and Stark, 2004). These findings suggest the possibility that the effect of Stat3 deletion in breast tissue may be mediated indirectly by increased activation of other STAT proteins, especially Stat5.

Figure 13:
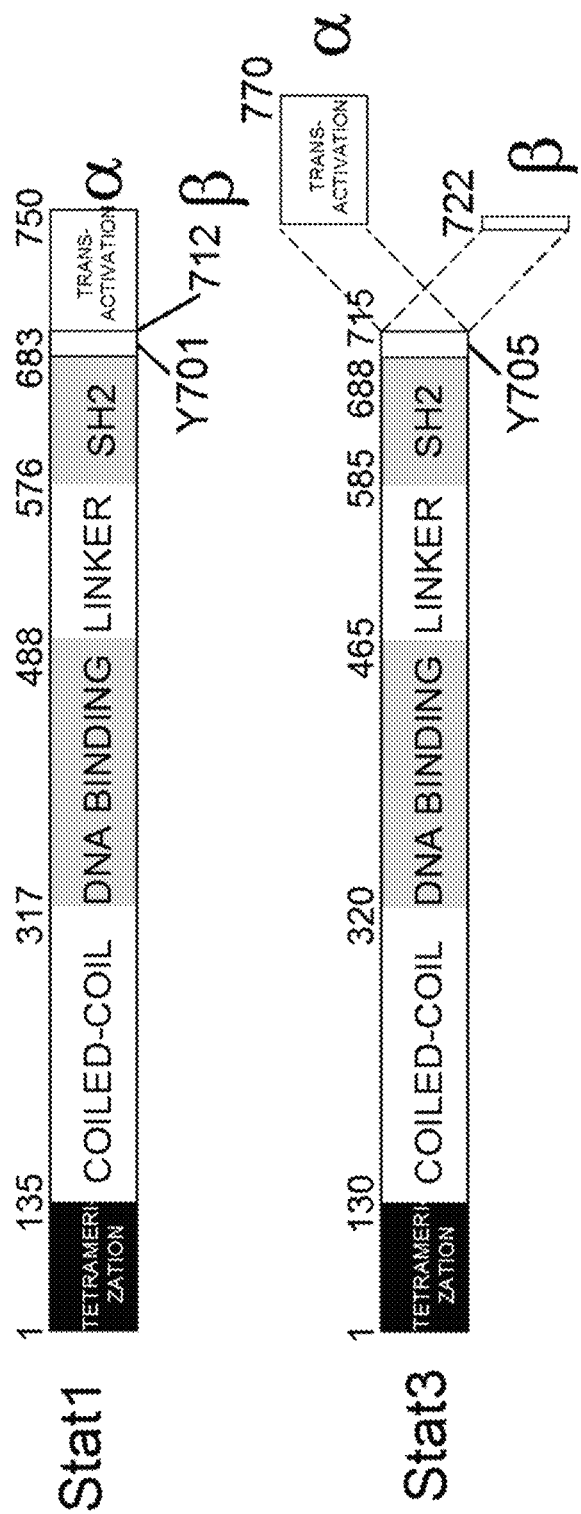
FIG. 13 illustrates schematic diagrams of Stat1 and Stat3.
Figure 14:
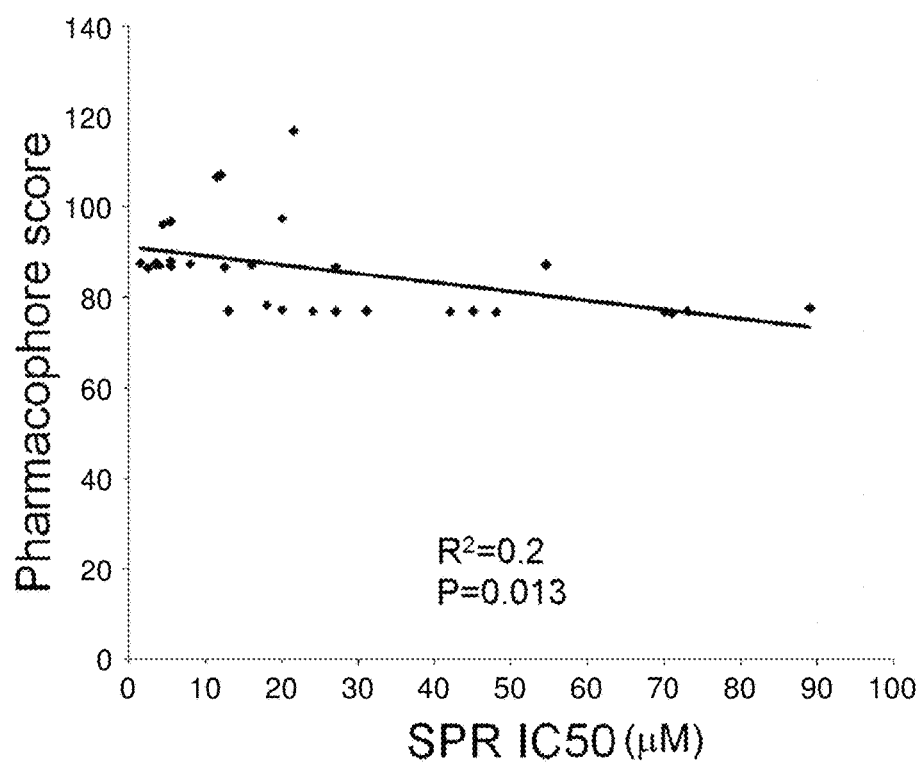
FIG. 14 demonstrates that SPR $IC_{50}$ of 2nd generation Stat3 chemical probes is inversely correlated with 3-D pharmacophore score.
Figure 15A:
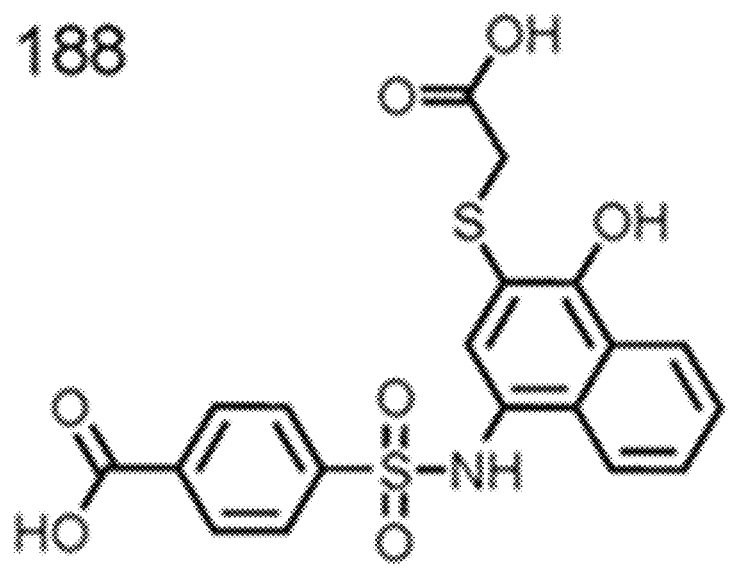
FIGS. 15A-15C shows SPR $IC_{50}$ and AML apoptosis $EC_{50}$ of parent Cpd188 and two 2nd generation 188-like Stat3 chemical probes.
Figure 15A:
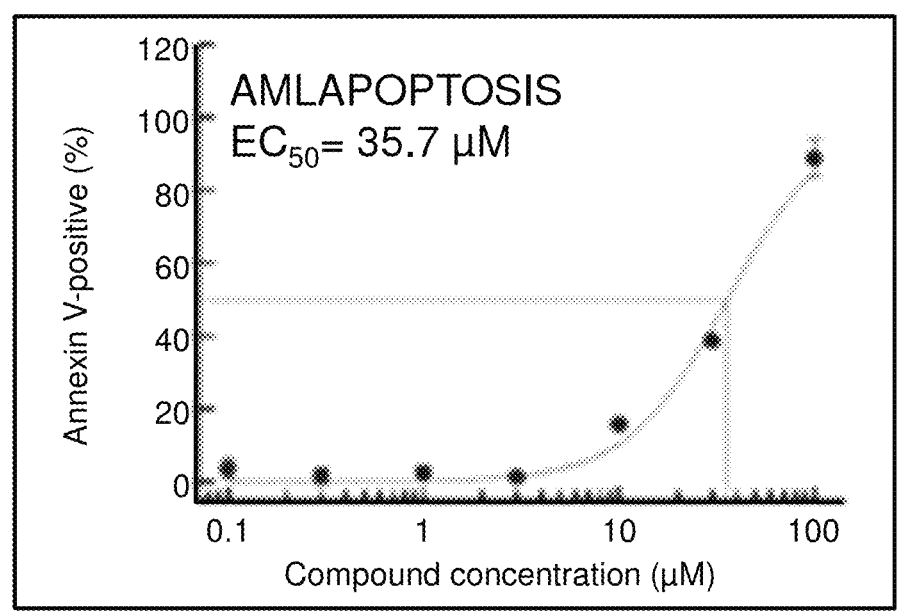
Figure 15B:
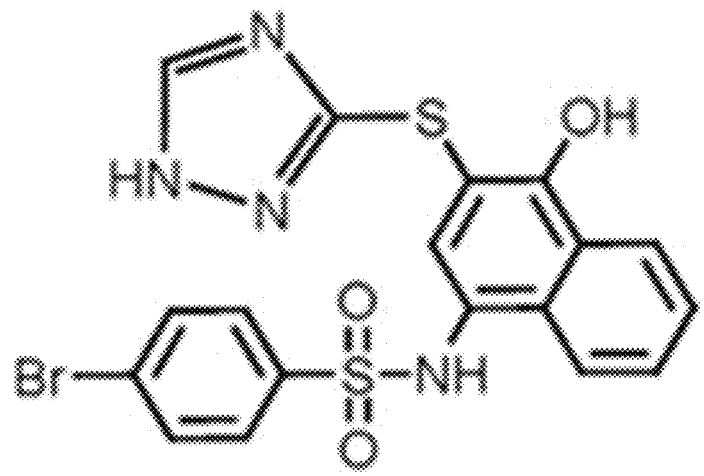
Figure 15B:
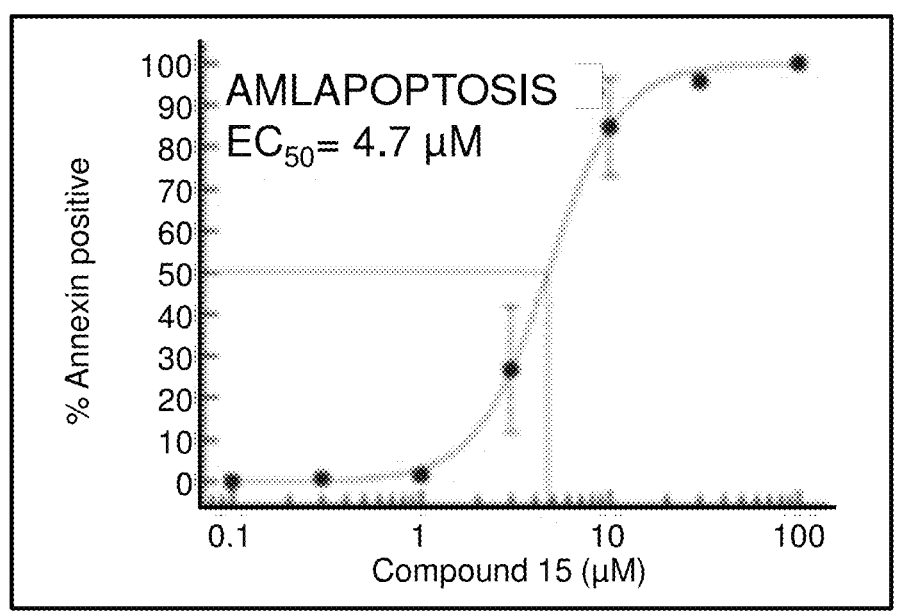
Figure 15C:
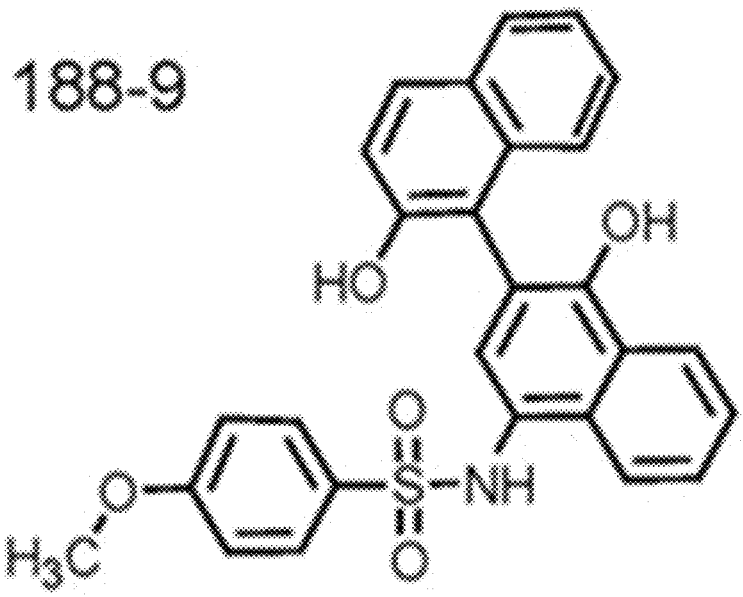
Figure 15C:
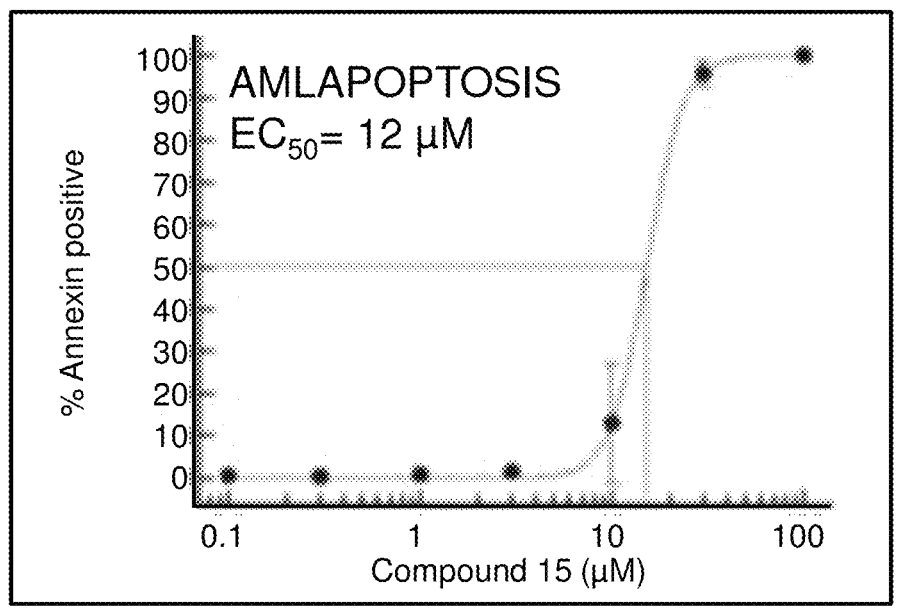

Stat1 and Stat3 Isoforms. Two isoforms of Stat1 and Stat3 have been identified—α(p91 and p92, respectively) and β (p84 and p83, respectively) (Schindler et al., 1992; Schaefer et al., 1995; Caldenhoven et al., 1996; Chakraborty et al., 1996)—that arise due to alternative mRNA splicing (FIG. 13). In contrast to Stat1β (712 aa), in which the C-terminal transactivation is simply deleted, the 55 amino acid residues of Stat3α are replaced in Stat3 β by 7 unique amino acid residues at its C-terminus. Unlike Stat1β, Stat3β is not simply a dominant-negative of Stat3α (Maritano et al., 2004) and regulates gene targets in a manner distinct from Stat3β (Maritano et al., 2004; Yoo et al., 2002). Stat3α has been demonstrated to contribute to transformation in cell models and many human cancers including breast cancer. Stat3α was shown to be constitutively activated in fibroblasts transformed by oncoproteins such as v-Src (Yu et al., 1995; Garcia and Jove, 1998) and to be essential for v-Src-mediated transformation (Turkson et al., 1998; Costa-Pereira et al., 2002). In contrast to Stat3α, Stat3β antagonized v-Src transformation mediated through Stat3α (Turkson et al., 1998). Overexpression of a constitutively active form of Stat3α in immortalized rat or mouse fibroblasts induced their transformation and conferred the ability to form tumors in nude mice (Bromberg et al., 1999). Stat3 has been shown to be constitutively activated in a variety of hematological and solid tumors including breast cancer (Dong et al., 2003; Redell and Tweardy, 2003) as a result of either autocrine growth factor production or dysregulation of protein tyrosine kinases. In virtually all cases, the isoform demonstrating increased activity is Stat3α.

Targeting Stat3α While Sparing Stat1.

Given its multiple contributory roles to oncogenesis, Stat3 has recently gained attention as a potential target for cancer therapy (Bromberg, 2002; Turkson, 2004). While several methods of Stat3 inhibition have been employed successfully and have established proof-of-principle that targeting Stat3 is potentially beneficial in a variety of tumor systems including breast cancer in which Stat3 is constitutively activated (Epling-Burnette et al., 2001; Yoshikawa et al., 2001; Li and Shaw, 2002; Catlett-Falcone et al., 1999; Mora et al., 2002; Grandis et al., 2000; Leong et al., 2003; Jing et al., 2003; Jing et al., 2004; Turkson et al., 2001; Ren et al., 2003; Shao et al., 2003; Turkson et al., 2004; Uddin et al., 2005); all have potential limitations for translation to clinical use for cancer therapy related to issues regarding delivery, specificity or toxicity.

Specific strategies that target Stat3 by identifying inhibitors of Stat3 recruitment and/or dimerization have been pursued by several groups (Turkson et al., 2001; Ren et al., 2003; Shao et al., 2003; Uddin et al., 2005; Song et al., 2005; Schust et al., 2006). As outlined below, this strategy has the potential to achieve specificity based on the observation that the preferred pY peptide motif of each STAT protein is distinct. When coupled to a small molecule approach, this strategy has the potential to overcome issues of delivery and toxicity.

Targeting Stat3α while Sparing Stat3β.

Some of the distinct biochemical features of Stat3β vs. Stat3α, notably constitutive activation and a 10-to-20 fold increased DNA binding affinity, have been attributed to the absence of the C-terminal transactivation domain (TAD) resulting in increased Stat3β dimer stability (Park et al., 1996; Park et al., 2000). Increased dimer stability likely results from higher binding affinity of the SH2 domain to pY peptide motifs when in the context of Stat3β compared to Stat3α because of reduced steric hindrance conferred by removal of the TAD. These differential biochemical features between Stat3α and Stat3β are exploited to develop a chemical compound that selectively targets Stat3 α, in some embodiments. This selectivity enhances the anti-tumor effect of such compounds, in certain cases, because they would spare Stat3β, which functions to antagonize the oncogenic functions of Stat3α.

In certain embodiments of the invention, specific therapies targeting Stat3 signaling are useful for treatment of fibrosis.

VI. Combination Therapy

It is an aspect of this invention that a composition as disclosed herein is used in combination with another agent or therapy method, such as another fibrosis treatment. In embodiments wherein the fibrosis is skin fibrosis, the additional therapy may be phototherapy, such as UVA1 phototherapy, ciprofloxacin, bosentan, methotrexate, E4 peptide (synthetic version of a peptide building block obtained from the natural protein endostatin; Yamaguchi et al., 2012), P144, a compound that is a known inhibitor of TGF-β (U.S. Pat. No. 7,582,609) and so forth.

The composition(s) (which may or may not be a Stat3 inhibitor) may precede or follow the other agent treatment by intervals ranging from minutes to weeks, for example. In embodiments where the other agent and the composition of the invention are applied separately to an individual with fibrosis, such as upon delivery to an individual suspected of having fibrosis, known to have fibrosis, or at risk for having fibrosis, one would generally ensure that a significant period of time did not expire between the time of each delivery, such that the agent and composition of the invention would still be able to exert an advantageously combined effect on the individual.

For example, in such instances, it is contemplated that one may contact the cell, tissue or organism with one, two, three, four or more modalities substantially simultaneously (i.e., within less than about a minute) with the composition of the invention. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the composition of the invention. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the composition of the invention, for example. In some situations, it may be desirable to extend the time period for treatment significantly, such as where several weeks (e.g., about 1, about 2, about 3, about 4, about 5, about 6, about 7 or about 8 weeks or more) lapse between the respective administrations. In some situations, it may be desirable to extend the time period for treatment significantly, such as where several months (e.g., about 1, about 2, about 3, about 4, about 5, about 6, about 7 or about 8 weeks or more) lapse between the respective administrations.

Various combinations may be employed, the composition of the invention is "A" and the secondary agent, which can be any other cancer therapeutic agent, is "B":

| A/B/A | B/A/B | B/B/A | A/A/B | A/B/B | B/A/A |
|-------|-------|-------|-------|-------|-------|
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of the therapeutic compositions of the present invention to a patient will follow general protocols for the administration of drugs, taking into account the toxicity. It is expected that the treatment cycles would be repeated as necessary.

In some cases, the combination therapy is an antimicrobial agents. Any antimicrobial agent(s) may be used, such as one or more of methyl propyl and chlorocresol, for example.

VII. Pharmaceutical Compositions

Pharmaceutical compositions of the present invention comprise an effective amount of a composition as disclosed herein dissolved or dispersed in a pharmaceutically acceptable carrier. The phrases "pharmaceutical" or "pharmacologically acceptable" refer to molecular entities and compositions that do not produce an adverse, allergic or other untoward reaction when administered to an animal, such as, for example, a human, as appropriate. The preparation of a pharmaceutical composition that contains at least one Stat3 inhibitor of the invention, and in some cases an additional active ingredient, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition(s) may comprise different types of carriers depending on whether it is to be administered in solid, liquid or aerosol form, and whether it needs to be sterile for such routes of administration such as injection. The composition(s) can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), as an aerosol, or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an individual can be determined by physical and physiological factors such as body weight, severity of condition, the type of disease being treated, previous or concurrent therapeutic interventions, and the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a composition. In other embodiments, the active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above. In certain embodiments of the invention, various dosing mechanisms are contemplated. For example, the composition may be given one or more times a day, one or more times a week, or one or more times a month, and so forth.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The composition may be formulated in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropylcellulose; or combinations thereof such methods. In many cases, it will be preferable to include isotonic agents, such as, for example, sugars, sodium chloride or combinations thereof.

Sterile injectable solutions are prepared by incorporating the instant invention in the required amount of the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VIII. Kits of the Invention

Any of the compositions described herein may be comprised in a kit, and they are housed in a suitable container. The kits will thus comprise, in suitable container means, one or more compositions and, in some cases, an additional agent of the present invention. In some cases, there are one or more agents other than the composition of the disclosure that are included in the kit, such as one or more other agents for the treatment of fibrosis and/or one or more agents for the treatment of an underlying condition associated with fibrosis. In particular embodiments, there is an apparatus or any kind of means for the diagnosing of fibrosis.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the composition, additional agent, and any other reagent containers in close confinement for commercial sale. Such containers may include injection or blow molded plastic containers into which the desired vials are retained.

Compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Materials and Methods

Virtual Ligand Screening.

The inventors isolated the three-dimensional structure of the Stat3 SH2 domain from the core fragment structure of phosphorylated Stat3 homodimers bound to DNA (Becker et al., 1998) deposited in the RCSB Protein Data Bank (PDB) databank (PDB code 1BG1) and converted it to be an Internal Coordinate Mechanics (ICM)-compatible system by adding hydrogen atoms, modifying unusual amino acids, making charge adjustments and performing additional cleanup steps. In addition, the inventors retrieved the coordinates of the Stat1 SH2 domain from the PDB databank (PDB code 1BF5) for use in computational selectivity analysis (Chen et al., 1998). Commercial chemical databases (Chembridge, Asinex, ChemDiv, Enamine, Keyorganics and Life Chemicals) were chosen as sources of compounds for screening in silico. Selection was of the amide hydrogen of E638 within the site that binds the +3 residue (Q, C or T) within the pY-peptide ligand (Shao et al., 2006) as the central point of the binding pocket, which consisted of a cube with dimensions 16.0×16.9×13.7 angstrom. In addition to the +3 binding site, this cube contained the pY residue binding site consisting mainly of R609 and K591 (Shao et al., 2006) and a hydrophobic binding site consisting of $Loop_{\beta C-\beta D}$ and $Loop_{\alpha B-\alpha C}$. Sequence alignment and overlay of the Stat3 and Stat1 structures revealed substantial differences in sequence of these loops; lack of their superimposition indicated that this region might serve as a selectivity filter (Cohen et al., 2005). A flexible docking calculation (Totrov and Abagyan 1997) was performed in order to determine the global minimum energy score and thereby predict the optimum conformation of the compound within the pocket. A compound was selected for purchase and biochemical testing based on fulfilling the criteria of interaction analysis (CIA): 1) global minimum energy score 30, 2) formation of a salt-bridge and/or H-bond network within the pY-residue binding site and 3) formation of a H-bond with or blocking access to the amide hydrogen of E638. Most, but not all, compounds also interacted with the hydrophobic binding site.

Stat3 SH2/pY-peptide binding assay. Stat3 binding assays were performed at 25° C. with a BIAcore 3000 biosensor using 20 mM Tris buffer pH 8 containing 2 mM mercaptoethanol and 5% DMSO as the running buffer (Kim et al., 2005). Phosphorylated and control non-phosphorylated biotinylated EGFR derived dodecapeptides based on the sequence surrounding Y1068 (Shao et al., 2004) were immobilized on a streptavidin coated sensor chip (BIAcore inc., Picataway N.J.). The binding of Stat3 was conducted in 20 mM Tris buffer pH 8 containing 2 mM β-mercaptoethanol at a flow rate of 10 uL/min for 1-2 minute. Aliquots of Stat3 at 500 nM were premixed with compound to achieve a final concentration of 1-1,000 uM and incubated at 4° C. prior to being injected onto the sensor chip. The chip was regenerated by injecting 10 uL of 100 mM glycine at pH 1.5 after each sample injection. A control (Stat3 with DMSO but without compound) was run at the beginning and the end of each cycle (40 sample injections) to ensure that the integrity of the sensor chip was maintained throughout the cycle run. The average of the two controls was normalized to 100% and used to evaluate the effect of each compound on Stat3 binding. Responses were normalized by dividing the value at 2 min by the response obtained in the absence of compounds at 2 min and multiplying by 100. $IC_{50}$ values were determined by plotting % maximum response as a function of log concentration of compound and fitting the experimental points to a competitive binding model using a four parameter logistic equation: $R=R_{high}-(R_{high}-R_{low})/(1+conc/A1)^{\wedge}A2$, where R=percent response at inhibitor concentration, $R_{high}$=percent response with no compound, $R_{low}$=percent response at highest compound concentration, A2=fitting parameter (slope) and A1=$IC_{50}$ (BIAevaluation Software version 4.1).

Immunoblot assay. The human hepatocellular carcinoma cell line (HepG2) was grown in 6-well plates under standard conditions. Cells were pretreated with compounds (0, 1, 3, 10, 30, 100 and 300 uM) for 1 hour then stimulated under optimal conditions with either interferon gamma (IFN-γ; 30 ng/ml for 30 min) to activate Stat1 or interleukin-6 (IL-6; 30 ng/ml for 30 min) to activate Stat3 (30-31). Cultures were then harvested and proteins extracted using high-salt buffer, as described (Shao et al., 2006). Briefly, extracts were mixed with 2× sodium dodecyl sulfate (SDS) sample buffer (125 mmol/L Tris-HCL pH 6.8; 4% SDS; 20% glycerol; 10% 2-mercaptoethanol) at a 1:1 ratio and heated for 5 minutes at 100° C. Proteins (20 µg) were separated by 7.5% SDS-PAGE and transferred to polyvinylidene fluoride (PVDF) membrane (Millipore, Waltham, Mass.) and immunoblotted. Prestained molecular weight markers (Biorad, Hercules, Calif.) were included in each gel. Membranes were probed serially with antibody against Stat1 $pY^{701}$ or Stat3 $pY^{705}$ followed by antibody against Stat1 or Stat3 (Transduction labs, Lexington, Ky.) then antibody against β-actin (Abcam, Cambridge, Mass.). Membranes were stripped between antibody probing using Restore™ Western Blot Stripping Buffer (Thermo Fisher Scientific Inc., Waltham, Mass.) per the manufacturer's instructions. Horseradish peroxidase-conjugated goat-anti-mouse IgG was used as the secondary antibody (Invitrogen Carlsbad, Calif.) and the membranes were developed with enhanced chemiluminescence (ECL) detection system (Amersham Life Sciences Inc.; Arlington Heights, Ill.).

Similarity screen. Three compounds identified in the initial virtual ligand screening (VLS)—Cpd3, Cpd30 and Cpd188—inhibited Stat3 SH2/pY-peptide binding and IL-6-mediated Stat3 phosphorylation and were chosen as reference molecules for similarity screening. A fingerprint similarity query for each reference compound was submitted to Molcart/ICM (Max Distance, 0.4). Similarity between each reference molecule and each database molecule was computed and the similarity results were ranked in decreasing order of ICM similarity score (Eckert and Bajorath 2007). The databases searched included ChemBridge, LifeChemicals, Enamine, ChemDiv, Asinex, AcbBlocks, KeyOrganics and PubChem for a total of 2.47 million compounds. All compounds identified were docked into the binding pocket of Stat3 SH2 domain in silico. Compounds that fulfilled CIA criteria were purchased and tested as described for compounds identified in the primary screen.

Electrophoretic Mobility Shift Assay (EMSA): EMSA was performed using the hSIE radiolabeled duplex oligonucleotide as a probe as described (Tweardy et al., 1995). Briefly, high salt extracts were prepared from HepG2 cells incubated without or with IL-6 (30 ng/ml) for 30 minutes. Protein concentration was determined by Bradford Assay and 20 ug of extract was incubated with compound (300 uM) for 60 minutes at 37° C. Bound and unbound hSIE probe was separated by polyacrylamide gel electrophoresis (4.5%). Gels were dried and autoradiographed.

Molecular modeling. All 3-D configurations of the Stat3 SH2 domain complexed with compounds were determined by global energy optimization that involves multiple steps: 1) location of organic molecules were adjusted as a whole in 2 Å amplitude by pseudo-Brownian random translations and rotations around the molecular center of gravity, 2) the internal variables of organic molecules were randomly changed. 3) coupled groups within the Stat3 SH2 domain side-chain torsion angles were sampled with biased probability shaking while the remaining variables of the protein were fixed, 4) local energy minimizations were performed using the Empirical Conformation Energy Program for Peptides type-3 (ECEPP3) in a vacuum (Nemethy et al., 1992) with distance-dependent dielectric constant ε=4r, surface-based solvent energy and entropic contributions from the protein side chains evaluated added and 5) conformations of the complex, which were determined by Metropolis criteria, were selected for the next conformation-scanning circle. The initial 3-dimensional configuration of the Stat1 SH2 domain in a complex with each compound was predicted and generated by superimposing, within the computational model, the 3-dimensional features of the Stat1 SH2 onto the 3-dimensional configuration of the Stat3 SH2 domain in a complex with each compound. The final computational model of Stat1 SH2 in a complex with each compound was determined by local minimization using Internal Coordinate Force Field (ICFF)-based molecular mechanics (Totrov and Abagyan 1997). The inventors computed the van der Waals energy of the complex of Stat1 or 3-SH2 bound with each compound using Lennard-Jones potential with ECEPP/3 force field (Nemethy et al., 1992).

Confocal and high-throughput fluorescence microscopy. Confocal and highthroughput fluorescence microscopy (HTFM) of MEF/GFP-Stat3α cells were performed as described (Huang et al., 2007). Briefly, for confocal fluorescence microscopy, cells were grown in 6-well plates containing a cover slip. For HTFM, cells were seeded into 96-well CC3 plates at a density of 5,000 cells/well using an automated plating system. Cells were cultured under standard conditions until 85-90% confluent. Cells were pretreated with compound for 1 hour at 37° C. then stimulated with IL-6 (200 ng/ml) and IL-6sR (250 ng/ml) for 30 minutes. Cells were fixed with 4% formaldehyde in PEM Buffer (80 mM Potassium PIPES, pH 6.8, 5 mM EGTA pH 7.0, 2 mM $MgCl_2$) for 30 minutes at 4° C., quenched in 1 mg/ml of NaBH4 (Sigma) in PEM buffer and counterstained for 1 min in 4,6-diamidino-2-phenylindole (DAPI; Sigma; 1 mg/ml) in PEM buffer. Cover slips were examined by confocal fluorescent microscopy. Plates were analyzed by automated HTFM using the Cell Lab IC Image Cytometer (IC100) platform and CytoshopVersion 2.1 analysis software (Beckman Coulter). Nuclear translocation is quantified by using the fraction localized in the nucleus (FLIN) measurement (Sharp et al., 2006).

Breast cancer cell line apoptosis assay. Human breast carcinoma cell lines MDA-MB-468, MDA-MB-231, MBA-MD-435 and MCF7 were kindly provided by Dr. Powel H. Brown (Breast Cancer Center, Baylor College of Medicine). Breast cancer cell line, MDA-MB-453 was kindly provided by Dr. Shou Jiang (Breast Cancer Center, Baylor College of Medicine). All cell lines were grown in DMEM medium supplemented with 10% fetal bovine serum (FBS), 25,000 units penicillin G, 25,000 ug streptomycin, and 131.4 mg L-Glutamine and cultured in the incubator under the condition of 95% air, 5% $CO_2$ at 37° C. (Garcia et al., 2001). Cells were seeded at 2,500 cells/$cm^2$ into 12-well plates. At 80% confluency, cells were washed with PBS and supplemented with fresh medium containing compound or the topoisomerase I-inhibitor, camptothecin, at 0, 0.1, 03, 1, 3, 10, 30, 100, 300 µM. At 24 hours, treatment was terminated by removing the medium from each well. Cells were lysed with cell lysis buffer (600 for 30 minutes at 25° C.). Cell lysate (200 µl) was centrifuged at 200×g for 10 minutes and 20 of each supernatant was assayed for nucleosomes using the Cell Death Detection ELISA (Roche Applied Science) as described by the manufacturer. The percent maximum nucleosome level was calculated by dividing the nucleosome level by the maximum nucleosome level achieved in the assay and multiplying by 100. This value was plotted as a function of the log compound concentration and the best-fitting curve generated using 4-Parameter Logistic Model/Dose Response/XLfit 4.2, IDBS software.

Example 2

Identification by VLS of Compounds that Blocked Stat3 Binding to its Phosphopeptide Ligand and Inhibited IL-6-Mediated Phosphorylation of Stat3

Figure 3:
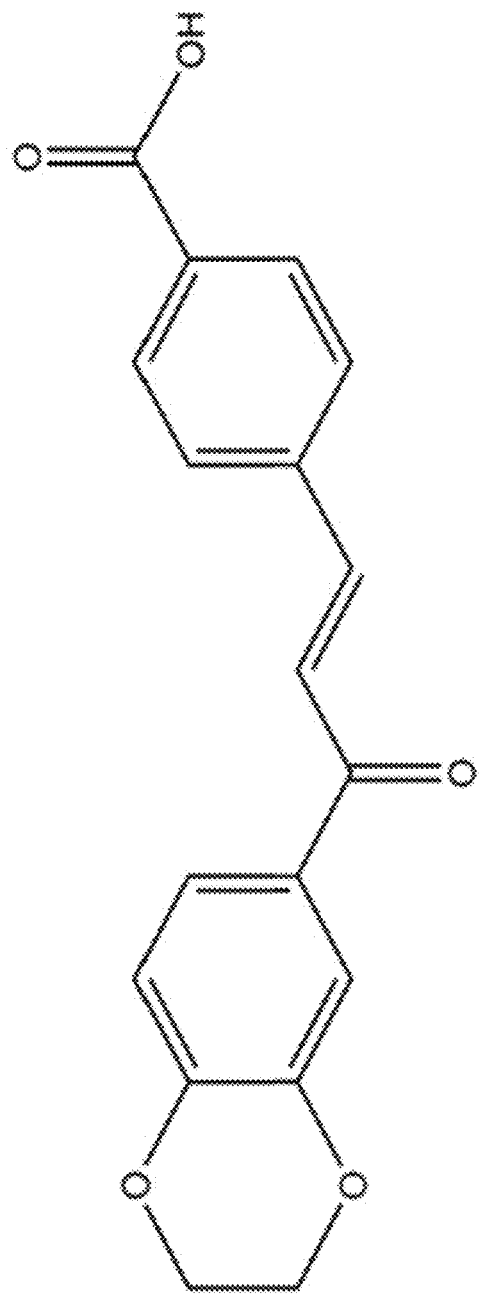
FIG. 3 provides exemplary chemical formulas and names of compounds. The chemical formulas and names are indicated for Cpd3 (panel A), Cpd30 (panel B), Cpd188 (panel C), Cpd3-2 (panel D), Cpd3-7 (panel E) and Cpd30-12 (panel F).
Figure 3:
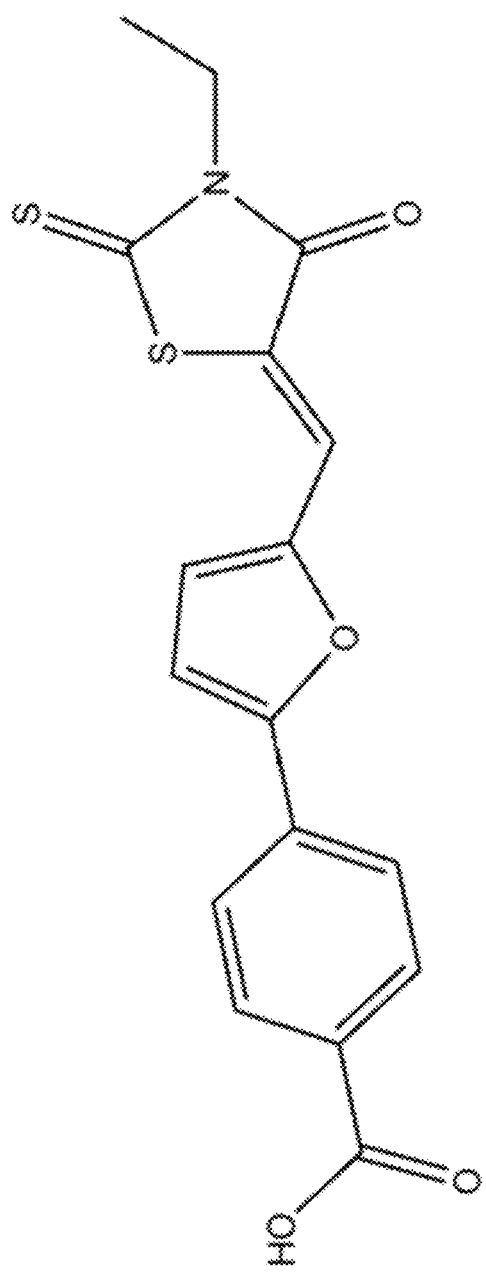
Figure 3:
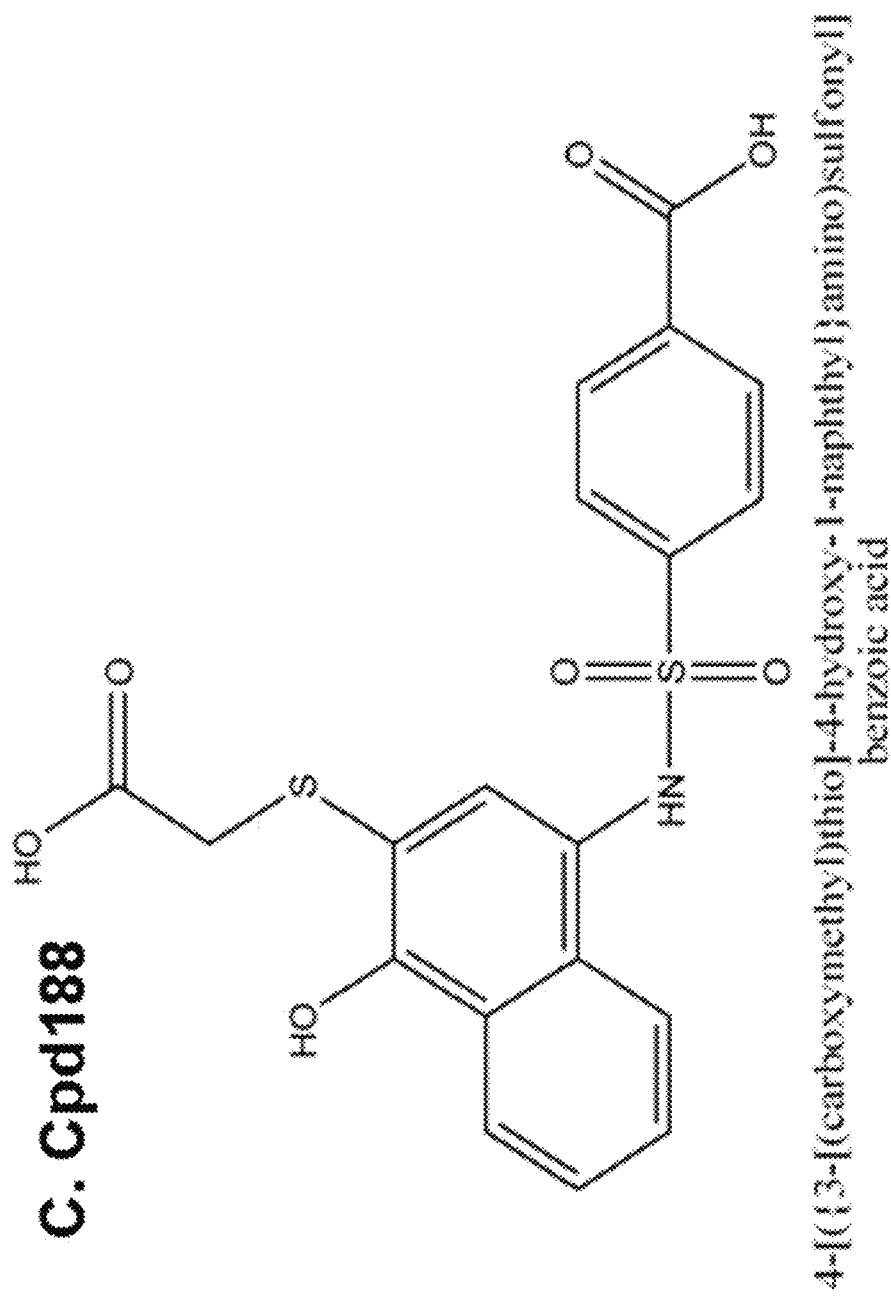
Figure 3:
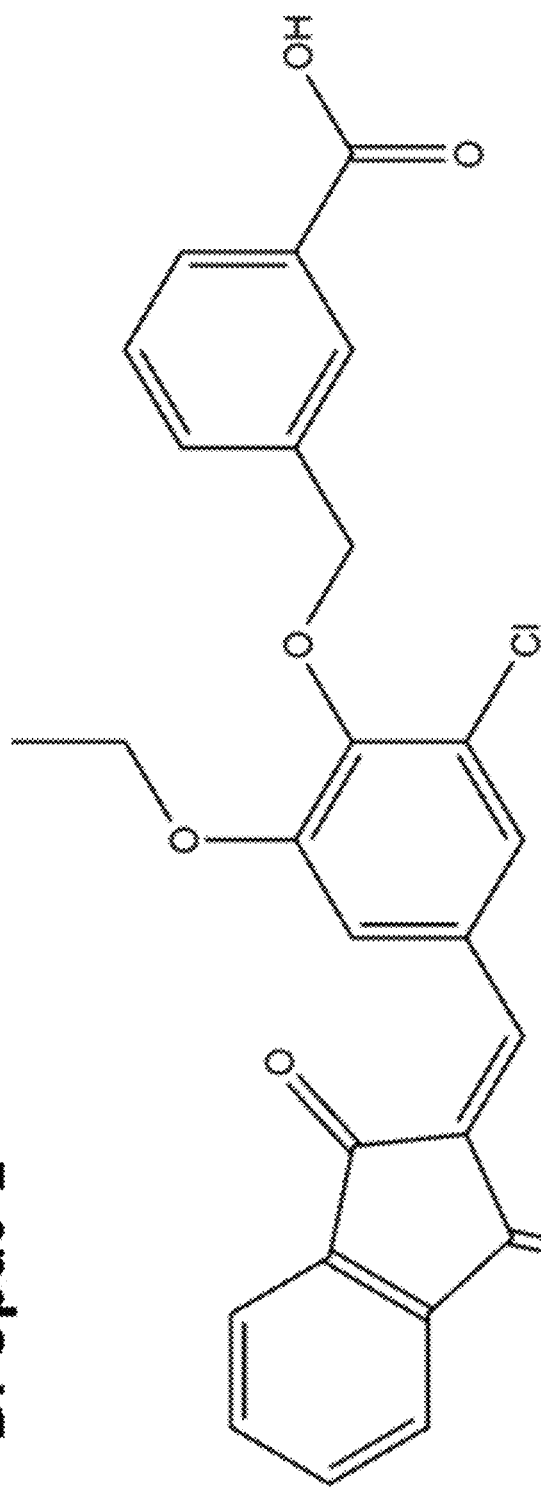
Figure 3:
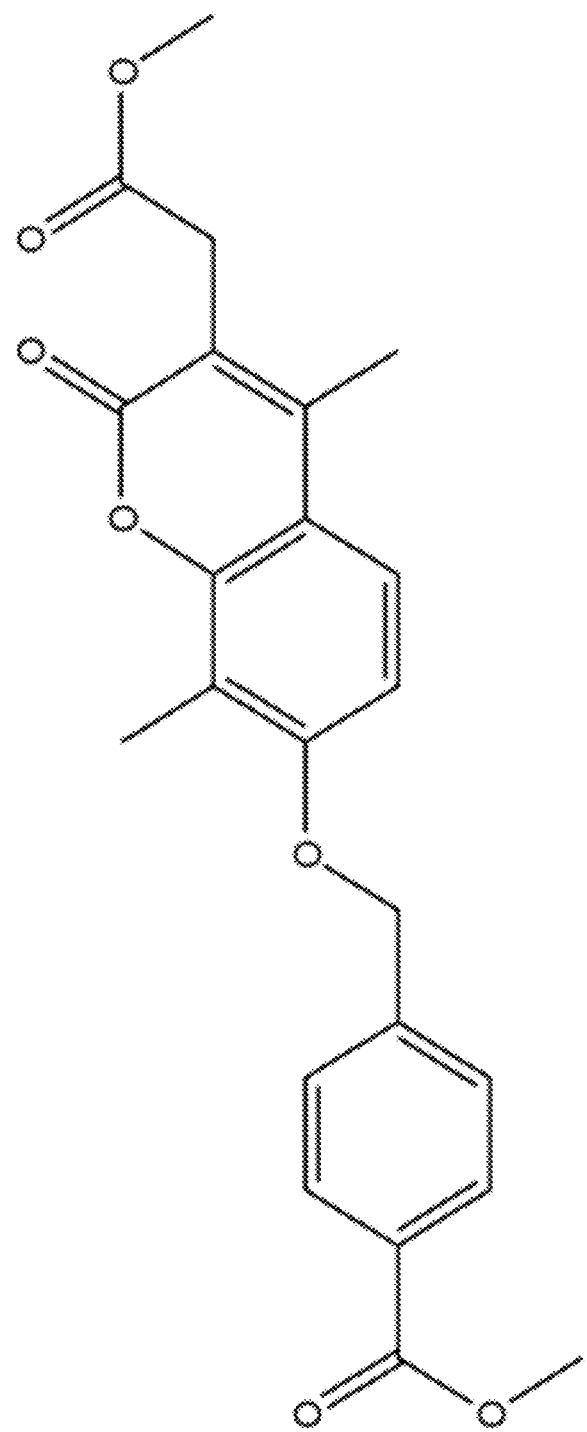
Figure 3:
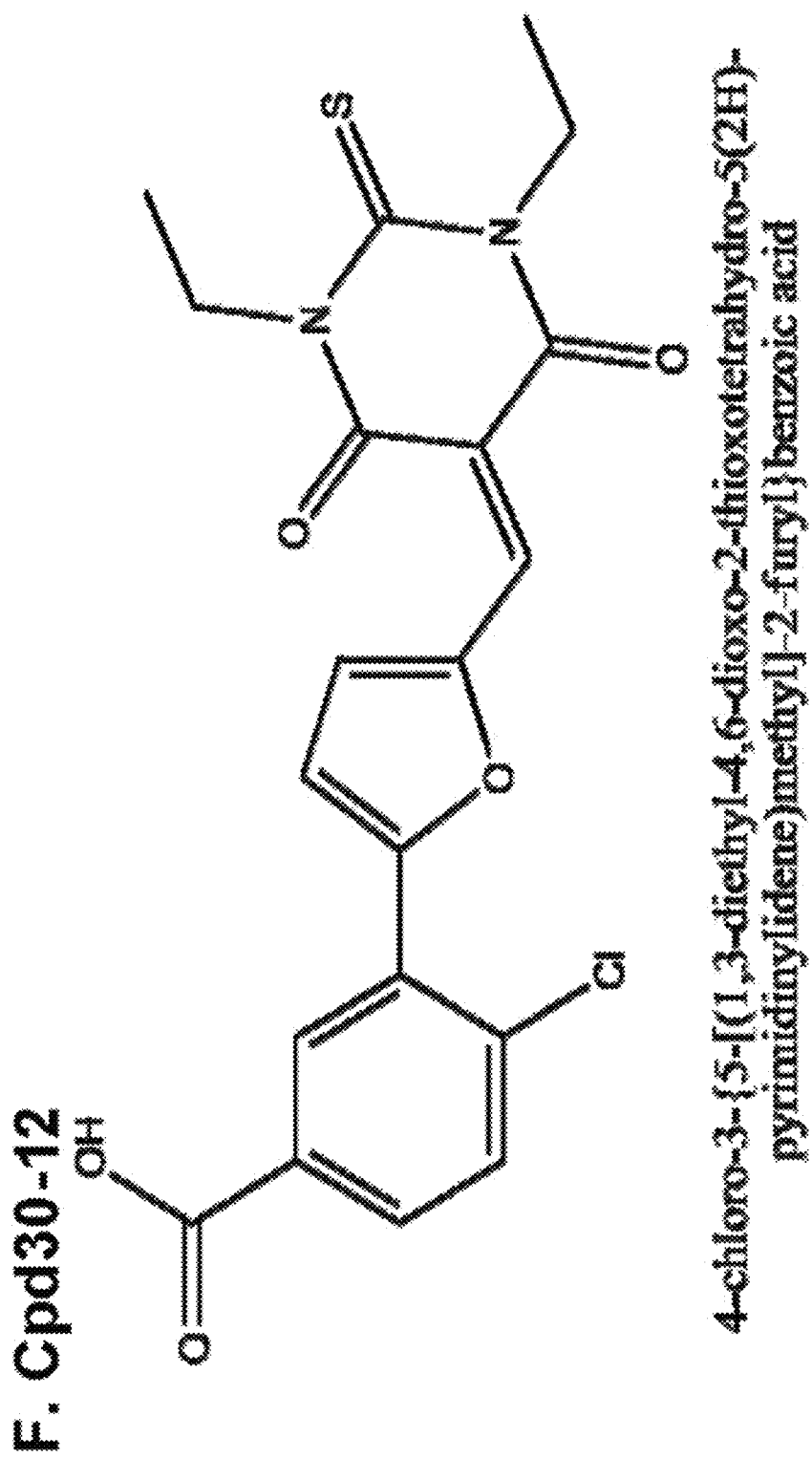

The VLS protocol was used to evaluate a total of 920,000 drug-like compounds. Of these, 142 compounds fulfilled CIA criteria. These compounds were purchased and tested for their ability to block Stat3 binding to its phosphopeptide ligand in a surface plasmon resonance (SPR)-based binding assay and to inhibit IL-6-mediated phosphorylation of Stat3. SPR competition experiments showed that of the 142 compounds tested, 3 compounds—Cpd3, Cpd30 and Cpd188—were able to directly compete with pY-peptide for binding to Stat3 with $IC_{50}$ values of 447, 30, and 20 µM, respectively (FIGS. 1 and 3; Table 4).

TABLE 4

$IC_{50}$ values (µM) of 6 active compounds

| Assay | Cpd3 | Cpd30 | Cpd188 | Cpd3-2 | Cpd3-7 | Cpd30-12 |
|---|---|---|---|---|---|---|
| SPR | 447[1] | 30 | 20 | 256 | 137 | 114 |
| pStat3 | 91 | 18 | 73 | 144 | 63 | 60 |
| HTM | 131 | 77 | 39 | 150 | 20 | >300 |

[1]Data presented are the mean or mean ± SD;
ND = not determined.

Figure 2:
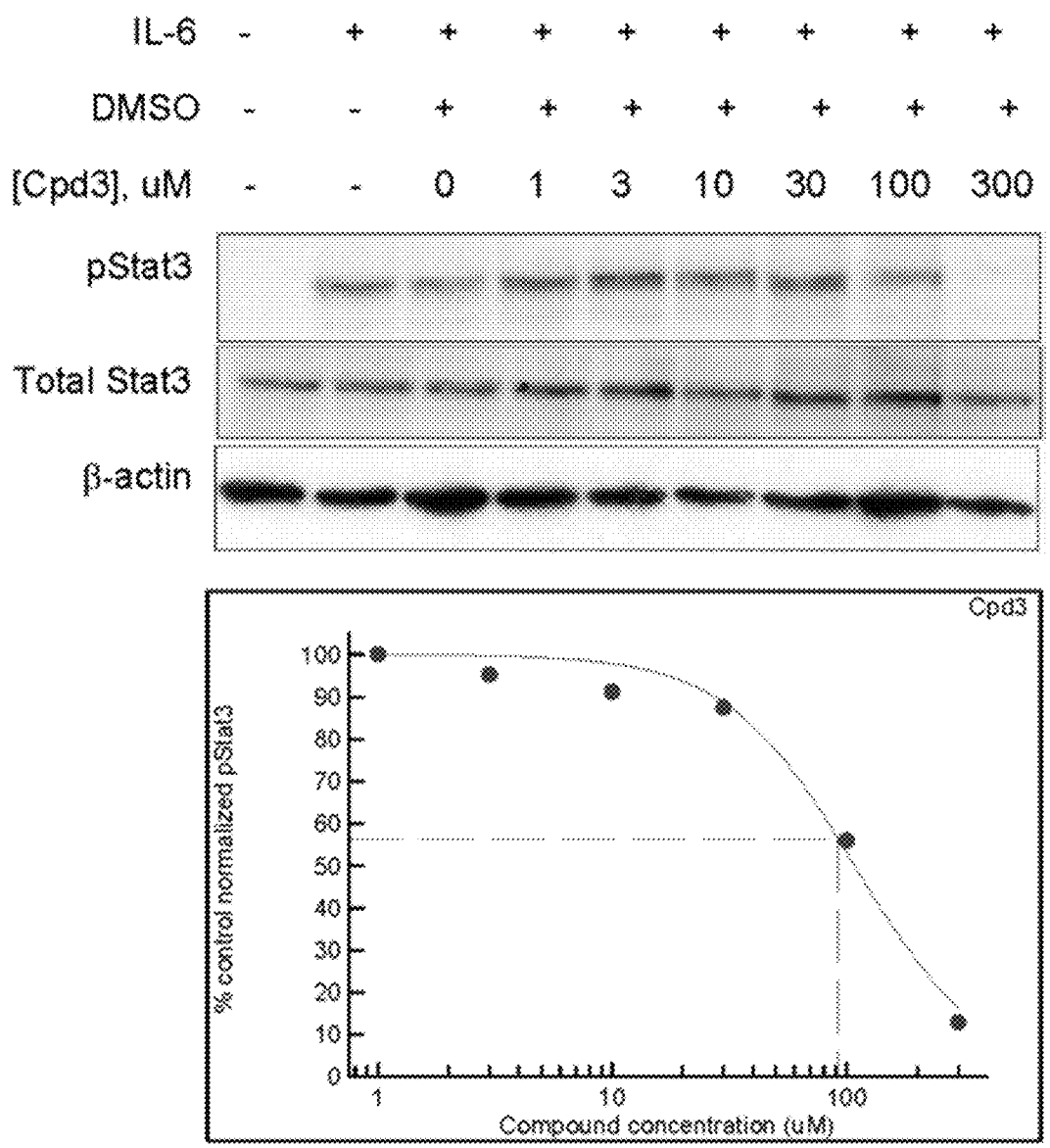
FIG. 2 demonstrates inhibition of IL-6-mediated activation of Stat3 by compounds. HepG2 cells were pretreated with DMSO alone or DMSO containing Cpd3 (panel A), Cpd188 (panel B), Cpd30 (panel C), Cpd3-2 (panel D), Cpd3-7 (panel E) or Cpd30-12 (panel F) at the indicated concentration for 60 min. Cells were then stimulated with IL-6 (30 ng/ml) for 30 min. Protein extracts of cells were separated by SDS-PAGE, blotted and developed serially with antibodies to pStat3, total Stat3 and β-actin. Blots were stripped between each antibody probing. The bands intensities of immunoblot were quantified by densitometry. The value of each pStat3 band's intensity was divided by each corresponding value of total Stat3 band intensity and the results normalized to the DMSO-treated control value and plotted as a function of the log compound concentration. The best-fit curves were generated based on 4 Parameter Logistic Model/Dose Response One Site/XLfit 4.2, IDBS. Each panel is representative of 3 or more experiments.
Figure 2:
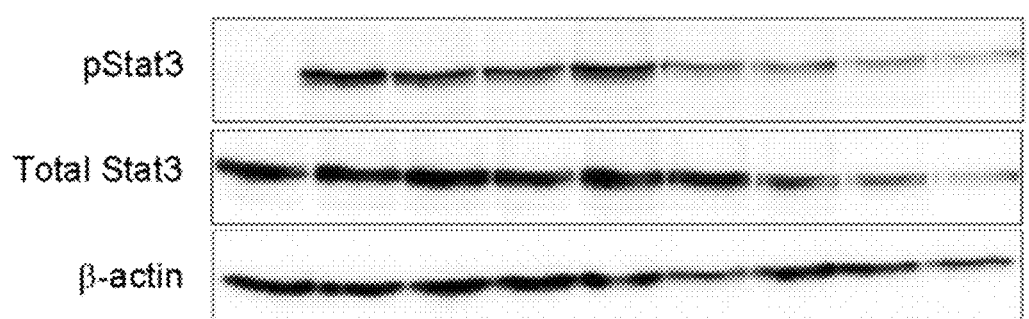
Figure 2:
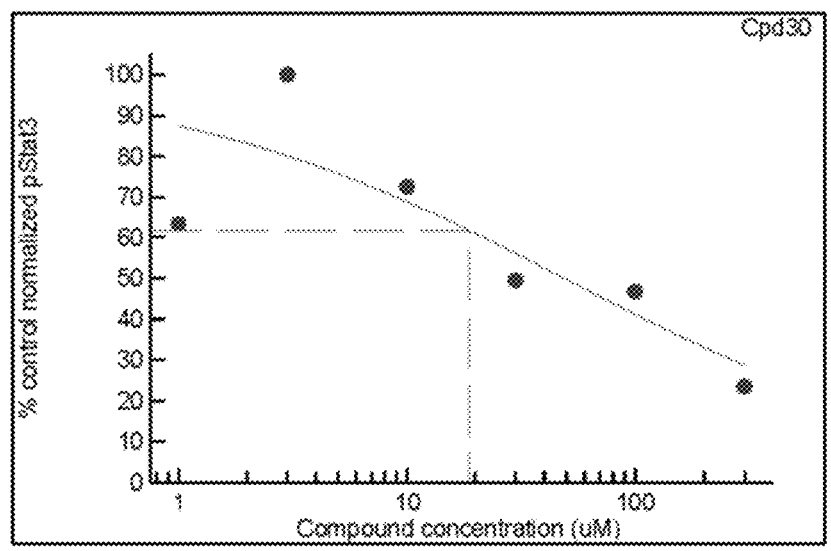
Figure 2:
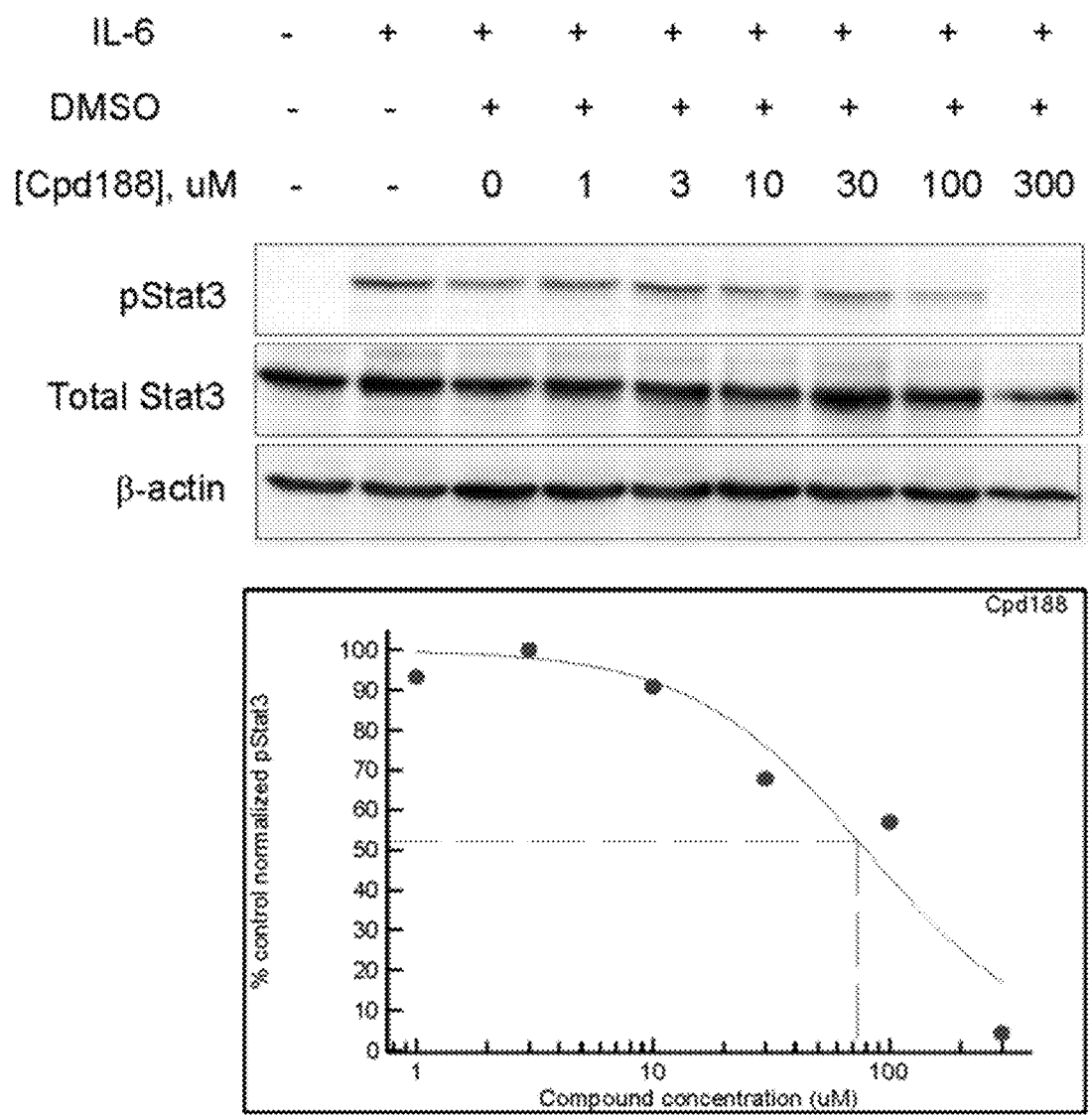
Figure 2:
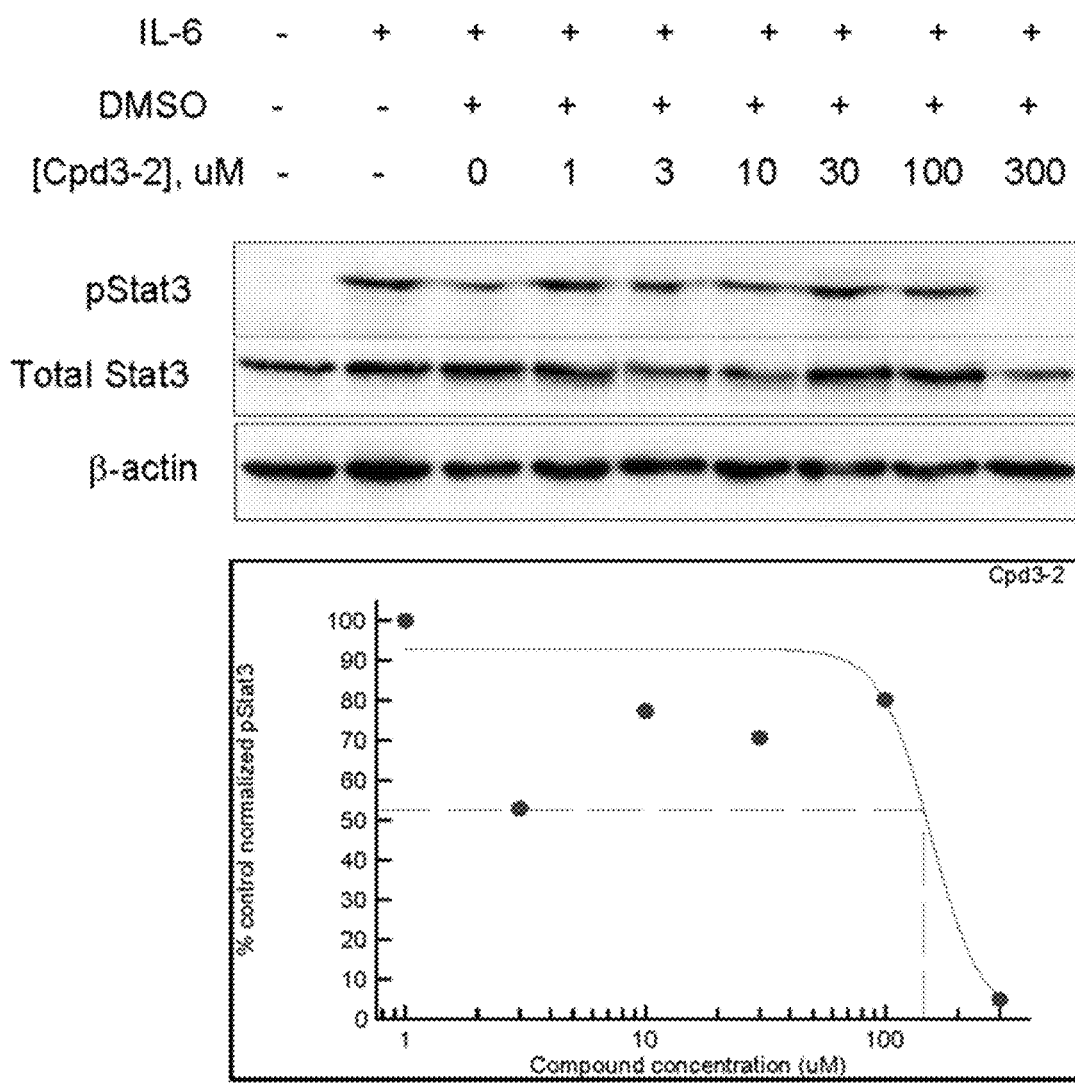
Figure 2:
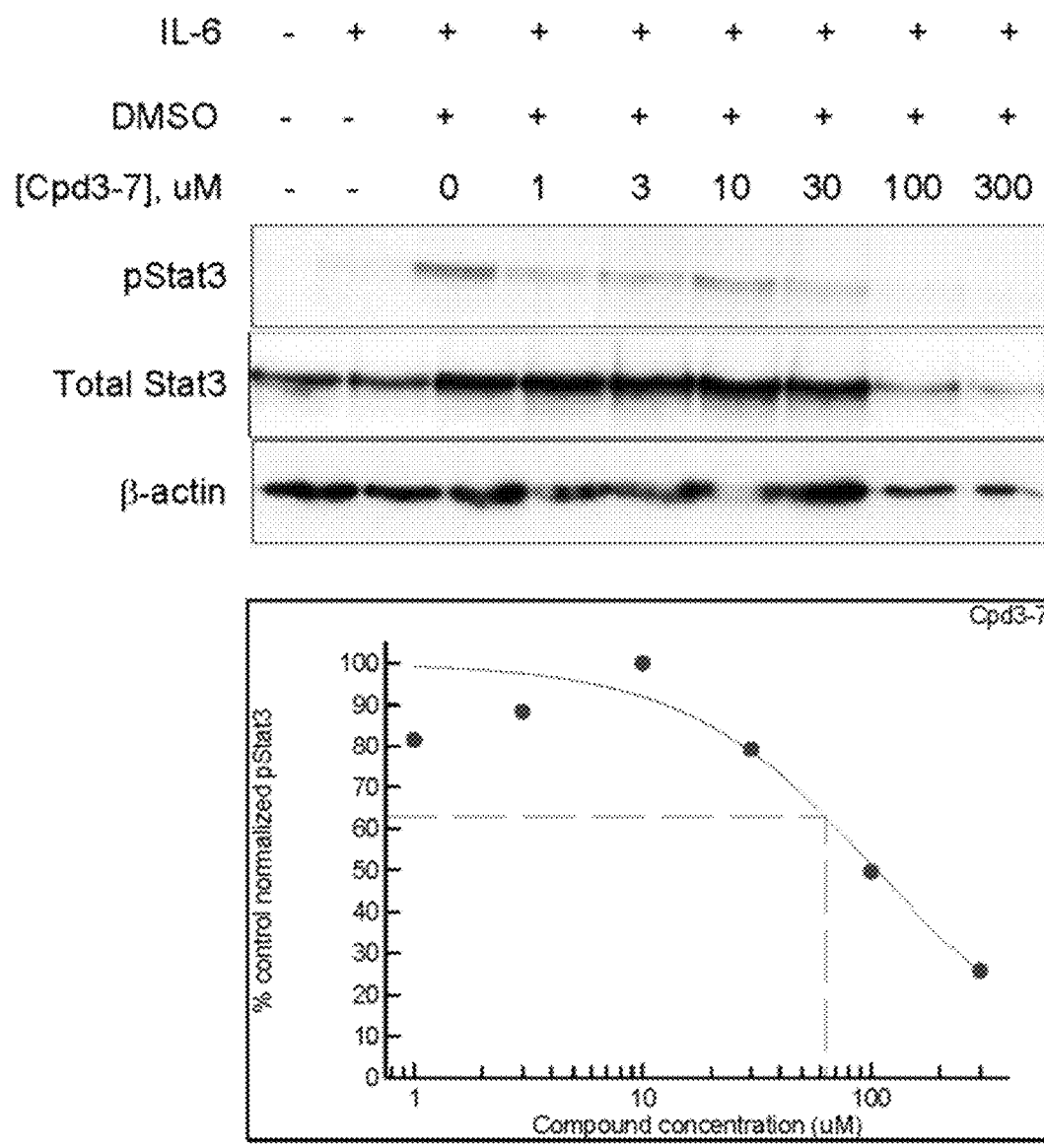
Figure 2:
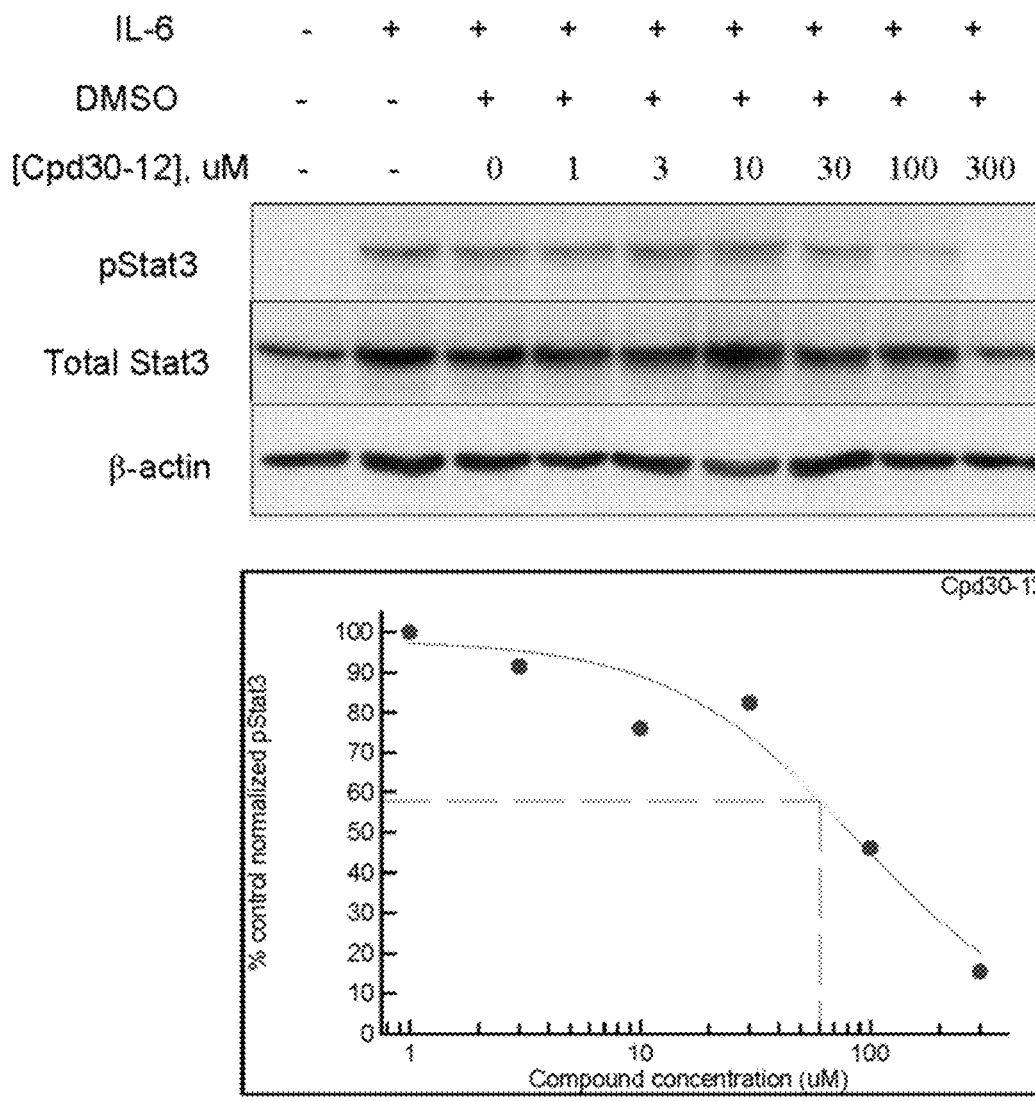

In addition, each compound inhibited IL-6-mediated phosphorylation of Stat3 with $IC_{50}$ values of 91, 18 and 73 µM respectively (FIG. 2; Table 4).

Similarity screening with Cpd3, Cpd30 and Cpd188 identified 4,302 additional compounds. VLS screening was performed with each of these compounds, which identified 41 compounds that fulfilled CIA criteria; these were purchased and tested. SPR competition experiments showed that of these 41 compounds, 3 compounds—Cpd3-2, Cpd3-7 and Cpd30-12—were able to directly compete with pY-peptide for binding to Stat3 with $IC_{50}$ values of 256, 137 and 114 µM, respectively (FIGS. 1 and 3; Table 4). In addition, each compound inhibited IL-6-mediated phosphorylation of Stat3 with IC50 values of 144, 63 and 60 µM, respectively (FIG. 2; Table 4).

Example 3

Compound-Mediated Inhibition of Ligand-Stimulated Phosphorylation of Stat3 is Specific for Stat3 Vs. Stat1

Figure 4:
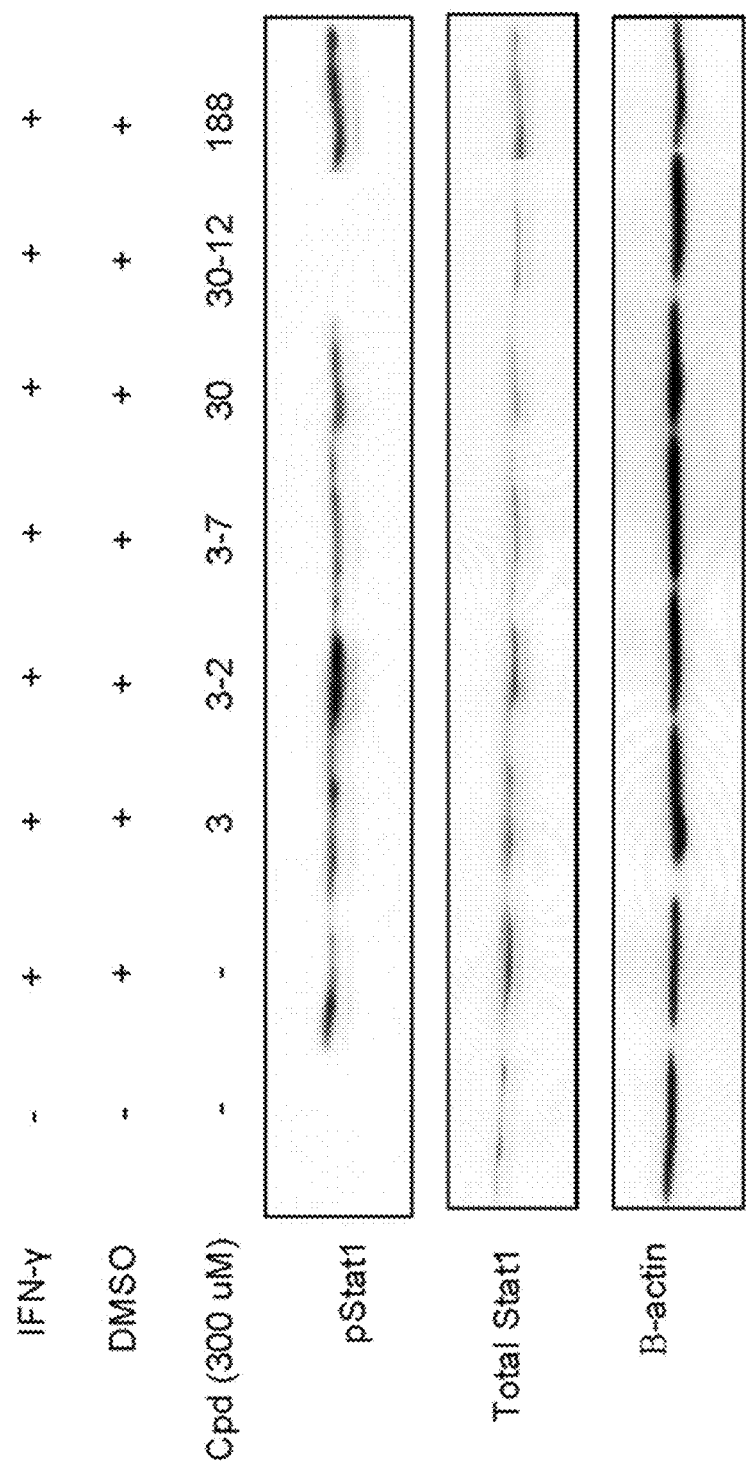
FIG. 4 shows effect of compounds on Stat1 activation. HepG2 cells were pretreated with DMSO alone or DMSO containing each of the compounds at a concentration of 300 μM for 60 min. Cells were then stimulated with IFN-γ (30 ng/ml) for 30 min. Protein extracts of cells were separated by SDS-PAGE and immunoblotted serially with antibodies to pStat1, total Stat1 and β-actin. Blots were stripped between each immunoblotting. The results shown are representative of 2 or more experiments.

While Stat3 contributes to oncogenesis, in part, through inhibition of apoptosis, Stat1 is anti-oncogenic; it mediates the apoptotic effects of interferons and contributes to tumor surveillance (Kaplan et al., 1998; Ramana et al., 2000). Consequently, compounds that target Stat3 while sparing Stat1, leaving its anti-oncogenic functions unopposed, may result in a synergistic anti-tumor effect. To assess the selectivity of the compounds for Stat3 vs. Stat1, HepG2 cells were incubated with Cpd3, Cpd30, Cpd188, Cpd3-2, Cpd3-7, and Cpd30-12 (300 µM) for 1 hour at 37° C. before IFN-γ stimulation (FIG. 4). Only treatment with Cpd30-12 blocked Stat1 phosphorylation while each of the other five compounds—Cpd3, Cpd30, Cpd188, Cpd3-2 and Cpd3-7—did not. Thus, five of the six exemplary compounds identified were selective and inhibited ligand-stimulated phosphorylation of Stat3 but not Stat1.

Example 4

Figure 5A:
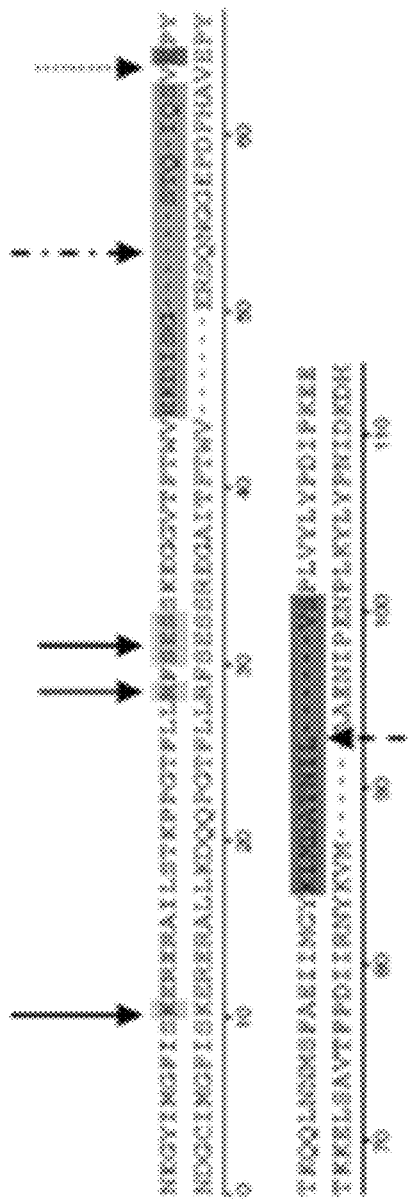
FIGS. 5A-5C provides comparisons of the Stat3 and Stat1 SH2 domain sequences, 3-D structures and van der Waals energies of compound binding. Sequence alignment of Stat3 and Stat1 SH2 domains is shown in panel A. The residues that bind the pY residue are highlighted in and pointed to by a solid arrow, the residue (E638) that binds to the +3 residue highlighted and pointed to by a dotted arrow and $Loop_{\beta C-\beta D}$ and $Loop_{\alpha B-\alpha C}$, which comprise the hydrophobic binding site consisting, are highlighted and pointed to by dot-dashed and dashed arrows, respectively. Panel B shows an overlay of a tube-and-fog van der Waals surface model of the Stat3 SH2 domain and a tube-and-fog van der Waals surface model of the Stat1 SH2. The residues of the Stat3 SH2 domain represents $Loop_{\beta C-\beta D}$ are highlighted and shown by dotted circles and the residues represent $Loop_{\alpha B-\alpha C}$ are highlighted and shown by a dotted-dashed circle; the corresponding loop residues within the Stat1 SH2 domain are shown in a light fog surrounding the circles. This overlay is shown bound by Cpd3-7 as it would bind to the Stat3 SH2 domain. The van der Waals energy of each compound bound to the Stat1 SH2 domain or the Stat3 SH2 domain was calculated, normalized to the value for Stat1 and depicted in panel C.
Figure 5B:
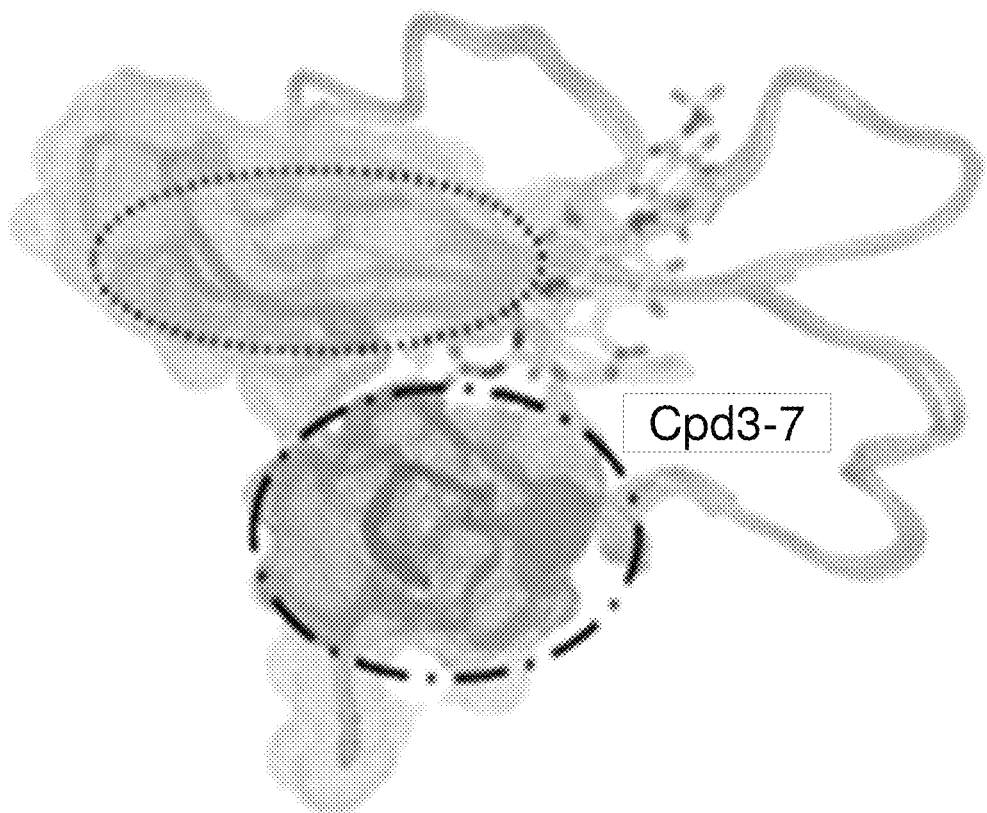

Sequence Analysis and Molecular Modeling of the Interaction of Each Compound with the Stat3 Vs. Stat1 Sh2 Domain To understand at the molecular level the basis for the selectivity of Cpds 3, 30, 188, 3-2 and 3-7 and the absence of selectivity in the case of Cpd 30-12, the amino acid sequence and available structures of the Stat1 and Stat3 SH2 domain were compared and also it was examined how each compound interacted with both. Sequence alignment revealed identity in the residues within Stat3 and Stat1 corresponding to the binding site for the pYresidue and the +3 residue (FIG. 5A). In addition, overlay of the Stat3 and Stat1 SH2 structures revealed that the loops that contained these binding sites were superimposed (FIG. 5B). In contrast, sequence alignment revealed substantial differences in the sequence of the regions of the SH2 domain corresponding to the loops forming the hydrophobic binding site (FIG. 5A). In addition, review of the overlay of Stat3 and Stat1 SH2 domains revealed that, in contrast to the close apposition of the two loops of Stat3 that form the hydrophobic binding site, the corresponding two loops of Stat1 are not closely apposed to form a pocket (FIG. 5B).

Figure 5C:
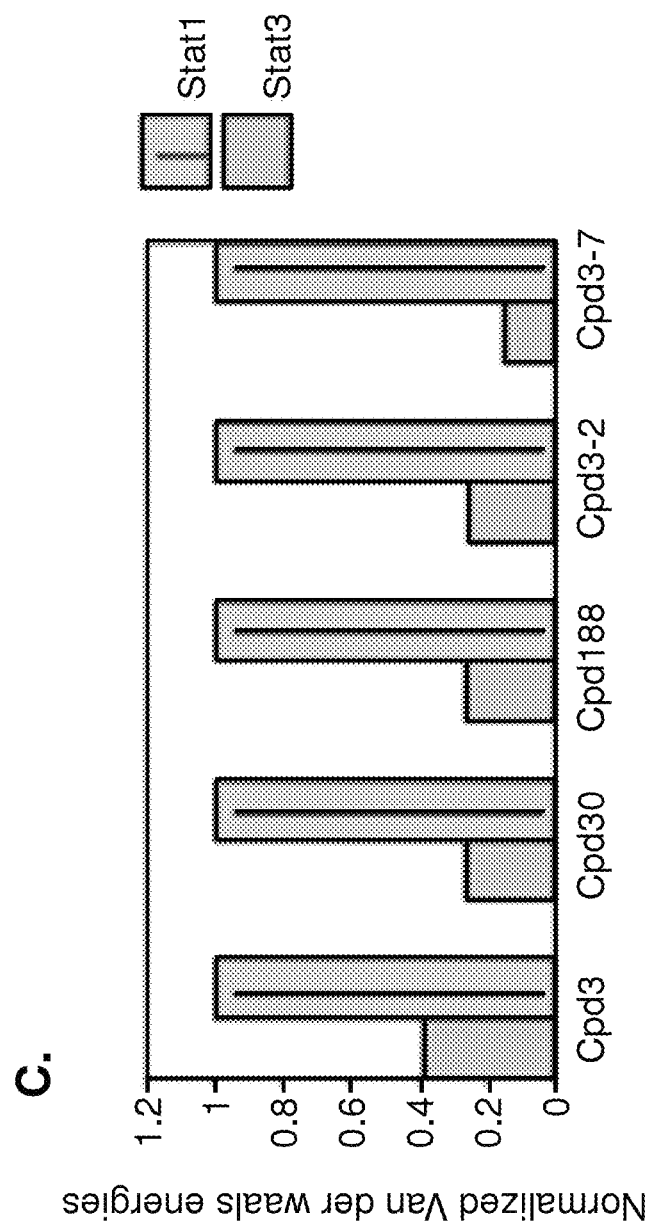
Figures 6A, 6B:
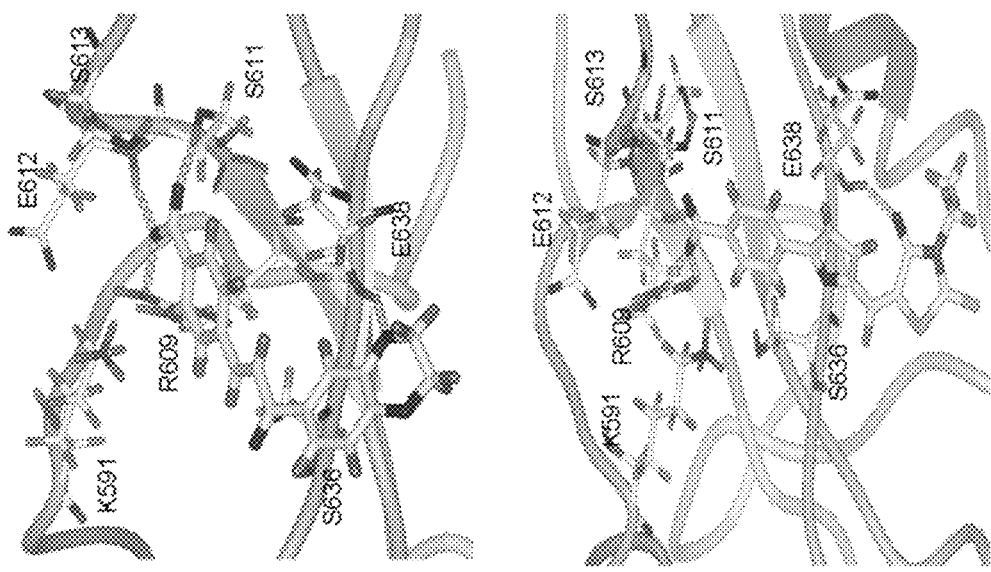
FIGS. 6A-6F shows a computer model of each compound bound by the Stat3 SH2 domain. The results of computer docking to the Stat3 SH2 domain is shown for Cpd3 (panel A), Cpd30 (panel B), Cpd188 (panel C), Cpd3-2 (panel D), Cpd3-7 (panel E) and Cpd30-12 (panel F). The image on the left of each panel shows the compound binding to a space-filling model of the Stat3 SH2 domain. The pY-residue binding site is represented by dashed circle, the +3 residue binding site is represented by a solid circle, loop $Loop_{\beta C-\beta D}$ is represented by dotted circle and loop $Loop_{\alpha B-\alpha C}$ is represented by dot-dashed circle. Residues R609 and K591 critical for binding pY are shown within a dashed circle, residue E638 that binds the +3 residue shown within a solid circle and the hydrophobic binding site consisting of $Loop_{\beta C-\beta D}$ and Loop$\alpha$B-$\alpha$C is shown within a dash-dot and dotted circle, respectively. The image on the right side of each panel is a closer view of this interaction with hydrogen bonds indicated by dotted lines.
Figure 6C:
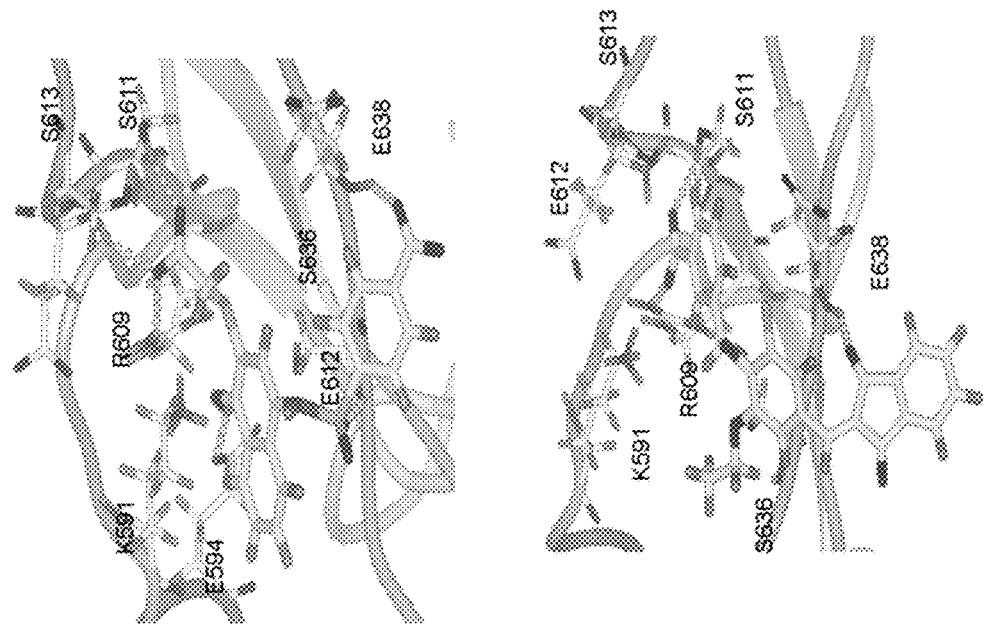
Figure 6D:
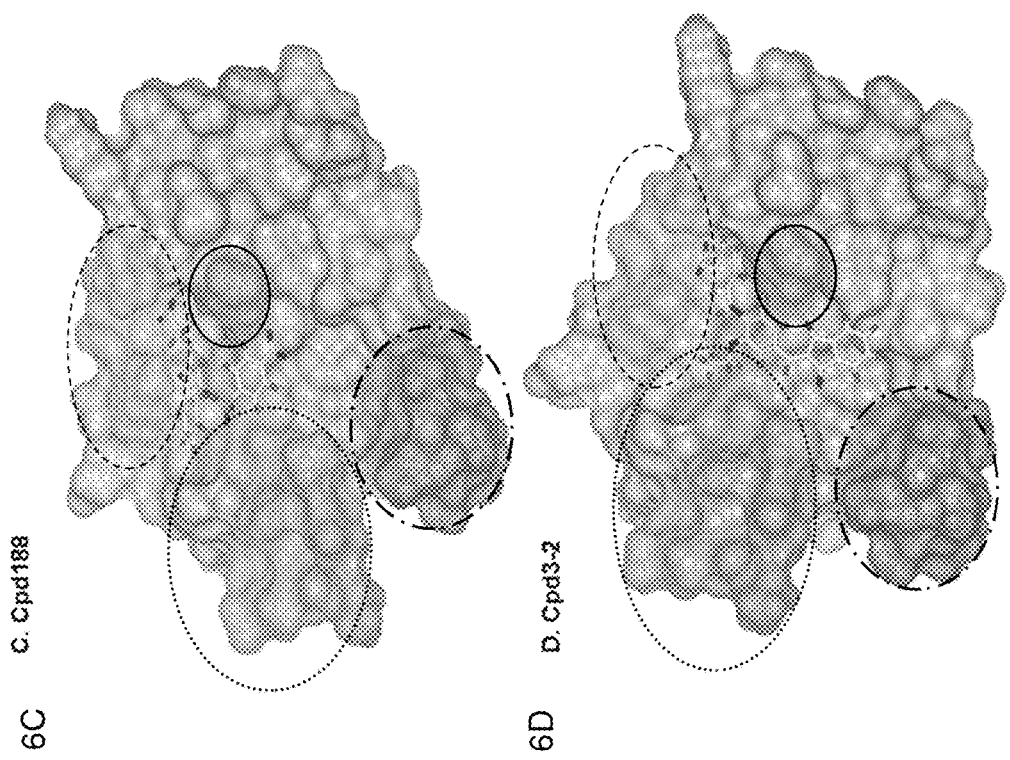
Figure 6E:
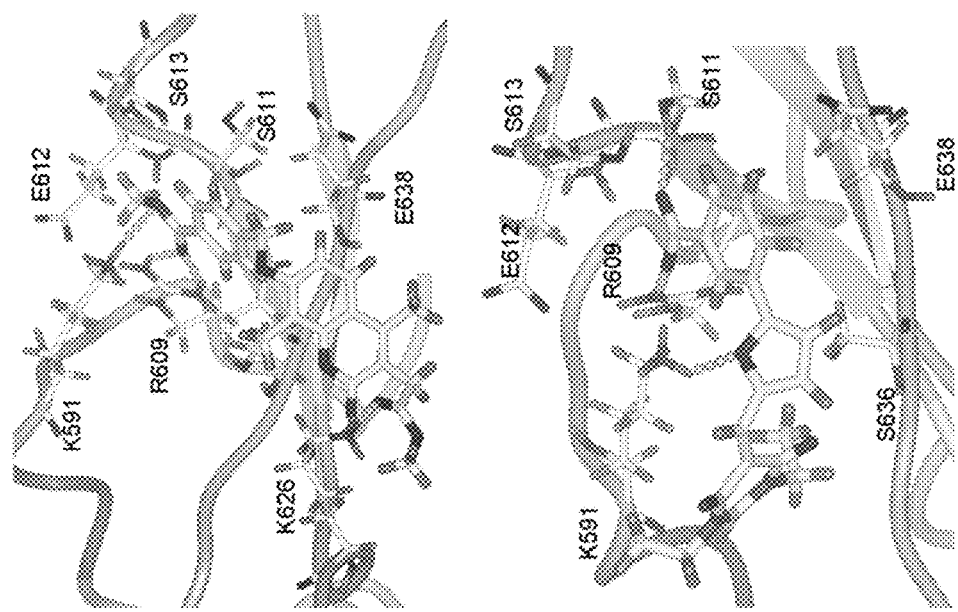
Figure 6F:
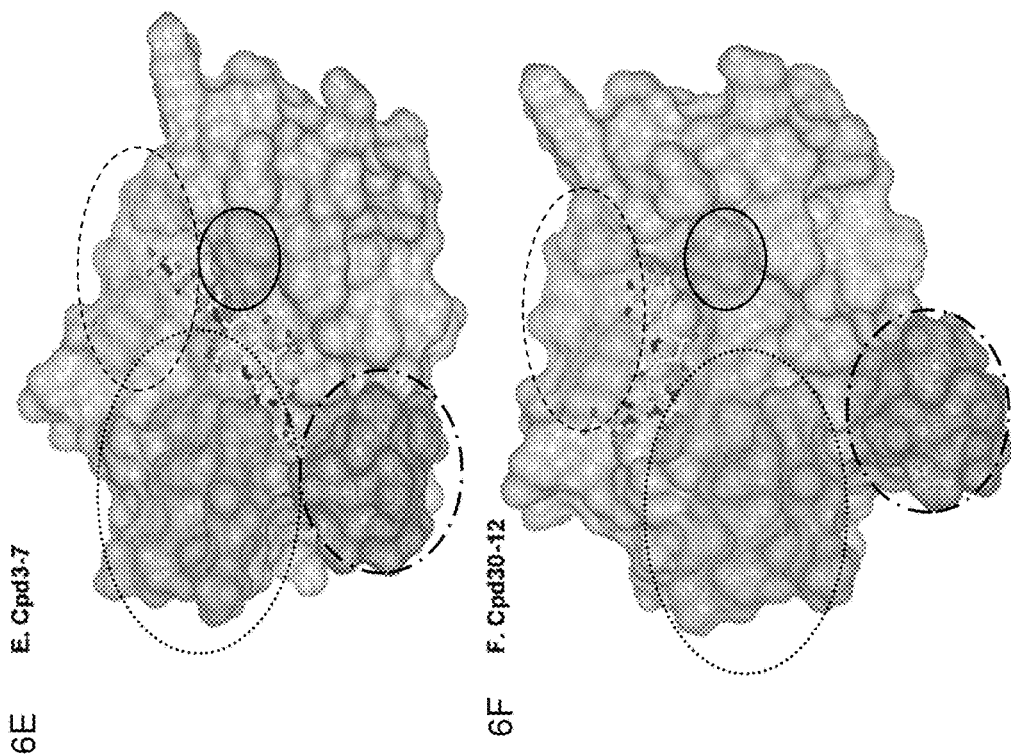

Review of computational models of Cpd3, Cpd30, Cpd188, Cpd3-2 and Cpd3-7 in a complex with the Stat3 SH2 domain revealed that each has significant interactions with the Stat3 SH2 domain binding pocket at all three binding sites, the pY-residue binding site, the +3 residue binding site and the hydrophobic binding site (FIGS. 6A, B, C, D, and E). In contrast, Cpd30-12 interacts with the pY-residue binding site and blocks access to the +3 residue-binding site but does not interact with or block access to the hydrophobic binding site (FIG. 6F). In addition, van der Waals energies of the 5 selective compounds were much more favorable for their interaction with the loops of Stat3 forming the hydrophobic binding site than with corresponding loops of Stat1 (FIG. 5C). Thus, computer modeling indicated that activity of compounds against Stat3 derives from their ability to interact with the binding sites for the pY and the +3 residues within the binding pocket, while selectivity for Stat3 vs. Stat1 derives from the ability of compounds to interact with the hydrophobic binding site within the Stat3 SH2 binding pocket, which served as a selectivity filter.

Example 5

Figure 7A:
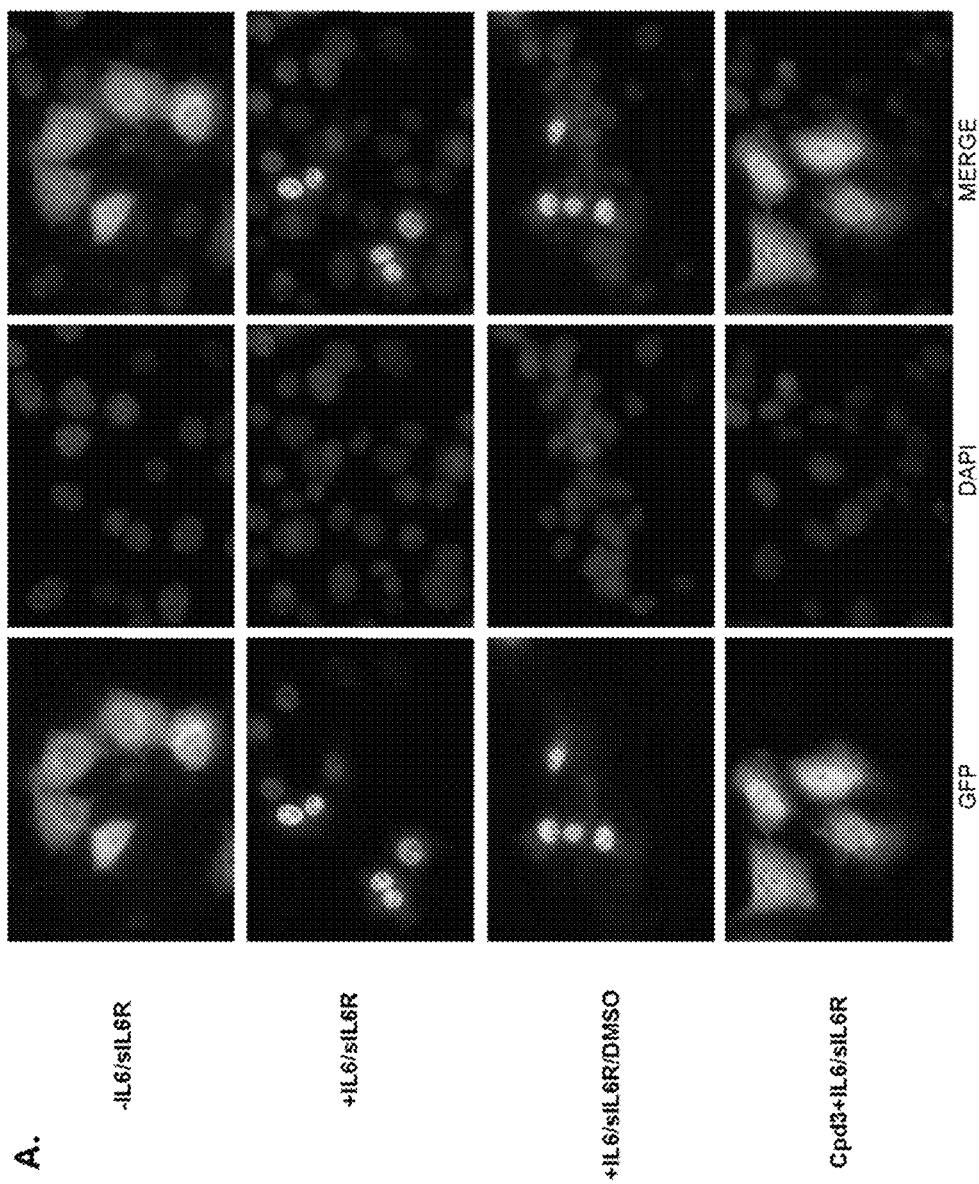
FIGS. 7A-7B shows inhibition of cytoplasmic-to-nuclear translocation of Stat3 assessed by confocal and high-throughput fluorescence microscopy. In panel A, MEF/GFP-Stat3 cells grown on coverslips were pretreated with DMSO that either contained (row four) or did not contain (row three) Cpd3 (300 µM) for 60 min before being stimulated without (row one) or with IL-6 (200 ng/ml) and IL-6sR (250 ng/ml) for 30 minutes (rows two, three and four). Coverslips were examined by confocal fluorescent microscopy using filters to detect GFP (column one), DAPI (column two) or both (merge; column three). In panel B, MEF-GFP-Stat3 cells were grown in 96-well plates with optical glass bottoms and pretreated with the indicated compound at the indicated concentrations in quadruplicate for 1 hour then stimulated with IL-6 (200 ng/ml) and IL-6sR (250 ng/ml) for 30 minutes. Cells were fixed and the plates were examined by high-throughput microscopy to determine the fluorescence intensity in the nucleus (FLIN) and the % $\Delta FLIN_{Max}$ was calculated as described in Example 1. Data shown are mean±SD and are representative of 2 or more studies. Best-fit curves were generated based on 4 Parameter Logistic Model/Dose Response One Site/XLfit 4.2, IDBS and were used to calculate $IC_{50}$ (Table 1).
Figure 7B:
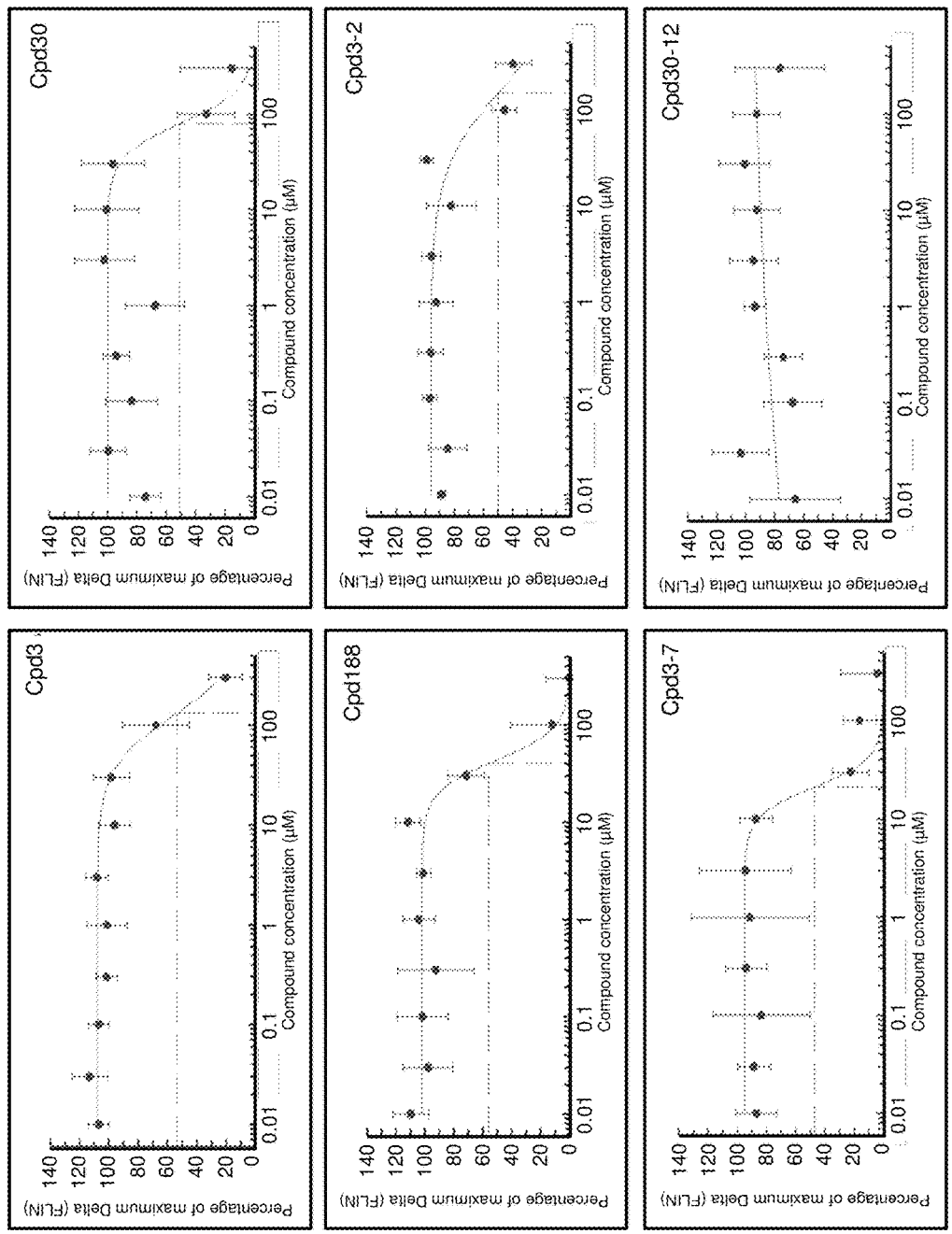

Inhibition of Nuclear Translocation of Phosphorylated Stat3 by CPD3, CPD30, CPD188, CPD3-2 and CPD3-7 Assessed by HTFM Following its phosphorylation on Y705, Stat3 undergoes a change in conformation from head-to-head dimerization mediated through its N-terminal oligomerization domain to tail-to-tail dimerization mediated by reciprocal SH2/pY705-peptide ligand interactions. This conformational change is followed by nuclear accumulation. Compounds that targeted SH2/pY-peptide ligand interactions of Stat3 would be expected to inhibit nuclear accumulation of Stat3. To determine if this was the case with the compounds herein, a nuclear translocation assay (FIG. 7) was employed using murine embryonic fibroblast (MEF) cells that are deficient in endogenous Stat3 but constitutively express GFP-tagged Stat3α at endogenous levels, MEF/GFP-Stat3 α (Huang et al., 2007). Preincubation of MEF/GFP-Stat3 cc cells with Cpd3, Cpd30, Cpd188, Cpd3-2 and Cpd3-7, but not Cpd30-12, blocked ligand-mediated nuclear translocation of GFP-Stat3 cc with $IC_{50}$ values of 131, 77, 39, 150 and 20 µM (FIG. 7 and Table 4).

Example 6

Destabilization of Stat3-DNA Complexes by CPD3 and CPD3-7

Figure 8:
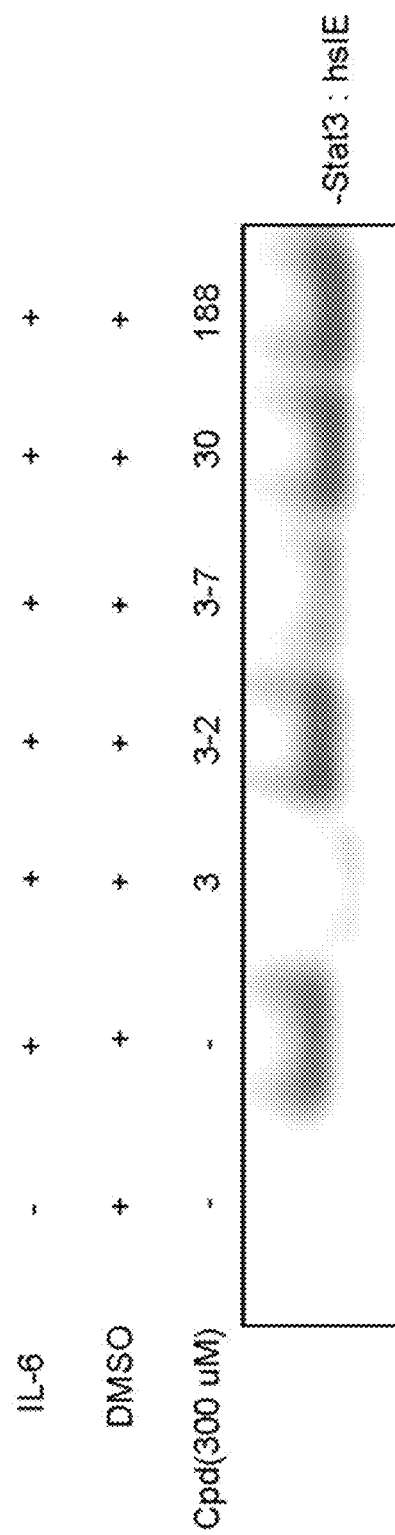
FIG. 8 demonstrates inhibition of Stat3 DNA binding by compounds. Electrophoretic mobility shift assays were performed using whole-cell extracts prepared from HepG2 cells without and with stimulation with IL-6 (30 ng/ml) for 30 min. Protein (20 µg) was incubated with radiolabeled duplex oligonucleotide (hSIE) and DMSO without or with the indicated compounds (300 uM) for 60 minutes at 37° C. then separated by PAGE. The gel was dried and autoradiographed; the portion of the gel corresponding to the Stat3-bound hSIE band is shown. Data shown are representative of 2 studies.
Figure 9:
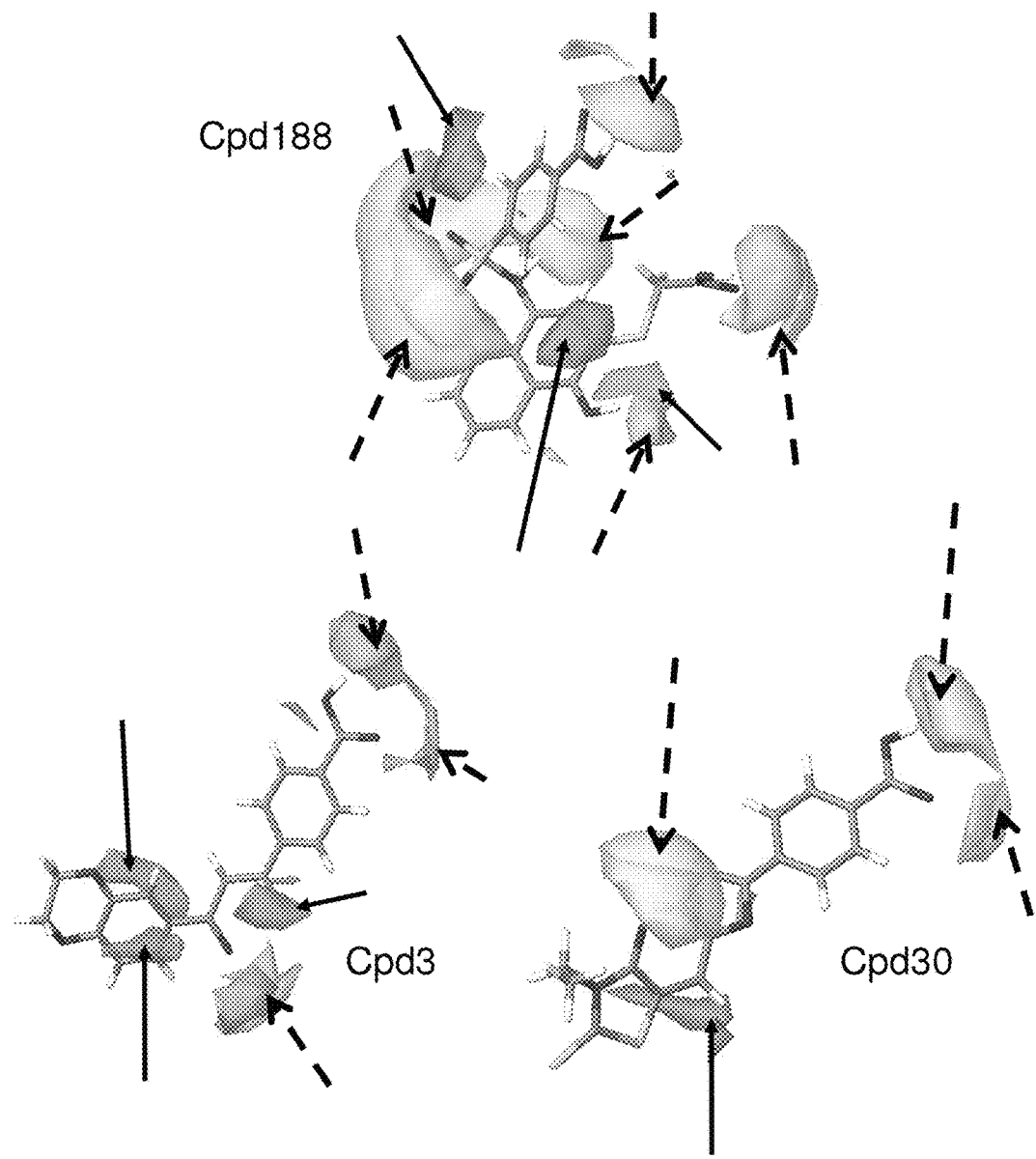
FIG. 9 shows Cpd3, Cpd30 and Cpd188 and the hydrophobicity or hydrophilicity of the surface of the molecule. The dashed arrows point to hydrophilic surfaces, and the solid arrows point to hydrophobic surfaces.
Figure 10:
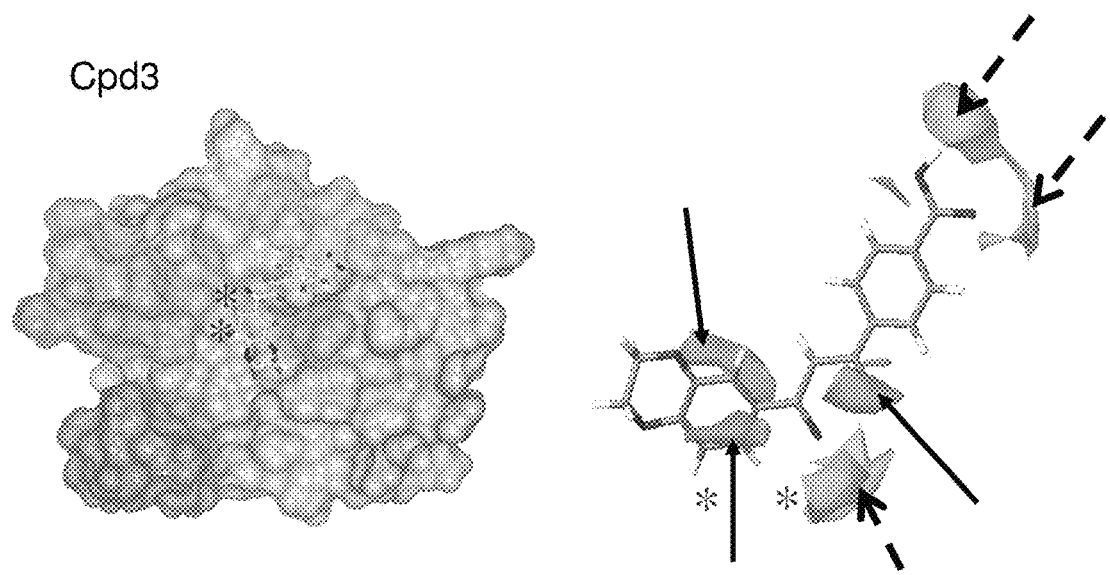
FIG. 10 illustrates exemplary compound 3 (Cpd3). The top-left picture of FIG. 11 shows Cpd3 docked into Stat3 and the interaction between Cpd3 and the surface of the protein and derivatives of Cpd3 that can fit into the surface of the protein. Stars represent atoms and chemical groups that can be replaced with other atoms or chemical groups to create one or more functional derivatives. The hydrophobic/hydrophilic surfaces of Cpd3 are also demonstrated on the top-right picture. The dashed arrows point to hydrophilic surfaces, and the solid arrows point to hydrophobic surfaces. $R_1$ and $R_2$ could be identical or different and may comprise hydrogen, carbon, sulfur, nitrogen, oxygen, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, or benzoic acid-based derivatives.
Figure 10:
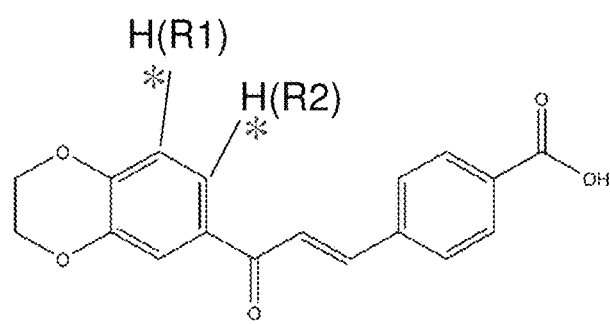
Figure 11:
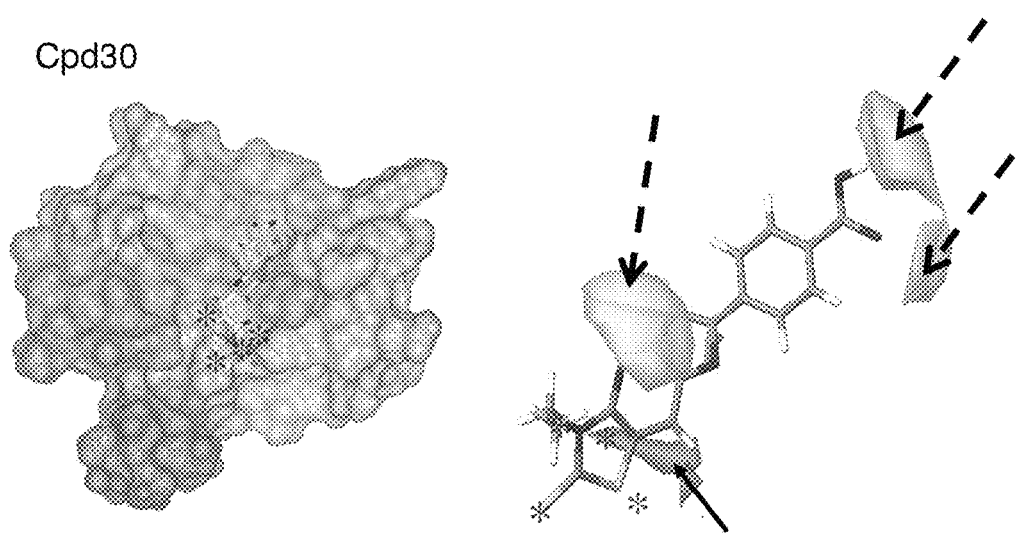
FIG. 11 illustrates exemplary compound 30 (Cpd30). The top-left picture of FIG. 12 shows Cpd30 docked into Stat3 and the interaction between Cpd30 and the surface of the protein, and derivatives of Cpd30 that fit into the surface of the protein. Stars represent atoms and chemical groups that can be replaced with other atoms or chemical groups to create one or more functional derivatives. The hydrophobic/hydrophilic surfaces of Cpd30 are also demonstrated on the top-right picture. The dashed arrows point to hydrophilic surfaces, and the solid arrows point to hydrophobic surfaces. 2-D structure of Cpd30 shown on the bottom picture, $R_1$, $R_2$, $R_3$ and $R_4$ could identical or different and may comprise be hydrogen, carbon, sulfur, nitrogen, oxygen, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, or benzoic acid-based derivatives.
Figure 11:
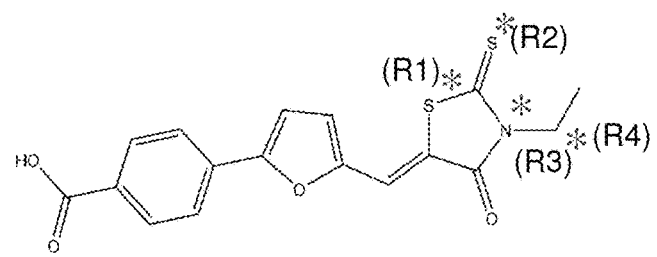
Figure 12:
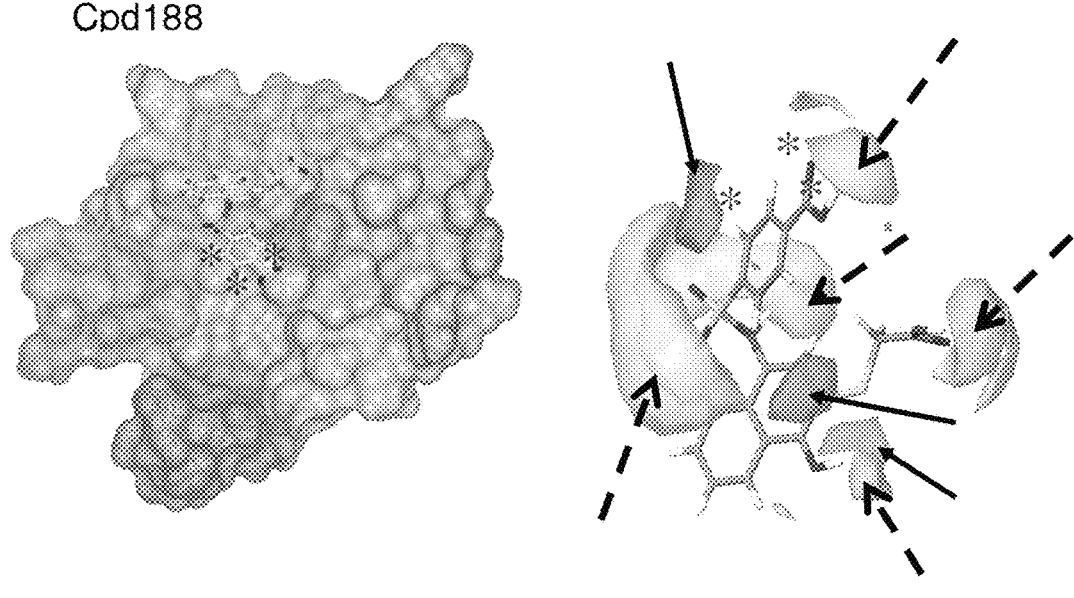
FIG. 12 illustrates exemplary compound 188 (Cpd188). The top picture of FIG. 12 shows Cpd188 docked into Stat3 SH2 domain and the interaction between Cpd188 and the surface of the protein, and derivatives of Cpd188 that fit into the surface of the protein. Stars represent atoms and chemical groups that can be replaced with other atoms or chemical groups to create one or more functional derivative. The hydrophobic/hydrophilic surfaces of Cpd188 are also demonstrated on the left picture on the bottom. The dashed arrows point to hydrophilic surfaces, and the solid arrows point to hydrophobic surfaces. Shown on the right bottom picture, $R_1$ and $R_2$ could be identical or different and may comprise hydrogen, carbon, sulfur, nitrogen, oxygen, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, or benzoic acid-based derivatives.
Figure 12:
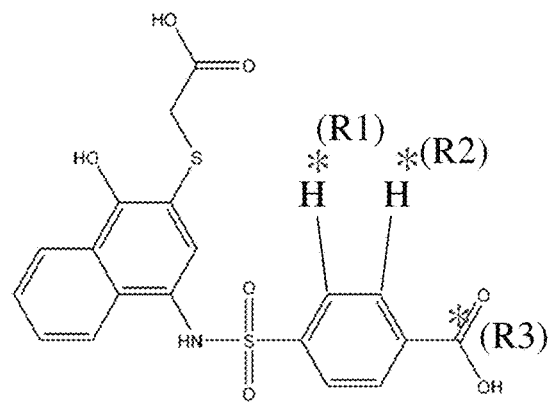

Once in the nucleus, Stat3 dimers bind to specific DNA elements to activate and, in some instances, repress gene transcription. Tyrosine-phosphorylated dodecapeptides based on motifs within receptors that recruit Stat3 have previously been shown to destabilize Stat3 (Chakraborty et al., 1999; Shao et al., 2003). Compounds that bind to the phosphopeptide-binding site of Stat3 might be expected to do the same. To determine if this was the case for any of the identified compounds, extracts of IL-6-stimulated HepG2 cells were incubated in binding reactions containing radiolabeled hSIE (FIG. 8) and each of the five selective compounds (300 µM). Incubation with Cpd3 or Cpd3-7 reduced the amount of hSIE shifted by half or greater. The other compounds did not have a detectable effect on the Stat3:hSIE band intensity. Thus, 2 of the 5 selective compounds destabilized Stat3:hSIE complexes.

Example 7

Exemplary Approach for Stat3 Inhibitors for Cancer Stem Cells

In the field of Stat3 probe development the inventors have focused on small molecule Stat3 probes (Xu et al., 2009), and several features of the small molecule program are useful, including: 1) a clearly defined mode of action of these probes: they target the Stat3 Src-homology (SH) 2 domain that is involved in 2 steps in the Stat3 activation pathway; 2) their specificity of action; and 3) the potential for using lead probes identified so far to identify probes with 2-to-3 logs greater activity based on recent and exemplary SAR analysis and medicinal chemistry considerations outlined below.

In specific embodiments, compound affinity is improved upon gaining a log greater affinity upon moving from $1^{St}$ generation to 2nd generation probes using 3-D pharmacophore analysis. In addition, selectivity is improved through modeling embodiments, in particular through identification of a distinct hydrophobic binding domain in the phosphopeptide binding pocket of Stat3 SH2 vs. the Stat1 SH2 (Xu et al., 2009).

Identification of 1st Generation Stat3 Chemical Probes.

To develop chemical probes that selectively target Stat3, the inventors virtually screened 920,000 small drug-like compounds by docking each into the peptide-binding pocket of the Stat3 SH2 domain, which consists of three sites—the pY-residue binding site, the +3 residue-binding site and a hydrophobic binding site, which served as a selectivity filter (Xu et al., 2009). Three compounds (Cpd3, Cpd30 and Cpd188) satisfied criteria of interaction analysis, competitively inhibited recombinant Stat3 binding to its immobilized pY-peptide ligand and inhibited IL-6-mediated tyrosine phosphorylation of Stat3. These compounds were used in a similarity screen of 2.47 million compounds, which identified 3 more compounds (Cpd3-2, Cpd3-7 and Cpd30-12) with similar activities. Examinations of the 6 active compounds for the ability to inhibit IFN-γ-mediated Stat1 phosphorylation revealed that all but Cpd30-12 were selective for Stat3. Molecular modeling of the SH2 domains of Stat3 and Stat1 bound to compound revealed that compound interaction with the hydrophobic binding site was the basis for selectivity. All 5 selective compounds inhibited nuclear-tocytoplasmic translocation of Stat3, while 3 of 5 compounds (Cpd3, Cpd30 and Cpd188) induced apoptosis preferentially of exemplary breast cancer cell lines with constitutive Stat3 activation.

Identification of 2nd Generation Stat3 Chemical Probes.

The similarity screening described above did not yield any hits using Cpd188, the most active of the 3 lead compounds, as the query compound. Consequently, the inventors repeated 2-D similarity screening using the scaffold of Cpd188 as the query structure and the Life Chemicals library, which yielded 207 hits. 3-D pharmacophore analysis was performed on these 207 compounds using Ligand Scout and the top 39 scoring compounds were purchased and tested for inhibition of Stat3 binding to its phosphopeptide ligand by SPR. All but six of these 39 compounds have measurable SPR IC50s, with 19 having IC50 values equal to or less than the parent compound and 2 (Cpd188-9 and Cpd188-15) having IC50 values one log lower. Examination of these 19 compounds has revealed a statistically significant correlation between 3-D pharmacophore scores and SPR IC50s and as well as 3-D pharmacophore score and IC50s for inhibition of ligand-mediated cytoplasmic-to-nuclear translocation. In addition, both Cpd188-9 and Cpd188-15 exhibited a log greater activity in inducing human leukemic cell line apoptosis than the parent Cpd188 (FIG. 15). In addition, Cpd188-38 exhibited a 2 logs greater activity than parent Cpd188 in inhibiting cytoplasmic-to-nuclear translocation in HTFM assay, while Cpd188-15 exhibited a 1 log greater activity than parent Cpd188 in decreasing MSFE (Table 5). Furthermore, several of the second-generation 188-like compounds represent a substantial improvement over Cpd188 from a medicinal chemistry, metabolism and bioavailability standpoint. In particular, Cpd188-9 lacked both carboxyl groups, which in particular cases improves cell permeability and/or the thioether group, which is subject to oxidation. $R^2=0.2$ P=0.013 (µM)

TABLE 5

Summary of Certain $2^{nd}$ Generation 188-like Compounds

| Compound | SPR $IC_{50}$, µM* | HTFM $IC_{50}$, µM* | Mammosphere ~$IC_{50}$, µM*** |
|---|---|---|---|
| 188 | 20** | 32 ± 4 | 30-100 |
| 188-1 | 6 ± 2 | 26 ± 4 | 30 |
| 188-9 | 3 ± 2 | 47 ± 21 | 10 |
| 188-10 | 8 ± 3 | 22 ± 19 | 30 |
| 188-15 | 2 ± 1 | 49 | 3 |
| 188-16 | 4 ± 0 | 9 ± 5 | 30 |
| 188-17 | 4 ± 2 | 76 | 30 |
| 188-18 | 4 ± 1 | 27 ± 8 | 30 |
| 188-38 | 19 ± 9 | 0.4 ± 0.1 | 10-30 |

*mean ± SD
**Xu et al PLoS ONE
***SUM159PT and HS578T cells plated (6 wells per test) without or with compound at 1, 10 or 100 µM, incubated 3 d; spheres counted on day 3.

Structure-Activity Relationship (SAR) Analysis of 2nd Generation Stat3 Probes.

Figure 16:
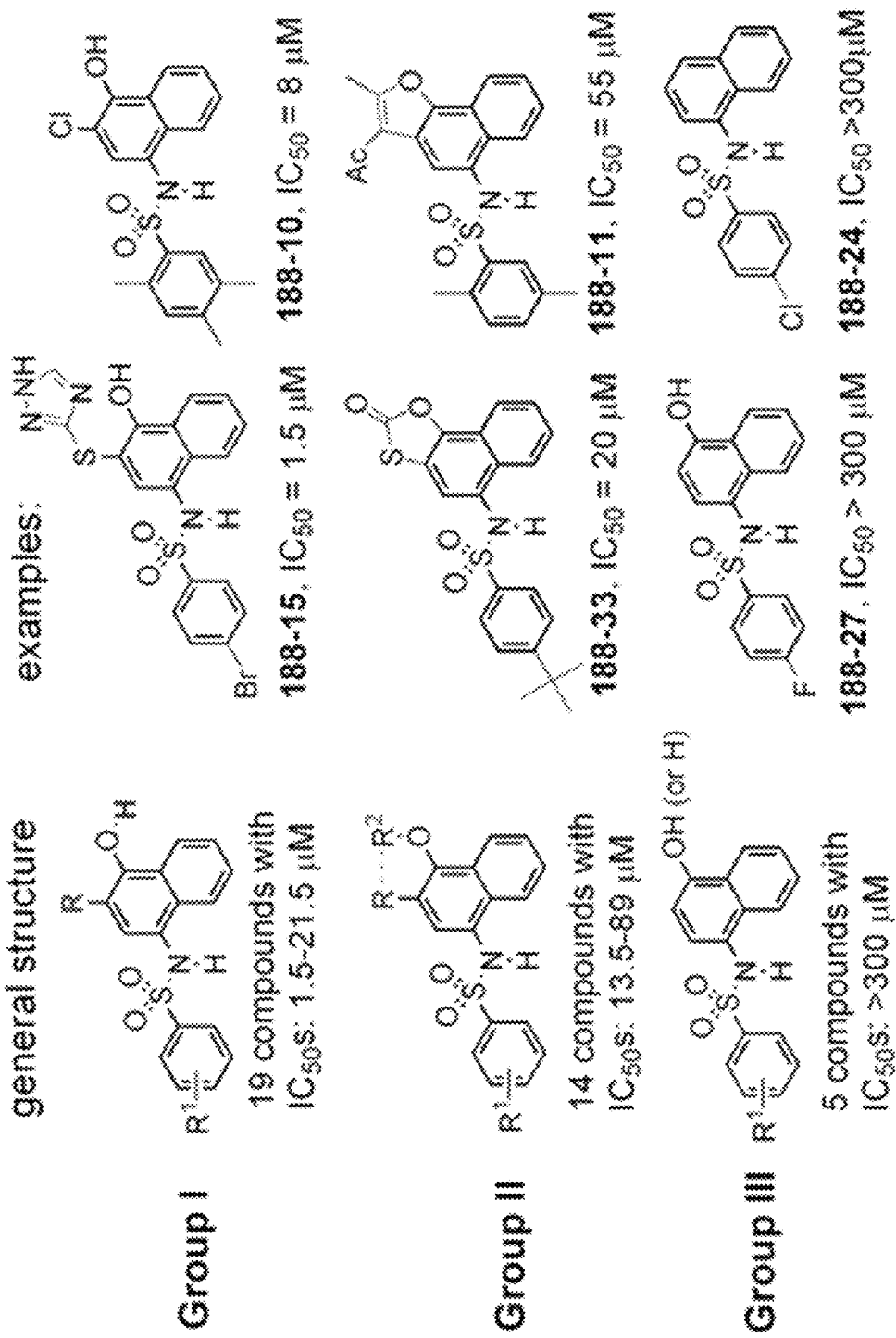
FIG. 16 provides an illustration of structure-activity relationships of 38 Cpd188-like, 2nd generation Stat3 probes.

All of the 39 second generation compounds described above, plus Cpd188 itself, are derivatives of N-naphth-1-yl benzenesulfamide. Upon careful analysis of their structure-activity relationships (SAR), the inventors found that most of these Cpd188-like compounds (38 out of 40: the rest of 2 are weak and will be described below in EXP ID) can be divided into three structural groups in a general trend of decreased activity, as shown in FIG. 16. Five compounds in Group III are actually the parents of compounds in Groups I and II. Addition of a variety of groups (the —R group highlighted in red in the general structure of Group I in FIG. 16), such as a triazole-3-yl-mercapto (188-15) or a chloro (188-10) group, to the 3-position of the naphthylamine ring led to the Group I compounds, which are the most potent series of Stat3 probes. In a specific embodiment, this is the most important contributor to the inhibitory activity: a total of eight 3-substituents are found in Group I compounds, which invariably enhance the activity by several orders of magnitude.

Most Stat3 probes in Group II contain a 5-membered ring that combines the 3-R and 4-OR2 groups, such as a furan (188-11). However, the compounds in this group are, in average, ~5× less active than the Group I compounds, which indicates that in certain aspects the H atom of the 4-hydroxy group (highlighted in blue in the general structure of Group I in FIG. 16) is important, e.g., involved in a favorable H-bond with the protein. Lacking the ability to form the H-bond attributes to the weaker activities of Group II probes, in particular cases. These considerations underlie a medicinal chemistry approach outlined below.

Example 8

Figure 18:
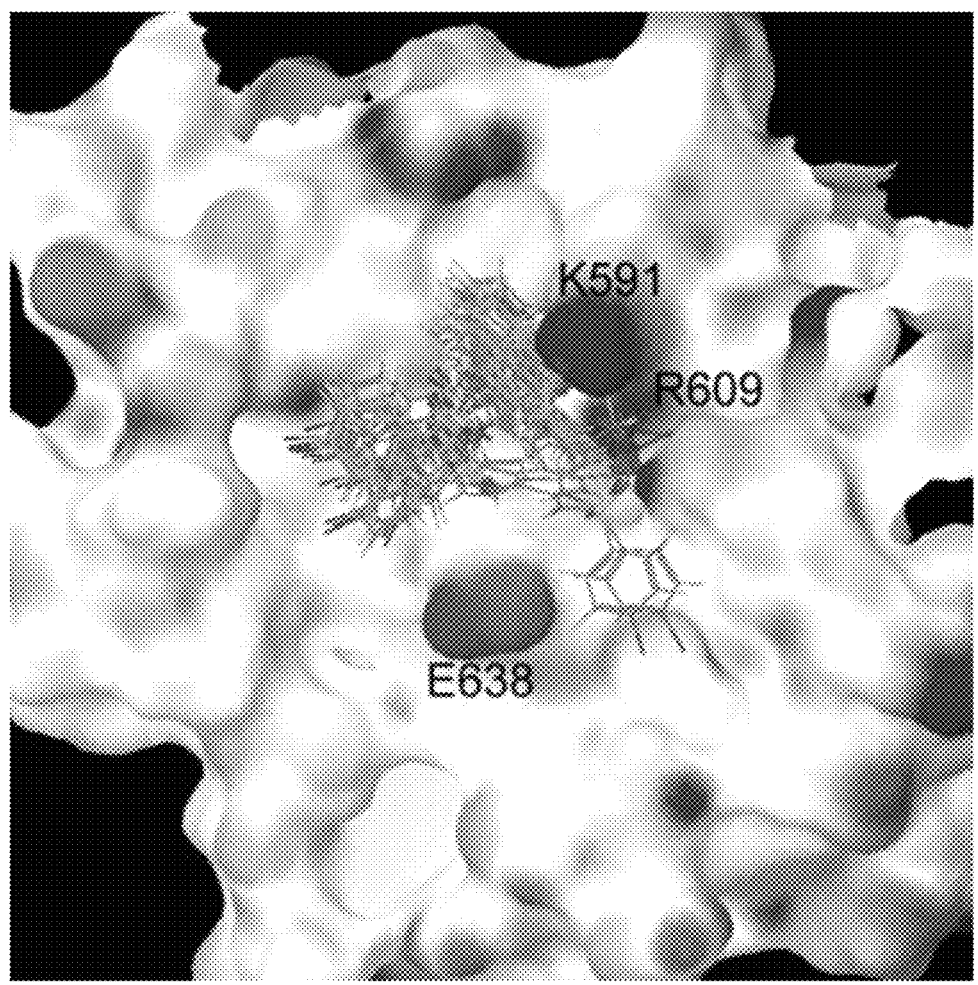
FIG. 18 provides illustration of the electrostatic surface of Stat3 SH2 domain (positive area in blue, neutral in white and negative in red in a color figure) and 20 docking poses of 5 ($R=CH_2PO_3^{2-}$), showing strong interactions between phosphonate groups (in purple and red) and K591/R609.

Medicinal Chemistry for Synthesis of $3^{RD}$ Generation 188-Like Sulfamide STAT3 Probes The crystal structure of Stat3 shows that the SH2 domain has a large, widely dispersed and generally shallow binding area with several valleys and hills that recognize the pY-peptide ligand (FIG. 18). Structure-based molecular modeling (docking) was useful in identifying the contribution of the hydrophobic binding surface of the Stat3 SH2 domain as a selectivity filter (Xu et al., 2009). However, different docking programs gave distinct binding poses for the same probe over the binding surface with similar predicted binding affinities. The inventors therefore in particular embodiments, based on initial SAR results outlined above, use traditional medicinal chemistry to further carry out an exemplary comprehensive structure activity relationship study, to optimize the activity as well as the selectivity of this novel class of sulfamide probes of Stat3. Compound 188-15 serves as a scaffold for making the new generation compounds, as shown schematically (FIG. 16).

In addition, chemistry for making these compounds is straightforward with a good yield, involving the reaction of a sulfonyl chloride with an aniline/amine, which can be either obtained commercially or synthesized readily.

Figure 17:
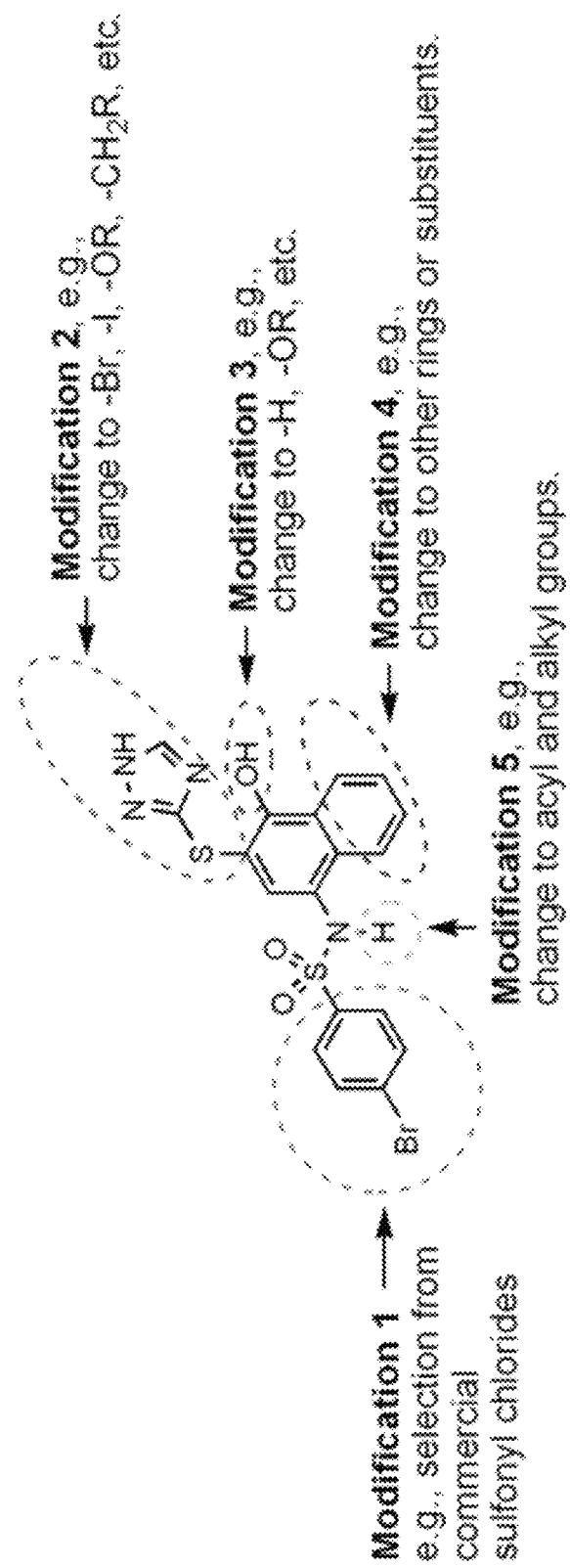
FIG. 17 shows an exemplary modification scheme for 3rd generation Stat3 probe development using Cpd188-15 as a scaffold.

For the proposed modifications described below, one can consult FIG. 17. EXP IA. Modification 1. Since almost all of the $2^{nd}$ generation probes contain a phenylsulfonyl group, the first step towards activity optimization focuses on synthesizing a series of compounds that have a larger (e.g., bicyclic or tricyclic) or an alkyl sulfonyl group. The general synthetic route is shown as follows:

There are about 4,300 commercially available sulfonyl chlorides, among which 25, such as those shown above, are selected to make probes. Aniline 2, which is the amine component of compound 188-10 (FIG. 16), one the most active probes, is readily made in a simple two step reaction from nitro compound 1. One can first make 25 (for example) compounds and test their activities in an in vitro rapid throughput SPR and in vivo HTFM assays. Based on the outcomes of structure-activity relationship study, more compounds can be designed and synthesized and tested in an iterative manner until optimization of this modification.

EXP IB. Modification 2. Next, one can modify the 3-substituent of the naphthylamine ring, based on either the structure of compound 188-15, for example. Prior SAR studies demonstrated this substituent is useful to the activity of this class of probes, in certain embodiments. However, a total of 8 groups at this position with a huge difference in size, from a single atom Cl to a large, bicyclic benzothiazole-2-ylmercapto group, showed similar activities. This feature indicates that in certain embodiments modifications at this position should be more focused on other properties, such as electrostatic interactions with the protein, as exemplified below. In addition, many of these groups are thio-ethers, which may be subjected to oxidation/degradation in vivo and lead to an unfavorable pharmacokinetic profile, in particular aspects. The central —S— atom is changed to a more metabolically stable isosteres, such as —CH$_2$—, —NH—, and —O—, in certain cases. In certain aspects one can synthesize the following compounds to optimize the 3-substituent:

The synthesis is also started from 1, in certain cases. Regio-selective halogenation and formylation at the 3-position gives rise to two compounds, i.e., bromo- or iodo-compound 3 and aldehyde 4, which are versatile, common starting compounds for introducing a wide range of substituents at this position (e.g., those listed above).

Moreover, the crystal structure of Stat3 SH2 domain also provides strong evidence that more compounds with different electrostatic properties are useful for characterization. The electrostatic molecular surface of the protein shows two distinct features, as shown in FIG. 18. The first one is the negatively charged Glu638 surface stands out in the center. Next, of particular interest is a positively charged area, composed of Arg609 and Lys591 located in the edge of the domain, which is actually the pY (phosphorylated tyrosine) binding site of the receptor. The inventors also found that introducing a negatively charged group targeting the pY binding site leads to particularly active probes, in certain embodiments. For example, the docking study of the 3-phosphomethyl compound 5 (R=CH$_2$PO$_3^{2-}$) showed all of the phosphonate groups of the 20 docking poses are tightly clustered together and located in the pY binding site, indicating strong electrostatic and H-bond interactions with the residues Arg609 and Lys591 (FIG. 18).

EXP IC. Modifications 3 and 4. Collectively, Modifications 3 and 4 test the effects of changing the substituents at the 4, 5, and 6-positions. The —OH at 4-position may be superior to —OR, in certain aspects. One can test whether the H atom in —OH is responsible for a better activity by synthesizing compounds 6 (acylated or alkylated 5), as schematically shown below. In addition, dehydroxy compounds 7 may also be made, starting from 3-bromonaphthyl-1-amine.

Regarding the general synthetic methods for modifying positions 5 and 6, one can first synthesize about a dozen of these compounds in this category and if very active compounds emerge, one can make more compounds to optimize the activity for these two positions.

EXP ID. Modification 5. The only two compounds not included in the SAR analysis (due to a different 4-substituent) are shown here, as well as their inhibitory activities against Stat3:

Despite the weak activity, masking the polar H of the sulfamide for the second compound is favorable, in certain aspects, which provides an easy route to making more potent probes. One can therefore use the following method to make a series of N-acyl or N-alkyl sulfamides 5:

Example 9

Identification of Stat3-Selective Chemical Probes from Sulfamide Compounds Synthesized in Example 11

Each novel sulfamide compound is tested for the ability to inhibit Stat3 binding to its phosphopeptide ligand by SPR and the ability to block IL-6-stimulated cytoplasmic-to-nuclear translocation in the HTFM assay. Probes with activity in these assays equivalent to or greater than the most active 2nd generation compounds are tested for inhibition of IL-6-stimulated Stat3 phosphorylation and lack of ability to inhibit IFN-γ-stimulated Stat1 phosphorylation as outlined below.

EXP IIA. Stat3/pY-peptide SPR binding inhibition assay. Stat3 pY-peptide binding assays is performed at 25° C. using a BIAcore 3000 biosensor as described (Xu et al., 2009). Briefly, phosphorylated and control nonphosphorylated biotinylated EGFR derived dodecapeptides based on the sequence surrounding Y1068 are immobilized on a streptavidin coated sensor chip (BIAcore Inc., Piscataway N.J.). The binding of Stat3 is performed in 20 mM Tris buffer pH 8 containing 2 mM β-mercaptoethanol at a flow rate of 10 uL/min for 1-2 minute. Aliquots of Stat3 at 500 nM are premixed with compound to achieve a final concentration of 1-1,000 uM and incubated at 4° C. prior to being injected onto the sensor chip. The chip is regenerated by injecting 10 uL of 100 mM glycine at pH 1.5 after each sample injection. A control (Stat3 with DMSO but without compound) is run at the beginning and the end of each cycle (40 sample injections) to ensure that the integrity of the sensor chip is maintained throughout the cycle run. The average of the two controls is normalized to 100% and used to evaluate the effect of each compound on Stat3 binding. Responses are normalized by dividing the value at 2 min by the response obtained in the absence of compounds at 2 min and multiplying by 100. $IC_{50}$ values are determined by plotting % maximum response as a function of log concentration of compound and fitting the experimental points to a competitive binding model using a four parameter logistic equation: $R=R_{high}-(R_{high}-R_{low})/(1+conc/A1)^{A2}$, where R=percent response at inhibitor concentration, $R_{high}$=percent response with no compound, $R_{low}$=percent response at highest compound concentration, A2=fitting parameter (slope) and A1=$IC_{50}$ (BIAevaluation Software version 4.1).

EXP IIB. High throughput fluorescence microscopy (HTFM), cytoplasm-to-nucleus translocation inhibition assays. HTFM of MEF/GFP-Stat3α cells is performed to assess the ability of probes to inhibit GFP-Stat3 cytoplasmic-to-nuclear translocation, as described (Xu et al., 2009), using the robotic system available as part of the John S. Dunn Gulf Coast Consortium for Chemical Genomics at the University of Texas-Houston School of Medicine. Briefly, cells are seeded into 96-well CC3 plates at a density of 5,000 cells/well and cultured under standard conditions until 85-90% confluent. Cells are pre-treated with compound for 1 hour at 37° C. then stimulated with IL-6 (100 ng/ml) and IL-6sR (150 ng/ml) for 30 minutes. Cells are fixed with 4% formaldehyde in PEM Buffer (80 mM Potassium PIPES, pH 6.8, 5 mM EGTA pH 7.0, 2 mM $MgCl_2$) for 30 minutes at 4° C., quenched in 1 mg/ml of $NaBH_4$ (Sigma) in PEM buffer and counterstained for 1 min in 4,6-diamidino-2-phenylindole (DAPI; Sigma; 1 mg/ml) in PEM buffer. Plates are analyzed by automated HTFM using the Cell Lab IC Image Cytometer (IC100) platform and CytoshopVersion 2.1 analysis software (Beckman Coulter).

Nuclear translocation is quantified by using the fraction localized in the nucleus (FLIN) measurement. FLIN values are normalized by subtracting the FLIN for unstimulated cells then dividing this difference by the maximum difference (delta, Δ) in FLIN (FLIN in cells stimulated with IL-6/sIL-6R in the absence of compound minus FLIN of unstimulated cells). This ratio is multiplied by 100 to obtain the percentage of maximum difference in FLIN and is plotted as a function of the log compound concentration. The best-fitting curve and $IC_{50}$ value are determined using 4-Parameter LogisticModel/Dose Response/XLfit 4.2, IDBS software.

EXP IIC. Ligand-mediated pStat3 and pStat1 inhibition assays. Newly synthesized Stat3 probes with activity equivalent to or greater than parent compound 188 in the SPR and HTFM assays will be tested for the ability to selectively inhibit ligand-mediated phosphorylation of Stat3 as described (Xu et al., 2009). Briefly, human hepatocellular carcinoma cells (HepG2) are grown in 6-well plates and pretreated with compounds (0, 0.1, 0.3, 1, 3, 10, 30, 100 μM) for 1 hour then stimulated under optimal conditions with either interleukin-6 (IL-6; 30 ng/ml for 30 min) to activate Stat3 or interferon gamma (IFN-γ; 30 ng/ml for 30 min) to activate Stat1. Cells are harvested and proteins extracted using high-salt buffer, mixed with 2× sodium dodecyl sulfate (SDS) sample buffer (125 mmol/L Tris-HCL pH 6.8; 4% SDS; 20% glycerol; 10%2-mercaptoethanol) at a 1:1 ratio then heated for 5 minutes at 100° C. Proteins (20 μg) are separated by 7.5% SDS-PAGE and transferred to polyvinylidene fluoride (PVDF) membrane (Millipore, Waltham, Mass.) and immunoblotted. Membranes are probed serially with antibody against Stat1 pY701 or Stat3 pY705 followed by antibody against Stat1 or Stat3 (Transduction labs, Lexington, Ky.) then antibody against β-actin (Abcam, Cambridge, Mass.). Membranes are stripped between antibody probings using Restore™ Western Blot Stripping Buffer (Thermo Fisher Scientific Inc., Waltham, Mass.) per the manufacturer's instructions. Horseradish peroxidase-conjugated goat-anti-mouse IgG is used as the secondary antibody (Invitrogen Carlsbad, Calif.) and the membranes are developed with enhanced chemiluminescence (ECL) detection system (Amersham Life Sciences Inc.; Arlington Heights, Ill.). Band intensities are quantified by densitometry. The value of each pStat3 band is divided by its corresponding total Stat3 band intensity; the results are normalized to the DMSO-treated control value. This value was plotted as a function of the log compound concentration. The best-fitting curve is determined using 4-Parameter Logistic Model/Dose Response/XLfit 4.2, IDBS software and was used to calculate the $IC_{50}$ value.

EXP IID. Molecular modeling of probe-Stat3 interactions. The results of modeling of the binding of the first generation probe to the Stat3 vs. Stat1 SH2 domains suggested that the basis for experimental selectivity of probes for Stat3 vs. Stat1 rested on the ability of the probes to have greater interaction with the hydrophobic binding site within the pY-peptide binding pocket of Stat3 compared to Stat1. Thus, the hydrophobic binding site served as a selectivity filter. To test if this remains the case for newly synthesized 3rd generation probes, one can use 2 complementary docking programs GLIDE (Schrödinger) and ICM (MolSoft) to determine the lowest energy docking configuration of each probe within the pY-peptide binding domain of Stat3 and Stat1 SH2 domain. One can review the computational models of each probe in a complex with the Stat3 vs. Stat1 SH2 domain and, in particular, compare the van der Waals energies and determine if they are equivalent for their interaction with the Stat3 SH2 domain vs. the Stat1 SH2 domain. It was this calculation that determined the selectivity of 1st generation probes for Stat3 vs. Stat1. In particular, van der Waals energy calculations implicated residues that form the hydrophobic binding site (W623, Q635, V637, Y640 and Y657) as critical for this selectivity.

In specific embodiments of the invention, there is identification of probes with one log or greater activity than $2^{nd}$ generation probes in SPR, HTFM and pStat3 assays. Furthermore, in certain aspects some of the most active $3^{rd}$ generation probes that emerge from this analysis are selective for Stat3 vs. Stat1 based on their greater interaction with the hydrophobic binding site within the Stat3 vs. Stat1 SH2 pY-peptide binding pocket.

Example 10

Exemplary Compositions of the Disclosure

Exemplary composition(s) of the disclosure are provided in Tables 6-11 below.

TABLE 6

| IDNUMBER | Structure | Formula structure | MW | LogP |
|---|---|---|---|---|
| F1566-0306 | 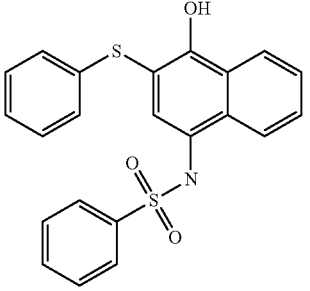 [SMILES: O=S(=O)(Nc1cc(Sc2ccccc2)c(O)c2ccccc12)c1ccccc1] | C22H17NO3S2 | 407.5137 | 5.846 |
| F1566-0318 | 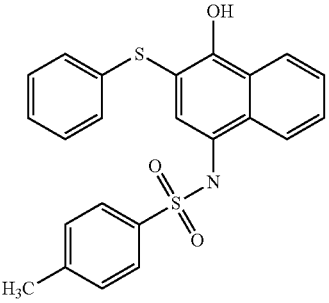 [SMILES: Cc1ccc(S(=O)(=O)Nc2cc(Sc3ccccc3)c(O)c3ccccc23)cc1] | C23H19NO3S2 | 421.5408 | 6.144 |
| F1566-0330 | 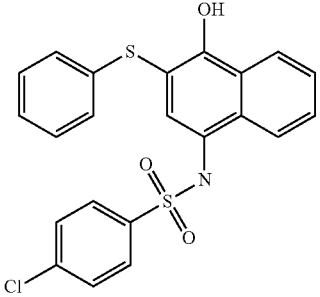 [SMILES: O=S(=O)(Nc1cc(Sc2ccccc2)c(O)c2ccccc12)c1ccc(Cl)cc1] | C22H16ClNO3S2 | 441.9587 | 6.438 |

TABLE 6-continued
| IDNUMBER | Structure | Formula structure | MW | LogP |
|---|---|---|---|---|
| F1566-0342 | 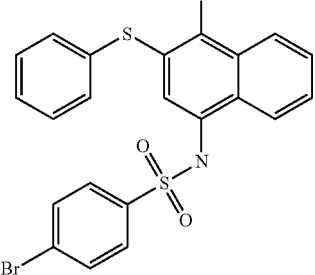 | C22H16BrNO3S2 | 486.4097 | 6.644 |
| F1566-0366 | 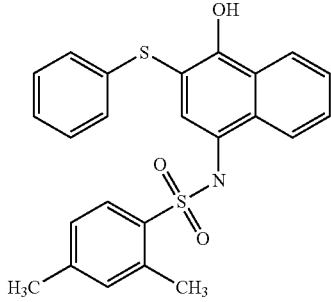 [SMILES: Cc1ccc(S(=O)(=O)Nc2cc(Sc3ccccc3)c(O)c3ccccc23)c(C)c1] | C24H21NO3S2 | 435.5679 | 6.477 |
| F1566-0414 | 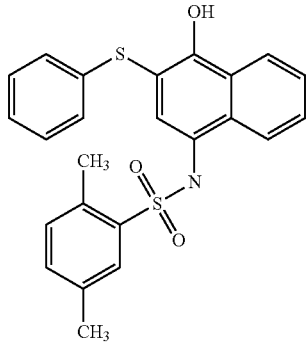 [SMILES: Cc1ccc(C)c(S(=O)(=O)Nc2cc(Sc3ccccc3)c(O)c3ccccc23)c1] | C24H21NO3S2 | 435.5679 | 6.477 |
| F1566-0438 | 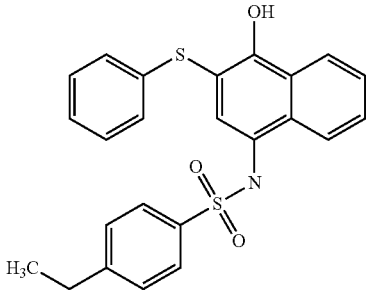 [SMILES: CCc1ccc(S(=O)(=O)Nc2cc(Sc3ccccc3)c(O)c3ccccc23)cc1] | C24H21NO3S2 | 435.5679 | 6.619 |

TABLE 6-continued
| IDNUMBER | Structure | Formula structure | MW | LogP |
|---|---|---|---|---|
| F1566-0450 | 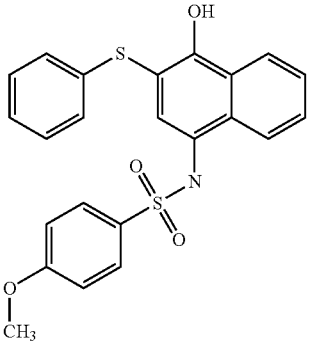 [SMILES: COc1ccc(S(=O)(=O)Nc2cc(Sc3ccccc3)c(O)c3ccccc23)cc1] | C23H19NO4S2 | 437.5402 | 5.802 |
| F1566-0462 | 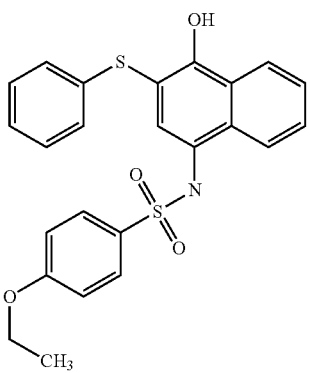 [SMILES: CCOc1ccc(S(=O)(=O)Nc2cc(Sc3ccccc3)c(O)c3ccccc23)cc1] | C24H21NO4S2 | 451.5673 | 6.143 |
| F1566-0486 | 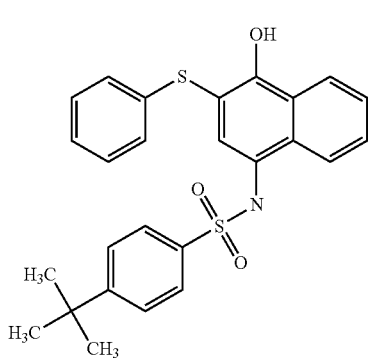 [SMILES: CC(C)(C)c1ccc(S(=O)(=O)Nc2cc(Sc3ccccc3)c(O)c3ccccc23)cc1] | C26H25NO3S2 | 463.6221 | 7.345 |
| F1566-0510 | 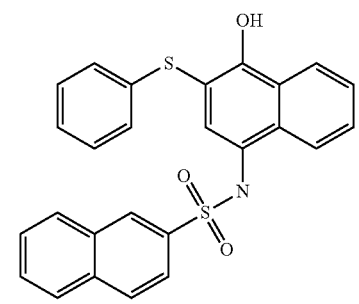 [SMILES: O=S(=O)(Nc1cc(Sc2ccccc2)c(O)c2ccccc12)c1ccc2ccccc2c1] | C26H19NO3S2 | 457.5742 | 7.105 |

TABLE 6-continued

| IDNUMBER | Structure | Formula structure | MW | LogP |
|---|---|---|---|---|
| F1566-0546 | 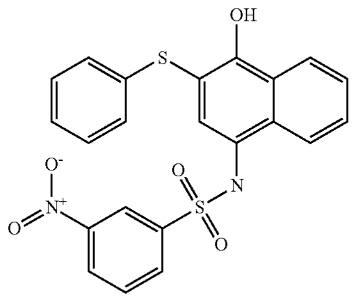 [SMILES: O=[N+]([O-])c1cccc(S(=O)(=O)Nc2cc(Sc3ccccc3)c(O)c3ccccc23)c1] | C22H16N2O5S2 | 452.5112 | 5.818 |
| F1566-0558 | 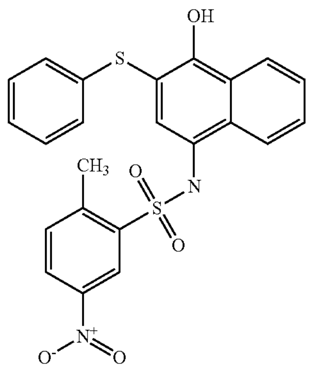 [SMILES: Cc1ccc([N+](=O)[O-])cc1S(=O)(=O)Nc1cc(Sc2ccccc2)c(O)c2ccccc12] | C23H18N2O5S2 | 466.5383 | 6.114 |
| F1566-0618 | 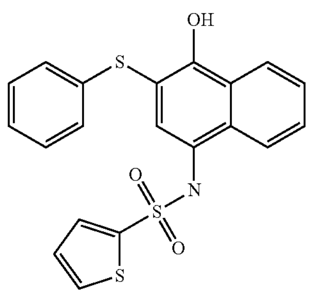 [SMILES: O=S(=O)(Nc1cc(Sc2ccccc2)c(O)c2ccccc12)c1cccs1] | C20H15NO3S3 | 413.5395 | 5.359 |
| F1566-1606 | 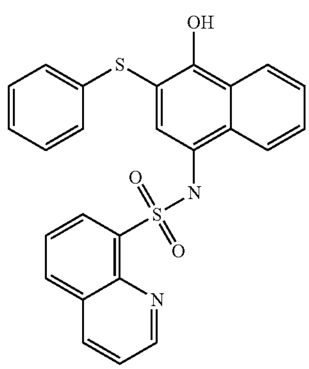 [SMILES: O=S(=O)(Nc1cc(Sc2ccccc2)c(O)c2ccccc12)c1cccc2cccnc12] | C25H18N2O3S2 | 458.5618 | 6.046 |
| F1566-1818 | 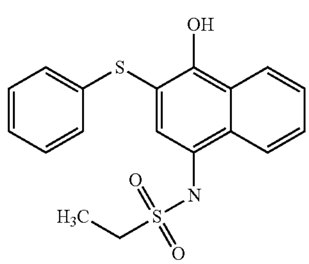 [SMILES: CCS(=O)(=O)Nc1cc(Sc2ccccc2)c(O)c2ccccc12] | C18H17NO3S2 | 359.4691 | 4.705 |

TABLE 6-continued

| IDNUMBER | Structure | Formula structure | MW | LogP |
| --- | --- | --- | --- | --- |
| F1566-1832 | 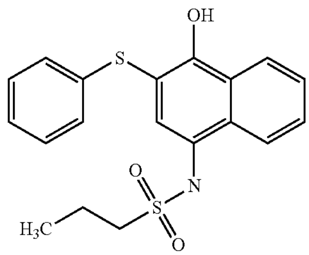 [SMILES: CCCS(=O)(=O)Nc1cc(Sc2ccccc2)c(O)c2ccccc12] | C19H19NO3S2 | 373.4962 | 5.147 |
| F1566-1846 | 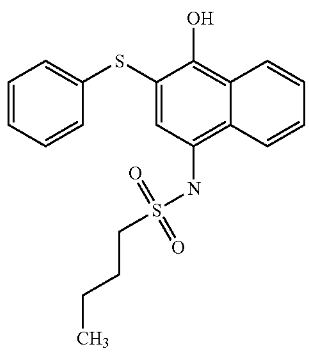 [SMILES: CCCCS(=O)(=O)Nc1cc(Sc2ccccc2)c(O)c2ccccc12] | C20H21NO3S2 | 387.5233 | 5.589 |
| F1566-1860 | 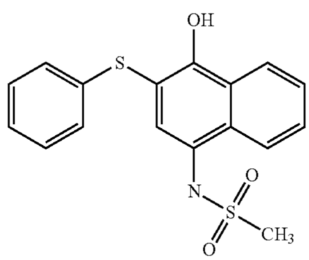 [SMILES: CS(=O)(=O)Nc1cc(Sc2ccccc2)c(O)c2ccccc12] | C17H15NO3S2 | 345.442 | 4.192 |
| F5749-0371 | 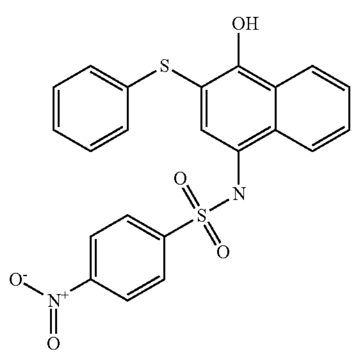 [SMILES: O=[N+]([O-])c1ccc(S(=O)(=O)Nc2cc(Sc3ccccc3)c(O)c3ccccc23)cc1] | C22H16N2O5S2 | 452.5112 | 5.781 |
| F5749-0372 | 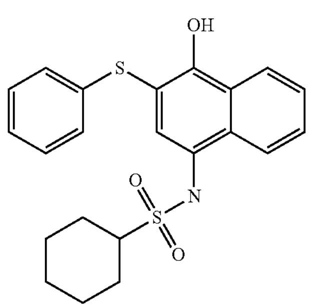 [SMILES: O=S(=O)(Nc1cc(Sc2ccccc2)c(O)c2ccccc12)C1CCCCC1] | C22H23NO3S2 | 413.5615 | 6.171 |

TABLE 6-continued
| IDNUMBER | Structure | Formula structure | MW | LogP |
|---|---|---|---|---|
| F5749-0373 | 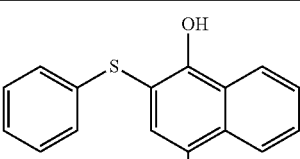 | C25H23NO4S2 | 465.5944 | 6.468 |
| F5749-0374 | 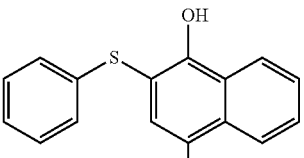 | C23H18ClNO4S2 | 471.9852 | 6.429 |
| F5749-0375 | 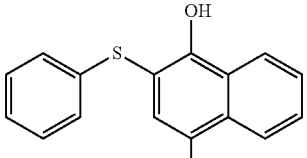 | C24H21NO3S2 | 435.5679 | 6.438 |
| F5749-0376 | 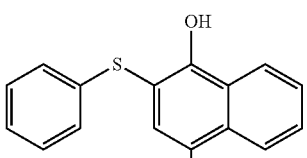 | C24H19NO5S2 | 465.5507 | 5.787 |

TABLE 6-continued
| IDNUMBER | Structure | Formula structure | MW | LogP |
|---|---|---|---|---|
| F5749-0377 | 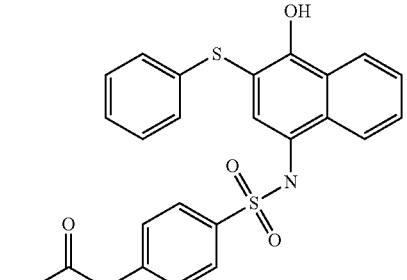 | C24H20N2O4S2 | 464.566 | 5.137 |
| F5749-0378 | 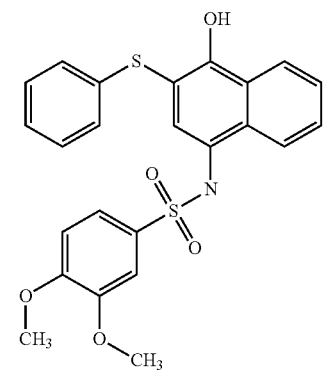 [SMILES: COc1ccc(S(=O)(=O)Nc2cc(Sc3ccccc3)c(O)c3ccccc23)cc1OC] | C24H21NO5S2 | 467.5667 | 5.54474 |
| F5749-0379 | 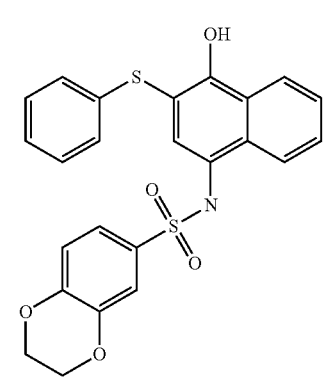 [SMILES: O=S(=O)(Nc1cc(Sc2ccccc2)c(O)c2ccccc12)c1ccc2c(c1)OCCO2] | C24H19NO5S2 | 465.5507 | 5.441 |
| F5749-0380 | 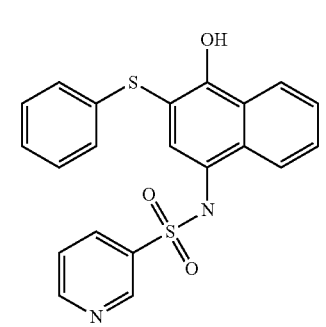 [SMILES: O=S(=O)(Nc1cc(Sc2ccccc2)c(O)c2ccccc12)c1cccnc1] | C21H16N2O3S2 | 408.5013 | 4.613 |

TABLE 6-continued

| IDNUMBER | Structure | Formula structure | MW | LogP |
|---|---|---|---|---|
| F5749-0381 | 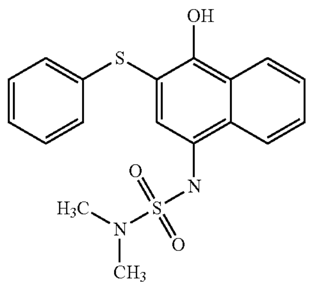 [SMILES: CN(C)S(=O)(=O)Nc1cc(Sc2ccccc2)c(O)c2ccccc12] | C18H18N2O3S2 | 374.4838 | 3.74 |
| F5749-0382 | 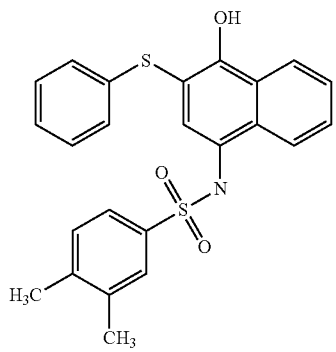 [SMILES: Cc1ccc(S(=O)(=O)Nc2cc(Sc3ccccc3)c(O)c3ccccc23)cc1C] | C24H21NO3S2 | 435.5679 | 6.477 |
| F5749-0383 | 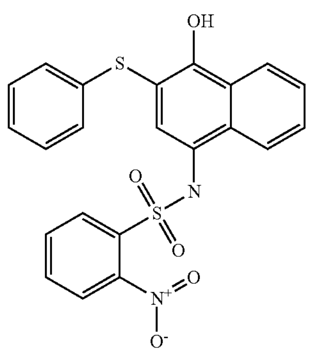 [SMILES: O=[N+]([O-])c1ccccc1S(=O)(=O)Nc1cc(Sc2ccccc2)c(O)c2ccccc12] | C22H16N2O5S2 | 452.5112 | 5.779 |
| F5749-0384 | 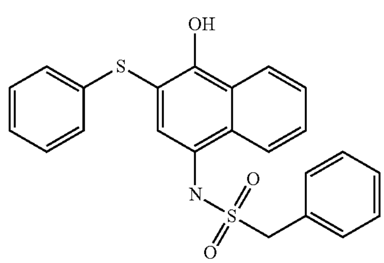 [SMILES: O=S(=O)(Cc1ccccc1)Nc1cc(Sc2ccccc2)c(O)c2ccccc12] | C23H19NO3S2 | 421.5408 | 5.98 |
| F5749-0385 | 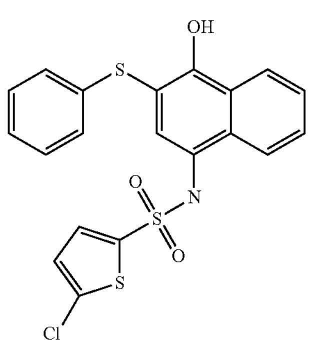 [SMILES: O=S(=O)(Nc1cc(Sc2ccccc2)c(O)c2ccccc12)c1ccc(Cl)s1] | C20H14ClNO3S3 | 447.9845 | 6.649 |

TABLE 6-continued

| IDNUMBER | Structure | Formula structure | MW | LogP |
|---|---|---|---|---|
| F5749-0386 | 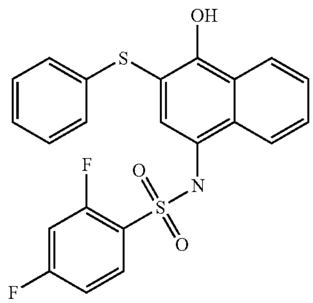 [SMILES: O=S(=O)(Nc1cc(Sc2ccccc2)c(O)c2ccccc12)c1ccc(F)cc1F] | C22H15F2NO3S2 | 443.4946 | 6.187 |
| F5749-0387 | 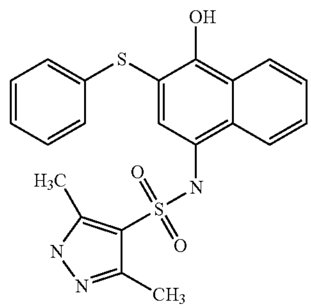 | C21H19N3O3S2 | 425.5319 | 4.956 |
| F5749-0388 | 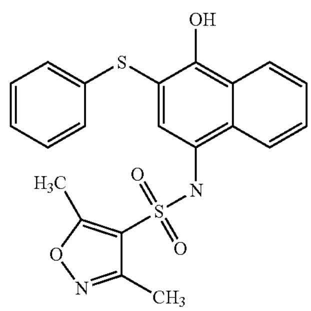 [SMILES: Cc1noc(C)c1S(=O)(=O)Nc1cc(Sc2ccccc2)c(O)c2ccccc12] | C21H18N2O4S2 | 426.5166 | 4.99 |
| F5749-0389 | 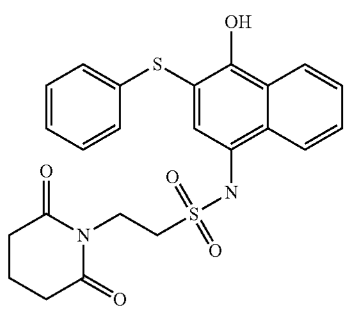 [SMILES: O=C1CCCC(=O)N1CCS(=O)(=O)Nc1cc(Sc2ccccc2)c(O)c2ccccc12] | C23H22N2O5S2 | 470.5702 | 3.633 |
| F5749-0390 | 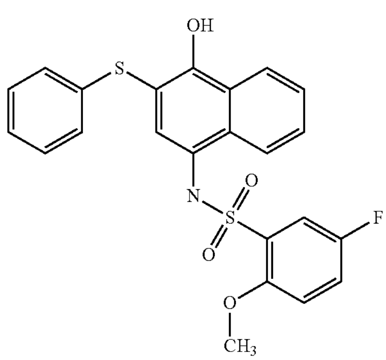 [SMILES: COc1ccc(F)cc1S(=O)(=O)Nc1cc(Sc2ccccc2)c(O)c2ccccc12] | C23H18FNO4S2 | 455.5306 | 5.99 |

TABLE 6-continued

| IDNUMBER | Structure | Formula structure | MW | LogP |
|---|---|---|---|---|
| F5749-0391 | 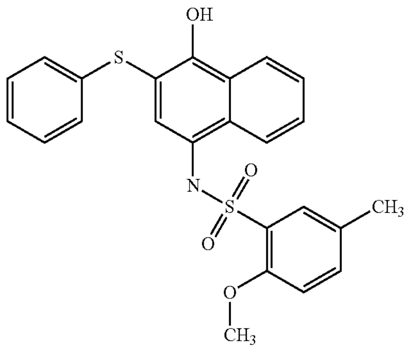 [SMILES: COc1ccc(C)cc1S(=O)(=O)Nc1cc(Sc2ccccc2)c(O)c2ccccc12] | C24H21NO4S2 | 451.5673 | 6.135 |
| F5749-0392 | 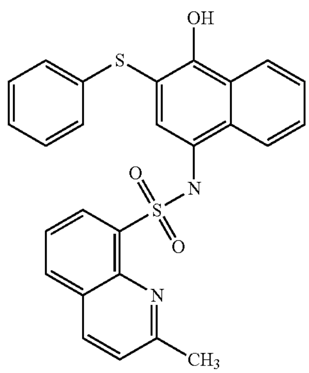 [SMILES: Cc1ccc2cccc(S(=O)(=O)Nc3cc(Sc4ccccc4)c(O)c4ccccc34)c2n1] | C26H20N2O3S2 | 472.5889 | 6.305 |
| F5749-0393 | 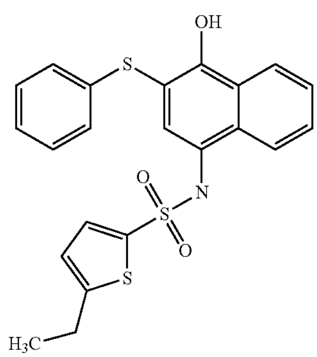 [SMILES: CCc1ccc(S(=O)(=O)Nc2cc(Sc3ccccc3)c(O)c3ccccc23)s1] | C22H19NO3S3 | 441.5936 | 6.497 |
| F5749-0394 | 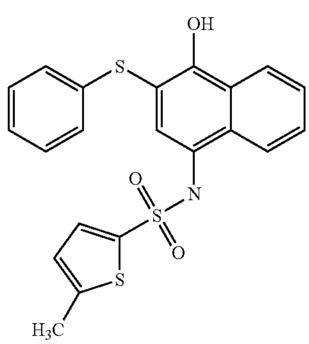 [SMILES: Cc1ccc(S(=O)(=O)Nc2cc(Sc3ccccc3)c(O)c3ccccc23)s1] | C21H17NO3S3 | 427.5665 | 6.022 |

TABLE 6-continued

| IDNUMBER | Structure | Formula structure | MW | LogP |
|---|---|---|---|---|
| F5749-0395 | 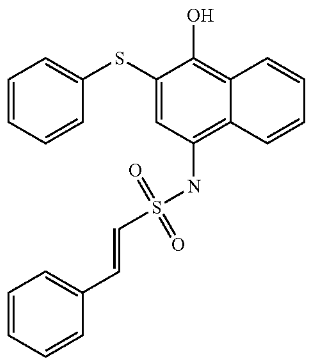 [SMILES: O=S(=O)(/C=C/c1ccccc1)Nc1cc(Sc2ccccc2)c(O)c2ccccc12] | C24H19NO3S2 | 433.5519 | 6.204 |
| F5749-0396 | 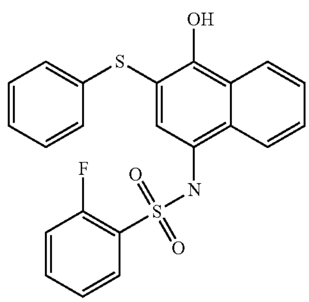 [SMILES: O=S(=O)(Nc1cc(Sc2ccccc2)c(O)c2ccccc12)c1ccccc1F] | C22H16FNO3S2 | 425.5041 | 5.997 |
| F5749-0397 | 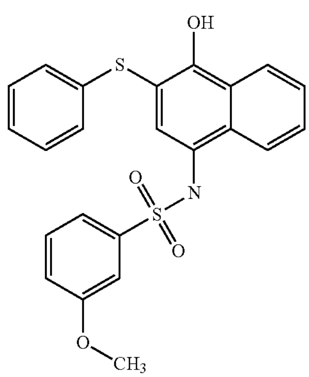 [SMILES: COc1cccc(S(=O)(=O)Nc2cc(Sc3ccccc3)c(O)c3ccccc23)c1] | C23H19NO4S2 | 437.5402 | 5.839 |
| F5749-0398 | 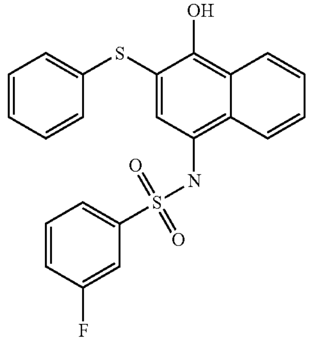 [SMILES: O=S(=O)(Nc1cc(Sc2ccccc2)c(O)c2ccccc12)c1cccc(F)c1] | C22H16FNO3S2 | 425.5041 | 6.036 |

TABLE 6-continued
| IDNUMBER | Structure | Formula structure | MW | LogP |
|---|---|---|---|---|
| F5749-0399 | 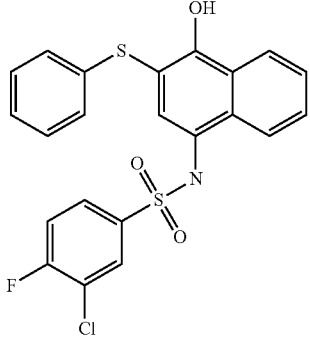 [SMILES: O=S(=O)(Nc1cc(Sc2ccccc2)c(O)c2ccccc12)c1ccc(F)c(Cl)c1] | C22H15ClFNO3S2 | 459.9492 | 6.626 |
| F5749-0400 | 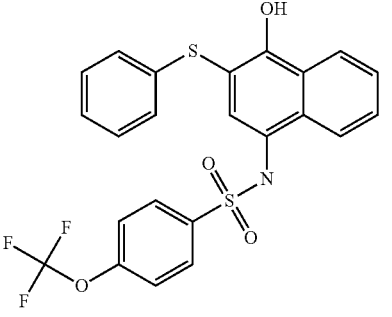 [SMILES: O=S(=O)(Nc1cc(Sc2ccccc2)c(O)c2ccccc12)c1ccc(OC(F)(F)F)cc1] | C23H16F3NO4S2 | 491.5115 | 7.24476 |
| F5749-0401 | 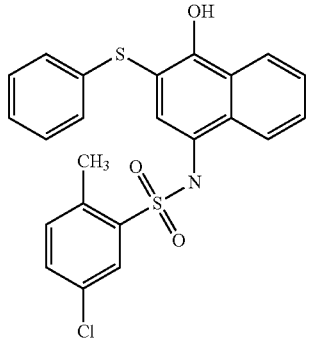 [SMILES: Cc1ccc(Cl)cc1S(=O)(=O)Nc1cc(Sc2ccccc2)c(O)c2ccccc12] | C23H18ClNO3S2 | 455.9858 | 6.771 |
| F5749-0402 | 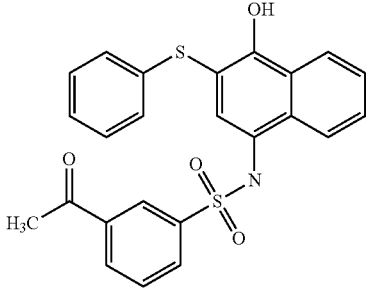 [SMILES: CC(=O)c1cccc(S(=O)(=O)Nc2cc(Sc3ccccc3)c(O)c3ccccc23)c1] | C24H19NO4S2 | 449.5513 | 5.736 |

TABLE 6-continued

| IDNUMBER | Structure | Formula structure | MW | LogP |
| --- | --- | --- | --- | --- |
| F5749-0403 | 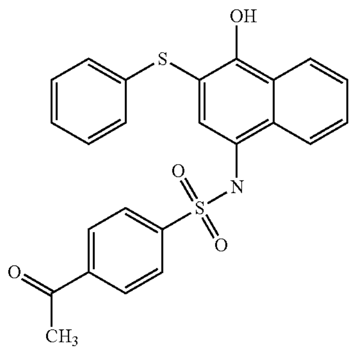 [SMILES: CC(=O)c1ccc(S(=O)(=O)Nc2cc(Sc3ccccc3)c(O)c3ccccc23)cc1] | C24H19NO4S2 | 449.5513 | 5.699 |
| F5749-0404 | 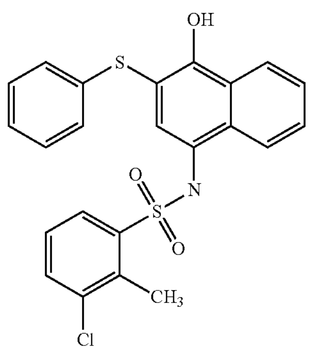 [SMILES: Cc1c(Cl)cccc1S(=O)(=O)Nc1cc(Sc2ccccc2)c(O)c2ccccc12] | C23H18ClNO3S2 | 455.9858 | 6.732 |
| F5749-0405 | 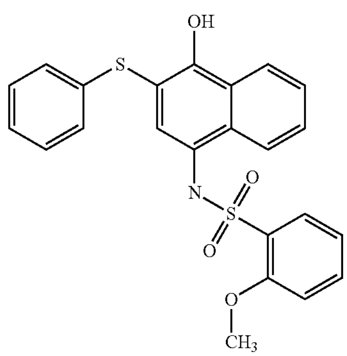 [SMILES: COc1ccccc1S(=O)(=O)Nc1cc(Sc2ccccc2)c(O)c2ccccc12] | C23H19NO4S2 | 437.5402 | 5.8 |
| F5749-0406 | 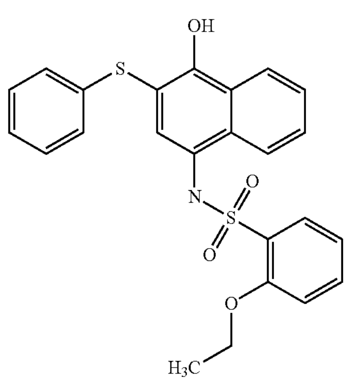 [SMILES: CCOc1ccccc1S(=O)(=O)Nc1cc(Sc2ccccc2)c(O)c2ccccc12] | C24H21NO4S2 | 451.5673 | 6.141 |

TABLE 6-continued

| IDNUMBER | Structure | Formula structure | MW | LogP |
|---|---|---|---|---|
| F5749-0407 | 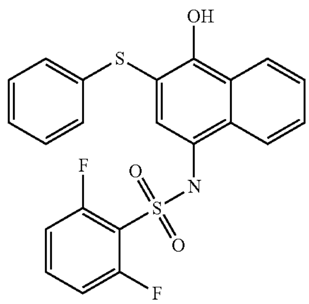 [SMILES: O=S(=O)(Nc1cc(Sc2ccccc2)c(O)c2ccccc12)c1c(F)cccc1F] | C22H15F2NO3S2 | 443.4946 | 6.148 |
| F5749-0408 | 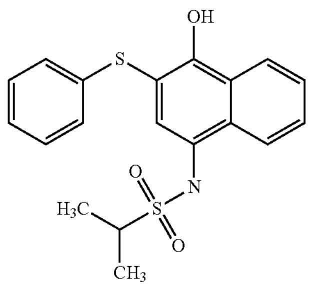 | C19H19NO3S2 | 373.4962 | 5.339 |
| F5749-0409 | 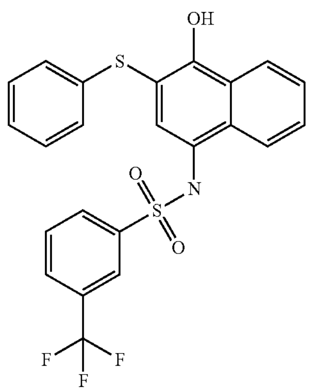 [SMILES: O=S(=O)(Nc1cc(Sc2ccccc2)c(O)c2ccccc12)c1cccc(C(F)(F)F)c1] | C23H16F3NO3S2 | 475.5121 | 6.81776 |
| F5749-0410 | 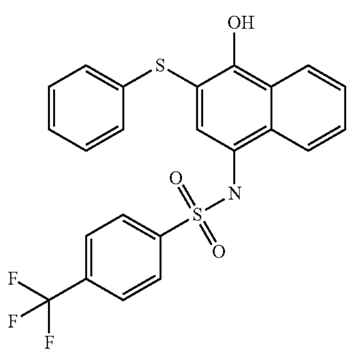 [SMILES: O=S(=O)(Nc1cc(Sc2ccccc2)c(O)c2ccccc12)c1ccc(C(F)(F)F)cc1] | C23H16F3NO3S2 | 475.5121 | 6.78076 |
| F5749-0411 | 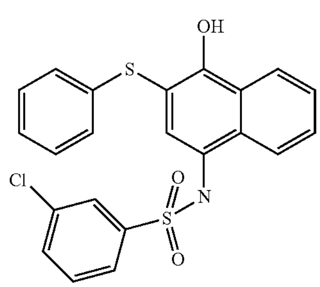 [SMILES: O=S(=O)(Nc1cc(Sc2ccccc2)c(O)c2ccccc12)c1cccc(Cl)c1] | C22H16ClNO3S2 | 441.9587 | 6.475 |

TABLE 6-continued
| IDNUMBER | Structure | Formula structure | MW | LogP |
|---|---|---|---|---|
| F5749-0412 | 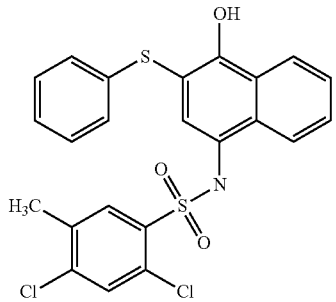 [SMILES: Cc1cc(S(=O)(=O)Nc2cc(Sc3ccccc3)c(O)c3ccccc23)c(Cl)cc1Cl] | C23H17Cl2NO3S2 | 490.4308 | 7.398 |
| F5749-0413 | 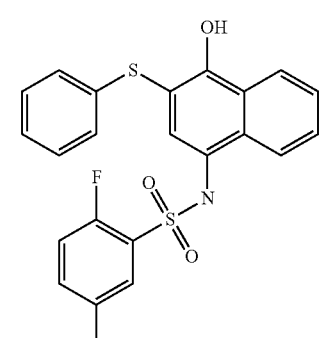 | C22H15F2NO3S2 | 443.4946 | 6.187 |
| F5749-0414 | 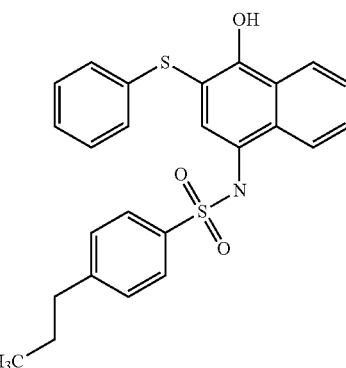 | C25H23NO3S2 | 449.595 | 7.061 |
| F5749-0415 | 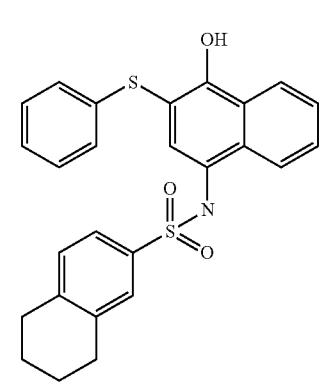 [SMILES: O=S(=O)(Nc1cc(Sc2ccccc2)c(O)c2ccccc12)c1ccc2c(c1)CCCC2] | C26H23NO3S2 | 461.6061 | 6.933 |

TABLE 6-continued

| IDNUMBER | Structure | Formula structure | MW | LogP |
|---|---|---|---|---|
| F5749-0416 | 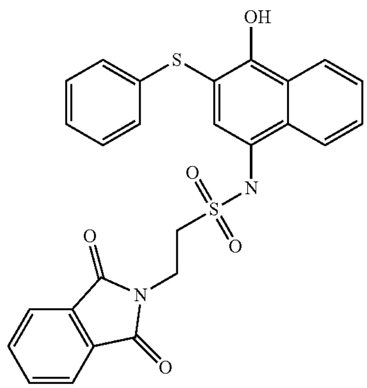 [SMILES: O=C1c2ccccc2C(=O)N1CCS(=O)(=O)Nc1cc(Sc2ccccc2)c(O)c2ccccc12] | C26H20N2O5S2 | 504.5877 | 4.973 |
| F5749-0417 | 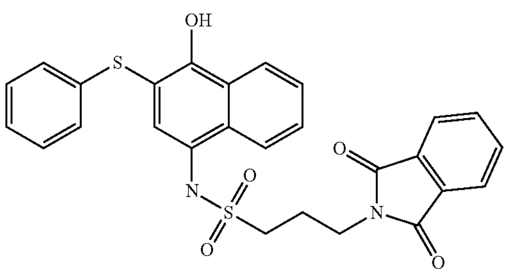 [SMILES: O=C1c2ccccc2C(=O)N1CCCS(=O)(=O)Nc1cc(Sc2ccccc2)c(O)c2ccccc12] | C27H22N2O5S2 | 518.6148 | 5.415 |
| F5749-0418 | 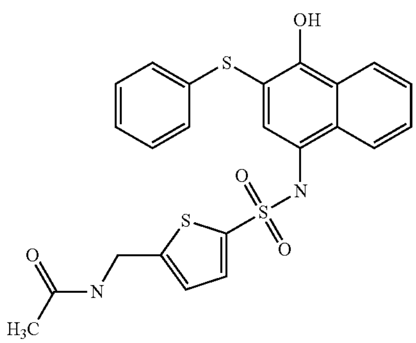 [SMILES: CC(=O)NCc1ccc(S(=O)(=O)Nc2cc(Sc3ccccc3)c(O)c3ccccc23)s1] | C23H20N2O4S3 | 484.6189 | 5.149 |
| F5749-0419 | 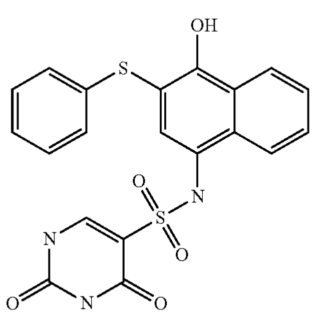 [SMILES: O=c1[nH]cc(S(=O)(=O)Nc2cc(Sc3ccccc3)c(O)c3ccccc23)c(=O)[nH]1] | C20H15N3O5S2 | 441.4877 | 2.891 |
| F5749-0420 | 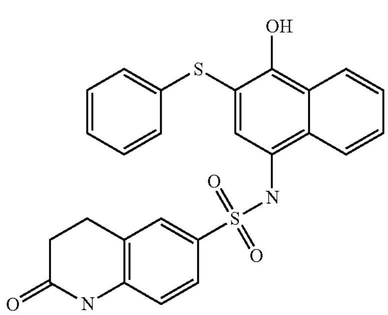 [SMILES: O=C1CCc2cc(S(=O)(=O)Nc3cc(Sc4ccccc4)c(O)c4ccccc34)ccc2N1] | C25H20N2O4S2 | 476.5772 | 5.042 |

TABLE 6-continued

| IDNUMBER | Structure | Formula structure | MW | LogP |
|---|---|---|---|---|
| F5749-0421 | 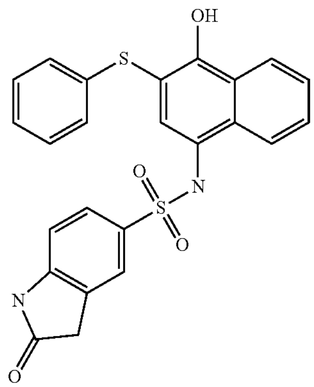 [SMILES: O=C1Cc2cc(S(=O)(=O)Nc3cc(Sc4ccccc4)c(O)c4ccccc34)ccc2N1] | C24H18N2O4S2 | 462.5501 | 4.954 |
| F5749-0422 | 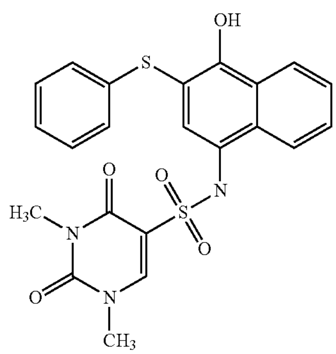 [SMILES: Cn1cc(S(=O)(=O)Nc2cc(Sc3ccccc3)c(O)c3ccccc23)c(=O)n(C)c1=O] | C22H19N3O5S2 | 469.5418 | 2.955 |
| F5749-0423 | 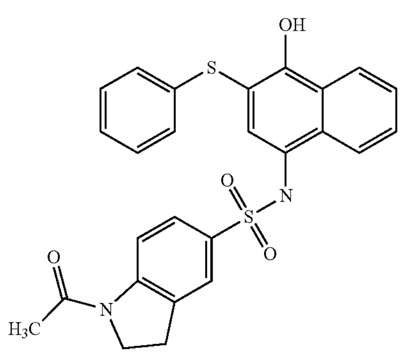 [SMILES: CC(=O)N1CCc2cc(S(=O)(=O)Nc3cc(Sc4ccccc4)c(O)c4ccccc34)ccc21] | C26H22N2O4S2 | 490.6042 | 5.277 |
| F5749-0424 | 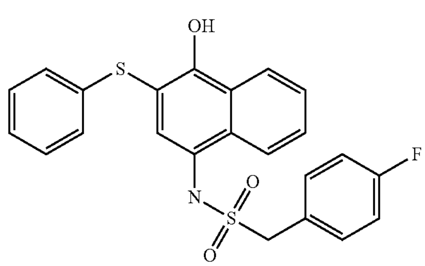 [SMILES: O=S(=O)(Cc1ccc(F)cc1)Nc1cc(Sc2ccccc2)c(O)c2ccccc12] | C23H18FNO3S2 | 439.5312 | 6.133 |

TABLE 6-continued

| IDNUMBER | Structure | Formula structure | MW | LogP |
|---|---|---|---|---|
| F5749-0425 | 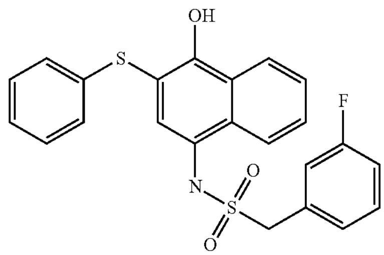 [SMILES: O=S(=O)(Cc1cccc(F)c1)Nc1cc(Sc2ccccc2)c(O)c2ccccc12] | C23H18FNO3S2 | 439.5312 | 6.17 |
| F5749-0426 | 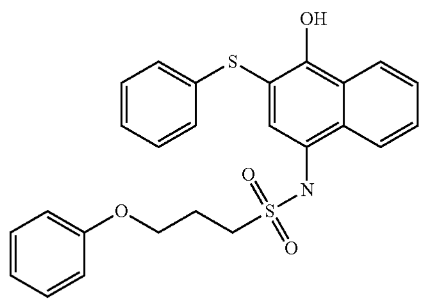 [SMILES: O=S(=O)(CCCOc1ccccc1)Nc1cc(Sc2ccccc2)c(O)c2ccccc12] | C25H23NO4S2 | 465.5944 | 6.206 |
| F5749-0427 | 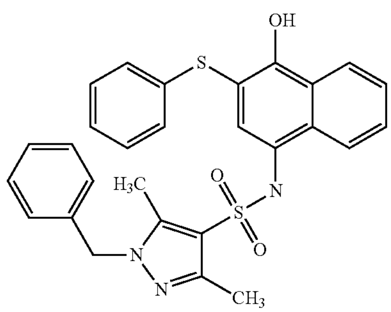 [SMILES: Cc1nn(Cc2ccccc2)c(C)c1S(=O)(=O)Nc1cc(Sc2ccccc2)c(O)c2ccccc12] | C28H25N3O3S2 | 515.6578 | 6.125 |
| F5749-0428 | 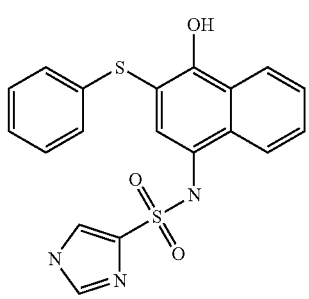 [SMILES: O=S(=O)(Nc1cc(Sc2ccccc2)c(O)c2ccccc12)c1c[nH]cn1] | C19H15N3O3S2 | 397.4777 | 3.986 |
| F5749-0429 | 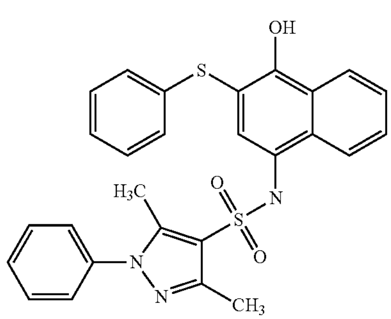 [SMILES: Cc1nn(-c2ccccc2)c(C)c1S(=O)(=O)Nc1cc(Sc2ccccc2)c(O)c2ccccc12] | C27H23N3O3S2 | 501.6307 | 5.991 |

| IDNUMBER | Structure | Formula structure | MW | LogP |
|---|---|---|---|---|
| F5749-0430 | 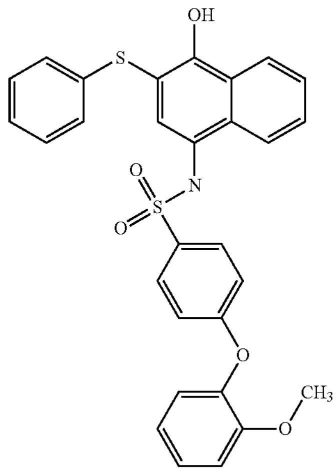 [SMILES: COc1ccccc1Oc1ccc(S(=O)(=O)Nc2cc(Sc3ccccc3)c(O)c3ccccc23)cc1] | C29H23NO5S2 | 529.6384 | 7.16174 |
| F5749-0431 | 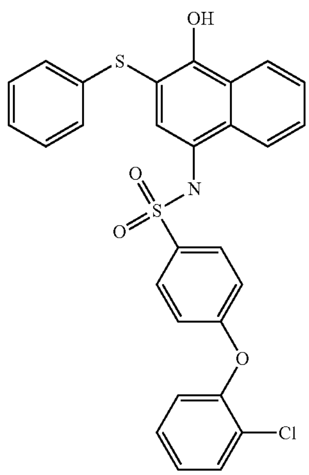 [SMILES: O=S(=O)(Nc1cc(Sc2ccccc2)c(O)c2ccccc12)c1ccc(Oc2ccccc2Cl)cc1] | C28H20ClNO4S2 | 534.0569 | 8.046 |
| F5749-0432 | 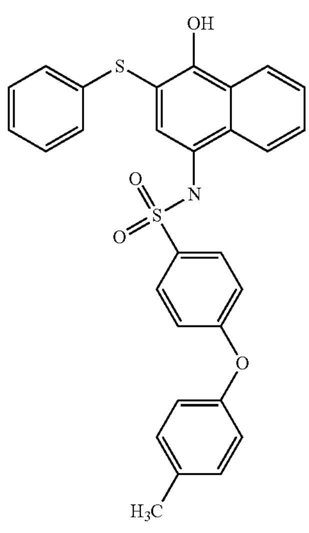 [SMILES: Cc1ccc(Oc2ccc(S(=O)(=O)Nc3cc(Sc4ccccc4)c(O)c4ccccc34)cc2)cc1] | C29H23NO4S2 | 513.639 | 7.754 |

TABLE 6-continued
| IDNUMBER | Structure | Formula structure | MW | LogP |
|---|---|---|---|---|
| F5749-0433 | 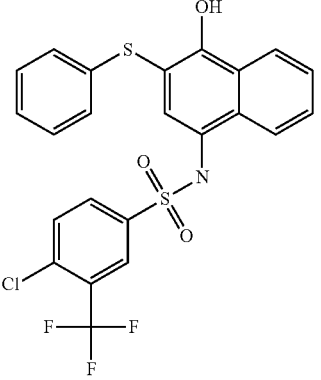 [SMILES: O=S(=O)(Nc1cc(Sc2ccccc2)c(O)c2ccccc12)c1ccc(Cl)c(C(F)(F)F)c1] | C23H15ClF3NO3S2 | 509.9571 | 7.40776 |
| F5749-0434 | 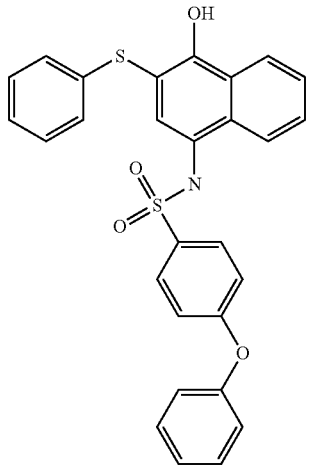 [SMILES: O=S(=O)(Nc1cc(Sc2ccccc2)c(O)c2ccccc12)c1ccc(Oc2ccccc2)cc1] | C28H21NO4S2 | 499.6119 | 7.456 |
| F5749-0435 | 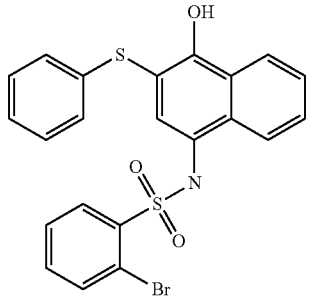 | C22H16BrNO3S2 | 486.4097 | 6.642 |
| F5749-0436 | 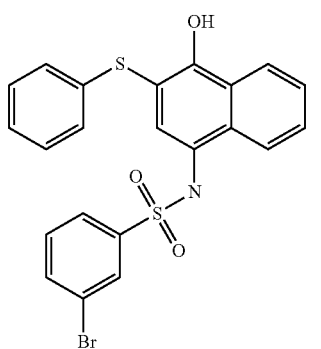 [SMILES: O=S(=O)(Nc1cc(Sc2ccccc2)c(O)c2ccccc12)c1cccc(Br)c1] | C22H16BrNO3S2 | 486.4097 | 6.681 |

TABLE 6-continued
| IDNUMBER | Structure | Formula structure | MW | LogP |
| --- | --- | --- | --- | --- |
| F5749-0437 | 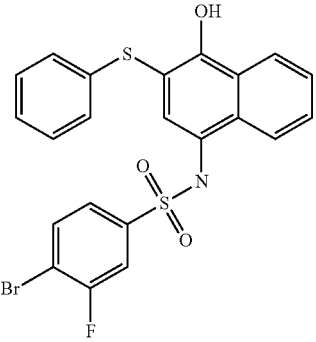 [SMILES: O=S(=O)(Nc1cc(Sc2ccccc2)c(O)c2ccccc12)c1ccc(Br)c(F)c1] | C22H15BrFNO3S2 | 504.4002 | 6.832 |
| F5749-0438 | 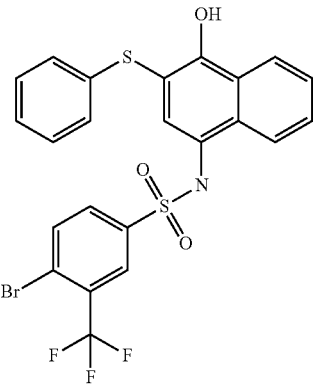 [SMILES: O=S(=O)(Nc1cc(Sc2ccccc2)c(O)c2ccccc12)c1ccc(Br)c(C(F)(F)F)c1] | C23H15BrF3NO3S2 | 554.4081 | 7.61376 |
| F5749-0439 | 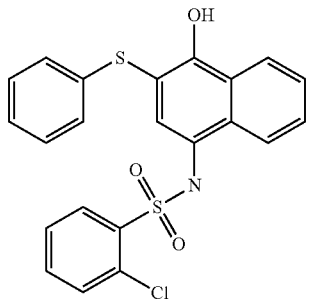 [SMILES: O=S(=O)(Nc1cc(Sc2ccccc2)c(O)c2ccccc12)c1ccccc1Cl] | C22H16ClNO3S2 | 441.9587 | 6.436 |
| F5749-0440 | 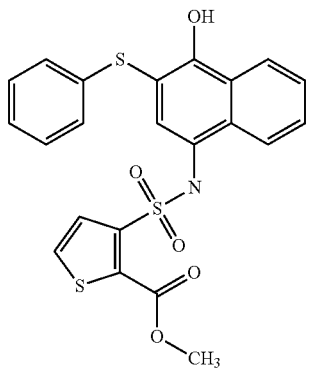 [SMILES: COC(=O)c1sccc1S(=O)(=O)Nc1cc(Sc2ccccc2)c(O)c2ccccc12] | C22H17NO5S3 | 471.5765 | 5.046 |

TABLE 6-continued
| IDNUMBER | Structure | Formula structure | MW | LogP |
|---|---|---|---|---|
| F5749-0441 | 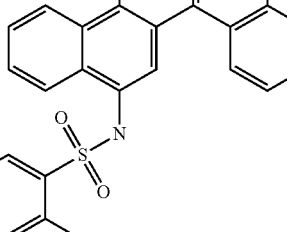 | C23H16F3NO4S2 | 491.5115 | 7.24276 |
TABLE 7
| IDNUMBER | Structure | Formula structure | MW | LogP |
|---|---|---|---|---|
| F0808-0081 | 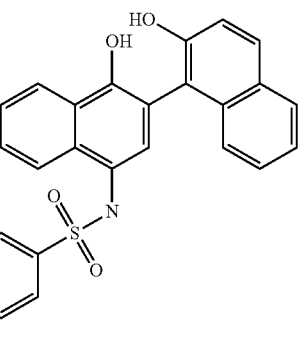 | C28H23NO4S | 469.5638 | 7.101 |
| F0808-0084 | 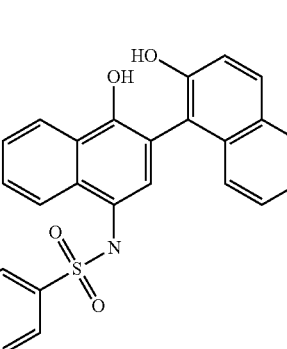 | C28H23NO5S | 485.5632 | 6.767 |
| F0808-0085 | 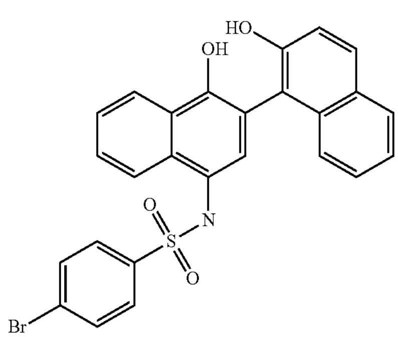 | C26H18BrNO4S | 520.4057 | 7.268 |

TABLE 7-continued
| IDNUMBER | Structure | Formula structure | MW | LogP |
|---|---|---|---|---|
| F0808-0086 | 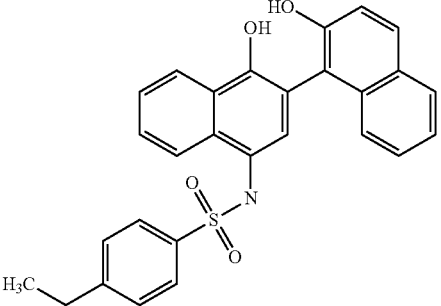 [SMILES: CCc1ccc(S(=O)(=O)Nc2cc(-c3c(O)ccc4ccccc34)c(O)c3ccccc23)cc1] | C28H23NO4S | 469.5638 | 7.243 |
| F0808-0089 | 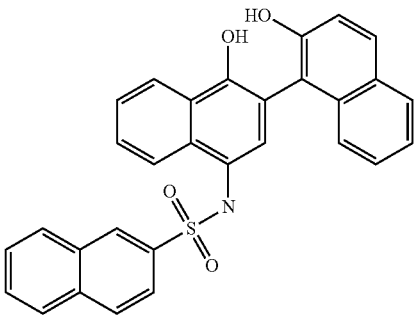 [SMILES: O=S(=O)(Nc1cc(-c2c(O)ccc3ccccc23)c(O)c2ccccc12)c1ccc2ccccc2c1] | C30H21NO4S | 491.5702 | 7.729 |
| F0808-0091 | 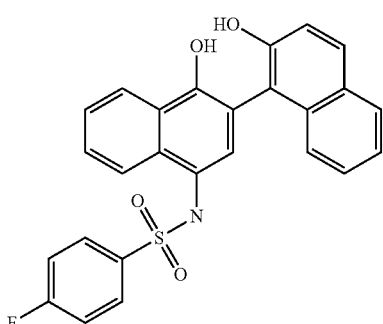 | C26H18FNO4S | 459.5001 | 6.623 |
| F0808-0092 | 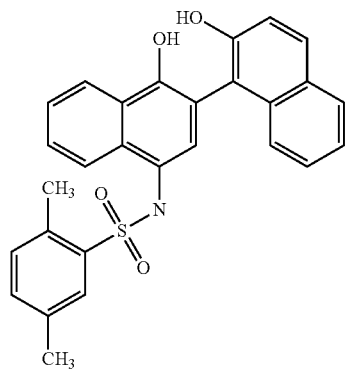 [SMILES: Cc1ccc(C)c(S(=O)(=O)Nc2cc(-c3c(O)ccc4ccccc34)c(O)c3ccccc23)c1] | C28H23NO4S | 469.5638 | 7.101 |

TABLE 7-continued

| IDNUMBER | Structure | Formula structure | MW | LogP |
|---|---|---|---|---|
| F0808-0094 | 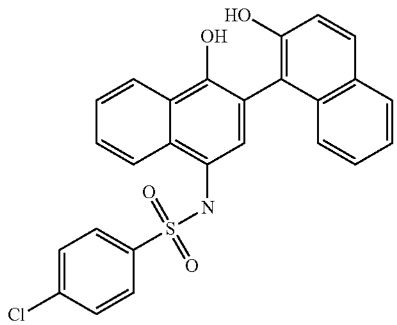 [SMILES: O=S(=O)(Nc1cc(-c2c(O)ccc3ccccc23)c(O)c2ccccc12)c1ccc(Cl)cc1] | C26H18ClNO4S | 475.9547 | 7.062 |
| F1269-0222 | 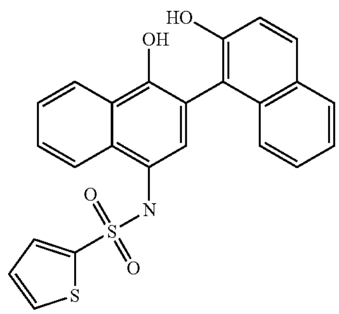 [SMILES: O=S(=O)(Nc1cc(-c2c(O)ccc3ccccc23)c(O)c2ccccc12)c1cccs1] | C24H17NO4S2 | 447.5354 | 5.983 |
| F1269-2003 | 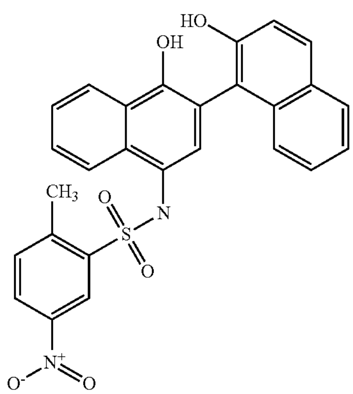 [SMILES: Cc1ccc([N+](=O)[O-])cc1S(=O)(=O)Nc1cc(-c2c(O)ccc3ccccc23)c(O)c2ccccc12] | C27H20N2O6S | 500.5343 | 6.738 |
| F1566-1138 | 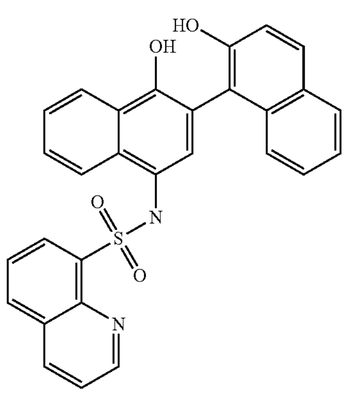 [SMILES: O=S(=O)(Nc1cc(-c2c(O)ccc3ccccc23)c(O)c2ccccc12)c1cccc2cccnc12] | C29H20N2O4S | 492.5578 | 6.67 |

TABLE 7-continued

| IDNUMBER | Structure | Formula structure | MW | LogP |
| --- | --- | --- | --- | --- |
| F5749-0001 | 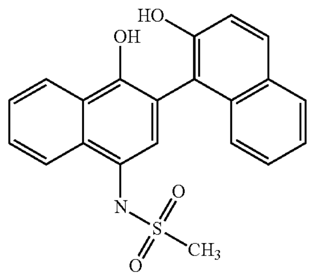 [SMILES: CS(=O)(=O)Nc1cc(-c2c(O)ccc3ccccc23)c(O)c2ccccc12] | C21H17NO4S | 379.4379 | 4.816 |
| F5749-0002 | 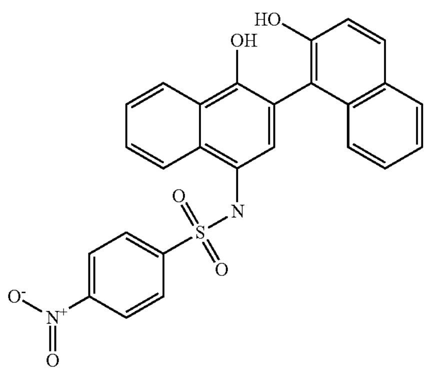 [SMILES: O=[N+]([O-])c1ccc(S(=O)(=O)Nc2cc(-c3c(O)ccc4ccccc34)c(O)c3ccccc23)cc1] | C26H18N2O6S | 486.5072 | 6.405 |
| F5749-0003 | 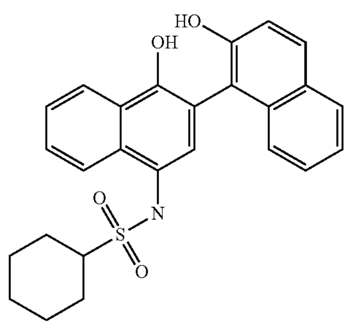 [SMILES: O=S(=O)(Nc1cc(-c2c(O)ccc3ccccc23)c(O)c2ccccc12)C1CCCCC1] | C26H25NO4S | 447.5575 | 6.795 |
| F5749-0004 | 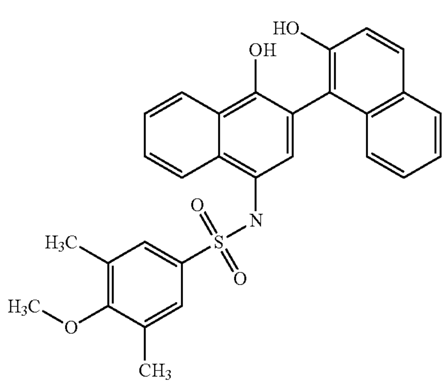 [SMILES: COc1c(C)cc(S(=O)(=O)Nc2cc(-c3c(O)ccc4ccccc34)c(O)c3ccccc23)cc1C] | C29H25NO5S | 499.5903 | 7.092 |

TABLE 7-continued
| IDNUMBER | Structure | Formula structure | MW | LogP |
|---|---|---|---|---|
| F5749-0005 | 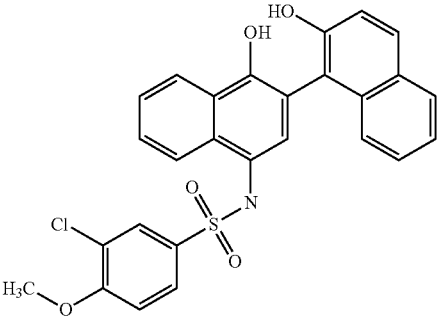 [SMILES: COc1ccc(S(=O)(=O)Nc2cc(-c3c(O)ccc4ccccc34)c(O)c3ccccc23)cc1Cl] | C27H20ClNO5S | 505.9812 | 7.053 |
| F5749-0006 | 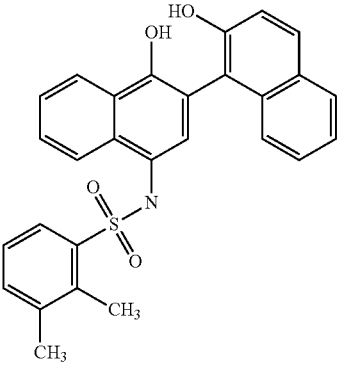 [SMILES: Cc1cccc(S(=O)(=O)Nc2cc(-c3c(O)ccc4ccccc34)c(O)c3ccccc23)c1C] | C28H23NO4S | 469.5638 | 7.062 |
| F5749-0007 | 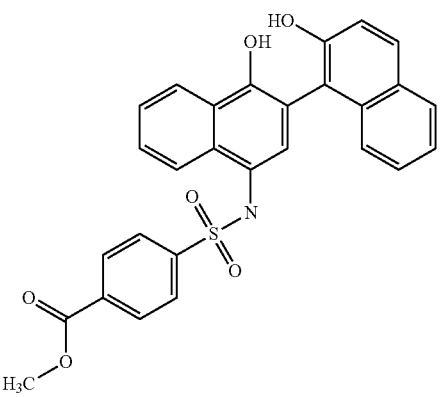 [SMILES: COC(=O)c1ccc(S(=O)(=O)Nc2cc(-c3c(O)ccc4ccccc34)c(O)c3ccccc23)cc1] | C28H21NO6S | 499.5467 | 6.411 |
| F5749-0008 | 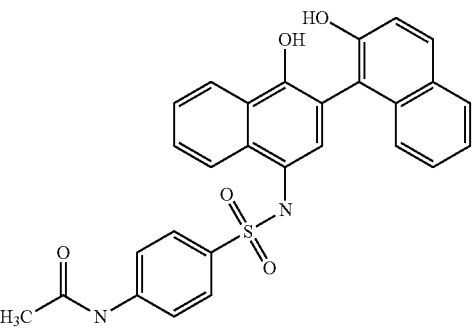 [SMILES: CC(=O)Nc1ccc(S(=O)(=O)Nc2cc(-c3c(O)ccc4ccccc34)c(O)c3ccccc23)cc1] | C28H22N2O5S | 498.5619 | 5.761 |

TABLE 7-continued
| IDNUMBER | Structure | Formula structure | MW | LogP |
|---|---|---|---|---|
| F5749-0009 | 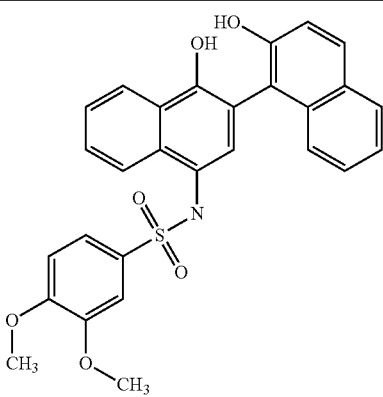 | C28H23NO6S | 501.5626 | 6.16874 |
| F5749-0010 | 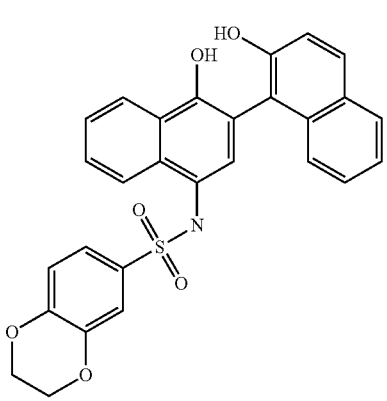 [SMILES: O=S(=O)(Nc1cc(-c2c(O)ccc3ccccc23)c(O)c2ccccc12)c1ccc2c(c1)OCCO2] | C28H21NO6S | 499.5467 | 6.065 |
| F5749-0011 | 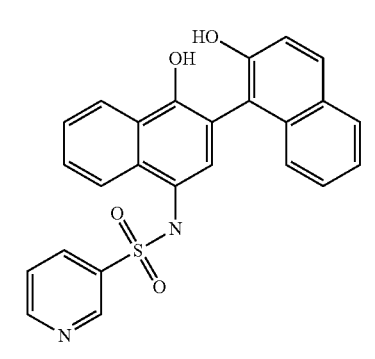 [SMILES: O=S(=O)(Nc1cc(-c2c(O)ccc3ccccc23)c(O)c2ccccc12)c1cccnc1] | C25H18N2O4S | 442.4972 | 5.237 |
| F5749-0012 | 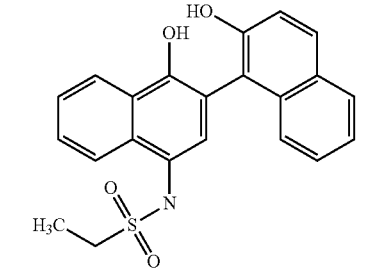 [SMILES: CCS(=O)(=O)Nc1cc(-c2c(O)ccc3ccccc23)c(O)c2ccccc12] | C22H19NO4S | 393.465 | 5.329 |

TABLE 7-continued

| IDNUMBER | Structure | Formula structure | MW | LogP |
|---|---|---|---|---|
| F5749-0013 | 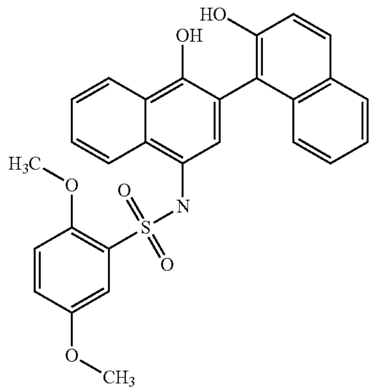 [SMILES: COc1ccc(OC)c(S(=O)(=O)Nc2cc(-c3c(O)ccc4ccccc34)c(O)c3ccccc23)c1] | C28H23NO6S | 501.5626 | 6.417 |
| F5749-0014 | 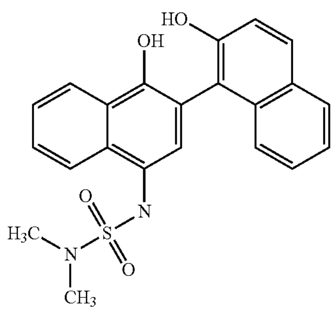 [SMILES: CN(C)S(=O)(=O)Nc1cc(-c2c(O)ccc3ccccc23)c(O)c2ccccc12] | C22H20N2O4S | 408.4797 | 4.364 |
| F5749-0015 | 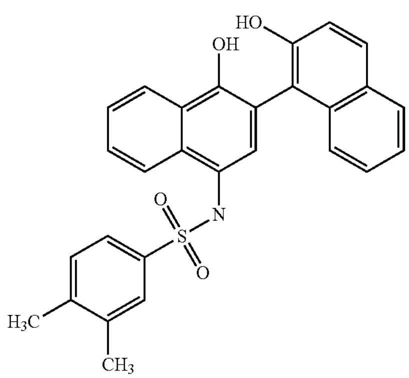 [SMILES: Cc1ccc(S(=O)(=O)Nc2cc(-c3c(O)ccc4ccccc34)c(O)c3ccccc23)cc1C] | C28H23NO4S | 469.5638 | 7.101 |
| F5749-0016 | 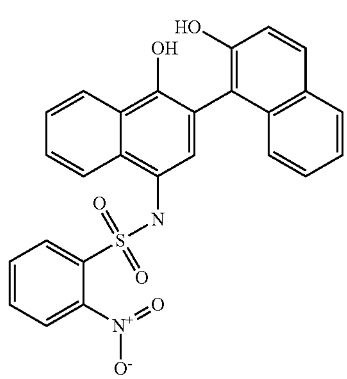 [SMILES: O=[N+]([O-])c1ccccc1S(=O)(=O)Nc1cc(-c2c(O)ccc3ccccc23)c(O)c2ccccc12] | C26H18N2O6S | 486.5072 | 6.403 |

TABLE 7-continued

| IDNUMBER | Structure | Formula structure | MW | LogP |
|---|---|---|---|---|
| F5749-0017 | 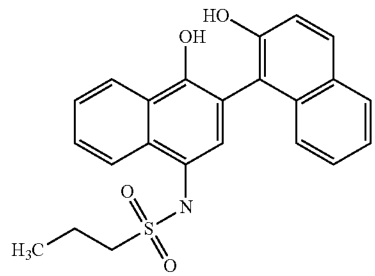 [SMILES: CCCS(=O)(=O)Nc1cc(-c2c(O)ccc3ccccc23)c(O)c2ccccc12] | C23H21NO4S | 407.4921 | 5.771 |
| F5749-0018 | 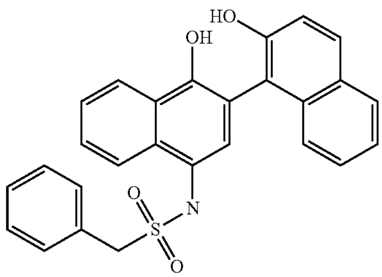 [SMILES: O=S(=O)(Cc1ccccc1)Nc1cc(-c2c(O)ccc3ccccc23)c(O)c2ccccc12] | C27H21NO4S | 455.5367 | 6.604 |
| F5749-0019 | 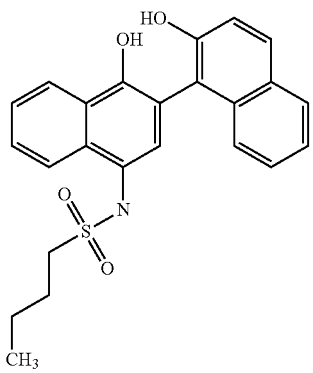 [SMILES: CCCCS(=O)(=O)Nc1cc(-c2c(O)ccc3ccccc23)c(O)c2ccccc12] | C24H23NO4S | 421.5192 | 6.213 |
| F5749-0020 | 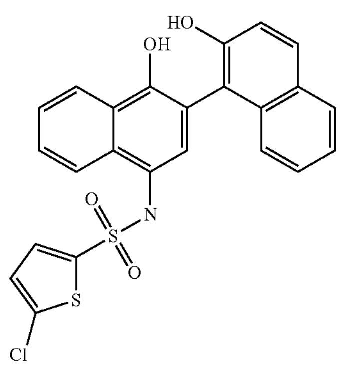 [SMILES: O=S(=O)(Nc1cc(-c2c(O)ccc3ccccc23)c(O)c2ccccc12)c1ccc(Cl)s1] | C24H16ClNO4S2 | 481.9804 | 7.273 |
| F5749-0021 | 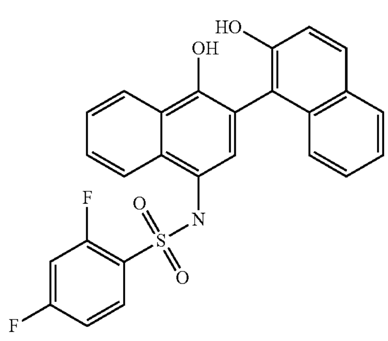 [SMILES: O=S(=O)(Nc1cc(-c2c(O)ccc3ccccc23)c(O)c2ccccc12)c1ccc(F)cc1F] | C26H17F2NO4S | 477.4905 | 6.811 |

TABLE 7-continued
| IDNUMBER | Structure | Formula structure | MW | LogP |
|---|---|---|---|---|
| F5749-0022 | 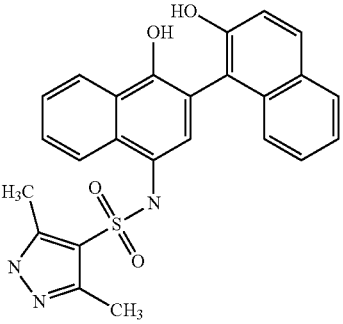 | C25H21N3O4S | 459.5278 | 5.58 |
| F5749-0023 | 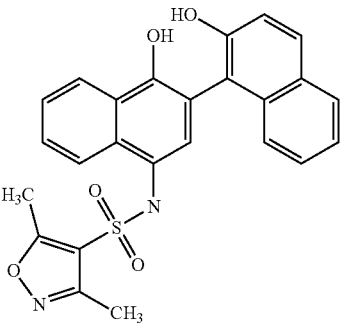 [SMILES: Cc1n[nH]c(C)c1S(=O)(=O)Nc1cc(-c2c(O)ccc3ccccc23)c(O)c2ccccc12] | C25H20N2O5S | 460.5126 | 5.614 |
| F5749-0024 | 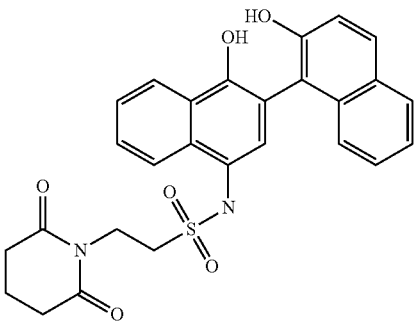 [SMILES: O=C1CCCC(=O)N1CCS(=O)(=O)Nc1cc(-c2c(O)ccc3ccccc23)c(O)c2ccccc12] | C27H24N2O6S | 504.5661 | 4.257 |
| F5749-0025 | 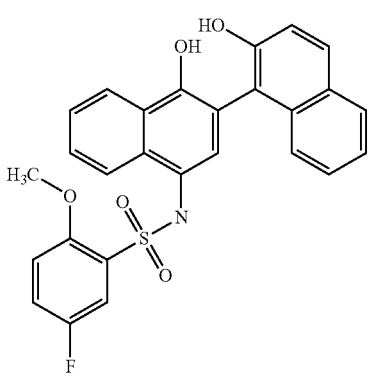 [SMILES: COc1ccc(F)cc1S(=O)(=O)Nc1cc(-c2c(O)ccc3ccccc23)c(O)c2ccccc12] | C27H20FNO5S | 489.5266 | 6.614 |

TABLE 7-continued

| IDNUMBER | Structure | Formula structure | MW | LogP |
|---|---|---|---|---|
| F5749-0026 | 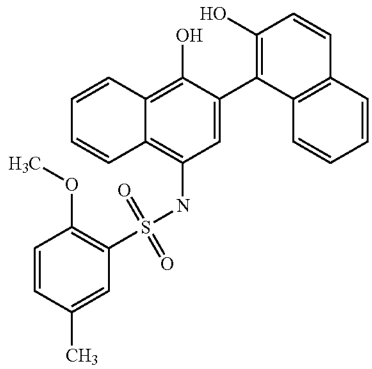 [SMILES: COc1ccc(C)cc1S(=O)(=O)Nc1cc(-c2c(O)ccc3ccccc23)c(O)c2ccccc12] | C28H23NO5S | 485.5632 | 6.759 |
| F5749-0027 | 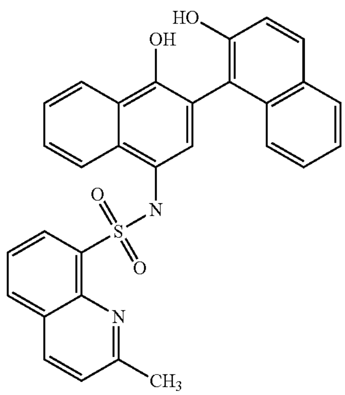 [SMILES: Cc1ccc2cccc(S(=O)(=O)Nc3cc(-c4c(O)ccc5ccccc45)c(O)c4ccccc34)c2n1] | C30H22N2O4S | 506.5848 | 6.929 |
| F5749-0028 | 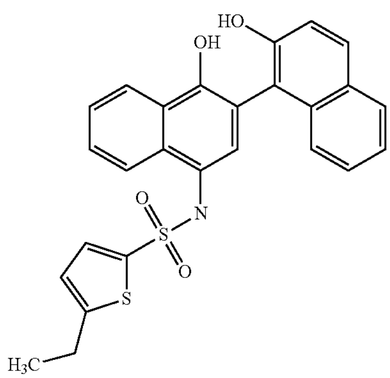 [SMILES: CCc1ccc(S(=O)(=O)Nc2cc(-c3c(O)ccc4ccccc34)c(O)c3ccccc23)s1] | C26H21NO4S2 | 475.5896 | 7.121 |
| F5749-0029 | 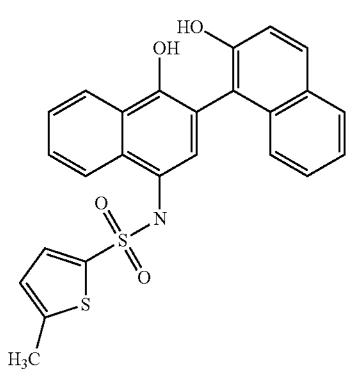 [SMILES: Cc1ccc(S(=O)(=O)Nc2cc(-c3c(O)ccc4ccccc34)c(O)c3ccccc23)s1] | C25H19NO4S2 | 461.5625 | 6.646 |

| IDNUMBER | Structure | Formula structure | MW | LogP |
|---|---|---|---|---|
| F5749-0030 | 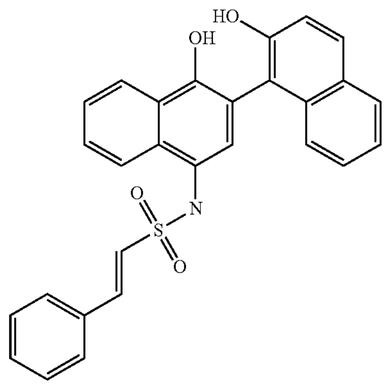 [SMILES: O=S(=O)(/C=C/c1ccccc1)Nc1cc(-c2c(O)ccc3ccccc23)c(O)c2ccccc12] | C28H21NO4S | 467.5479 | 6.828 |
| F5749-0031 | 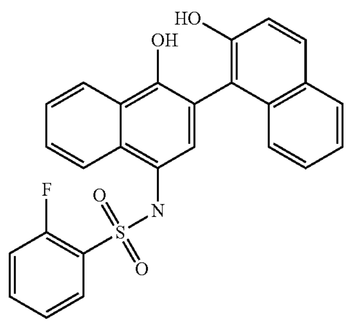 [SMILES: O=S(=O)(Nc1cc(-c2c(O)ccc3ccccc23)c(O)c2ccccc12)c1ccccc1F] | C26H18FNO4S | 459.5001 | 6.621 |
| F5749-0032 | 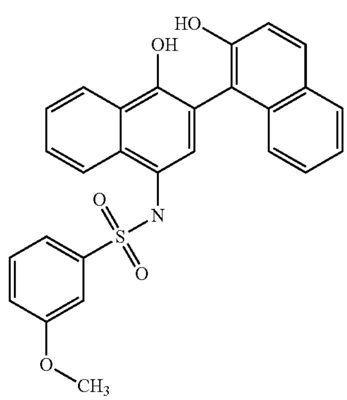 [SMILES: COc1cccc(S(=O)(=O)Nc2cc(-c3c(O)ccc4ccccc34)c(O)c3ccccc23)c1] | C27H21NO5S | 471.5361 | 6.463 |
| F5749-0033 | 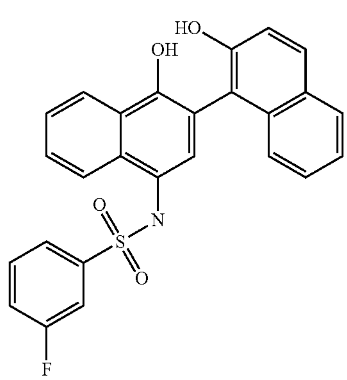 [SMILES: O=S(=O)(Nc1cc(-c2c(O)ccc3ccccc23)c(O)c2ccccc12)c1cccc(F)c1] | C26H18FNO4S | 459.5001 | 6.66 |

TABLE 7-continued
| IDNUMBER | Structure | Formula structure | MW | LogP |
|---|---|---|---|---|
| F5749-0034 | 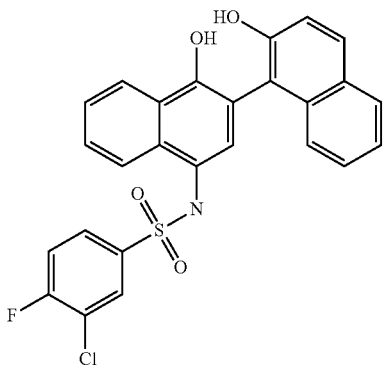 [SMILES: O=S(=O)(Nc1cc(-c2c(O)ccc3ccccc23)c(O)c2ccccc12)c1ccc(F)c(Cl)c1] | C26H17ClFNO4S | 493.9451 | 7.25 |
| F5749-0035 | 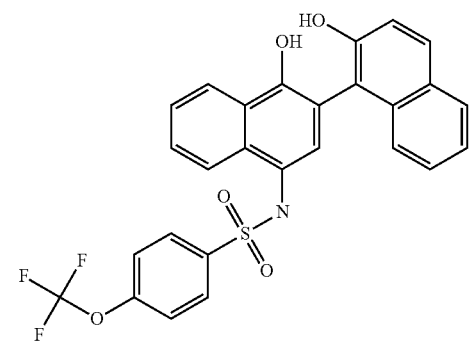 [SMILES: O=S(=O)(Nc1cc(-c2c(O)ccc3ccccc23)c(O)c2ccccc12)c1ccc(OC(F)(F)F)cc1] | C27H18F3NO5S | 525.5074 | 7.86876 |
| F5749-0036 | 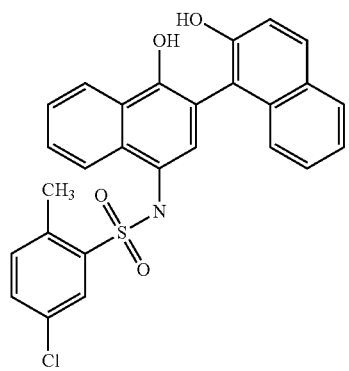 [SMILES: Cc1ccc(Cl)cc1S(=O)(=O)Nc1cc(-c2c(O)ccc3ccccc23)c(O)c2ccccc12] | C27H20ClNO4S | 489.9818 | 7.395 |
| F5749-0037 | 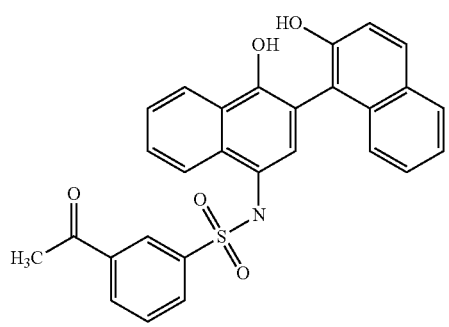 [SMILES: CC(=O)c1cccc(S(=O)(=O)Nc2cc(-c3c(O)ccc4ccccc34)c(O)c3ccccc23)c1] | C28H21NO5S | 483.5473 | 6.36 |

TABLE 7-continued
| IDNUMBER | Structure | Formula structure | MW | LogP |
|---|---|---|---|---|
| F5749-0038 | 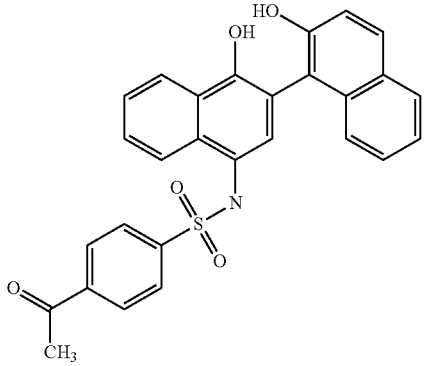 [SMILES: CC(=O)c1ccc(S(=O)(=O)Nc2cc(-c3c(O)ccc4ccccc34)c(O)c3ccccc23)cc1] | C28H21NO5S | 483.5473 | 6.323 |
| F5749-0039 | 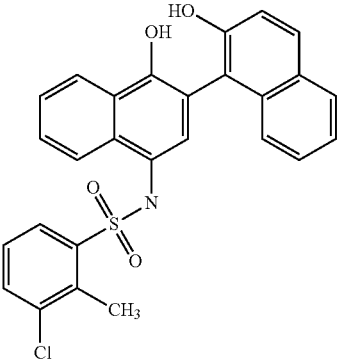 [SMILES: Cc1c(Cl)cccc1S(=O)(=O)Nc1cc(-c2c(O)ccc3ccccc23)c(O)c2ccccc12] | C27H20ClNO4S | 489.9818 | 7.356 |
| F5749-0040 | 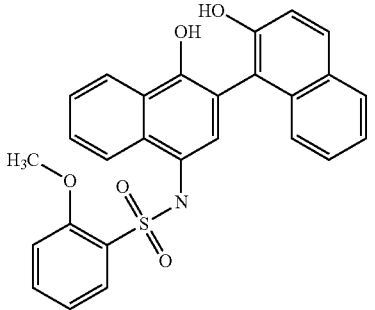 [SMILES: COc1ccccc1S(=O)(=O)Nc1cc(-c2c(O)ccc3ccccc23)c(O)c2ccccc12] | C27H21NO5S | 471.5361 | 6.424 |
| F5749-0041 | 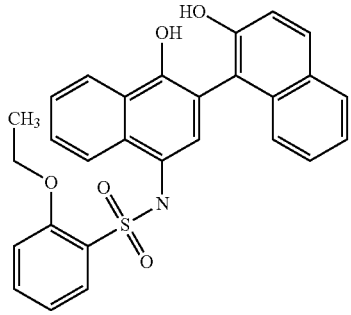 [SMILES: CCOc1ccccc1S(=O)(=O)Nc1cc(-c2c(O)ccc3ccccc23)c(O)c2ccccc12] | C28H23NO5S | 485.5632 | 6.765 |

TABLE 7-continued

| IDNUMBER | Structure | Formula structure | MW | LogP |
|---|---|---|---|---|
| F5749-0042 | 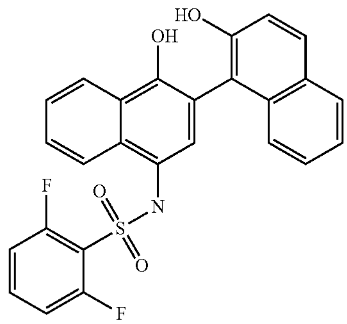 [SMILES: O=S(=O)(Nc1cc(-c2c(O)ccc3ccccc23)c(O)c2ccccc12)c1c(F)cccc1F] | C26H17F2NO4S | 477.4905 | 6.772 |
| F5749-0043 | 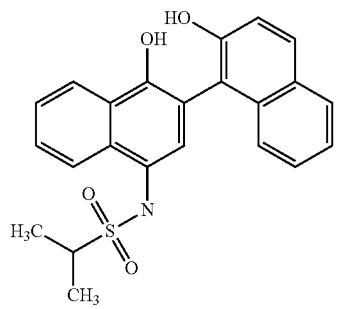 | C23H21NO4S | 407.4921 | 5.963 |
| F5749-0044 | 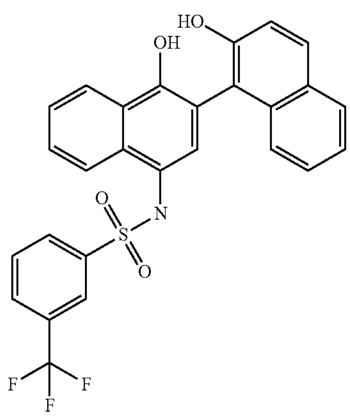 [SMILES: O=S(=O)(Nc1cc(-c2c(O)ccc3ccccc23)c(O)c2ccccc12)c1cccc(C(F)(F)F)c1] | C27H18F3NO4S | 509.508 | 7.44176 |
| F5749-0045 | | C27H18F3NO4S | 509.508 | 7.40476 |

TABLE 7-continued

| IDNUMBER | Structure | Formula structure | MW | LogP |
| --- | --- | --- | --- | --- |
| F5749-0046 | 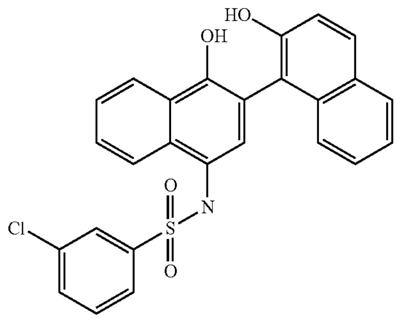 [SMILES: O=S(=O)(Nc1cc(-c2c(O)ccc3ccccc23)c(O)c2ccccc12)c1cccc(Cl)c1] | C26H18ClNO4S | 475.9547 | 7.099 |
| F5749-0047 | 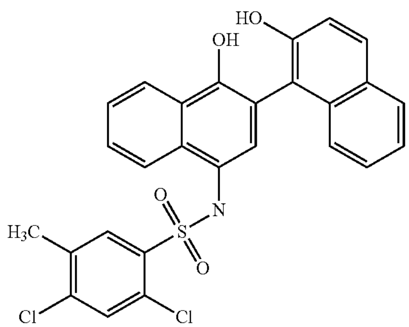 [SMILES: Cc1cc(S(=O)(=O)Nc2cc(-c3c(O)ccc4ccccc34)c(O)c3ccccc23)c(Cl)cc1Cl] | C27H19Cl2NO4S | 524.4268 | 8.022 |
| F5749-0048 | 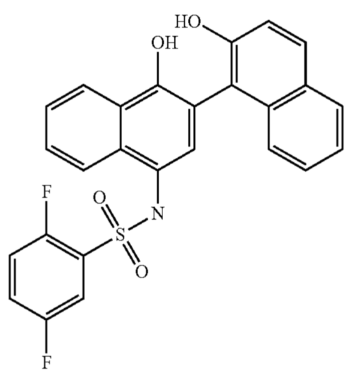 [SMILES: O=S(=O)(Nc1cc(-c2c(O)ccc3ccccc23)c(O)c2ccccc12)c1cc(F)ccc1F] | C26H17F2NO4S | 477.4905 | 6.811 |
| F5749-0049 | 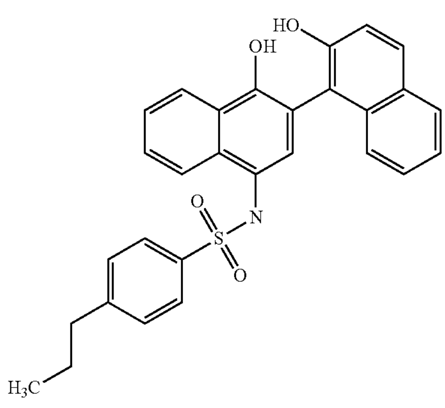 [SMILES: CCCc1ccc(S(=O)(=O)Nc2cc(-c3c(O)ccc4ccccc34)c(O)c3ccccc23)cc1] | C29H25NO4S | 483.5909 | 7.685 |

TABLE 7-continued

| IDNUMBER | Structure | Formula structure | MW | LogP |
|---|---|---|---|---|
| F5749-0050 | 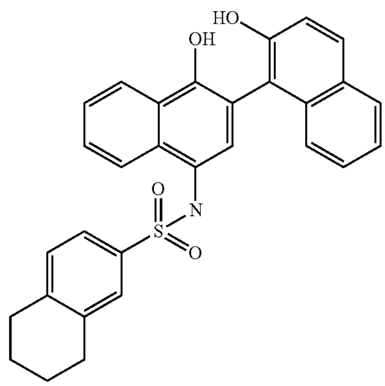 [SMILES: O=S(=O)(Nc1cc(-c2c(O)ccc3ccccc23)c(O)c2ccccc12)c1ccc2c(c1)CCCC2] | C30H25NO4S | 495.6021 | 7.557 |
| F5749-0051 | 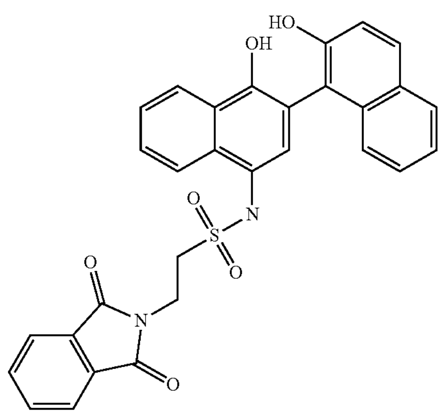 [SMILES: O=C1c2ccccc2C(=O)N1CCS(=O)(=O)Nc1cc(-c2c(O)ccc3ccccc23)c(O)c2ccccc12] | C30H22N2O6S | 538.5836 | 5.597 |
| F5749-0052 | 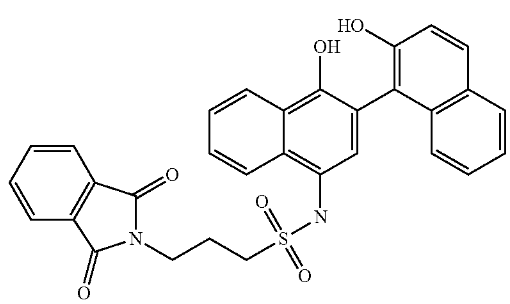 [SMILES: O=C1c2ccccc2C(=O)N1CCCS(=O)(=O)Nc1cc(-c2c(O)ccc3ccccc23)c(O)c2ccccc12] | C31H24N2O6S | 552.6107 | 6.039 |
| F5749-0053 | 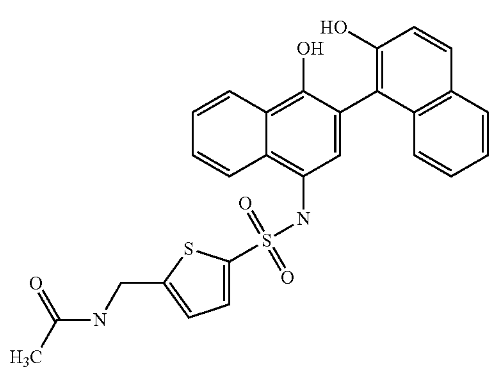 [SMILES: CC(=O)NCc1ccc(S(=O)(=O)Nc2cc(-c3c(O)ccc4ccccc34)c(O)c3ccccc23)s1] | C27H22N2O5S2 | 518.6148 | 5.773 |

TABLE 7-continued
| IDNUMBER | Structure | Formula structure | MW | LogP |
|---|---|---|---|---|
| F5749-0054 | 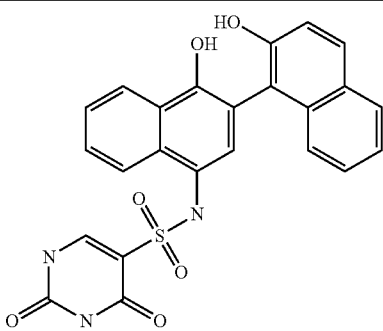 | C24H17N3O6S | 475.4836 | 3.515 |
| F5749-0055 | 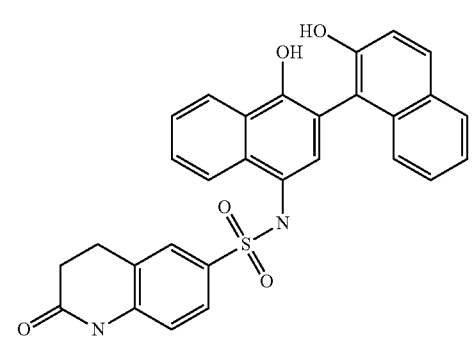 [SMILES: O=C1CCc2cc(S(=O)(=O)Nc3cc(-c4c(O)ccc5ccccc45)c(O)c4ccccc34)ccc2N1] | C29H22N2O5S | 510.5731 | 5.666 |
| F5749-0056 | 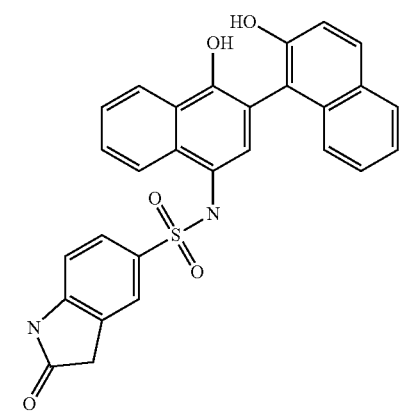 [SMILES: O=C1Cc2cc(S(=O)(=O)Nc3cc(-c4c(O)ccc5ccccc45)c(O)c4ccccc34)ccc2N1] | C28H20N2O5S | 496.546 | 5.578 |
| F5749-0057 | 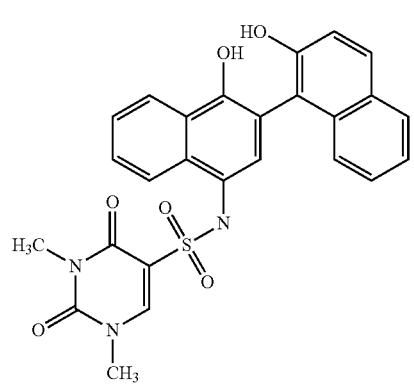 [SMILES: Cn1cc(S(=O)(=O)Nc2cc(-c3c(O)ccc4ccccc34)c(O)c3ccccc23)c(=O)n(C)c1=O] | C26H21N3O6S | 503.5378 | 3.579 |

TABLE 7-continued

| IDNUMBER | Structure | Formula structure | MW | LogP |
|---|---|---|---|---|
| F5749-0058 | 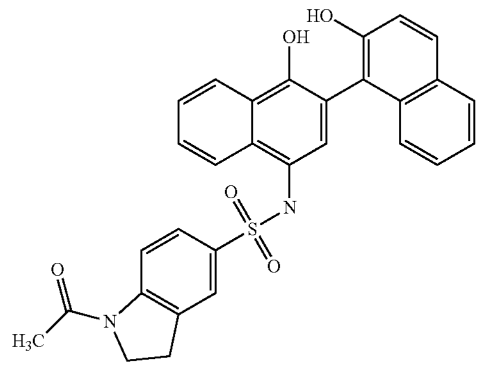 [SMILES: CC(=O)N1CCc2cc(S(=O)(=O)Nc3cc(-c4c(O)ccc5ccccc45)c(O)c4ccccc34)ccc21] | C30H24N2O5S | 524.6002 | 5.901 |
| F5749-0059 | 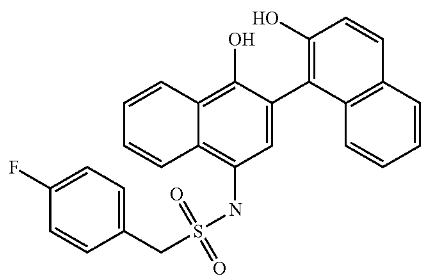 [SMILES: O=S(=O)(Cc1ccc(F)cc1)Nc1cc(-c2c(O)ccc3ccccc23)c(O)c2ccccc12] | C27H20FNO4S | 473.5272 | 6.757 |
| F5749-0060 | 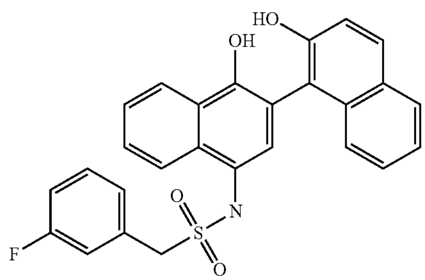 [SMILES: O=S(=O)(Cc1cccc(F)c1)Nc1cc(-c2c(O)ccc3ccccc23)c(O)c2ccccc12] | C27H20FNO4S | 473.5272 | 6.794 |
| F5749-0061 | 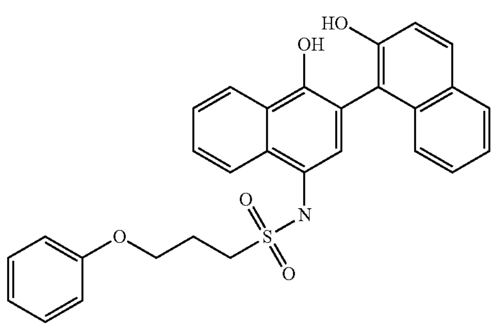 [SMILES: O=S(=O)(CCCOc1ccccc1)Nc1cc(-c2c(O)ccc3ccccc23)c(O)c2ccccc12] | C29H25NO5S | 499.5903 | 6.83 |
| F5749-0062 | 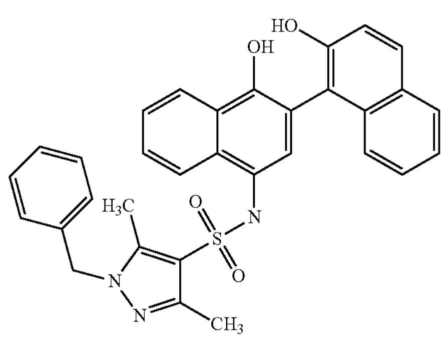 [SMILES: Cc1nn(Cc2ccccc2)c(C)c1S(=O)(=O)Nc1cc(-c2c(O)ccc3ccccc23)c(O)c2ccccc12] | C32H27N3O4S | 549.6537 | 6.749 |

TABLE 7-continued

| IDNUMBER | Structure | Formula structure | MW | LogP |
|---|---|---|---|---|
| F5749-0063 | 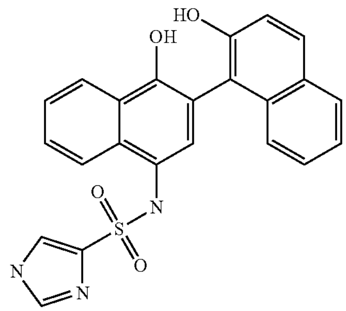 [SMILES: O=S(=O)(Nc1cc(-c2c(O)ccc3ccccc23)c(O)c2ccccc12)c1c[nH]cn1] | C23H17N3O4S | 431.4736 | 4.61 |
| F5749-0064 | 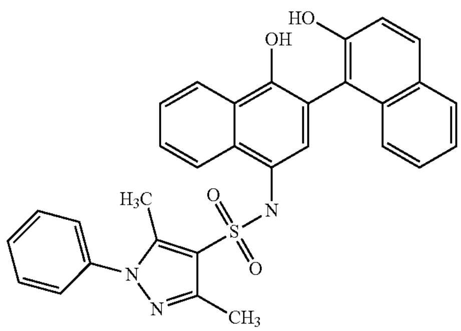 [SMILES: Cc1nn(-c2ccccc2)c(C)c1S(=O)(=O)Nc1cc(-c2c(O)ccc3ccccc23)c(O)c2ccccc12] | C31H25N3O4S | 535.6266 | 6.615 |
| F5749-0065 | 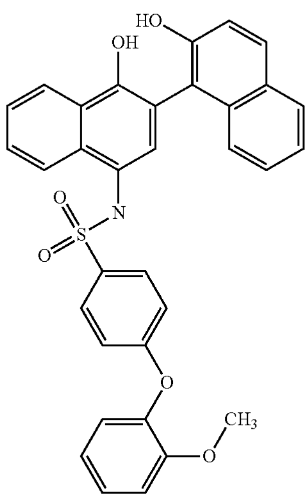 [SMILES: COc1ccccc1Oc1ccc(S(=O)(=O)Nc2cc(-c3c(O)ccc4ccccc34)c(O)c3ccccc23)cc1] | C33H25NO6S | 563.6343 | 7.78574 |
| F5749-0066 | 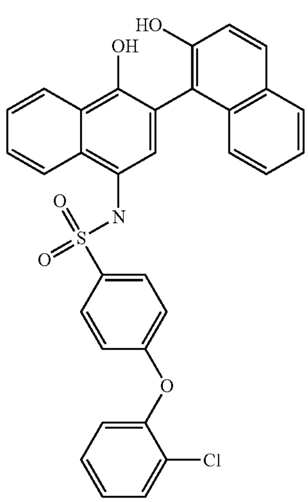 [SMILES: O=S(=O)(Nc1cc(-c2c(O)ccc3ccccc23)c(O)c2ccccc12)c1ccc(Oc2ccccc2Cl)cc1] | C32H22ClNO5S | 568.0528 | 8.67 |

TABLE 7-continued
| IDNUMBER | Structure | Formula structure | MW | LogP |
|---|---|---|---|---|
| F5749-0067 | 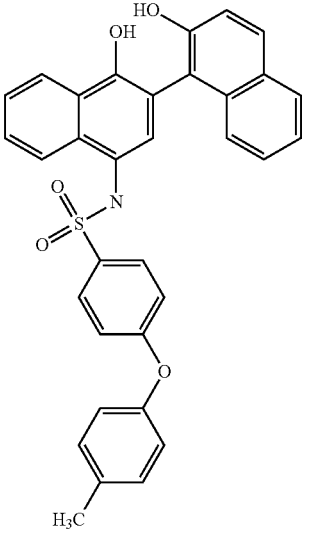 [SMILES: Cc1ccc(Oc2ccc(S(=O)(=O)Nc3cc(-c4c(O)ccc5ccccc45)c(O)c4ccccc34)cc2)cc1] | C33H25NO5S | 547.6349 | 8.378 |
| F5749-0068 | 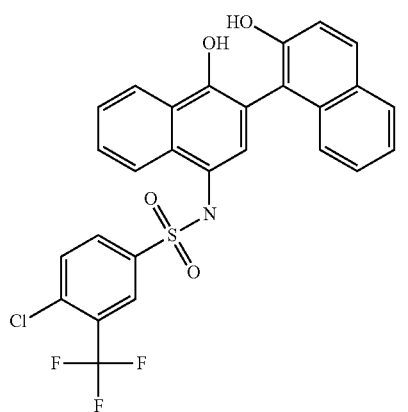 [SMILES: O=S(=O)(Nc1cc(-c2c(O)ccc3ccccc23)c(O)c2ccccc12)c1ccc(Cl)c(C(F)(F)F)c1] | C27H17ClF3NO4S | 543.953 | 8.03176 |
| F5749-0069 | 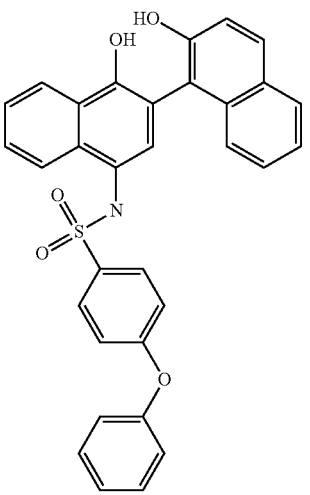 [SMILES: O=S(=O)(Nc1cc(-c2c(O)ccc3ccccc23)c(O)c2ccccc12)c1ccc(Oc2ccccc2)cc1] | C32H23NO5S | 533.6078 | 8.08 |

TABLE 7-continued

| IDNUMBER | Structure | Formula structure | MW | LogP |
|---|---|---|---|---|
| F5749-0070 | 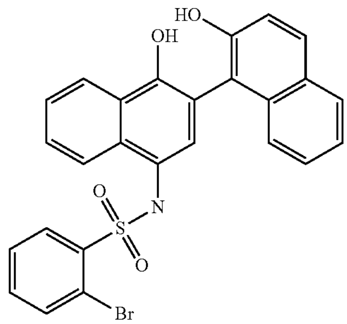 [SMILES: O=S(=O)(Nc1cc(-c2c(O)ccc3ccccc23)c(O)c2ccccc12)c1ccccc1Br] | C26H18BrNO4S | 520.4057 | 7.266 |
| F5749-0071 | 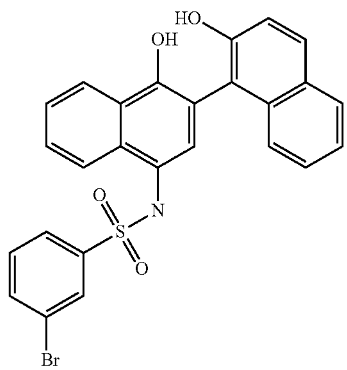 | C26H18BrNO4S | 520.4057 | 7.305 |
| F5749-0072 | 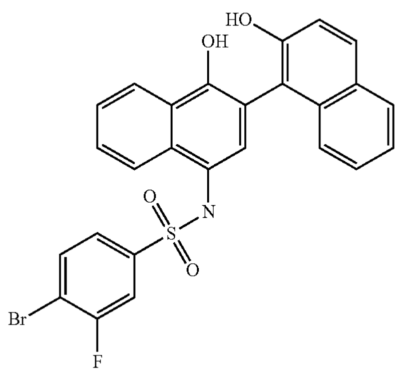 [SMILES: O=S(=O)(Nc1cc(-c2c(O)ccc3ccccc23)c(O)c2ccccc12)c1ccc(Br)c(F)c1] | C26H17BrFNO4S | 538.3961 | 7.456 |
| F5749-0073 | 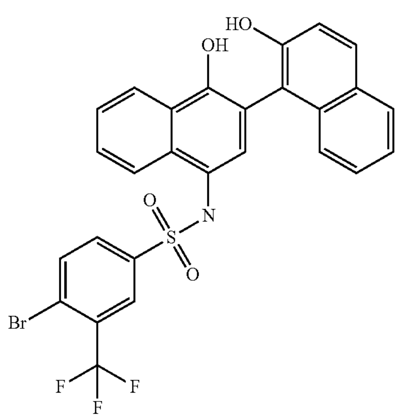 [SMILES: O=S(=O)(Nc1cc(-c2c(O)ccc3ccccc23)c(O)c2ccccc12)c1ccc(Br)c(C(F)(F)F)c1] | C27H17BrF3NO4S | 588.404 | 8.23776 |

TABLE 7-continued
| IDNUMBER | Structure | Formula structure | MW | LogP |
|---|---|---|---|---|
| F5749-0074 | 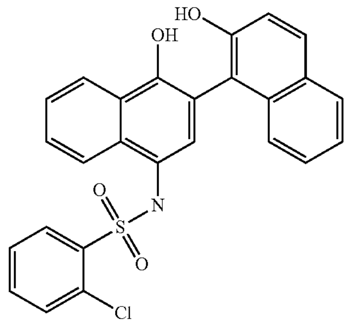 [SMILES: O=S(=O)(Nc1cc(-c2c(O)ccc3ccccc23)c(O)c2ccccc12)c1ccccc1Cl] | C26H18ClNO4S | 475.9547 | 7.06 |
| F5749-0075 | 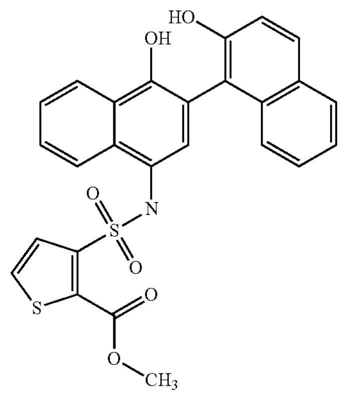 [SMILES: COC(=O)c1sccc1S(=O)(=O)Nc1cc(-c2c(O)ccc3ccccc23)c(O)c2ccccc12] | C26H19NO6S2 | 505.5724 | 5.67 |
| F5749-0076 | 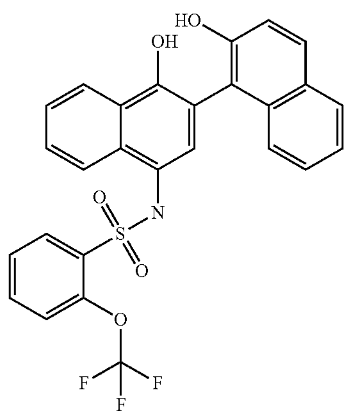 [SMILES: O=S(=O)(Nc1cc(-c2c(O)ccc3ccccc23)c(O)c2ccccc12)c1ccccc1OC(F)(F)F] | C27H18F3NO5S | 525.5074 | 7.86676 |
TABLE 8
| IDNUMBER | Structure | Formula structure | MW | Log P |
|---|---|---|---|---|
| F1566-0329 | 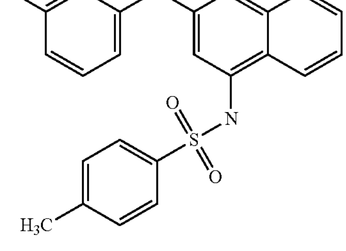 | C26H20N2O3S2 | 472.5889 | 6.344 |

TABLE 8-continued

| IDNUMBER | Structure | Formula structure | MW | Log P |
| --- | --- | --- | --- | --- |
| F1566-0341 | 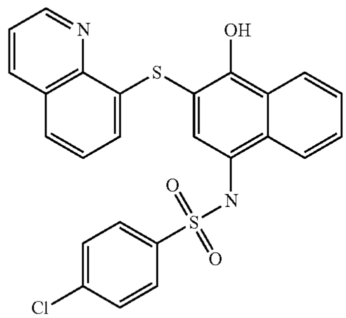 [SMILES: O=S(=O)(Nc1cc(Sc2cccc3cccnc23)c(O)c2ccccc12)c1ccc(Cl)cc1] | C25H17ClN2O3S2 | 493.0068 | 6.638 |
| F1566-0353 | 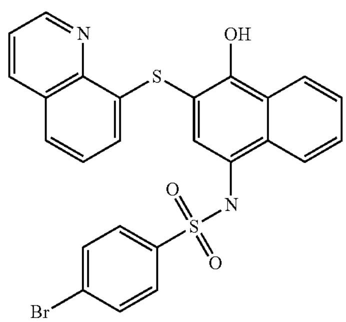 | C25H17BrN2O3S2 | 537.4578 | 6.844 |
| F1566-0377 | 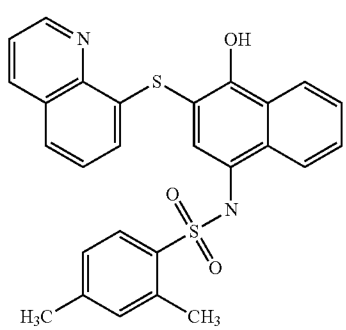 [SMILES: Cc1ccc(S(=O)(=O)Nc2cc(Sc3cccc4cccnc34)c(O)c3ccccc23)c(C)c1] | C27H22N2O3S2 | 486.616 | 6.677 |
| F1566-0425 | 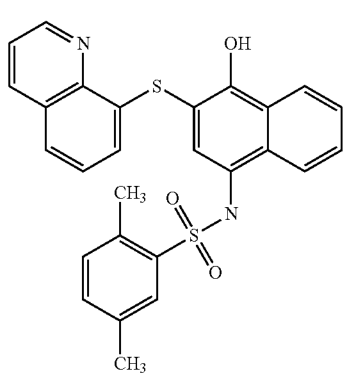 [SMILES: Cc1ccc(C)c(S(=O)(=O)Nc2cc(Sc3cccc4cccnc34)c(O)c3ccccc23)c1] | C27H22N2O3S2 | 486.616 | 6.677 |

TABLE 8-continued
| IDNUMBER | Structure | Formula structure | MW | Log P |
| --- | --- | --- | --- | --- |
| F1566-0449 | 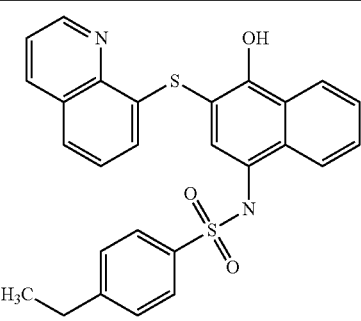 | C27H22N2O3S2 | 486.616 | 6.819 |
| F1566-0473 | 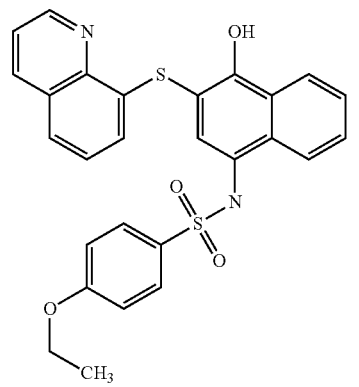 [SMILES: CCOc1ccc(S(=O)(=O)Nc2cc(Sc3cccc4cccnc34)c(O)c3ccccc23)cc1] | C27H22N2O4S2 | 502.6154 | 6.343 |
| F1566-0497 | 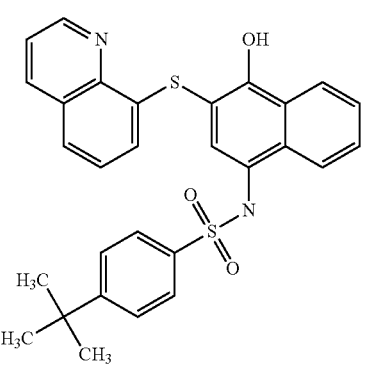 [SMILES: CC(C)(C)c1ccc(S(=O)(=O)Nc2cc(Sc3cccc4cccnc34)c(O)c3ccccc23)cc1] | C29H26N2O3S2 | 514.6702 | 7.545 |
| F1566-0521 | 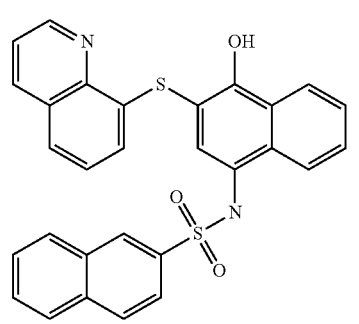 [SMILES: O=S(=O)(Nc1cc(Sc2cccc3cccnc23)c(O)c2ccccc12)c1ccc2ccccc2c1] | C29H20N2O3S2 | 508.6224 | 7.305 |

TABLE 8-continued

| IDNUMBER | Structure | Formula structure | MW | Log P |
| --- | --- | --- | --- | --- |
| F1566-0557 | 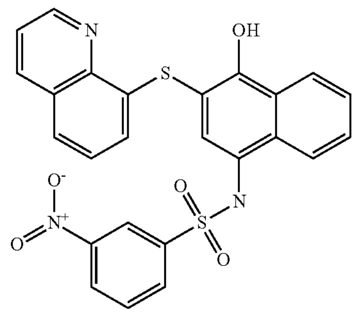 [SMILES: O=[N+]([O-])c1cccc(S(=O)(=O)Nc2cc(Sc3cccc4cccnc34)c(O)c3ccccc23)c1] | C25H17N3O5S2 | 503.5593 | 6.018 |
| F1566-0569 | 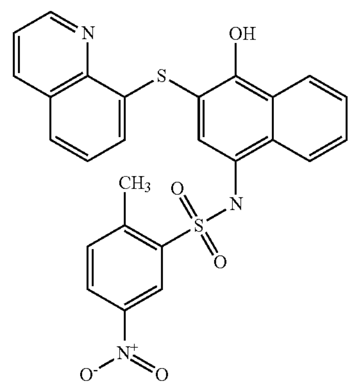 [SMILES: Cc1ccc([N+](=O)[O-])cc1S(=O)(=O)Nc1cc(Sc2cccc3cccnc23)c(O)c2ccccc12] | C26H19N3O5S2 | 517.5864 | 6.314 |
| F1566-0617 | 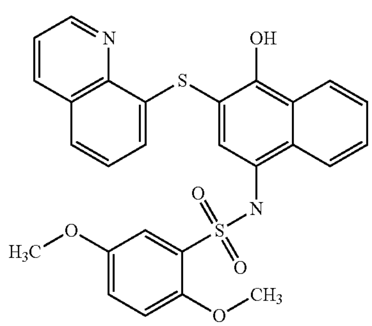 [SMILES: COc1ccc(OC)c(S(=O)(=O)Nc2cc(Sc3cccc4cccnc34)c(O)c3ccccc23)c1] | C27H22N2O5S2 | 518.6148 | 5.993 |
| F1566-0629 | 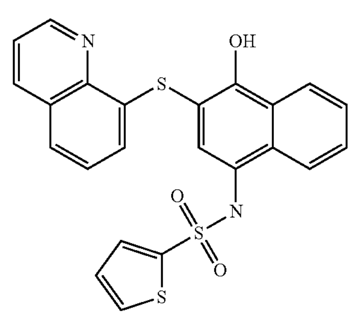 [SMILES: O=S(=O)(Nc1cc(Sc2cccc3cccnc23)c(O)c2ccccc12)c1cccs1] | C23H16N2O3S3 | 464.5876 | 5.559 |

TABLE 8-continued

| IDNUMBER | Structure | Formula structure | MW | Log P |
|---|---|---|---|---|
| F1566-1608 | 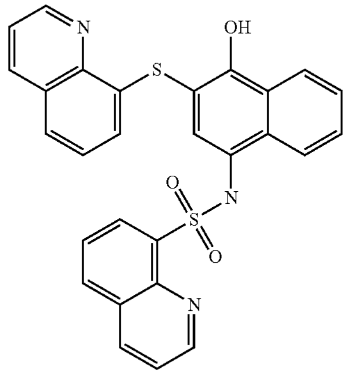 [SMILES: O=S(=O)(Nc1cc(Sc2cccc3cccnc23)c(O)c2ccccc12)c1cccc2cccnc12] | C28H19N3O3S2 | 509.6099 | 6.246 |
| F1566-1821 | 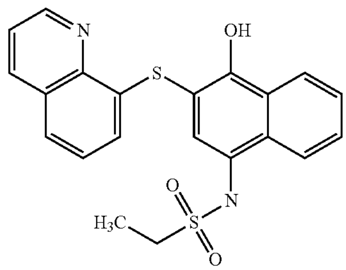 [SMILES: CCS(=O)(=O)Nc1cc(Sc2cccc3cccnc23)c(O)c2ccccc12] | C21H18N2O3S2 | 410.5172 | 4.905 |
| F1566-1835 | 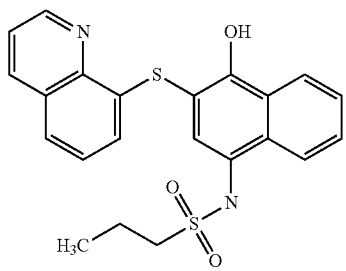 [SMILES: CCCS(=O)(=O)Nc1cc(Sc2cccc3cccnc23)c(O)c2ccccc12] | C22H20N2O3S2 | 424.5443 | 5.347 |
| F1566-1849 | 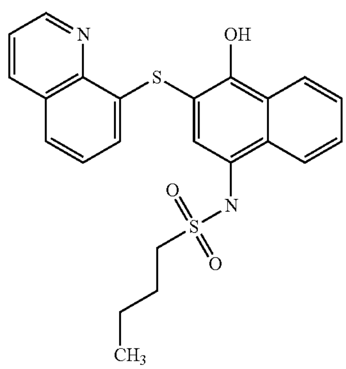 [SMILES: CCCCS(=O)(=O)Nc1cc(Sc2cccc3cccnc23)c(O)c2ccccc12] | C23H22N2O3S2 | 438.5714 | 5.789 |
| F1566-1863 | 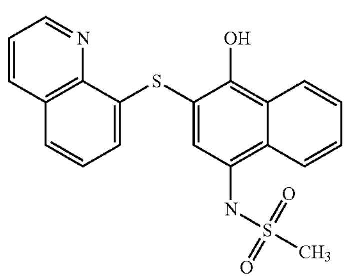 [SMILES: CS(=O)(=O)Nc1cc(Sc2cccc3cccnc23)c(O)c2ccccc12] | C20H16N2O3S2 | 396.4901 | 4.392 |

TABLE 8-continued

| IDNUMBER | Structure | Formula structure | MW | Log P |
|---|---|---|---|---|
| F5749-0077 | 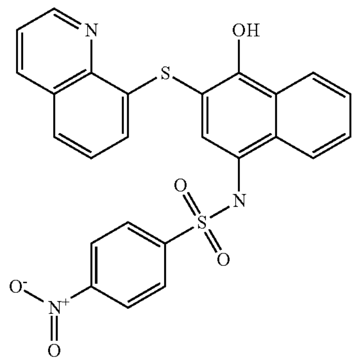 [SMILES: O=[N+]([O-])c1ccc(S(=O)(=O)Nc2cc(Sc3cccc4cccnc34)c(O)c3ccccc23)cc1] | C25H17N3O5S2 | 503.5593 | 5.981 |
| F5749-0078 | 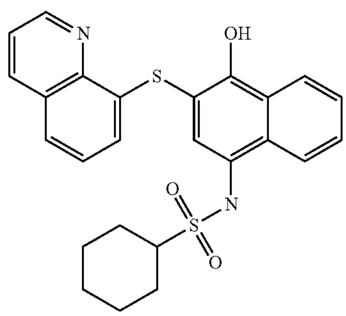 [SMILES: O=S(=O)(Nc1cc(Sc2cccc3cccnc23)c(O)c2ccccc12)C1CCCCC1] | C25H24N2O3S2 | 464.6096 | 6.371 |
| F5749-0079 | 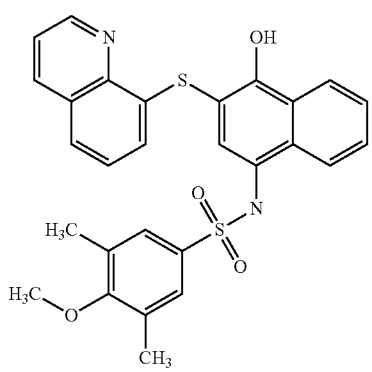 [SMILES: COc1c(C)cc(S(=O)(=O)Nc2cc(Sc3cccc4cccnc34)c(O)c3ccccc23)cc1C] | C28H24N2O4S2 | 516.6425 | 6.668 |
| F5749-0080 | 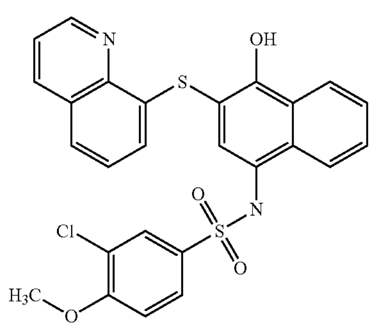 [SMILES: COc1ccc(S(=O)(=O)Nc2cc(Sc3cccc4cccnc34)c(O)c3ccccc23)cc1Cl] | C26H19ClN2O4S2 | 523.0333 | 6.629 |

TABLE 8-continued

| IDNUMBER | Structure | Formula structure | MW | Log P |
| --- | --- | --- | --- | --- |
| F5749-0081 | 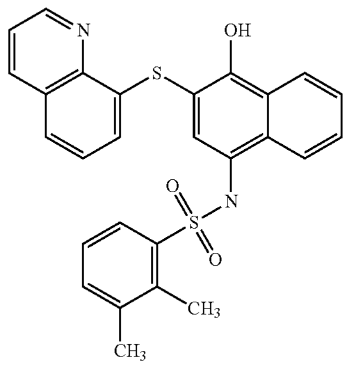 [SMILES: Cc1cccc(S(=O)(=O)Nc2cc(Sc3cccc4cccnc34)c(O)c3ccccc23)c1C] | C27H22N2O3S2 | 486.616 | 6.638 |
| F5749-0082 | 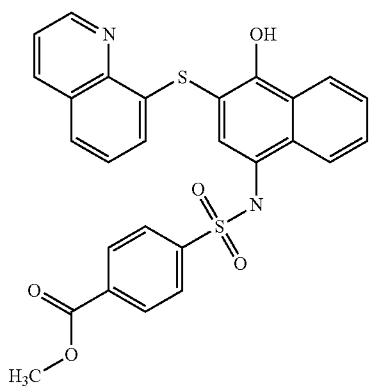 [SMILES: COC(=O)c1ccc(S(=O)(=O)Nc2cc(Sc3cccc4cccnc34)c(O)c3ccccc23)cc1] | C27H20N2O5S2 | 516.5989 | 5.987 |
| F5749-0083 | 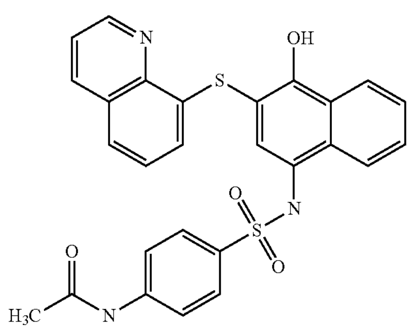 [SMILES: CC(=O)Nc1ccc(S(=O)(=O)Nc2cc(Sc3cccc4cccnc34)c(O)c3ccccc23)cc1] | C27H21N3O4S2 | 515.6141 | 5.337 |
| F5749-0084 | 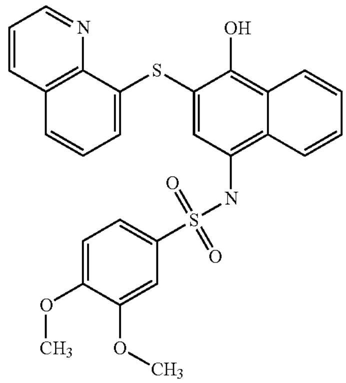 [SMILES: COc1ccc(S(=O)(=O)Nc2cc(Sc3cccc4cccnc34)c(O)c3ccccc23)cc1OC] | C27H22N2O5S2 | 518.6148 | 5.74474 |

TABLE 8-continued

| IDNUMBER | Structure | Formula structure | MW | Log P |
|---|---|---|---|---|
| F5749-0085 | 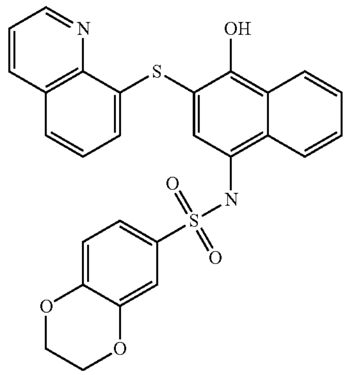 [SMILES: O=S(=O)(Nc1cc(Sc2cccc3cccnc23)c(O)c2ccccc12)c1ccc2c(c1)OCCO2] | C27H20N2O5S2 | 516.5989 | 5.641 |
| F5749-0086 | 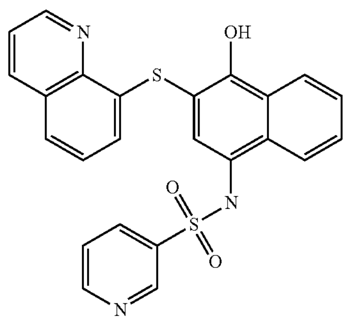 [SMILES: O=S(=O)(Nc1cc(Sc2cccc3cccnc23)c(O)c2ccccc12)c1cccnc1] | C24H17N3O3S2 | 459.5494 | 4.813 |
| F5749-0087 | 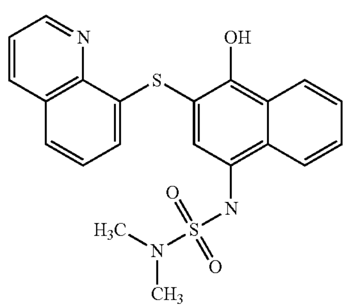 [SMILES: CN(C)S(=O)(=O)Nc1cc(Sc2cccc3cccnc23)c(O)c2ccccc12] | C21H19N3O3S2 | 425.5319 | 3.94 |
| F5749-0088 | 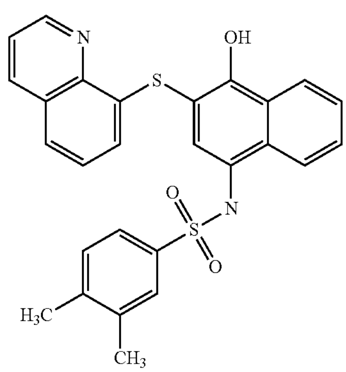 [SMILES: Cc1ccc(S(=O)(=O)Nc2cc(Sc3cccc4cccnc34)c(O)c3ccccc23)cc1C] | C27H22N2O3S2 | 486.616 | 6.677 |

TABLE 8-continued
| IDNUMBER | Structure | Formula structure | MW | Log P |
|---|---|---|---|---|
| F5749-0089 | 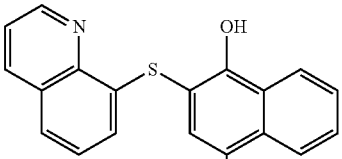 | C25H17N3O5S2 | 503.5593 | 5.979 |
| F5749-0090 | 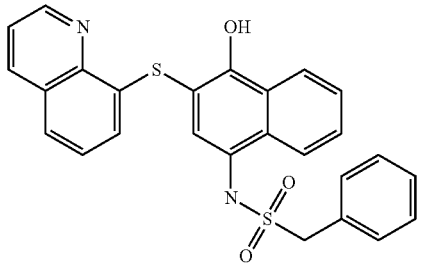 [SMILES: O=S(=O)(Cc1ccccc1)Nc1cc(Sc2cccc3cccnc23)c(O)c2ccccc12] | C26H20N2O3S2 | 472.5889 | 6.18 |
| F5749-0091 | 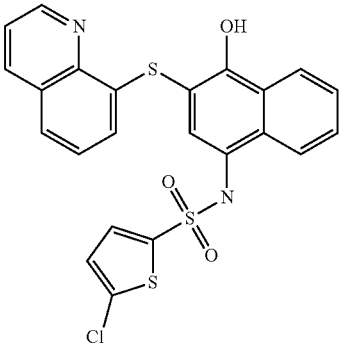 [SMILES: O=S(=O)(Nc1cc(Sc2cccc3cccnc23)c(O)c2ccccc12)c1ccc(Cl)s1] | C23H15ClN2O3S3 | 499.0326 | 6.849 |
| F5749-0092 | 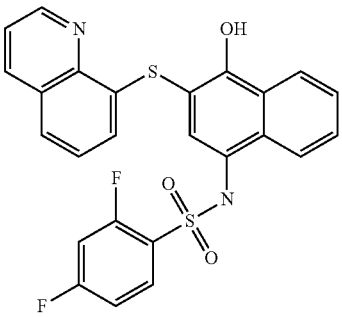 [SMILES: O=S(=O)(Nc1cc(Sc2cccc3cccnc23)c(O)c2ccccc12)c1ccc(F)cc1F] | C25H16F2N2O3S2 | 494.5427 | 6.387 |

TABLE 8-continued

| IDNUMBER | Structure | Formula structure | MW | Log P |
|---|---|---|---|---|
| F5749-0093 | 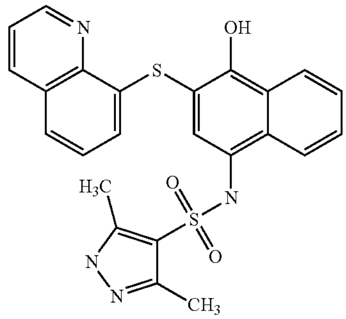 [SMILES: Cc1noc(C)c1S(=O)(=O)Nc1cc(Sc2cccc3cccnc23)c(O)c2ccccc12] | C24H20N4O3S2 | 476.58 | 5.156 |
| F5749-0094 | 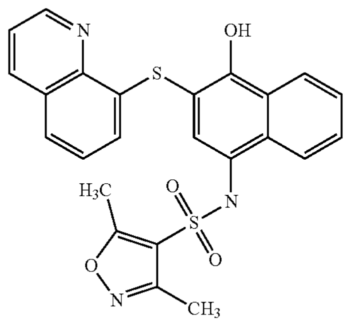 | C24H19N3O4S2 | 477.5647 | 5.19 |
| F5749-0095 | 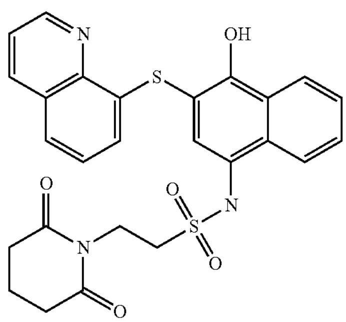 [SMILES: O=C1CCCC(=O)N1CCS(=O)(=O)Nc1cc(Sc2cccc3cccnc23)c(O)c2ccccc12] | C26H23N3O5S2 | 521.6183 | 3.833 |
| F5749-0096 | 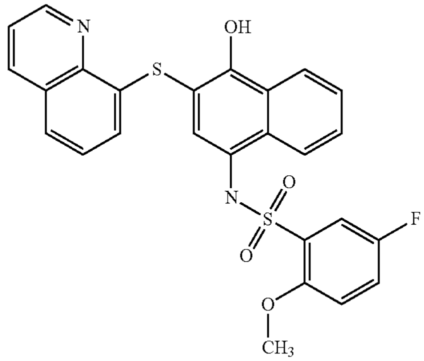 [SMILES: COc1ccc(F)cc1S(=O)(=O)Nc1cc(Sc2cccc3cccnc23)c(O)c2ccccc12] | C26H19FN2O4S2 | 506.5787 | 6.19 |

TABLE 8-continued

| IDNUMBER | Structure | Formula structure | MW | Log P |
|---|---|---|---|---|
| F5749-0097 | 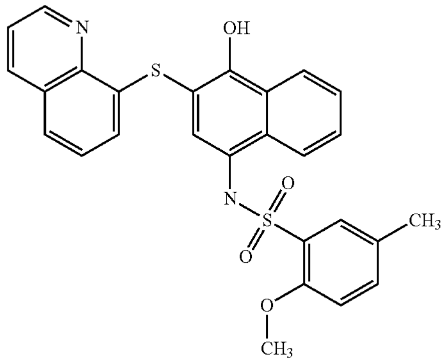 [SMILES: COc1ccc(C)cc1S(=O)(=O)Nc1cc(Sc2cccc3cccnc23)c(O)c2ccccc12] | C27H22N2O4S2 | 502.6154 | 6.335 |
| F5749-0098 | 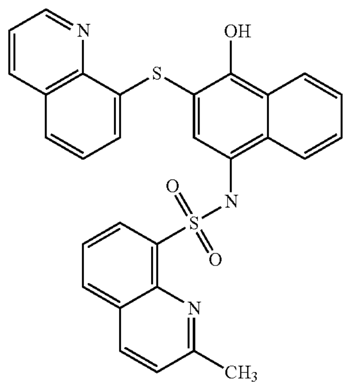 [SMILES: Cc1ccc2cccc(S(=O)(=O)Nc3cc(Sc4cccc5cccnc45)c(O)c4ccccc34)c2n1] | C29H21N3O3S2 | 523.637 | 6.505 |
| F5749-0099 | 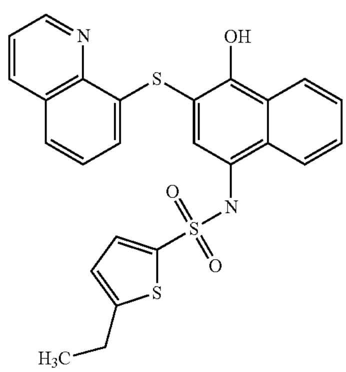 [SMILES: CCc1ccc(S(=O)(=O)Nc2cc(Sc3cccc4cccnc34)c(O)c3ccccc23)s1] | C25H20N2O3S3 | 492.6418 | 6.697 |
| F5749-0100 | 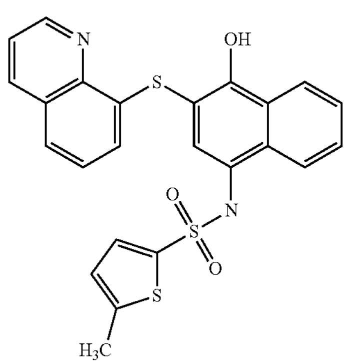 [SMILES: Cc1ccc(S(=O)(=O)Nc2cc(Sc3cccc4cccnc34)c(O)c3ccccc23)s1] | C24H18N2O3S3 | 478.6147 | 6.222 |

TABLE 8-continued
| IDNUMBER | Structure | Formula structure | MW | Log P |
|---|---|---|---|---|
| F5749-0101 | 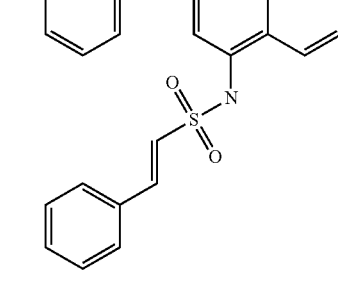 | C27H20N2O3S2 | 484.6001 | 6.404 |
| F5749-0102 | 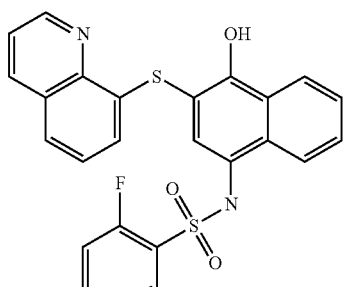 | C25H17FN2O3S2 | 476.5522 | 6.197 |
| F5749-0103 | 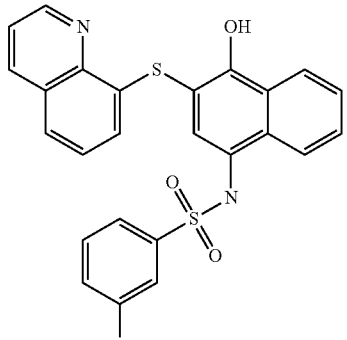 | C26H20N2O4S2 | 488.5883 | 6.039 |
| F5749-0104 | 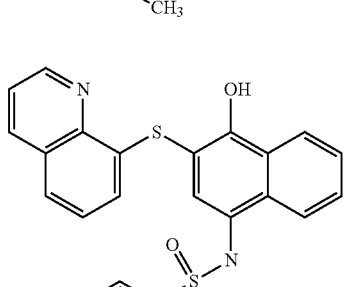 | C25H17FN2O3S2 | 476.5522 | 6.236 |

TABLE 8-continued
| IDNUMBER | Structure | Formula structure | MW | Log P |
|---|---|---|---|---|
| F5749-0105 | 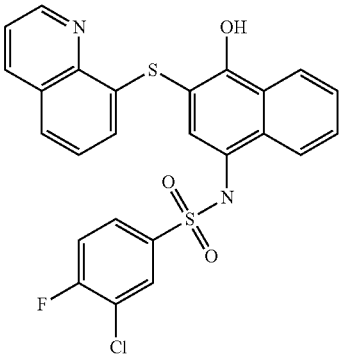 [SMILES: O=S(=O)(Nc1cc(Sc2cccc3cccnc23)c(O)c2ccccc12)c1ccc(F)c(Cl)c1] | C25H16ClFN2O3S2 | 510.9973 | 6.826 |
| F5749-0106 | 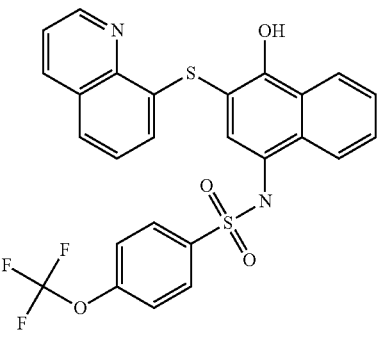 [SMILES: O=S(=O)(Nc1cc(Sc2cccc3cccnc23)c(O)c2ccccc12)c1ccc(OC(F)(F)F)cc1] | C26H17F3N2O4S2 | 542.5596 | 7.44476 |
| F5749-0107 | 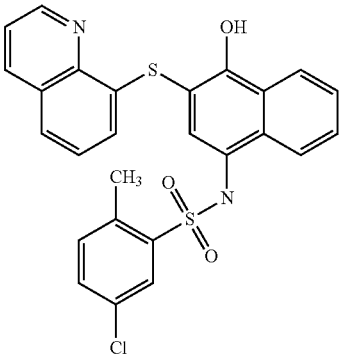 [SMILES: Cc1ccc(Cl)cc1S(=O)(=O)Nc1cc(Sc2cccc3cccnc23)c(O)c2ccccc12] | C26H19ClN2O3S2 | 507.0339 | 6.971 |
| F5749-0108 | 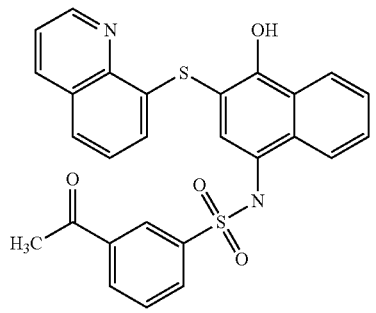 [SMILES: CC(=O)c1cccc(S(=O)(=O)Nc2cc(Sc3cccc4cccnc34)c(O)c3ccccc23)c1] | C27H20N2O4S2 | 500.5995 | 5.936 |

TABLE 8-continued

| IDNUMBER | Structure | Formula structure | MW | Log P |
| --- | --- | --- | --- | --- |
| F5749-0109 | 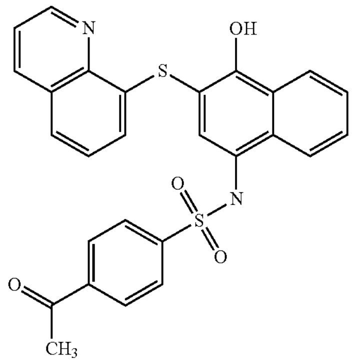 [SMILES: CC(=O)c1ccc(S(=O)(=O)Nc2cc(Sc3cccc4cccnc34)c(O)c3ccccc23)cc1] | C27H20N2O4S2 | 500.5995 | 5.899 |
| F5749-0110 | 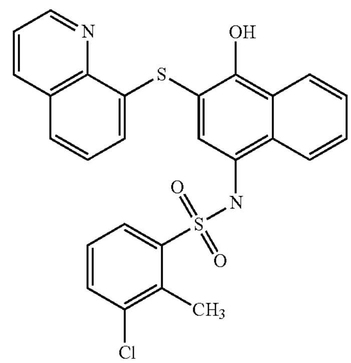 [SMILES: Cc1c(Cl)cccc1S(=O)(=O)Nc1cc(Sc2cccc3cccnc23)c(O)c2ccccc12] | C26H19ClN2O3S2 | 507.0339 | 6.932 |
| F5749-0111 | 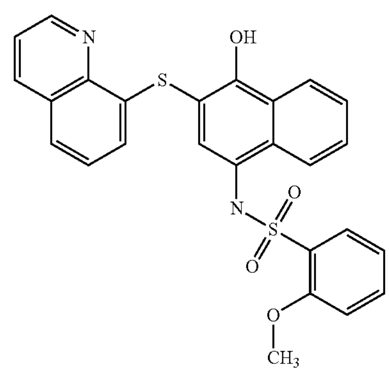 [SMILES: COc1ccccc1S(=O)(=O)Nc1cc(Sc2cccc3cccnc23)c(O)c2ccccc12] | C26H20N2O4S2 | 488.5883 | 6 |
| F5749-0112 | 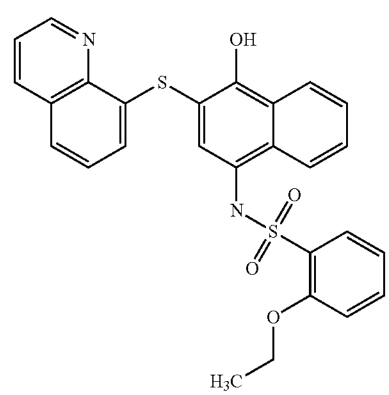 [SMILES: CCOc1ccccc1S(=O)(=O)Nc1cc(Sc2cccc3cccnc23)c(O)c2ccccc12] | C27H22N2O4S2 | 502.6154 | 6.341 |

TABLE 8-continued

| IDNUMBER | Structure | Formula structure | MW | Log P |
|---|---|---|---|---|
| F5749-0113 | 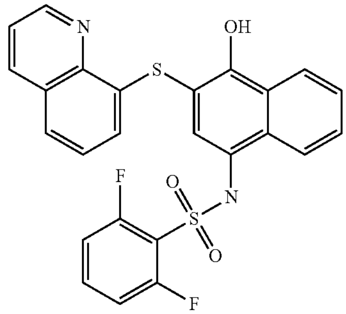 [SMILES: O=S(=O)(Nc1cc(Sc2cccc3cccnc23)c(O)c2ccccc12)c1c(F)cccc1F] | C25H16F2N2O3S2 | 494.5427 | 6.348 |
| F5749-0114 | 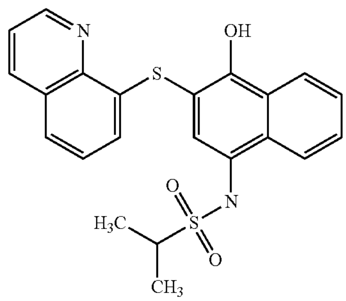 | C22H20N2O3S2 | 424.5443 | 5.539 |
| F5749-0115 | 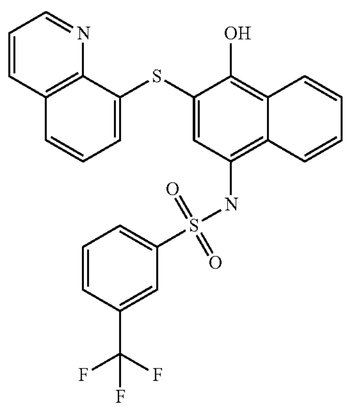 [SMILES: O=S(=O)(Nc1cc(Sc2cccc3cccnc23)c(O)c2ccccc12)c1cccc(C(F)(F)F)c1] | C26H17F3N2O3S2 | 526.5602 | 7.01776 |
| F5749-0116 | 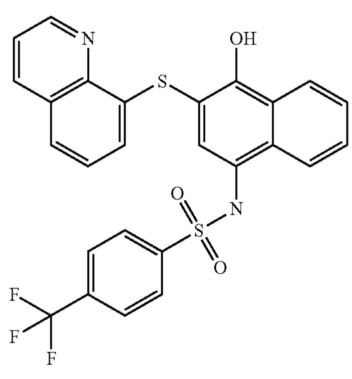 [SMILES: O=S(=O)(Nc1cc(Sc2cccc3cccnc23)c(O)c2ccccc12)c1ccc(C(F)(F)F)cc1] | C26H17F3N2O3S2 | 526.5602 | 6.98076 |

TABLE 8-continued

| IDNUMBER | Structure | Formula structure | MW | Log P |
|---|---|---|---|---|
| F5749-0117 | 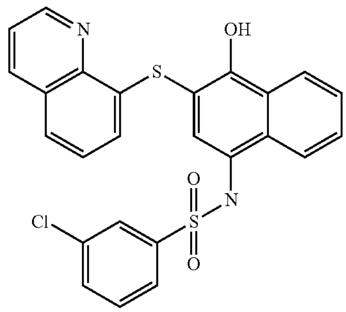 [SMILES: O=S(=O)(Nc1cc(Sc2cccc3cccnc23)c(O)c2ccccc12)c1cccc(Cl)c1] | C25H17ClN2O3S2 | 493.0068 | 6.675 |
| F5749-0118 | 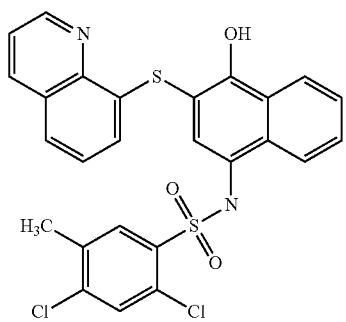 [SMILES: Cc1cc(S(=O)(=O)Nc2cc(Sc3cccc4cccnc34)c(O)c3ccccc23)c(Cl)cc1Cl] | C26H18Cl2N2O3S2 | 541.479 | 7.598 |
| F5749-0119 | 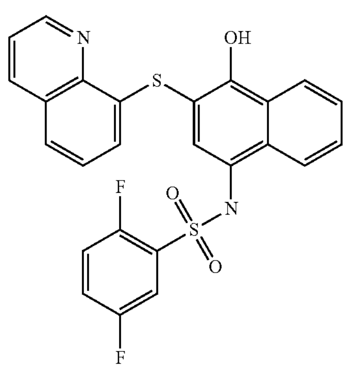 [SMILES: O=S(=O)(Nc1cc(Sc2cccc3cccnc23)c(O)c2ccccc12)c1cc(F)ccc1F] | C25H16F2N2O3S2 | 494.5427 | 6.387 |
| F5749-0120 | 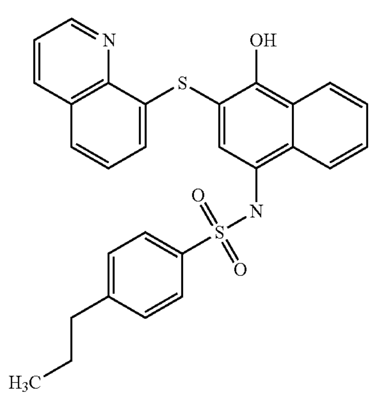 [SMILES: CCCc1ccc(S(=O)(=O)Nc2cc(Sc3cccc4cccnc34)c(O)c3ccccc23)cc1] | C28H24N2O3S2 | 500.6431 | 7.261 |

TABLE 8-continued
| IDNUMBER | Structure | Formula structure | MW | Log P |
|---|---|---|---|---|
| F5749-0121 | 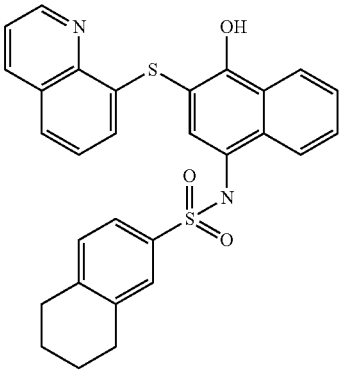 [SMILES: O=S(=O)(Nc1cc(Sc2cccc3cccnc23)c(O)c2ccccc12)c1ccc2c(c1)CCCC2] | C29H24N2O3S2 | 512.6542 | 7.133 |
| F5749-0122 | 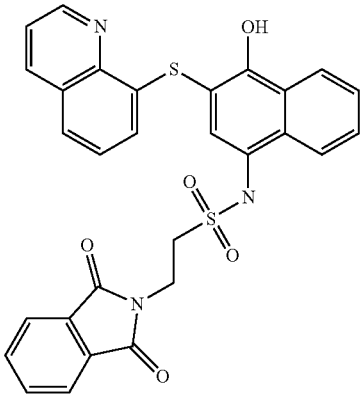 [SMILES: O=C1c2ccccc2C(=O)N1CCS(=O)(=O)Nc1cc(Sc2cccc3cccnc23)c(O)c2ccccc12] | C29H21N3O5S2 | 555.6358 | 5.173 |
| F5749 0123 | 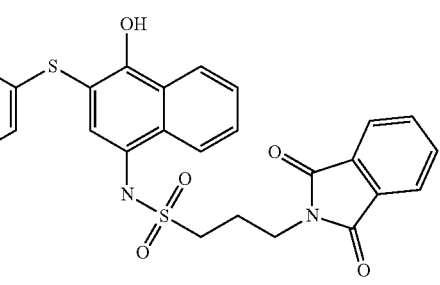 | C30H23N3O5S2 | 569.6629 | 5.615 |
| F5749-0124 | 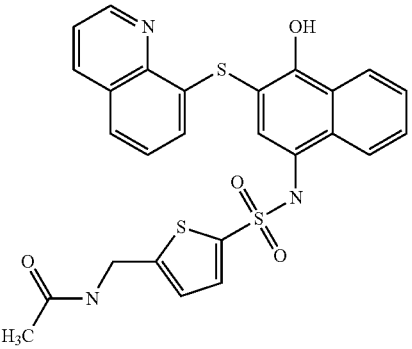 [SMILES: CC(=O)NCc1ccc(S(=O)(=O)Nc2cc(Sc3cccc4cccnc34)c(O)c3ccccc23)s1] | C26H21N3O4S3 | 535.667 | 5.349 |

TABLE 8-continued

| IDNUMBER | Structure | Formula structure | MW | Log P |
|---|---|---|---|---|
| F5749-0125 | 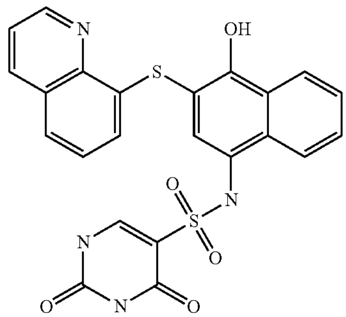 [SMILES: O=c1[nH]cc(S(=O)(=O)Nc2cc(Sc3cccc4cccnc34)c(O)c3ccccc23)c(=O)[nH]1] | C23H16N4O5S2 | 492.5358 | 3.091 |
| F5749-0126 | 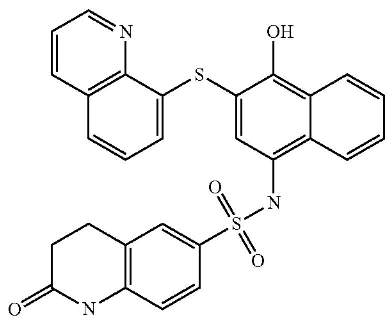 [SMILES: O=C1CCc2cc(S(=O)(=O)Nc3cc(Sc4cccc5cccnc45)c(O)c4ccccc34)ccc2N1] | C28H21N3O4S2 | 527.6253 | 5.242 |
| F5749-0127 | 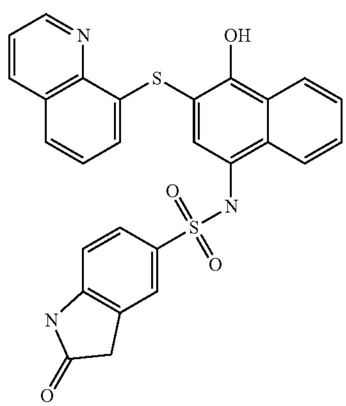 [SMILES: O=C1Cc2cc(S(=O)(=O)Nc3cc(Sc4cccc5cccnc45)c(O)c4ccccc34)ccc2N1] | C27H19N3O4S2 | 513.5982 | 5.154 |
| F5749-0128 | 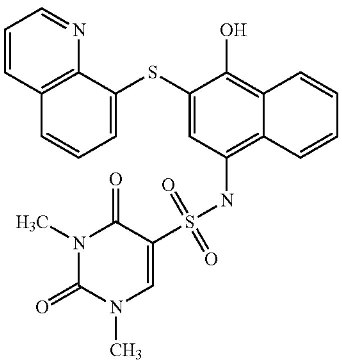 [SMILES: Cn1cc(S(=O)(=O)Nc2cc(Sc3cccc4cccnc34)c(O)c3ccccc23)c(=O)n(C)c1=O] | C25H20N4O5S2 | 520.59 | 3.155 |

TABLE 8-continued

| IDNUMBER | Structure | Formula structure | MW | Log P |
|---|---|---|---|---|
| F5749-0129 | 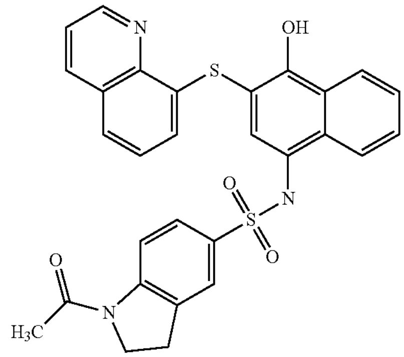 [SMILES: CC(=O)N1CCc2cc(S(=O)(=O)Nc3cc(Sc4cccc5cccnc45)c(O)c4ccccc34)ccc21] | C29H23N3O4S2 | 541.6524 | 5.477 |
| F5749-0130 | 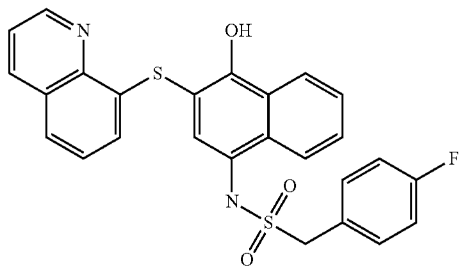 [SMILES: O=S(=O)(Cc1ccc(F)cc1)Nc1cc(Sc2cccc3cccnc23)c(O)c2ccccc12] | C26H19FN2O3S2 | 490.5793 | 6.333 |
| F5749-0131 | 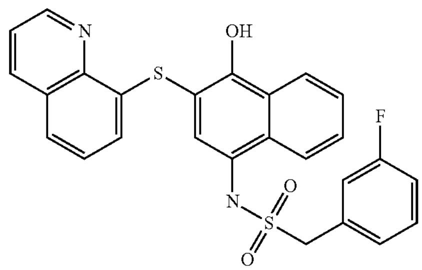 [SMILES: O=S(=O)(Cc1cccc(F)c1)Nc1cc(Sc2cccc3cccnc23)c(O)c2ccccc12] | C26H19FN2O3S2 | 490.5793 | 6.37 |
| F5749-0132 | 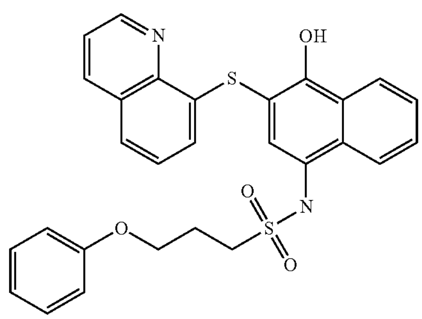 [SMILES: O=S(=O)(CCCOc1ccccc1)Nc1cc(Sc2cccc3cccnc23)c(O)c2ccccc12] | C28H24N2O4S2 | 516.6425 | 6.406 |
| F5749-0133 | 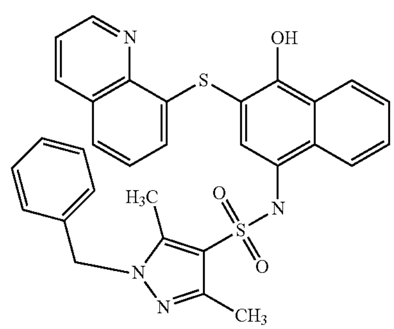 [SMILES: Cc1nn(Cc2ccccc2)c(C)c1S(=O)(=O)Nc1cc(Sc2cccc3cccnc23)c(O)c2ccccc12] | C31H26N4O3S2 | 566.7059 | 6.325 |

TABLE 8-continued

| IDNUMBER | Structure | Formula structure | MW | Log P |
|---|---|---|---|---|
| F5749-0134 | 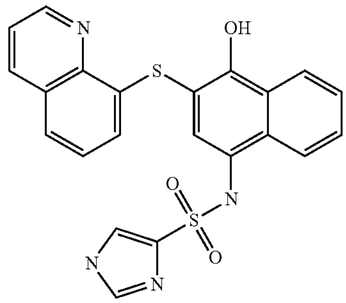 [SMILES: O=S(=O)(Nc1cc(Sc2cccc3cccnc23)c(O)c2ccccc12)c1c[nH]cn1] | C22H16N4O3S2 | 448.5258 | 4.186 |
| F5749-0135 | 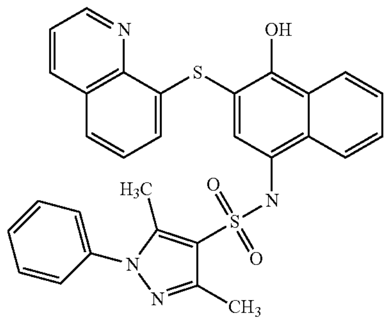 [SMILES: Cc1nn(-c2ccccc2)c(C)c1S(=O)(=O)Nc1cc(Sc2cccc3cccnc23)c(O)c2ccccc12] | C30H24N4O3S2 | 552.6788 | 6.191 |
| F5749-0136 | 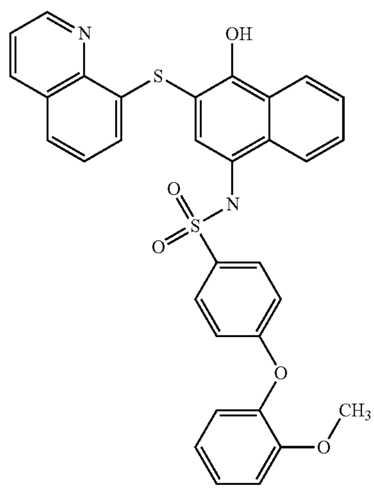 [SMILES: COc1ccccc1Oc1ccc(S(=O)(=O)Nc2cc(Sc3cccc4cccnc34)c(O)c3ccccc23)cc1] | C32H24N2O5S2 | 580.6865 | 7.36174 |
| F5749-0137 | 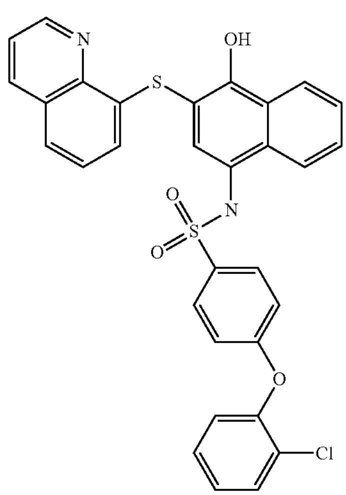 [SMILES: O=S(=O)(Nc1cc(Sc2cccc3cccnc23)c(O)c2ccccc12)c1ccc(Oc2ccccc2Cl)cc1] | C31H21ClN2O4S2 | 585.105 | 8.246 |

TABLE 8-continued

| IDNUMBER | Structure | Formula structure | MW | Log P |
| --- | --- | --- | --- | --- |
| F5749-0138 | 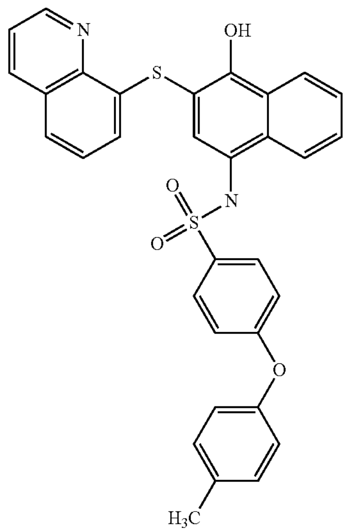 [SMILES: Cc1ccc(Oc2ccc(S(=O)(=O)Nc3cc(Sc4cccc5cccnc45)c(O)c4ccccc34)cc2)cc1] | C32H24N2O4S2 | 564.6871 | 7.954 |
| F5749-0139 | 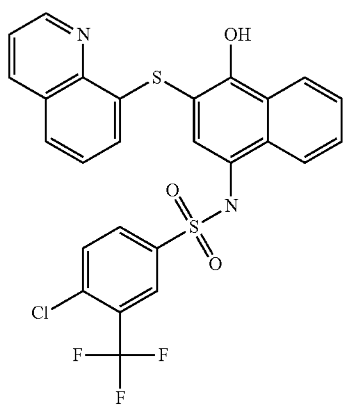 [SMILES: O=S(=O)(Nc1cc(Sc2cccc3cccnc23)c(O)c2ccccc12)c1ccc(Cl)c(C(F)(F)F)c1] | C26H16ClF3N2O3S2 | 561.0052 | 7.60776 |
| F5749-0140 | 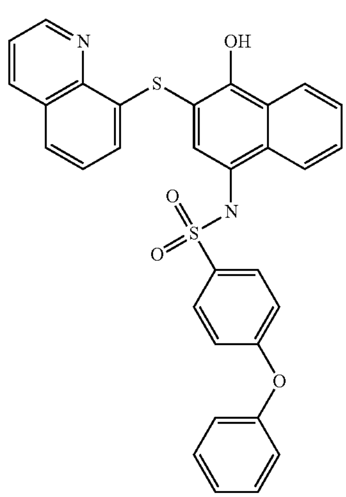 [SMILES: O=S(=O)(Nc1cc(Sc2cccc3cccnc23)c(O)c2ccccc12)c1ccc(Oc2ccccc2)cc1] | C31H22N2O4S2 | 550.66 | 7.656 |

TABLE 8-continued

| IDNUMBER | Structure | Formula structure | MW | Log P |
|---|---|---|---|---|
| F5749-0141 | 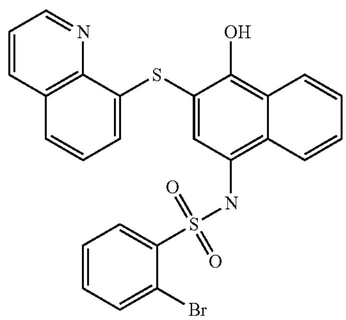 | C25H17BrN2O3S2 | 537.4578 | 6.842 |
| F5749-0142 | 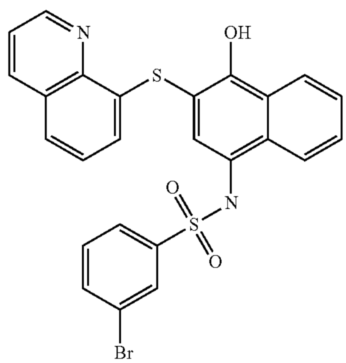 [SMILES: O=S(=O)(Nc1cc(Sc2cccc3cccnc23)c(O)c2ccccc12)c1cccc(Br)c1] | C25H17BrN2O3S2 | 537.4578 | 6.881 |
| F5749-0143 | 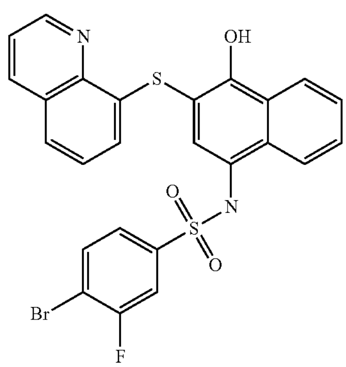 [SMILES: O=S(=O)(Nc1cc(Sc2cccc3cccnc23)c(O)c2ccccc12)c1ccc(Br)c(F)c1] | C25H16BrFN2O3S2 | 555.4483 | 7.032 |
| F5749-0144 | 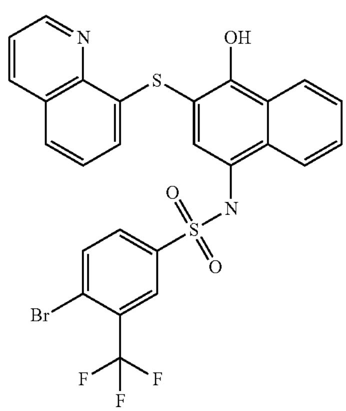 [SMILES: O=S(=O)(Nc1cc(Sc2cccc3cccnc23)c(O)c2ccccc12)c1ccc(Br)c(C(F)(F)F)c1] | C26H16BrF3N2O3S2 | 605.4562 | 7.81376 |

TABLE 8-continued

| IDNUMBER | Structure | Formula structure | MW | Log P |
|---|---|---|---|---|
| F5749-0145 | 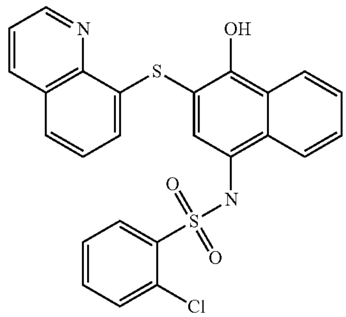 [SMILES: O=S(=O)(Nc1cc(Sc2cccc3cccnc23)c(O)c2ccccc12)c1ccccc1Cl] | C25H17ClN2O3S2 | 493.0068 | 6.636 |
| F5749-0146 | 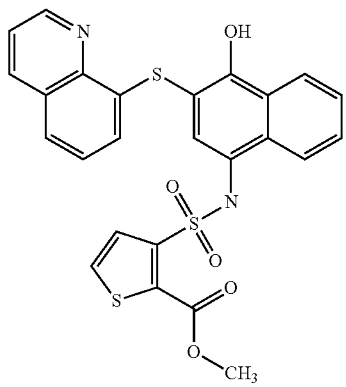 [SMILES: COC(=O)c1sccc1S(=O)(=O)Nc1cc(Sc2cccc3cccnc23)c(O)c2ccccc12] | C25H18N2O5S3 | 522.6246 | 5.246 |
| F5749-0147 | 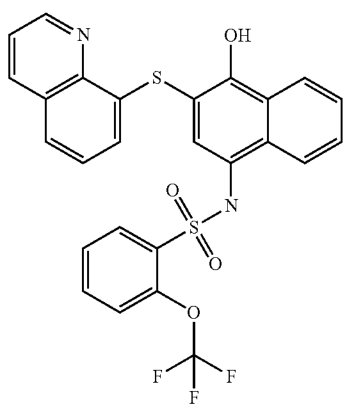 [SMILES: O=S(=O)(Nc1cc(Sc2cccc3cccnc23)c(O)c2ccccc12)c1ccccc1OC(F)(F)F] | C26H17F3N2O4S2 | 542.5596 | 7.44276 |

TABLE 9

| IDNUMBER | Structure | Formula structure | MW | LogP |
|---|---|---|---|---|
| F1565-0253 | 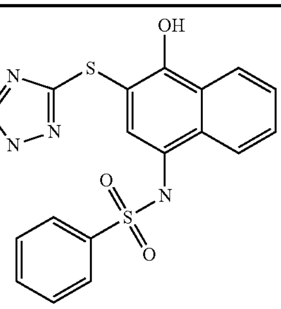 | C18H14N4O3S2 | 398.4653 | 3.698 |

TABLE 9-continued

| IDNUMBER | Structure | Formula structure | MW | LogP |
|---|---|---|---|---|
| F1566-0328 | 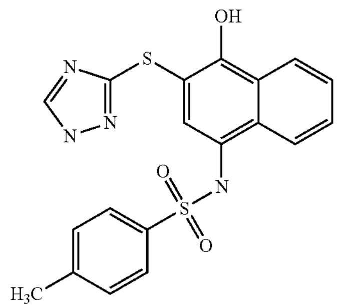 [SMILES: Cc1ccc(S(=O)(=O)Nc2cc(Sc3nc[nH]n3)c(O)c3ccccc23)cc1] | C19H16N4O3S2 | 412.4924 | 3.996 |
| F1566-0340 | 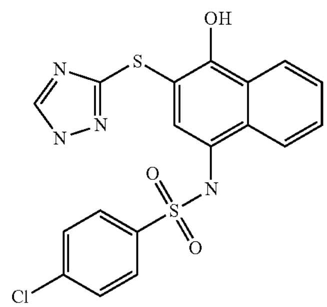 [SMILES: O=S(=O)(Nc1cc(Sc2nc[nH]n2)c(O)c2ccccc12)c1ccc(Cl)cc1] | C18H13ClN4O3S2 | 432.9103 | 4.29 |
| F1566-0520 | 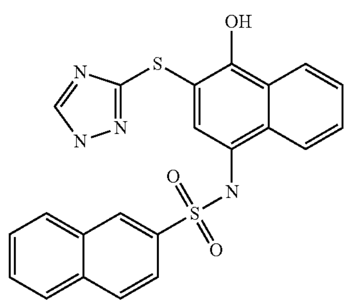 [SMILES: O=S(=O)(Nc1cc(Sc2nc[nH]n2)c(O)c2ccccc12)c1ccc2ccccc2c1] | C22H16N4O3S2 | 448.5258 | 4.957 |
| F1566-0556 | 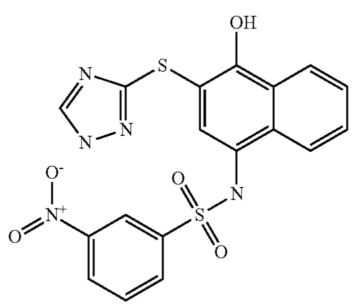 [SMILES: O=[N+]([O-])c1cccc(S(=O)(=O)Nc2cc(Sc3nc[nH]n3)c(O)c3ccccc23)c1] | C18H13N5O5S2 | 443.4628 | 3.67 |
| F1566-0568 | 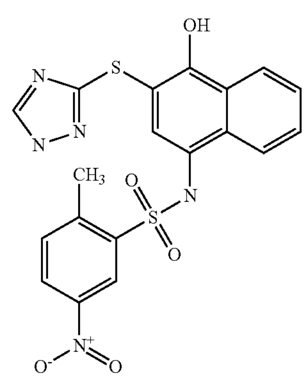 [SMILES: Cc1ccc([N+](=O)[O-])cc1S(=O)(=O)Nc1cc(Sc2nc[nH]n2)c(O)c2ccccc12] | C19H15N5O5S2 | 457.4899 | 3.966 |

TABLE 9-continued

| IDNUMBER | Structure | Formula structure | MW | LogP |
|---|---|---|---|---|
| F1566-0616 | 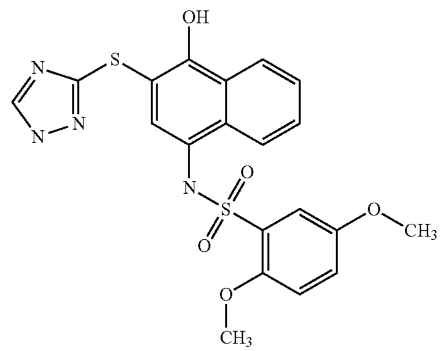 [SMILES: COc1ccc(OC)c(S(=O)(=O)Nc2cc(Sc3nc[nH]n3)c(O)c3ccccc23)c1] | C20H18N4O5S2 | 458.5183 | 3.645 |
| F1566-0628 | 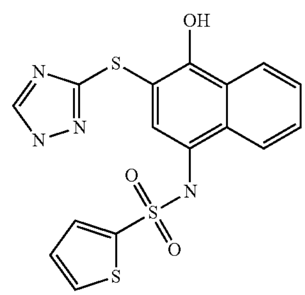 [SMILES: O=S(=O)(Nc1cc(Sc2nc[nH]n2)c(O)c2ccccc12)c1cccs1] | C16H12N4O3S3 | 404.491 | 3.211 |
| F5749-0148 | 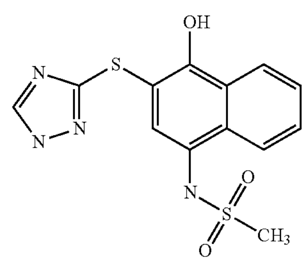 [SMILES: CS(=O)(=O)Nc1cc(Sc2nc[nH]n2)c(O)c2ccccc12] | C13H12N4O3S2 | 336.3936 | 2.044 |
| F5749-0149 | 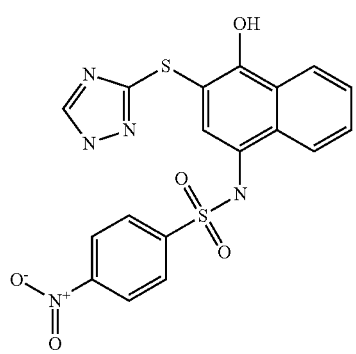 [SMILES: O=[N+]([O-])c1ccc(S(=O)(=O)Nc2cc(Sc3nc[nH]n3)c(O)c3ccccc23)cc1] | C18H13N5O5S2 | 443.4628 | 3.633 |
| F5749-0150 | 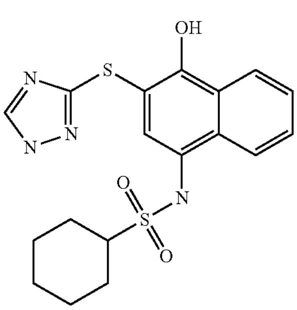 [SMILES: O=S(=O)(Nc1cc(Sc2nc[nH]n2)c(O)c2ccccc12)C1CCCCC1] | C18H20N4O3S2 | 404.5131 | 4.023 |

TABLE 9-continued
| IDNUMBER | Structure | Formula structure | MW | LogP |
|---|---|---|---|---|
| F5749-0151 | 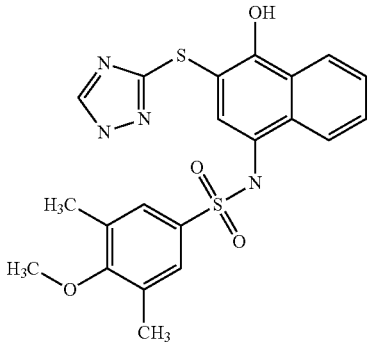 [SMILES: COc1c(C)cc(S(=O)(=O)Nc2cc(Sc3nc[nH]n3)c(O)c3ccccc23)cc1C] | C21H20N4O4S2 | 456.546 | 4.32 |
| F5749-0152 | 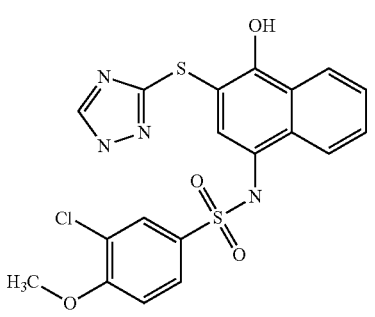 [SMILES: COc1ccc(S(=O)(=O)Nc2cc(Sc3nc[nH]n3)c(O)c3ccccc23)cc1Cl] | C19H15ClN4O4S2 | 462.9368 | 4.281 |
| F5749-0153 | 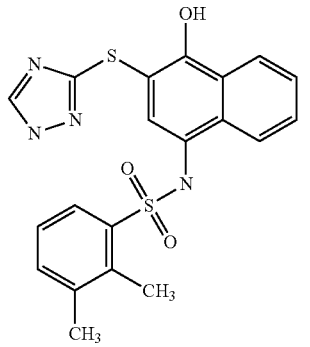 [SMILES: Cc1cccc(S(=O)(=O)Nc2cc(Sc3nc[nH]n3)c(O)c3ccccc23)c1C] | C20H18N4O3S2 | 426.5195 | 4.29 |
| F5749-0154 | 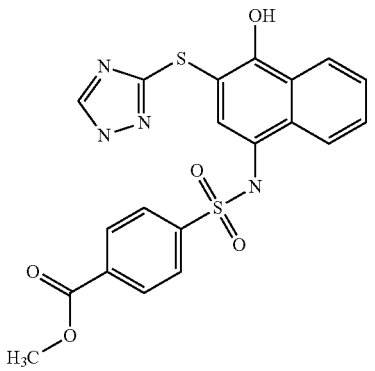 [SMILES: COC(=O)c1ccc(S(=O)(=O)Nc2cc(Sc3nc[nH]n3)c(O)c3ccccc23)cc1] | C20H16N4O5S2 | 456.5023 | 3.639 |

TABLE 9-continued

| IDNUMBER | Structure | Formula structure | MW | LogP |
|---|---|---|---|---|
| F5749-0155 | 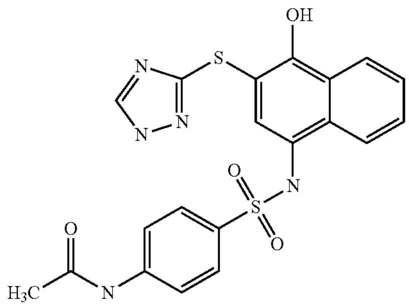 [SMILES: CC(=O)Nc1ccc(S(=O)(=O)Nc2cc(Sc3nc[nH]n3)c(O)c3ccccc23)cc1] | C20H17N5O4S2 | 455.5176 | 2.989 |
| F5749-0156 | 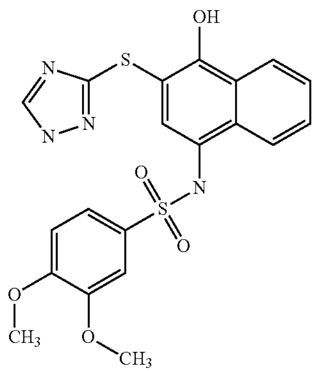 [SMILES: COc1ccc(S(=O)(=O)Nc2cc(Sc3nc[nH]n3)c(O)c3ccccc23)cc1OC] | C20H18N4O5S2 | 458.5183 | 3.39674 |
| F5749-0157 | 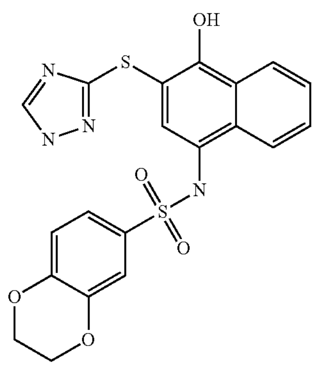 [SMILES: O=S(=O)(Nc1cc(Sc2nc[nH]n2)c(O)c2ccccc12)c1ccc2c(c1)OCCO2] | C20H16N4O5S2 | 456.5023 | 3.293 |
| F5749-0158 | 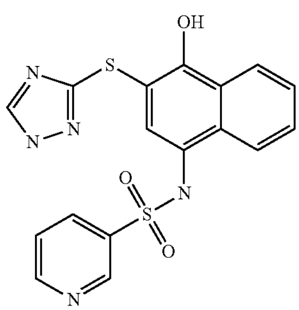 [SMILES: O=S(=O)(Nc1cc(Sc2nc[nH]n2)c(O)c2ccccc12)c1cccnc1] | C17H13N5O3S2 | 399.4529 | 2.465 |
| F5749-0159 | 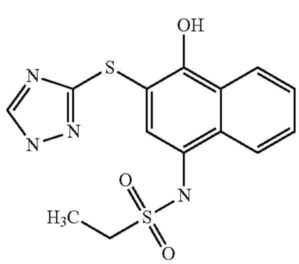 [SMILES: CCS(=O)(=O)Nc1cc(Sc2nc[nH]n2)c(O)c2ccccc12] | C14H14N4O3S2 | 350.4207 | 2.557 |

TABLE 9-continued

| IDNUMBER | Structure | Formula structure | MW | LogP |
| --- | --- | --- | --- | --- |
| F5749-0160 | 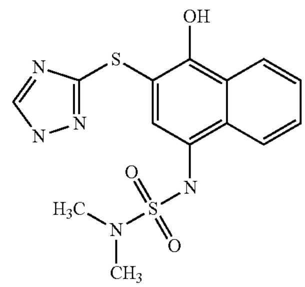 [SMILES: CN(C)S(=O)(=O)Nc1cc(Sc2nc[nH]n2)c(O)c2ccccc12] | C14H15N5O3S2 | 365.4354 | 1.592 |
| F5749-0161 | 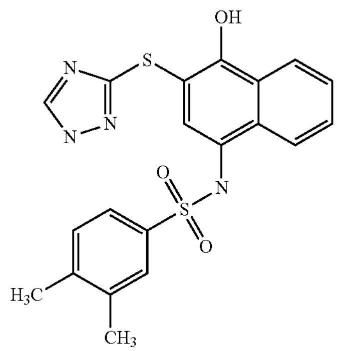 [SMILES: Cc1ccc(S(=O)(=O)Nc2cc(Sc3nc[nH]n3)c(O)c3ccccc23)cc1C] | C20H18N4O3S2 | 426.5195 | 4.329 |
| F5749-0162 | 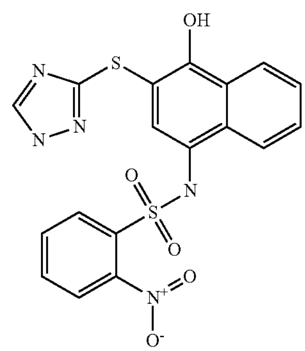 [SMILES: O=[N+]([O-])c1ccccc1S(=O)(=O)Nc1cc(Sc2nc[nH]n2)c(O)c2ccccc12] | C18H13N5O5S2 | 443.4628 | 3.631 |
| F5749-0163 | 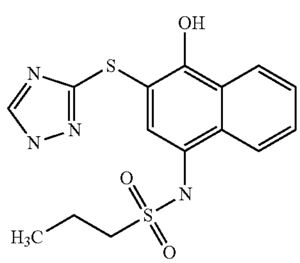 [SMILES: CCCS(=O)(=O)Nc1cc(Sc2nc[nH]n2)c(O)c2ccccc12] | C15H16N4O3S2 | 364.4478 | 2.999 |
| F5749-0164 | 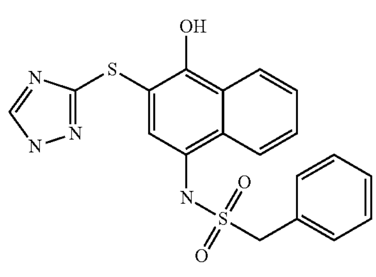 [SMILES: O=S(=O)(Cc1ccccc1)Nc1cc(Sc2nc[nH]n2)c(O)c2ccccc12] | C19H16N4O3S2 | 412.4924 | 3.832 |

TABLE 9-continued

| IDNUMBER | Structure | Formula structure | MW | LogP |
| --- | --- | --- | --- | --- |
| F5749-0165 | 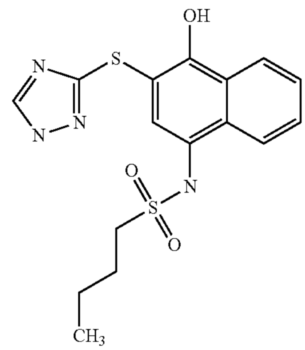 [SMILES: CCCCS(=O)(=O)Nc1cc(Sc2nc[nH]n2)c(O)c2ccccc12] | C16H18N4O3S2 | 378.4749 | 3.441 |
| F5749-0166 | 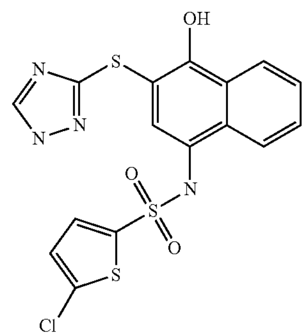 [SMILES: O=S(=O)(Nc1cc(Sc2nc[nH]n2)c(O)c2ccccc12)c1ccc(Cl)s1] | C16H11ClN4O3S3 | 438.9361 | 4.501 |
| F5749-0167 | 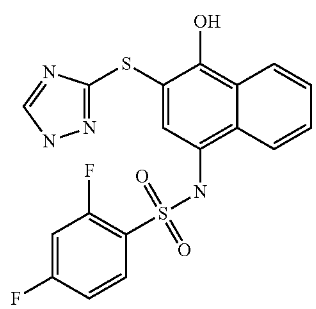 [SMILES: O=S(=O)(Nc1cc(Sc2nc[nH]n2)c(O)c2ccccc12)c1ccc(F)cc1F] | C18H12F2N4O3S2 | 434.4461 | 4.039 |
| F5749-0168 | 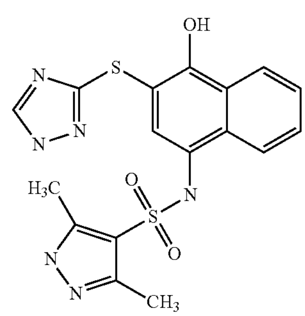 [SMILES: Cc1n[nH]c(C)c1S(=O)(=O)Nc1cc(Sc2nc[nH]n2)c(O)c2ccccc12] | C17H16N6O3S2 | 416.4835 | 2.808 |
| F5749-0169 | 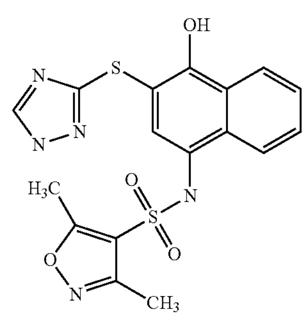 | C17H15N5O4S2 | 417.4682 | 2.842 |

TABLE 9-continued

| IDNUMBER | Structure | Formula structure | MW | LogP |
|---|---|---|---|---|
| F5749-0170 | 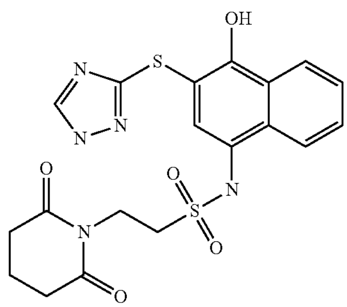 [SMILES: O=C1CCCC(=O)N1CCS(=O)(=O)Nc1cc(Sc2nc[nH]n2)c(O)c2ccccc12] | C19H19N5O5S2 | 461.5218 | 1.485 |
| F5749-0171 | 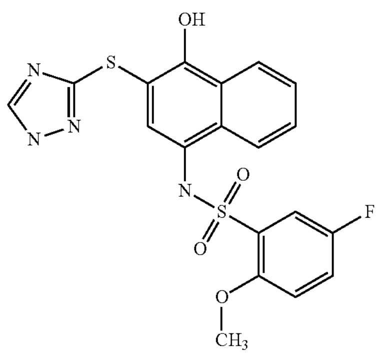 [SMILES: COc1ccc(F)cc1S(=O)(=O)Nc1cc(Sc2nc[nH]n2)c(O)c2ccccc12] | C19H15FN4O4S2 | 446.4822 | 3.842 |
| F5749-0172 | 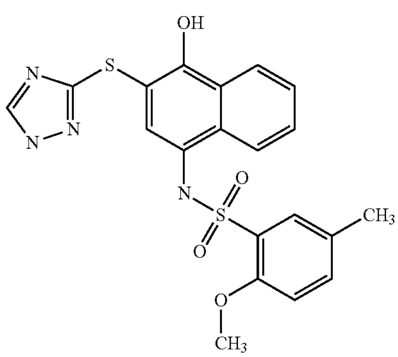 [SMILES: COc1ccc(C)cc1S(=O)(=O)Nc1cc(Sc2nc[nH]n2)c(O)c2ccccc12] | C20H18N4O4S2 | 442.5189 | 3.987 |
| F5749-0173 | 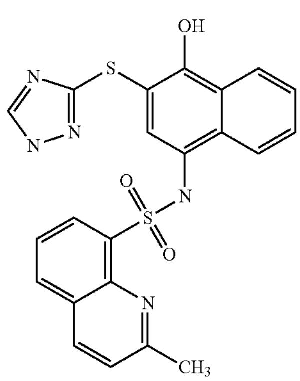 [SMILES: Cc1ccc2cccc(S(=O)(=O)Nc3cc(Sc4nc[nH]n4)c(O)c4ccccc34)c2n1] | C22H17N5O3S2 | 463.5405 | 4.157 |

TABLE 9-continued

| IDNUMBER | Structure | Formula structure | MW | LogP |
| --- | --- | --- | --- | --- |
| F5749-0174 | 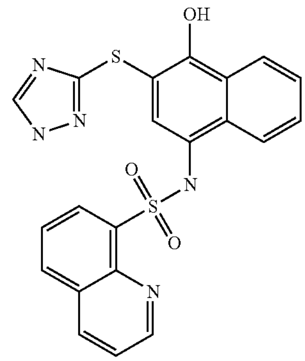 [SMILES: O=S(=O)(Nc1cc(Sc2nc[nH]n2)c(O)c2ccccc12)c1cccc2cccnc12] | C21H15N5O3S2 | 449.5134 | 3.898 |
| F5749-0175 | 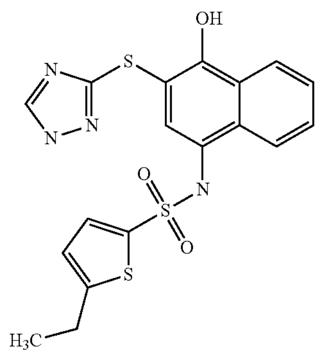 [SMILES: CCc1ccc(S(=O)(=O)Nc2cc(Sc3nc[nH]n3)c(O)c3ccccc23)s1] | C18H16N4O3S3 | 432.5452 | 4.349 |
| F5749-0176 | 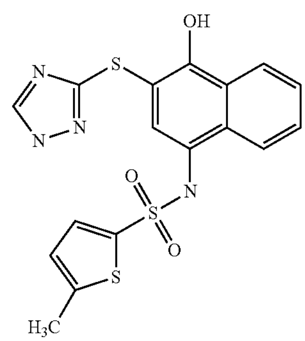 [SMILES: Cc1ccc(S(=O)(=O)Nc2cc(Sc3nc[nH]n3)c(O)c3ccccc23)s1] | C17H14N4O3S3 | 418.5181 | 3.874 |
| F5749-0177 | 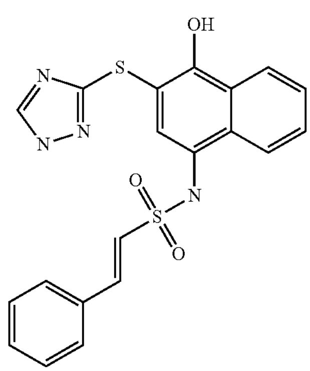 [SMILES: O=S(=O)(/C=C/c1ccccc1)Nc1cc(Sc2nc[nH]n2)c(O)c2ccccc12] | C20H16N4O3S2 | 424.5035 | 4.056 |

TABLE 9-continued

| IDNUMBER | Structure | Formula structure | MW | LogP |
| --- | --- | --- | --- | --- |
| F5749-0178 | 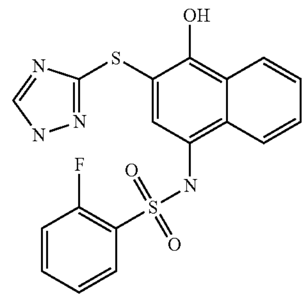 [SMILES: O=S(=O)(Nc1cc(Sc2nc[nH]n2)c(O)c2ccccc12)c1ccccc1F] | C18H13FN4O3S2 | 416.4557 | 3.849 |
| F5749-0179 | 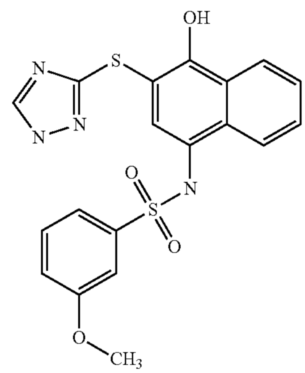 [SMILES: COc1cccc(S(=O)(=O)Nc2cc(Sc3nc[nH]n3)c(O)c3ccccc23)c1] | C19H16N4O4S2 | 428.4918 | 3.691 |
| F5749-0180 | 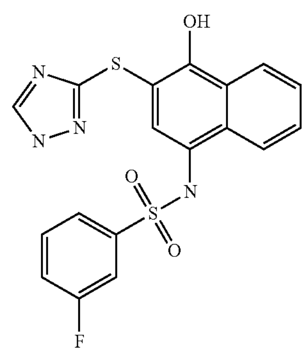 [SMILES: O=S(=O)(Nc1cc(Sc2nc[nH]n2)c(O)c2ccccc12)c1cccc(F)c1] | C18H13FN4O3S2 | 416.4557 | 3.888 |
| F5749-0181 | 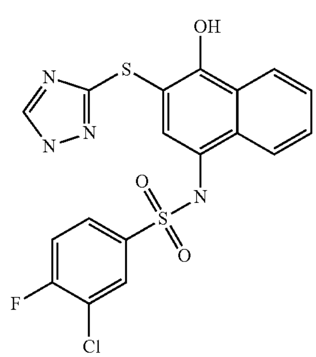 [SMILES: O=S(=O)(Nc1cc(Sc2nc[nH]n2)c(O)c2ccccc12)c1ccc(F)c(Cl)c1] | C18H12ClFN4O3S2 | 450.9007 | 4.478 |

TABLE 9-continued

| IDNUMBER | Structure | Formula structure | MW | LogP |
|---|---|---|---|---|
| F5749-0182 | 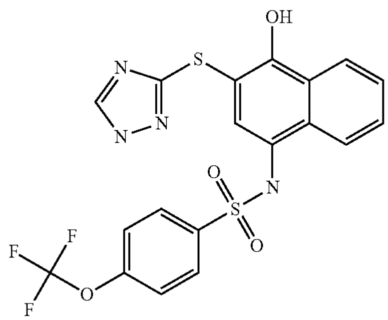 [SMILES: O=S(=O)(Nc1cc(Sc2nc[nH]n2)c(O)c2ccccc12)c1ccc(OC(F)(F)F)cc1] | C19H13F3N4O4S2 | 482.4631 | 5.09676 |
| F5749-0183 | 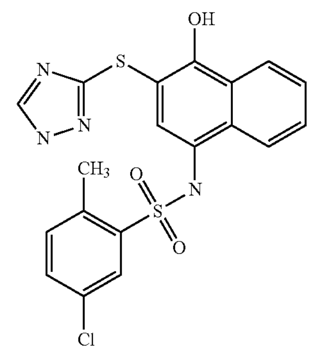 [SMILES: Cc1ccc(Cl)cc1S(=O)(=O)Nc1cc(Sc2nc[nH]n2)c(O)c2ccccc12] | C19H15ClN4O3S2 | 446.9374 | 4.623 |
| F5749-0184 | 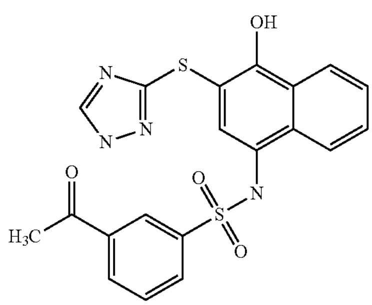 [SMILES: CC(=O)c1cccc(S(=O)(=O)Nc2cc(Sc3nc[nH]n3)c(O)c3ccccc23)c1] | C20H16N4O4S2 | 440.5029 | 3.588 |
| F5749-0185 | 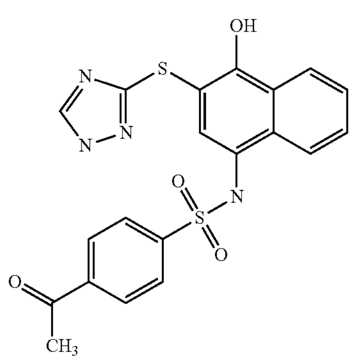 [SMILES: CC(=O)c1ccc(S(=O)(=O)Nc2cc(Sc3nc[nH]n3)c(O)c3ccccc23)cc1] | C20H16N4O4S2 | 440.5029 | 3.551 |

TABLE 9-continued

| IDNUMBER | Structure | Formula structure | MW | LogP |
|---|---|---|---|---|
| F5749-0186 | 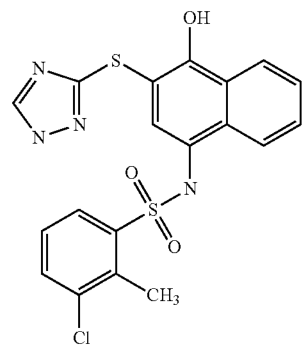 [SMILES: Cc1c(Cl)cccc1S(=O)(=O)Nc1cc(Sc2nc[nH]n2)c(O)c2ccccc12] | C19H15ClN4O3S2 | 446.9374 | 4.584 |
| F5749-0187 | 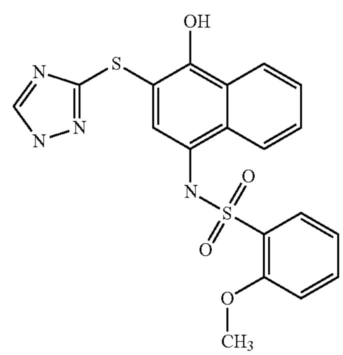 [SMILES: COc1ccccc1S(=O)(=O)Nc1cc(Sc2nc[nH]n2)c(O)c2ccccc12] | C19H16N4O4S2 | 428.4918 | 3.652 |
| F5749-0188 | 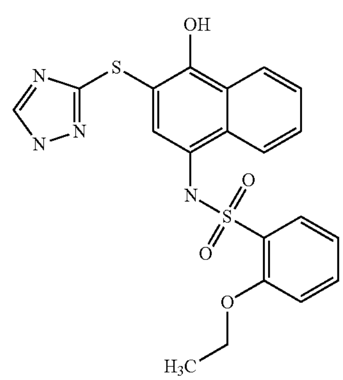 [SMILES: CCOc1ccccc1S(=O)(=O)Nc1cc(Sc2nc[nH]n2)c(O)c2ccccc12] | C20H18N4O4S2 | 442.5189 | 3.993 |
| F5749-0189 | 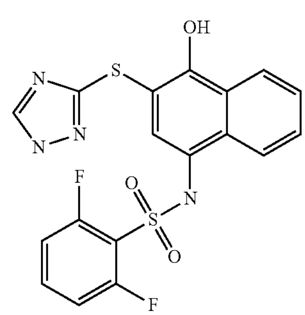 [SMILES: O=S(=O)(Nc1cc(Sc2nc[nH]n2)c(O)c2ccccc12)c1c(F)cccc1F] | C18H12F2N4O3S2 | 434.4461 | 4 |

TABLE 9-continued

| IDNUMBER | Structure | Formula structure | MW | LogP |
|---|---|---|---|---|
| F5749-0190 | 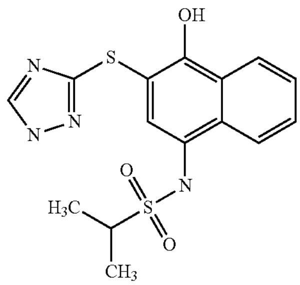 [SMILES: CC(C)S(=O)(=O)Nc1cc(Sc2nc[nH]n2)c(O)c2ccccc12] | C15H16N4O3S2 | 364.4478 | 3.191 |
| F5749-0191 | 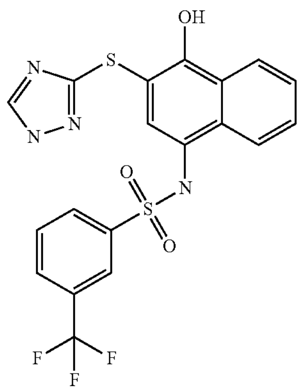 [SMILES: O=S(=O)(Nc1cc(Sc2nc[nH]n2)c(O)c2ccccc12)c1cccc(C(F)(F)F)c1] | C19H13F3N4O3S2 | 466.4637 | 4.66976 |
| F5749-0192 | 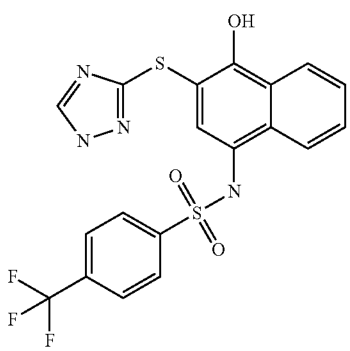 [SMILES: O=S(=O)(Nc1cc(Sc2nc[nH]n2)c(O)c2ccccc12)c1ccc(C(F)(F)F)cc1] | C19H13F3N4O3S2 | 466.4637 | 4.63276 |
| F5749-0193 | 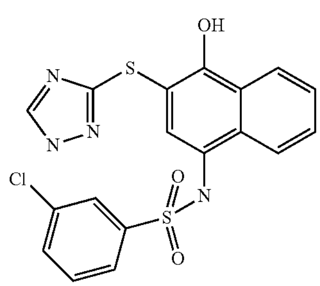 [SMILES: O=S(=O)(Nc1cc(Sc2nc[nH]n2)c(O)c2ccccc12)c1cccc(Cl)c1] | C18H13ClN4O3S2 | 432.9103 | 4.327 |
| F5749-0194 | 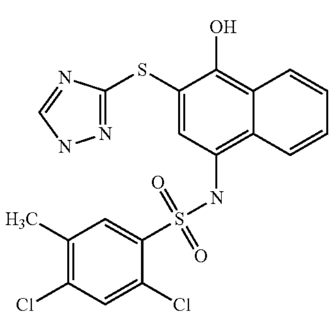 [SMILES: Cc1cc(S(=O)(=O)Nc2cc(Sc3nc[nH]n3)c(O)c3ccccc23)c(Cl)cc1Cl] | C19H14Cl2N4O3S2 | 481.3824 | 5.25 |

TABLE 9-continued

| IDNUMBER | Structure | Formula structure | MW | LogP |
|---|---|---|---|---|
| F5749-0195 | 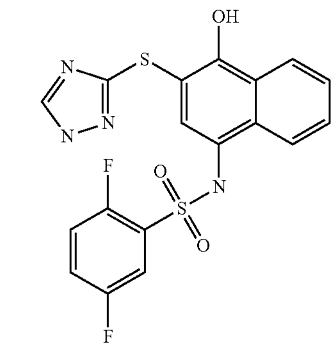 [SMILES: O=S(=O)(Nc1cc(Sc2nc[nH]n2)c(O)c2ccccc12)c1cc(F)ccc1F] | C18H12F2N4O3S2 | 434.4461 | 4.039 |
| F5749-0196 | 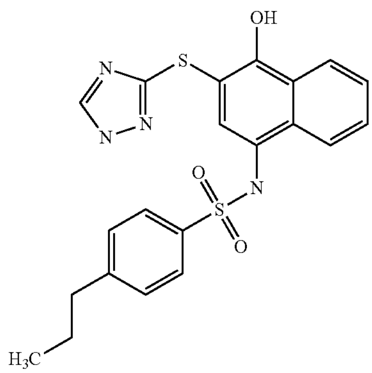 [SMILES: CCCc1ccc(S(=O)(=O)Nc2cc(Sc3nc[nH]n3)c(O)c3ccccc23)cc1] | C21H20N4O3S2 | 440.5466 | 4.913 |
| F5749-0197 | 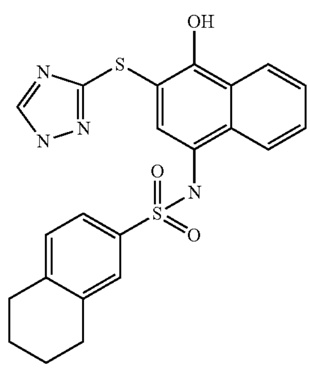 [SMILES: O=S(=O)(Nc1cc(Sc2nc[nH]n2)c(O)c2ccccc12)c1ccc2c(c1)CCCC2] | C22H20N4O3S2 | 452.5577 | 4.785 |
| F5749-0198 | 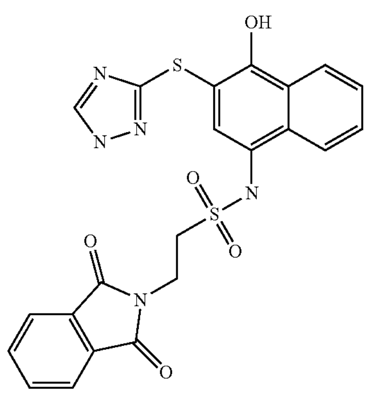 [SMILES: O=C1c2ccccc2C(=O)N1CCS(=O)(=O)Nc1cc(Sc2nc[nH]n2)c(O)c2ccccc12] | C22H17N5O5S2 | 495.5393 | 2.825 |

TABLE 9-continued
| IDNUMBER | Structure | Formula structure | MW | LogP |
|---|---|---|---|---|
| F5749-0199 | 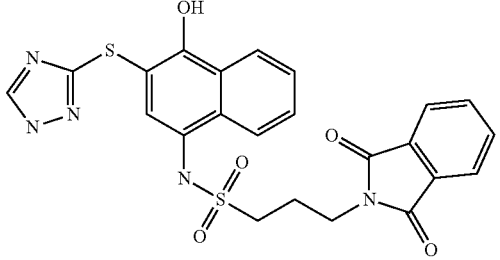 [SMILES: O=C1c2ccccc2C(=O)N1CCCS(=O)(=O)Nc1cc(Sc2nc[nH]n2)c(O)c2ccccc12] | C23H19N5O5S2 | 509.5664 | 3.267 |
| F5749-0200 | 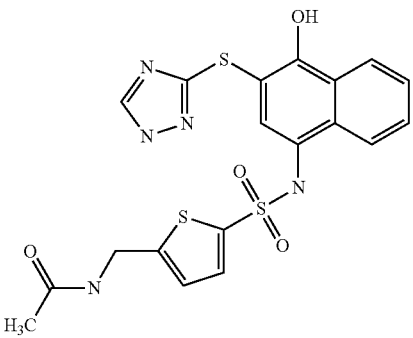 [SMILES: CC(=O)NCc1ccc(S(=O)(=O)Nc2cc(Sc3nc[nH]n3)c(O)c3ccccc23)s1] | C19H17N5O4S3 | 475.5704 | 3.001 |
| F5749-0201 | 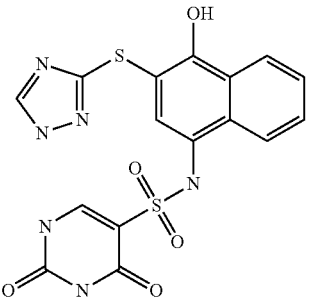 [SMILES: O=c1[nH]cc(S(=O)(=O)Nc2cc(Sc3nc[nH]n3)c(O)c3ccccc23)c(=O)[nH]1] | C16H12N6O5S2 | 432.4392 | 0.743 |
| F5749-0202 | 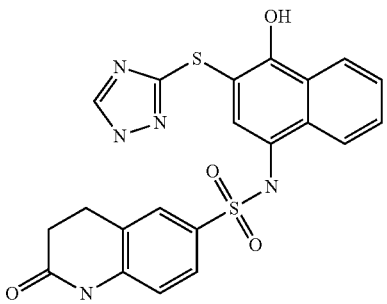 [SMILES: O=C1CCc2cc(S(=O)(=O)Nc3cc(Sc4nc[nH]n4)c(O)c4ccccc34)ccc2N1] | C21H17N5O4S2 | 467.5287 | 2.894 |
| F5749-0203 | 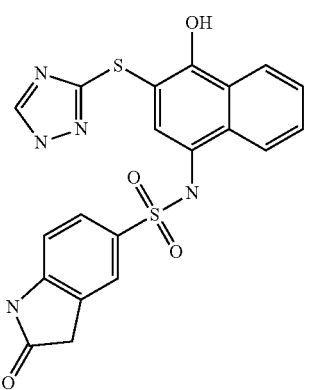 [SMILES: O=C1Cc2cc(S(=O)(=O)Nc3cc(Sc4nc[nH]n4)c(O)c4ccccc34)ccc2N1] | C20H15N5O4S2 | 453.5017 | 2.806 |

TABLE 9-continued

| IDNUMBER | Structure | Formula structure | MW | LogP |
|---|---|---|---|---|
| F5749-0204 | 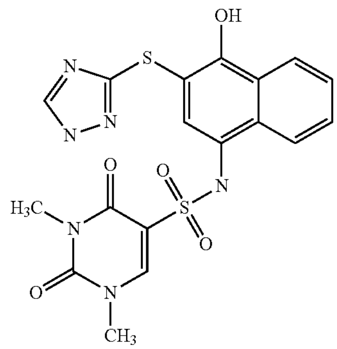 [SMILES: Cn1cc(S(=O)(=O)Nc2cc(Sc3nc[nH]n3)c(O)c3ccccc23)c(=O)n(C)c1=O] | C18H16N6O5S2 | 460.4934 | 0.807 |
| F5749-0205 | 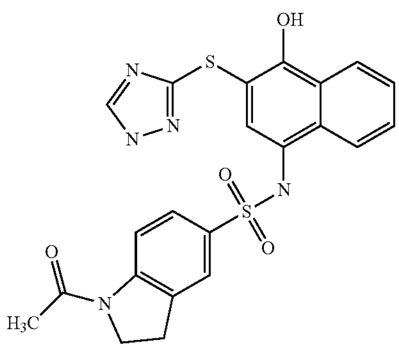 [SMILES: CC(=O)N1CCc2cc(S(=O)(=O)Nc3cc(Sc4nc[nH]n4)c(O)c4ccccc34)ccc21] | C22H19N5O4S2 | 481.5558 | 3.129 |
| F5749-0206 | 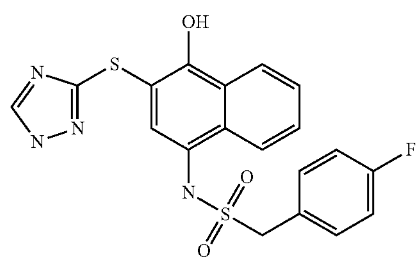 [SMILES: O=S(=O)(Cc1ccc(F)cc1)Nc1cc(Sc2nc[nH]n2)c(O)c2ccccc12] | C19H15FN4O3S2 | 430.4828 | 3.985 |
| F5749-0207 | 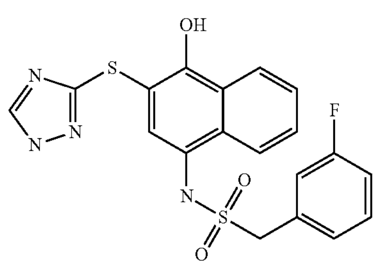 [SMILES: O=S(=O)(Cc1cccc(F)c1)Nc1cc(Sc2nc[nH]n2)c(O)c2ccccc12] | C19H15FN4O3S2 | 430.4828 | 4.022 |
| F5749-0208 | 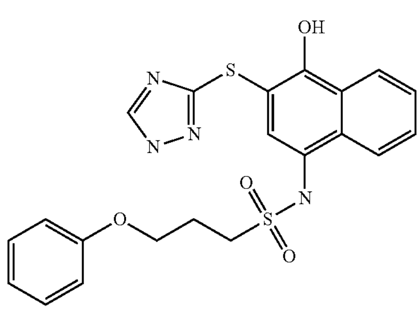 [SMILES: O=S(=O)(CCCOc1ccccc1)Nc1cc(Sc2nc[nH]n2)c(O)c2ccccc12] | C21H20N4O4S2 | 456.546 | 4.058 |

TABLE 9-continued

| IDNUMBER | Structure | Formula structure | MW | LogP |
|---|---|---|---|---|
| F5749-0209 | 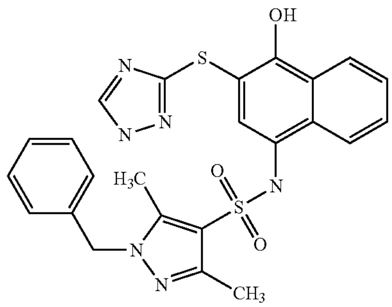 [SMILES: Cc1nn(Cc2ccccc2)c(C)c1S(=O)(=O)Nc1cc(Sc2nc[nH]n2)c(O)c2ccccc12] | C24H22N6O3S2 | 506.6093 | 3.977 |
| F5749-0210 | 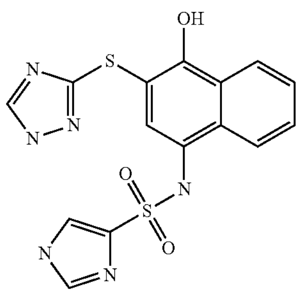 [SMILES: O=S(=O)(Nc1cc(Sc2nc[nH]n2)c(O)c2ccccc12)c1c[nH]cn1] | C15H12N6O3S2 | 388.4293 | 1.838 |
| F5749-0211 | 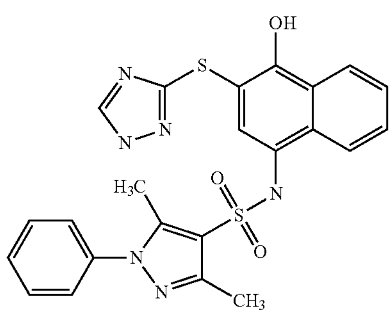 [SMILES: Cc1nn(-c2ccccc2)c(C)c1S(=O)(=O)Nc1cc(Sc2nc[nH]n2)c(O)c2ccccc12] | C23H20N6O3S2 | 492.5823 | 3.843 |
| F5749-0212 | 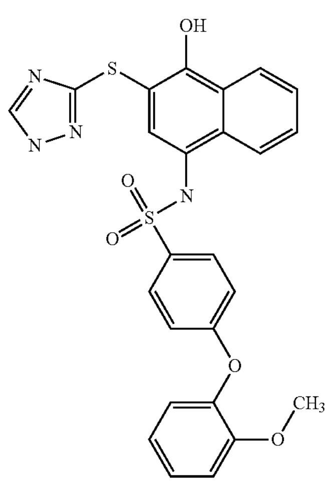 [SMILES: COc1ccccc1Oc1ccc(S(=O)(=O)Nc2cc(Sc3nc[nH]n3)c(O)c3ccccc23)cc1] | C25H20N4O5S2 | 520.59 | 5.01374 |

TABLE 9-continued

| IDNUMBER | Structure | Formula structure | MW | LogP |
|---|---|---|---|---|
| F5749-0213 | 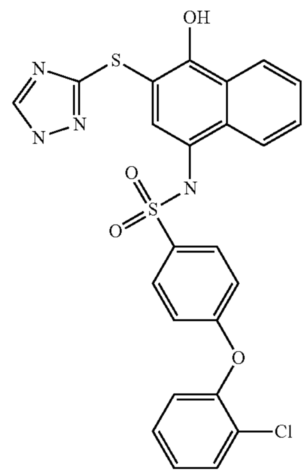 [SMILES: O=S(=O)(Nc1cc(Sc2nc[nH]n2)c(O)c2ccccc12)c1ccc(Oc2ccccc2Cl)cc1] | C24H17ClN4O4S2 | 525.0085 | 5.898 |
| F5749-0214 | 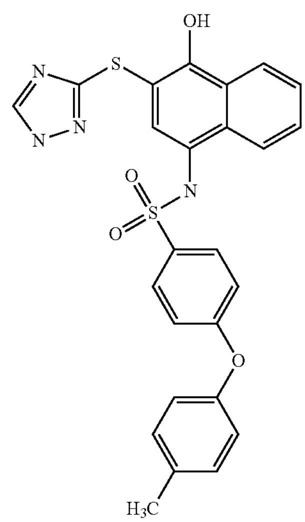 [SMILES: Cc1ccc(Oc2ccc(S(=O)(=O)Nc3cc(Sc4nc[nH]n4)c(O)c4ccccc34)cc2)cc1] | C25H20N4O4S2 | 504.5906 | 5.606 |
| F5749-0215 | 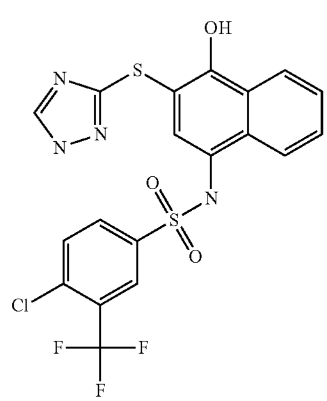 [SMILES: O=S(=O)(Nc1cc(Sc2nc[nH]n2)c(O)c2ccccc12)c1ccc(Cl)c(C(F)(F)F)c1] | C19H12ClF3N4O3S2 | 500.9087 | 5.25976 |

TABLE 9-continued

| IDNUMBER | Structure | Formula structure | MW | LogP |
|---|---|---|---|---|
| F5749-0216 | 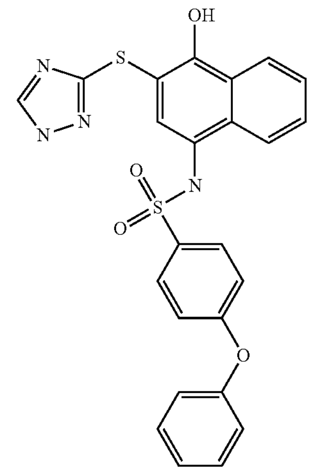 [SMILES: O=S(=O)(Nc1cc(Sc2nc[nH]n2)c(O)c2ccccc12)c1ccc(Oc2ccccc2)cc1] | C24H18N4O4S2 | 490.5635 | 5.308 |
| F5749-0217 | 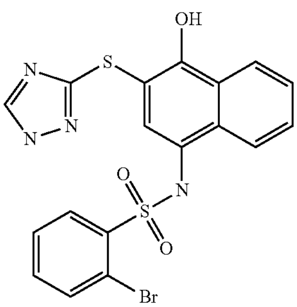 [SMILES: O=S(=O)(Nc1cc(Sc2nc[nH]n2)c(O)c2ccccc12)c1ccccc1Br] | C18H13BrN4O3S2 | 477.3613 | 4.494 |
| F5749-0218 | 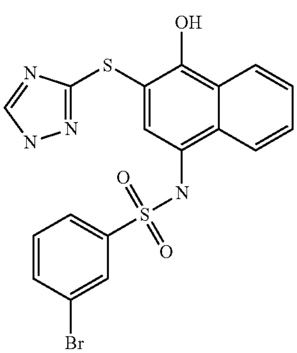 | C18H13BrN4O3S2 | 477.3613 | 4.533 |
| F5749-0219 | 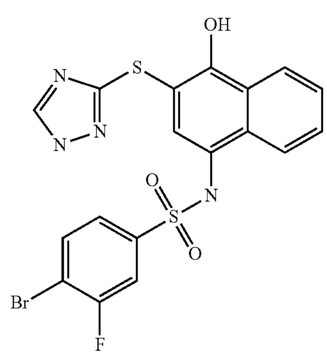 [SMILES: O=S(=O)(Nc1cc(Sc2nc[nH]n2)c(O)c2ccccc12)c1ccc(Br)c(F)c1] | C18H12BrFN4O3S2 | 495.3517 | 4.684 |

TABLE 9-continued

| IDNUMBER | Structure | Formula structure | MW | LogP |
|---|---|---|---|---|
| F5749-0220 | 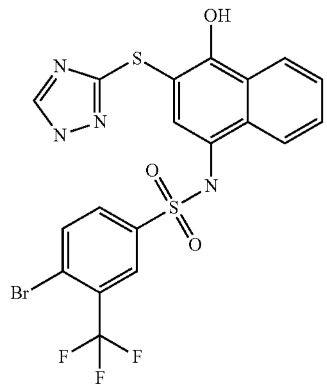 [SMILES: O=S(=O)(Nc1cc(Sc2nc[nH]n2)c(O)c2ccccc12)c1ccc(Br)c(C(F)(F)F)c1] | C19H12BrF3N4O3S2 | 545.3597 | 5.46576 |
| F5749-0221 | 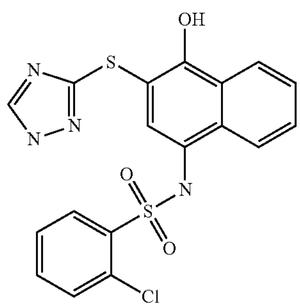 | C18H13ClN4O3S2 | 432.9103 | 4.288 |
| F5749-0222 | 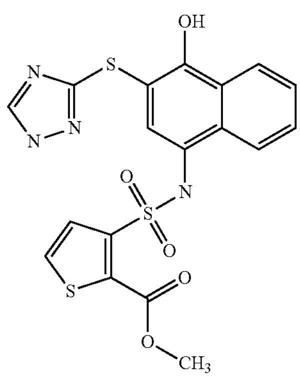 [SMILES: COC(=O)c1sccc1S(=O)(=O)Nc1cc(Sc2nc[nH]n2)c(O)c2ccccc12] | C18H14N4O5S3 | 462.5281 | 2.898 |
| F5749-0223 | 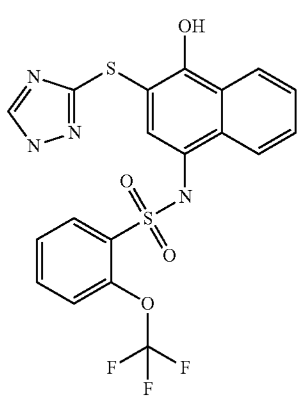 [SMILES: O=S(=O)(Nc1cc(Sc2nc[nH]n2)c(O)c2ccccc12)c1ccccc1OC(F)(F)F] | C19H13F3N4O4S2 | 482.4631 | 5.09476 |

TABLE 10

| IDNUMBER | Structure | Formula structure | MW | LogP |
| --- | --- | --- | --- | --- |
| F0808-0128 | 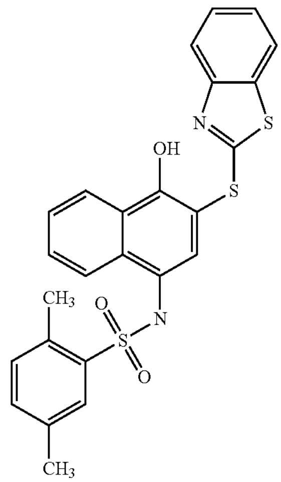 [SMILES: Cc1ccc(C)c(S(=O)(=O)Nc2cc(Sc3nc4ccccc4s3)c(O)c3ccccc23)c1] | C25H20N2O3S3 | 492.6418 | 6.892 |
| F0808-0132 | 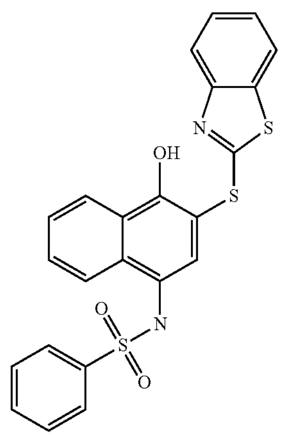 [SMILES: O=S(=O)(Nc1cc(Sc2nc3ccccc3s2)c(O)c2ccccc12)c1ccccc1] | C23H16N2O3S3 | 464.5876 | 6.261 |
| F0808-0133 | 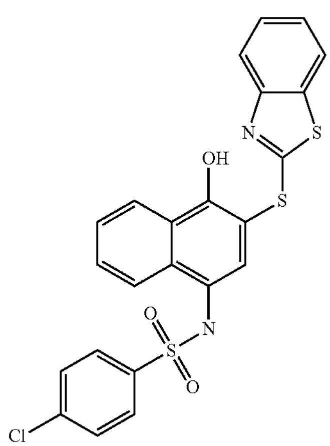 [SMILES: O=S(=O)(Nc1cc(Sc2nc3ccccc3s2)c(O)c2ccccc12)c1ccc(Cl)cc1] | C23H15ClN2O3S3 | 499.0326 | 6.853 |

TABLE 10-continued
| IDNUMBER | Structure | Formula structure | MW | LogP |
|---|---|---|---|---|
| F0808-0134 | 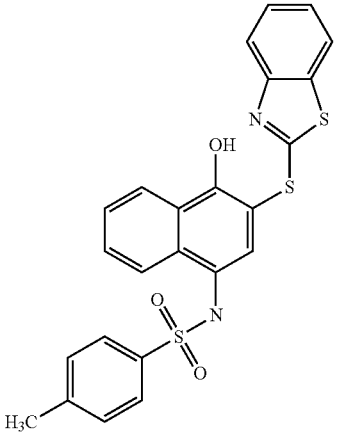 [SMILES: Cc1ccc(S(=O)(=O)Nc2cc(Sc3nc4ccccc4s3)c(O)c3ccccc23)cc1] | C24H18N2O3S3 | 478.6147 | 6.559 |
| F0808-0136 | 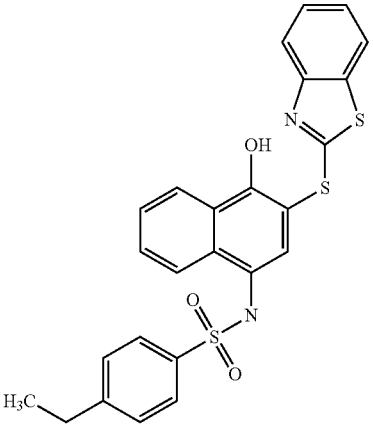 [SMILES: CCc1ccc(S(=O)(=O)Nc2cc(Sc3nc4ccccc4s3)c(O)c3ccccc23)cc1] | C25H20N2O3S3 | 492.6418 | 7.034 |
| F0808-0137 | 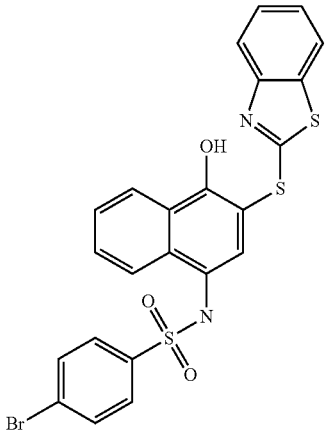 [SMILES: O=S(=O)(Nc1cc(Sc2nc3ccccc3s2)c(O)c2ccccc12)c1ccc(Br)cc1] | C23H15BrN2O3S3 | 543.4836 | 7.059 |

TABLE 10-continued
| IDNUMBER | Structure | Formula structure | MW | LogP |
|---|---|---|---|---|
| F1269-0225 | 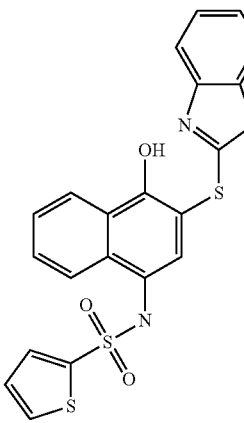 | C21H14N2O3S4 | 470.6133 | 5.774 |
| F1269-1420 | 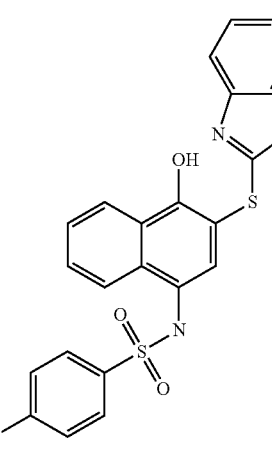 | C24H18N2O4S3 | 494.6141 | 6.217 |
| F1566-1144 | 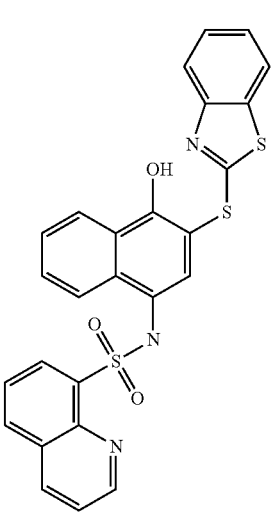 [SMILES: O=S(=O)(Nc1cc(Sc2nc3ccccc3s2)c(O)c2ccccc12)c1cccc2cccnc12] | C26H17N3O3S3 | 515.6357 | 6.461 |

TABLE 10-continued

| IDNUMBER | Structure | Formula structure | MW | LogP |
|---|---|---|---|---|
| F1566-1584 | 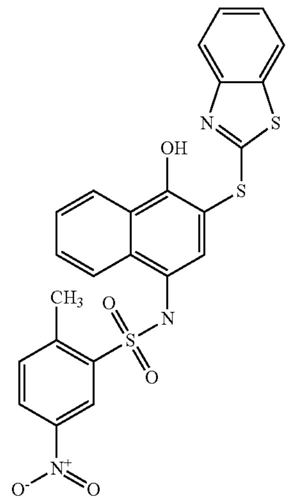 [SMILES: Cc1ccc([N+](=O)[O-])cc1S(=O)(=O)Nc1cc(Sc2nc3ccccc3s2)c(O)c2ccccc12] | C24H17N3O5S3 | 523.6122 | 6.529 |
| F1566-1596 | 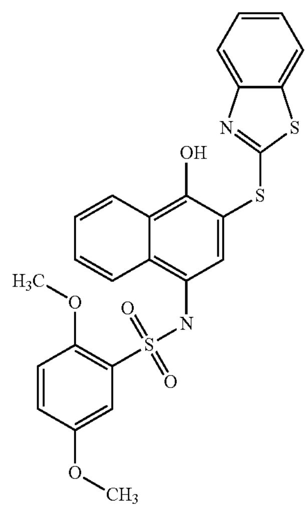 [SMILES: COc1ccc(OC)c(S(=O)(=O)Nc2cc(Sc3nc4ccccc4s3)c(O)c3ccccc23)c1] | C25H20N2O5S3 | 524.6406 | 6.208 |
| F1566-1816 | 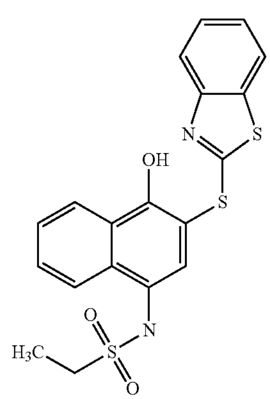 [SMILES: CCS(=O)(=O)Nc1cc(Sc2nc3ccccc3s2)c(O)c2ccccc12] | C19H16N2O3S3 | 416.543 | 5.12 |

TABLE 10-continued

| IDNUMBER | Structure | Formula structure | MW | LogP |
|---|---|---|---|---|
| F1566-1830 | 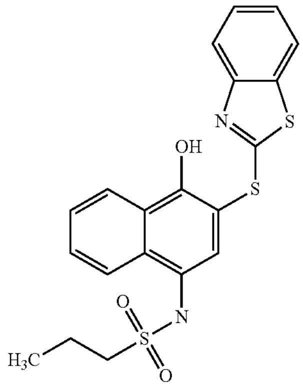 [SMILES: CCCS(=O)(=O)Nc1cc(Sc2nc3ccccc3s2)c(O)c2ccccc12] | C20H18N2O3S3 | 430.5701 | 5.562 |
| F1566-1844 | 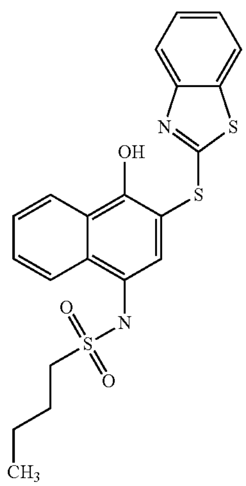 [SMILES: CCCCS(=O)(=O)Nc1cc(Sc2nc3ccccc3s2)c(O)c2ccccc12] | C21H20N2O3S3 | 444.5972 | 6.004 |
| F1566-1858 | 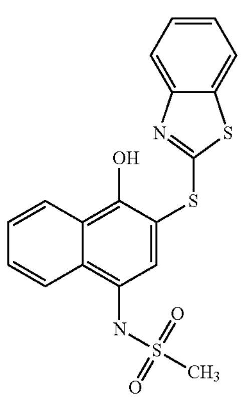 [SMILES: CS(=O)(=O)Nc1cc(Sc2nc3ccccc3s2)c(O)c2ccccc12] | C18H14N2O3S3 | 402.5159 | 4.607 |

TABLE 10-continued

| IDNUMBER | Structure | Formula structure | MW | LogP |
|---|---|---|---|---|
| F5749-0224 | 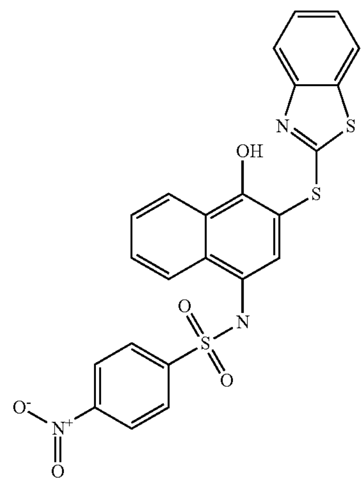 [SMILES: O=[N+]([O-])c1ccc(S(=O)(=O)Nc2cc(Sc3nc4ccccc4s3)c(O)c3ccccc23)cc1] | C23H15N3O5S3 | 509.5851 | 6.196 |
| F5749-0225 | 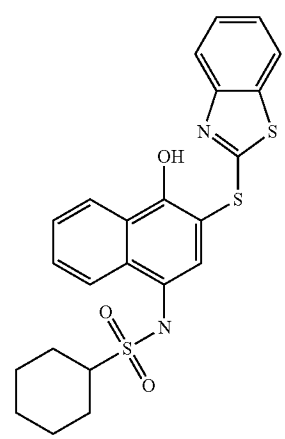 [SMILES: O=S(=O)(Nc1cc(Sc2nc3ccccc3s2)c(O)c2ccccc12)C1CCCCC1] | C23H22N2O3S3 | 470.6354 | 6.586 |
| F5749-0226 | 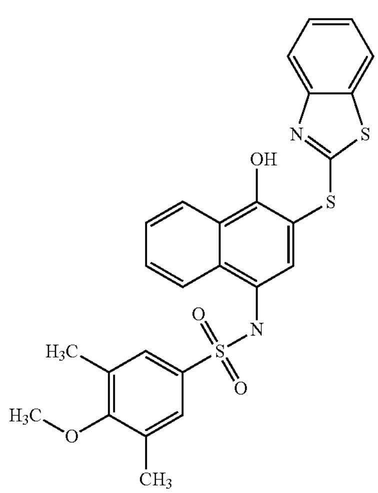 [SMILES: COc1c(C)cc(S(=O)(=O)Nc2cc(Sc3nc4ccccc4s3)c(O)c3ccccc23)cc1C] | C26H22N2O4S3 | 522.6682 | 6.883 |

TABLE 10-continued

| IDNUMBER | Structure | Formula structure | MW | LogP |
| --- | --- | --- | --- | --- |
| F5749-0227 | 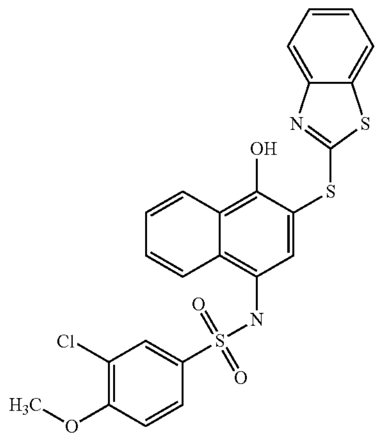 [SMILES: COc1ccc(S(=O)(=O)Nc2cc(Sc3nc4ccccc4s3)c(O)c3ccccc23)cc1Cl] | C24H17ClN2O4S3 | 529.0591 | 6.844 |
| F5749-0228 | 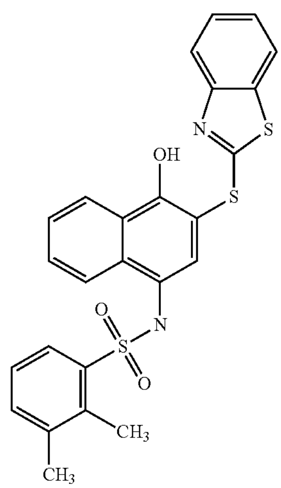 [SMILES: Cc1cccc(S(=O)(=O)Nc2cc(Sc3nc4ccccc4s3)c(O)c3ccccc23)c1C] | C25H20N2O3S3 | 492.6418 | 6.853 |
| F5749-0229 | 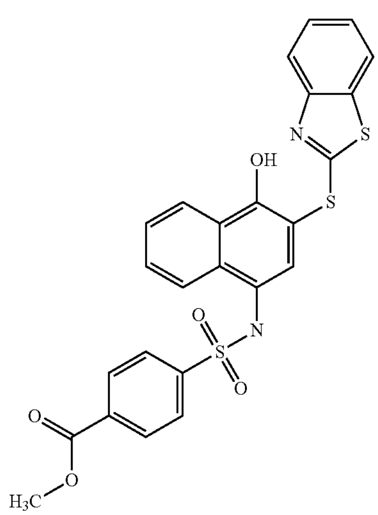 [SMILES: COC(=O)c1ccc(S(=O)(=O)Nc2cc(Sc3nc4ccccc4s3)c(O)c3ccccc23)cc1] | C25H18N2O5S3 | 522.6246 | 6.202 |

TABLE 10-continued

| IDNUMBER | Structure | Formula structure | MW | LogP |
|---|---|---|---|---|
| F5749-0230 | 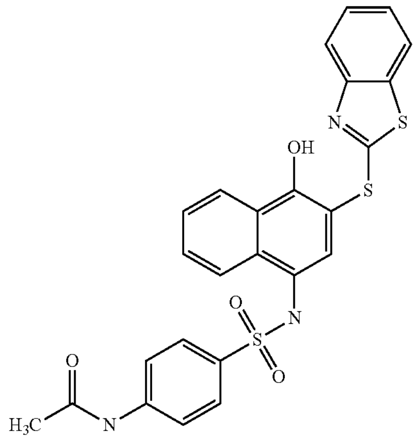 [SMILES: CC(=O)Nc1ccc(S(=O)(=O)Nc2cc(Sc3nc4ccccc4s3)c(O)c3ccccc23)cc1] | C25H19N3O4S3 | 521.6399 | 5.552 |
| F5749-0231 | 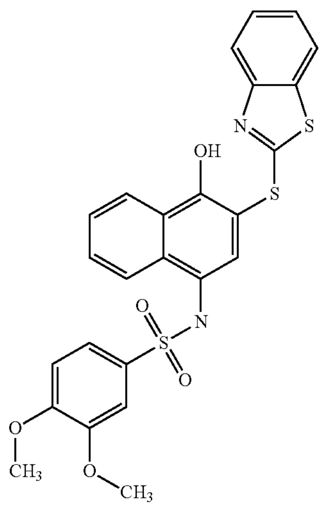 [SMILES: COc1ccc(S(=O)(=O)Nc2cc(Sc3nc4ccccc4s3)c(O)c3ccccc23)cc1OC] | C25H20N2O5S3 | 524.6406 | 5.95974 |
| F5749-0232 | 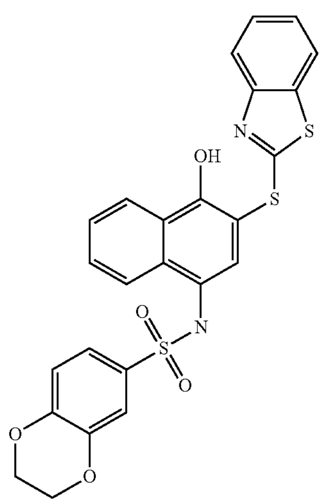 [SMILES: O=S(=O)(Nc1cc(Sc2nc3ccccc3s2)c(O)c2ccccc12)c1ccc2c(c1)OCCO2] | C25H18N2O5S3 | 522.6246 | 5.856 |

TABLE 10-continued

| IDNUMBER | Structure | Formula structure | MW | LogP |
| --- | --- | --- | --- | --- |
| F5749-0233 | 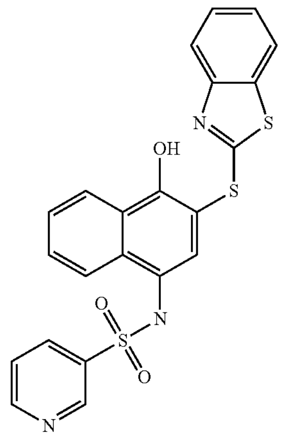 [SMILES: O=S(=O)(Nc1cc(Sc2nc3ccccc3s2)c(O)c2ccccc12)c1cccnc1] | C22H15N3O3S3 | 465.5752 | 5.028 |
| F5749-0234 | 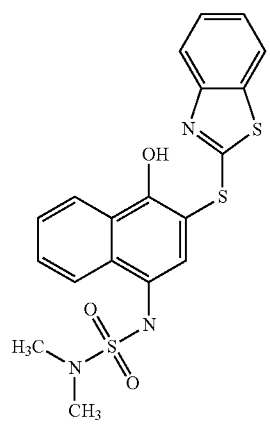 | C19H17N3O3S3 | 431.5576 | 4.155 |
| F5749-0235 | 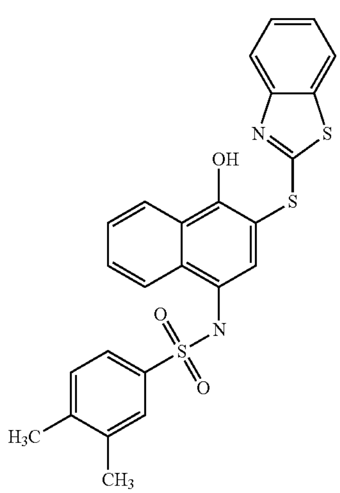 [SMILES: Cc1ccc(S(=O)(=O)Nc2cc(Sc3nc4ccccc4s3)c(O)c3ccccc23)cc1C] | C25H20N2O3S3 | 492.6418 | 6.892 |

TABLE 10-continued

| IDNUMBER | Structure | Formula structure | MW | LogP |
|---|---|---|---|---|
| F5749-0236 | 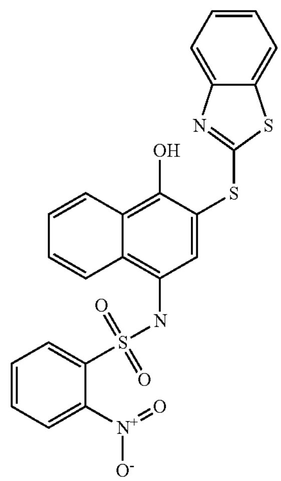 [SMILES: O=[N+]([O-])c1ccccc1S(=O)(=O)Nc1cc(Sc2nc3ccccc3s2)c(O)c2ccccc12] | C23H15N3O5S3 | 509.5851 | 6.194 |
| F5749-0237 | 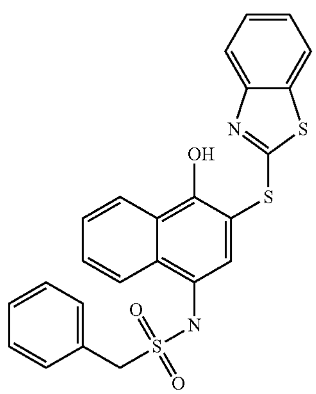 [SMILES: O=S(=O)(Cc1ccccc1)Nc1cc(Sc2nc3ccccc3s2)c(O)c2ccccc12] | C24H18N2O3S3 | 478.6147 | 6.395 |
| F5749-0238 | 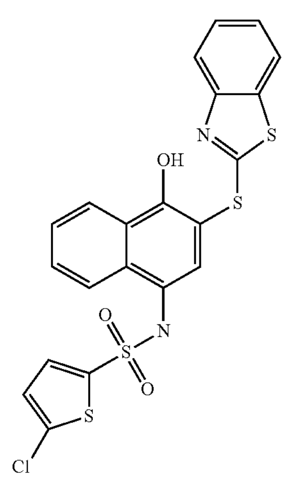 [SMILES: O=S(=O)(Nc1cc(Sc2nc3ccccc3s2)c(O)c2ccccc12)c1ccc(Cl)s1] | C21H13ClN2O3S4 | 505.0584 | 7.064 |

TABLE 10-continued

| IDNUMBER | Structure | Formula structure | MW | LogP |
|---|---|---|---|---|
| F5749-0239 | 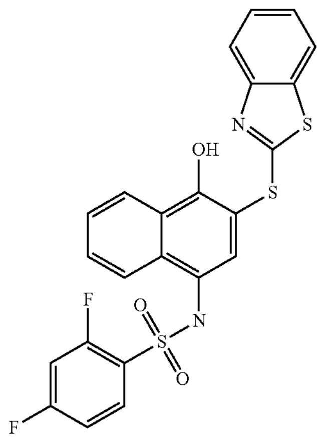 [SMILES: O=S(=O)(Nc1cc(Sc2nc3ccccc3s2)c(O)c2ccccc12)c1ccc(F)cc1F] | C23H14F2N2O3S3 | 500.5684 | 6.602 |
| F5749-0240 | 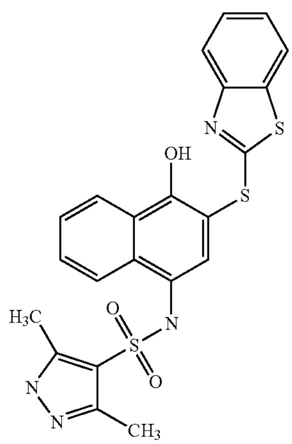 [SMILES: Cc1n[nH]c(C)c1S(=O)(=O)Nc1cc(Sc2nc3ccccc3s2)c(O)c2ccccc12] | C22H18N4O3S3 | 482.6058 | 5.371 |
| F5749-0241 | 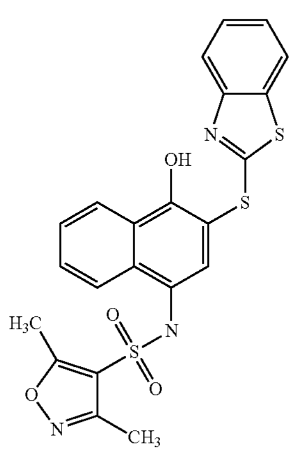 [SMILES: Cc1noc(C)c1S(=O)(=O)Nc1cc(Sc2nc3ccccc3s2)c(O)c2ccccc12] | C22H17N3O4S3 | 483.5905 | 5.405 |

TABLE 10-continued

| IDNUMBER | Structure | Formula structure | MW | LogP |
| --- | --- | --- | --- | --- |
| F5749-0242 | 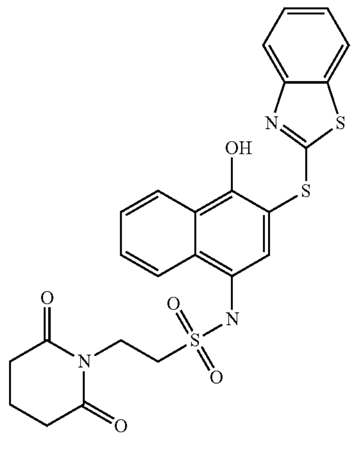 [SMILES: O=C1CCCC(=O)N1CCS(=O)(=O)Nc1cc(Sc2nc3ccccc3s2)c(O)c2ccccc12] | C24H21N3O5S3 | 527.6441 | 4.048 |
| F5749-0243 | 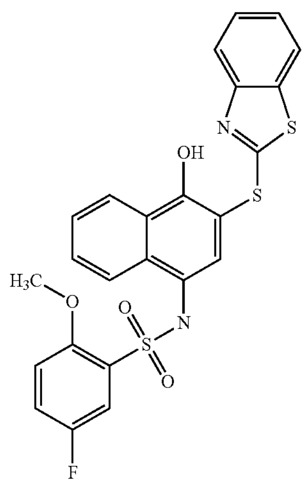 [SMILES: COc1ccc(F)cc1S(=O)(=O)Nc1cc(Sc2nc3ccccc3s2)c(O)c2ccccc12] | C24H17FN2O4S3 | 512.6045 | 6.405 |
| F5749-0244 | 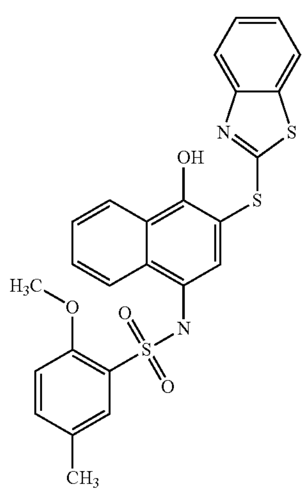 [SMILES: COc1ccc(C)cc1S(=O)(=O)Nc1cc(Sc2nc3ccccc3s2)c(O)c2ccccc12] | C25H20N2O4S3 | 508.6412 | 6.55 |

TABLE 10-continued

| IDNUMBER | Structure | Formula structure | MW | LogP |
|---|---|---|---|---|
| F5749-0245 | 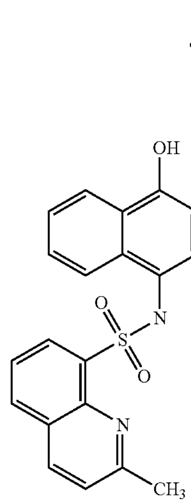 | C27H19N3O3S3 | 529.6628 | 6.72 |
| F5749-0246 | 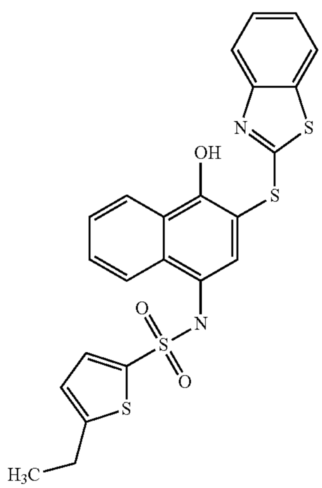 [SMILES: CCc1ccc(S(=O)(=O)Nc2cc(Sc3nc4ccccc4s3)c(O)c3ccccc23)s1] | C23H18N2O3S4 | 498.6675 | 6.912 |
| F5749-0247 | 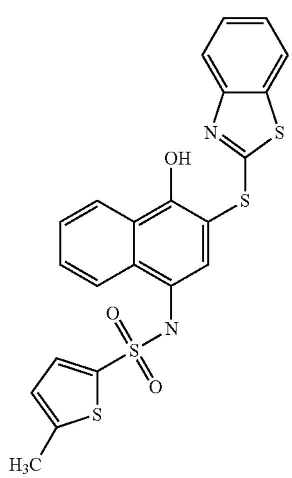 [SMILES: Cc1ccc(S(=O)(=O)Nc2cc(Sc3nc4ccccc4s3)c(O)c3ccccc23)s1] | C22H16N2O3S4 | 484.6404 | 6.437 |

TABLE 10-continued

| IDNUMBER | Structure | Formula structure | MW | LogP |
| --- | --- | --- | --- | --- |
| F5749-0248 | 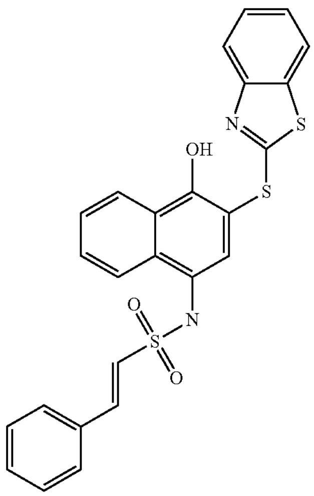 [SMILES: O=S(=O)(/C=C/c1ccccc1)Nc1cc(Sc2nc3ccccc3s2)c(O)c2ccccc12] | C25H18N2O3S3 | 490.6258 | 6.619 |
| F5749-0249 | 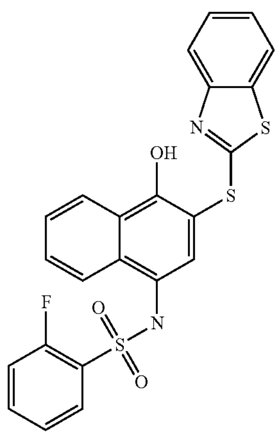 [SMILES: O=S(=O)(Nc1cc(Sc2nc3ccccc3s2)c(O)c2ccccc12)c1ccccc1F] | C23H15FN2O3S3 | 482.578 | 6.412 |
| F5749-0250 | 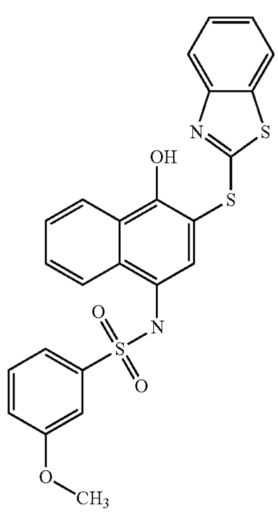 [SMILES: COc1cccc(S(=O)(=O)Nc2cc(Sc3nc4ccccc4s3)c(O)c3ccccc23)c1] | C24H18N2O4S3 | 494.6141 | 6.254 |

TABLE 10-continued

| IDNUMBER | Structure | Formula structure | MW | LogP |
|---|---|---|---|---|
| F5749-0251 | 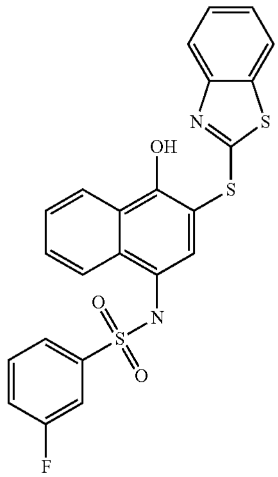 [SMILES: O=S(=O)(Nc1cc(Sc2nc3ccccc3s2)c(O)c2ccccc12)c1cccc(F)c1] | C23H15FN2O3S3 | 482.578 | 6.451 |
| F5749-0252 | 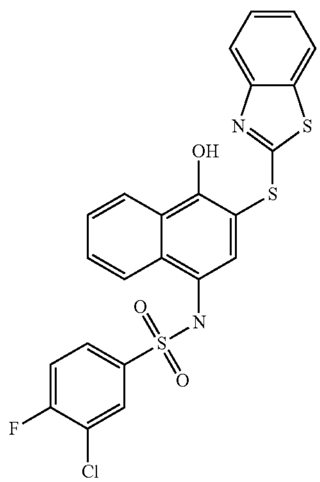 [SMILES: O=S(=O)(Nc1cc(Sc2nc3ccccc3s2)c(O)c2ccccc12)c1ccc(F)c(Cl)c1] | C23H14ClFN2O3S3 | 517.023 | 7.041 |
| F5749-0253 | 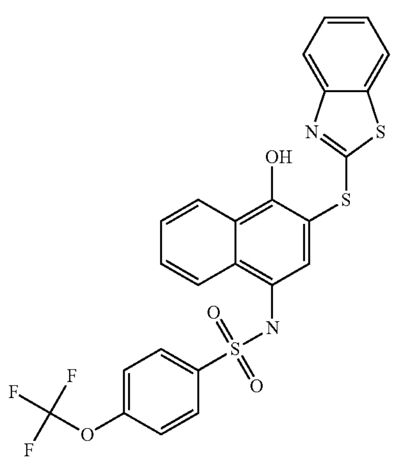 [SMILES: O=S(=O)(Nc1cc(Sc2nc3ccccc3s2)c(O)c2ccccc12)c1ccc(OC(F)(F)F)cc1] | C24H15F3N2O4S3 | 548.5854 | 7.65976 |

TABLE 10-continued

| IDNUMBER | Structure | Formula structure | MW | LogP |
| --- | --- | --- | --- | --- |
| F5749-0254 | 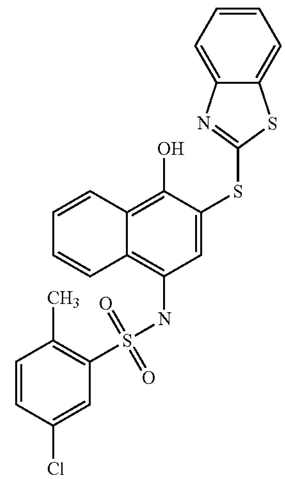 [SMILES: Cc1ccc(Cl)cc1S(=O)(=O)Nc1cc(Sc2nc3ccccc3s2)c(O)c2ccccc12] | C24H17ClN2O3S3 | 513.0597 | 7.186 |
| F5749-0255 | 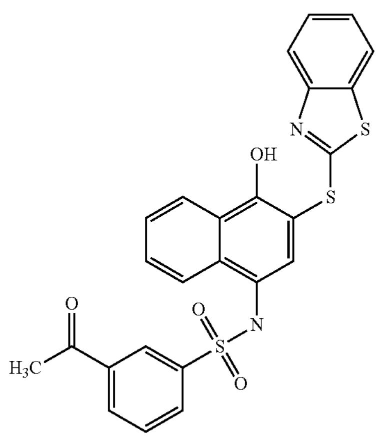 [SMILES: CC(=O)c1cccc(S(=O)(=O)Nc2cc(Sc3nc4ccccc4s3)c(O)c3ccccc23)c1] | C25H18N2O4S3 | 506.6252 | 6.151 |
| F5749-0256 | 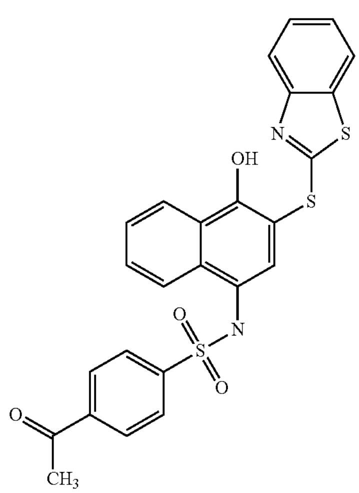 [SMILES: CC(=O)c1ccc(S(=O)(=O)Nc2cc(Sc3nc4ccccc4s3)c(O)c3ccccc23)cc1] | C25H18N2O4S3 | 506.6252 | 6.114 |

TABLE 10-continued

| IDNUMBER | Structure | Formula structure | MW | LogP |
| --- | --- | --- | --- | --- |
| F5749-0257 | 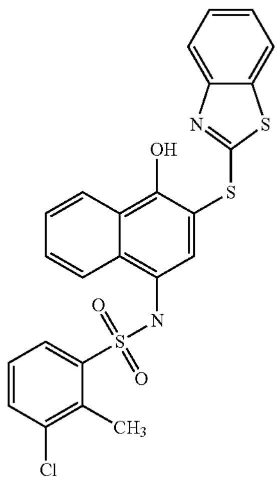 [SMILES: Cc1c(Cl)cccc1S(=O)(=O)Nc1cc(Sc2nc3ccccc3s2)c(O)c2ccccc12] | C24H17ClN2O3S3 | 513.0597 | 7.147 |
| F5749-0258 | 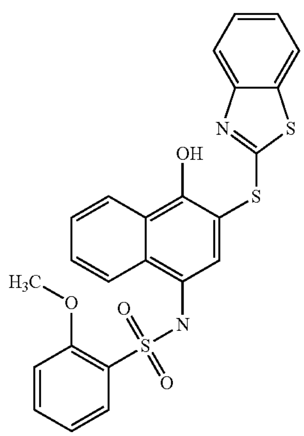 [SMILES: COc1ccccc1S(=O)(=O)Nc1cc(Sc2nc3ccccc3s2)c(O)c2ccccc12] | C24H18N2O4S3 | 494.6141 | 6.215 |
| F5749-0259 | 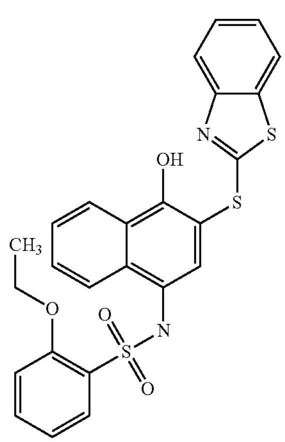 [SMILES: CCOc1ccccc1S(=O)(=O)Nc1cc(Sc2nc3ccccc3s2)c(O)c2ccccc12] | C25H20N2O4S3 | 508.6412 | 6.556 |

TABLE 10-continued

| IDNUMBER | Structure | Formula structure | MW | LogP |
|---|---|---|---|---|
| F5749-0260 | 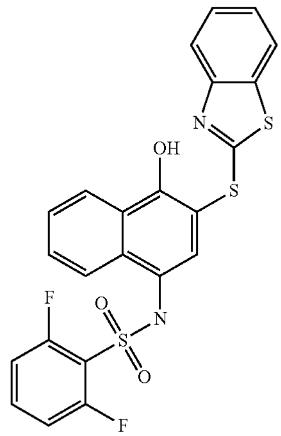 [SMILES: O=S(=O)(Nc1cc(Sc2nc3ccccc3s2)c(O)c2ccccc12)c1c(F)cccc1F] | C23H14F2N2O3S3 | 500.5684 | 6.563 |
| F5749-0261 | 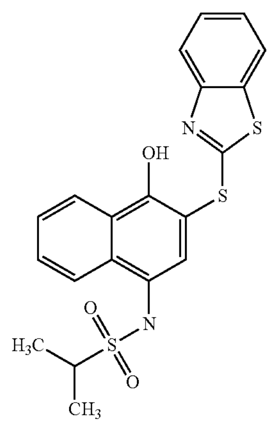 [SMILES: CC(C)S(=O)(=O)Nc1cc(Sc2nc3ccccc3s2)c(O)c2ccccc12] | C20H18N2O3S3 | 430.5701 | 5.754 |
| F5749-0262 | 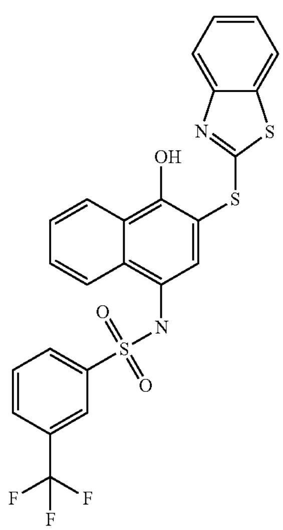 [SMILES: O=S(=O)(Nc1cc(Sc2nc3ccccc3s2)c(O)c2ccccc12)c1cccc(C(F)(F)F)c1] | C24H15F3N2O3S3 | 532.586 | 7.23276 |

TABLE 10-continued

| IDNUMBER | Structure | Formula structure | MW | LogP |
| --- | --- | --- | --- | --- |
| F5749-0263 | 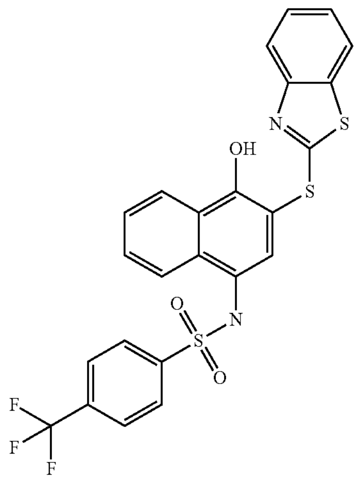 [SMILES: O=S(=O)(Nc1cc(Sc2nc3ccccc3s2)c(O)c2ccccc12)c1ccc(C(F)(F)F)cc1] | C24H15F3N2O3S3 | 532.586 | 7.19576 |
| F5749-0264 | 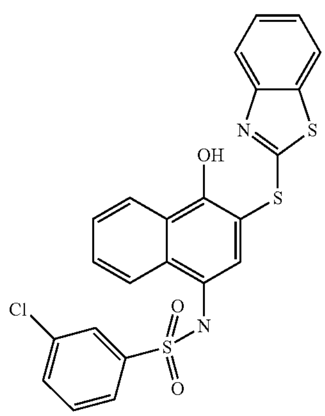 [SMILES: O=S(=O)(Nc1cc(Sc2nc3ccccc3s2)c(O)c2ccccc12)c1cccc(Cl)c1] | C23H15ClN2O3S3 | 499.0326 | 6.89 |
| F5749-0265 | 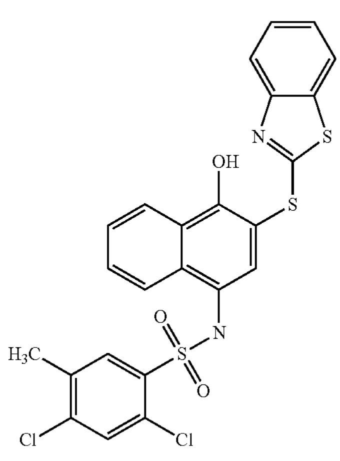 [SMILES: Cc1cc(S(=O)(=O)Nc2cc(Sc3nc4ccccc4s3)c(O)c3ccccc23)c(Cl)cc1Cl] | C24H16Cl2N2O3S3 | 547.5047 | 7.813 |

TABLE 10-continued

| IDNUMBER | Structure | Formula structure | MW | LogP |
|---|---|---|---|---|
| F5749-0266 | 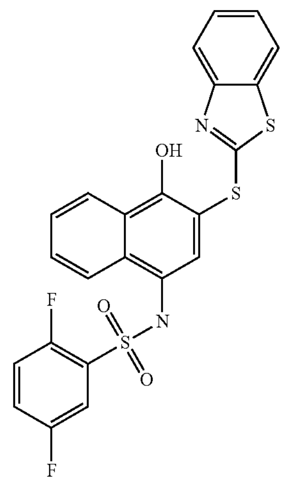 [SMILES: O=S(=O)(Nc1cc(Sc2nc3ccccc3s2)c(O)c2ccccc12)c1cc(F)ccc1F] | C23H14F2N2O3S3 | 500.5684 | 6.602 |
| F5749-0267 | 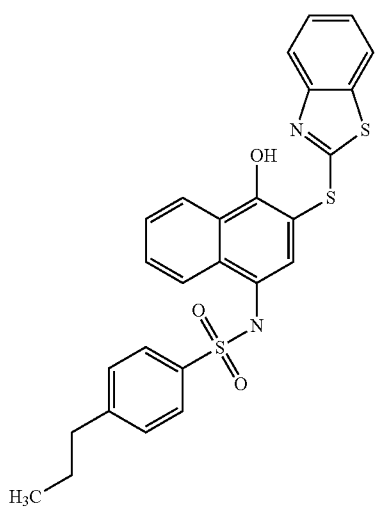 [SMILES: CCCc1ccc(S(=O)(=O)Nc2cc(Sc3nc4ccccc4s3)c(O)c3ccccc23)cc1] | C26H22N2O3S3 | 506.6688 | 7.476 |
| F5749-0268 | 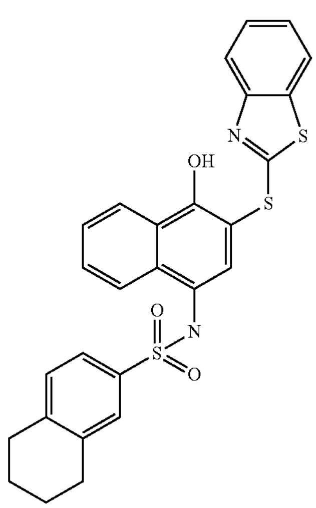 [SMILES: O=S(=O)(Nc1cc(Sc2nc3ccccc3s2)c(O)c2ccccc12)c1ccc2c(c1)CCCC2] | C27H22N2O3S3 | 518.68 | 7.348 |

TABLE 10-continued

| IDNUMBER | Structure | Formula structure | MW | LogP |
| --- | --- | --- | --- | --- |
| F5749-0269 | 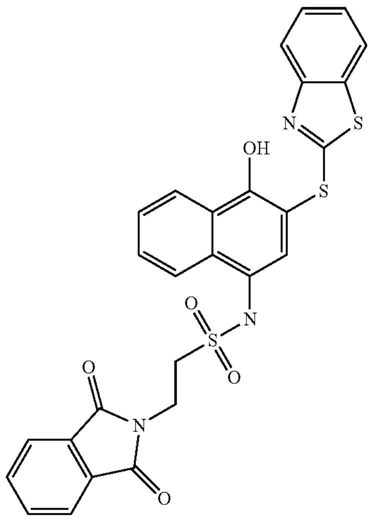 [SMILES: O=C1c2ccccc2C(=O)N1CCS(=O)(=O)Nc1cc(Sc2nc3ccccc3s2)c(O)c2ccccc12] | C27H19N3O5S3 | 561.6616 | 5.388 |
| F5749-0270 | 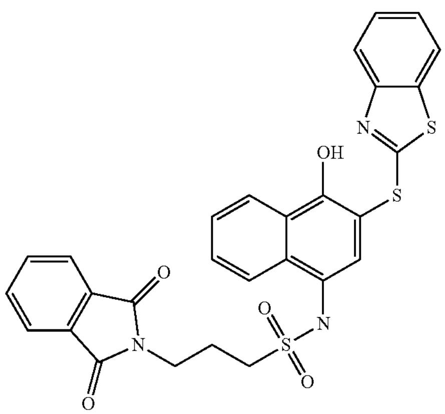 [SMILES: O=C1c2ccccc2C(=O)N1CCCS(=O)(=O)Nc1cc(Sc2nc3ccccc3s2)c(O)c2ccccc12] | C28H21N3O5S3 | 575.6887 | 5.83 |
| F5749-0271 | 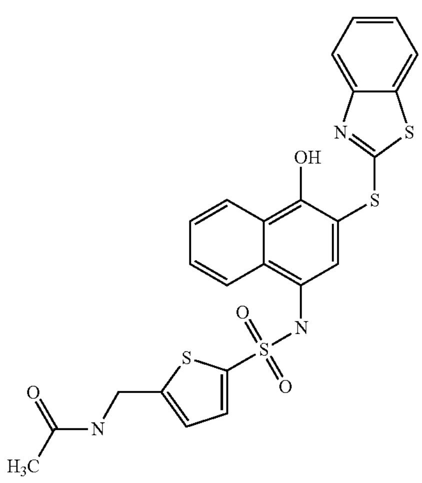 [SMILES: CC(=O)NCc1ccc(S(=O)(=O)Nc2cc(Sc3nc4ccccc4s3)c(O)c3ccccc23)s1] | C24H19N3O4S4 | 541.6927 | 5.564 |

TABLE 10-continued

| IDNUMBER | Structure | Formula structure | MW | LogP |
| --- | --- | --- | --- | --- |
| F5749-0272 | 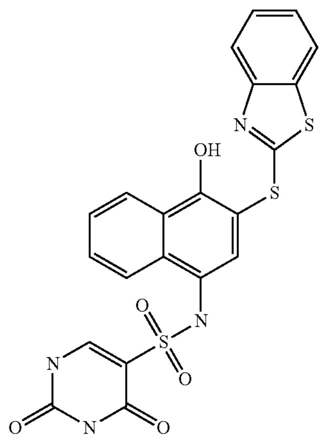 [SMILES: O=c1[nH]cc(S(=O)(=O)Nc2cc(Sc3nc4ccccc4s3)c(O)c3ccccc23)c(=O)[nH]1] | C21H14N4O5S3 | 498.5615 | 3.306 |
| F5749-0273 | 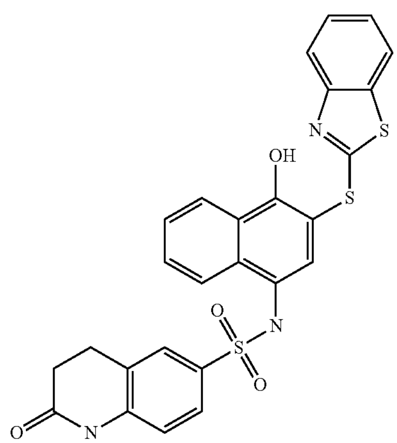 [SMILES: O=C1CCc2cc(S(=O)(=O)Nc3cc(Sc4nc5ccccc5s4)c(O)c4ccccc34)ccc2N1] | C26H19N3O4S3 | 533.651 | 5.457 |
| F5749-0274 | 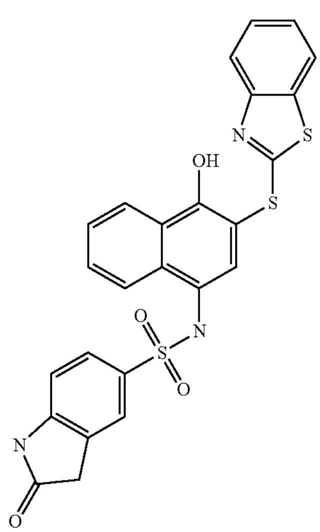 [SMILES: O=C1Cc2cc(S(=O)(=O)Nc3cc(Sc4nc5ccccc5s4)c(O)c4ccccc34)ccc2N1] | C25H17N3O4S3 | 519.6239 | 5.369 |

TABLE 10-continued

| IDNUMBER | Structure | Formula structure | MW | LogP |
|---|---|---|---|---|
| F5749-0275 | 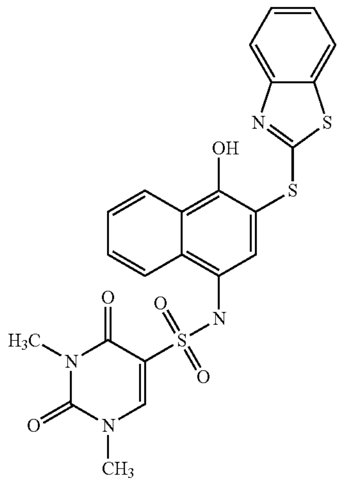 [SMILES: Cn1cc(S(=O)(=O)Nc2cc(Sc3nc4ccccc4s3)c(O)c3ccccc23)c(=O)n(C)c1=O] | C23H18N4O5S3 | 526.6157 | 3.37 |
| F5749-0276 | 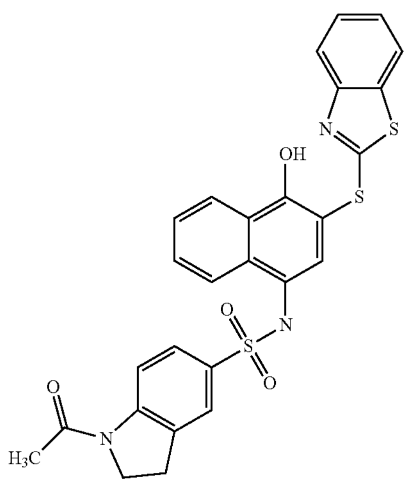 [SMILES: CC(=O)N1CCc2cc(S(=O)(=O)Nc3cc(Sc4nc5ccccc5s4)c(O)c4ccccc34)ccc21] | C27H21N3O4S3 | 547.6781 | 5.692 |
| F5749-0277 | 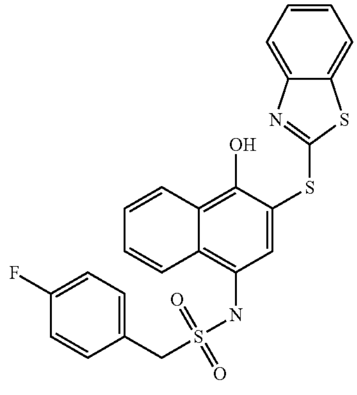 [SMILES: O=S(=O)(Cc1ccc(F)cc1)Nc1cc(Sc2nc3ccccc3s2)c(O)c2ccccc12] | C24H17FN2O3S3 | 496.6051 | 6.548 |

TABLE 10-continued

| IDNUMBER | Structure | Formula structure | MW | LogP |
|---|---|---|---|---|
| F5749-0278 | 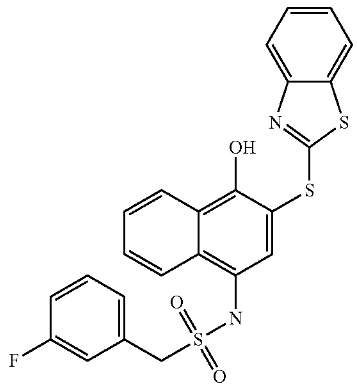 [SMILES: O=S(=O)(Cc1cccc(F)c1)Nc1cc(Sc2nc3ccccc3s2)c(O)c2ccccc12] | C24H17FN2O3S3 | 496.6051 | 6.585 |
| F5749-0279 | 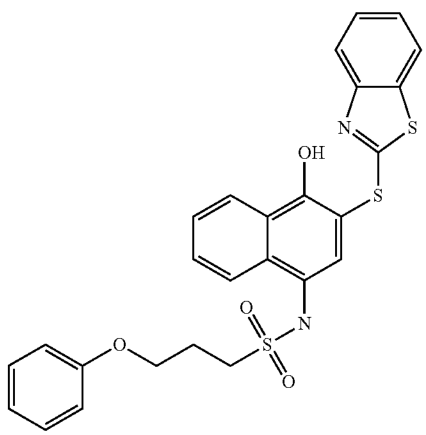 [SMILES: O=S(=O)(CCCOc1ccccc1)Nc1cc(Sc2nc3ccccc3s2)c(O)c2ccccc12] | C26H22N2O4S3 | 522.6682 | 6.621 |
| F5749-0280 | 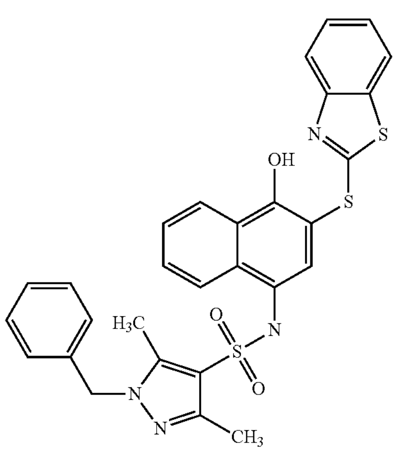 [SMILES: Cc1nn(Cc2ccccc2)c(C)c1S(=O)(=O)Nc1cc(Sc2nc3ccccc3s2)c(O)c2ccccc12] | C29H24N4O3S3 | 572.7316 | 6.54 |

TABLE 10-continued

| IDNUMBER | Structure | Formula structure | MW | LogP |
| --- | --- | --- | --- | --- |
| F5749-0281 | 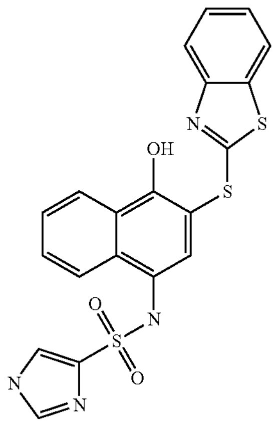 [SMILES: O=S(=O)(Nc1cc(Sc2nc3ccccc3s2)c(O)c2ccccc12)c1c[nH]cn1] | C20H14N4O3S3 | 454.5516 | 4.401 |
| F5749-0282 | 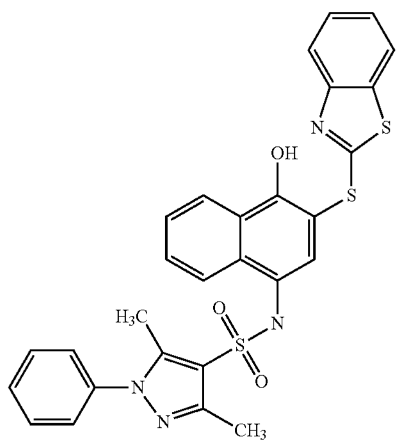 [SMILES: Cc1nn(-c2ccccc2)c(C)c1S(=O)(=O)Nc1cc(Sc2nc3ccccc3s2)c(O)c2ccccc12] | C28H22N4O3S3 | 558.7045 | 6.406 |
| F5749-0283 | 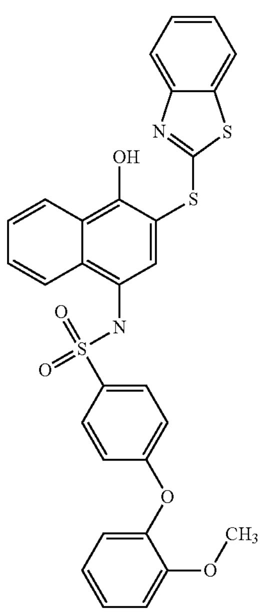 [SMILES: COc1ccccc1Oc1ccc(S(=O)(=O)Nc2cc(Sc3nc4ccccc4s3)c(O)c3ccccc23)cc1] | C30H22N2O5S3 | 586.7122 | 7.57674 |

| IDNUMBER | Structure | Formula structure | MW | LogP |
|---|---|---|---|---|
| F5749-0284 | 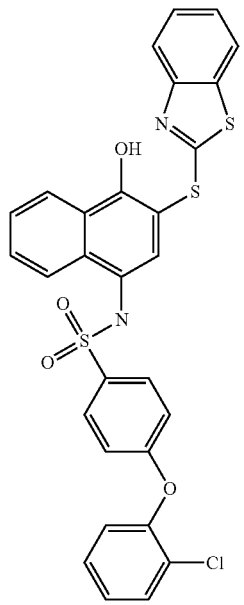 [SMILES: O=S(=O)(Nc1cc(Sc2nc3ccccc3s2)c(O)c2ccccc12)c1ccc(Oc2ccccc2Cl)cc1] | C29H19ClN2O4S3 | 591.1308 | 8.461 |
| F5749-0285 | 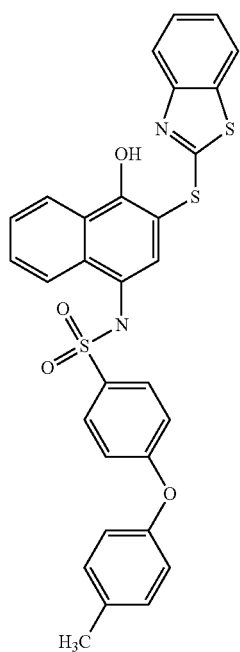 [SMILES: Cc1ccc(Oc2ccc(S(=O)(=O)Nc3cc(Sc4nc5ccccc5s4)c(O)c4ccccc34)cc2)cc1] | C30H22N2O4S3 | 570.7128 | 8.169 |

TABLE 10-continued

| IDNUMBER | Structure | Formula structure | MW | LogP |
| --- | --- | --- | --- | --- |
| F5749-0286 | 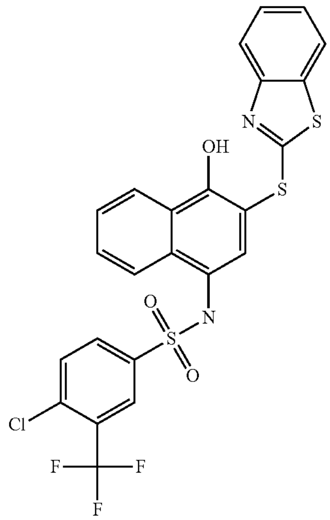 [SMILES: O=S(=O)(Nc1cc(Sc2nc3ccccc3s2)c(O)c2ccccc12)c1ccc(Cl)c(C(F)(F)F)c1] | C24H14ClF3N2O3S3 | 567.031 | 7.82276 |
| F5749-0287 | 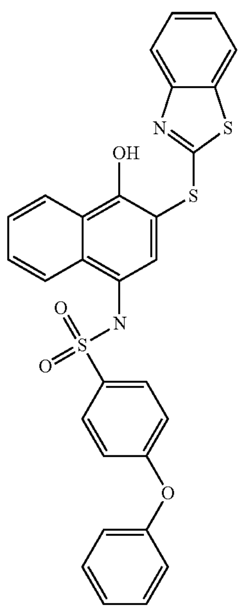 [SMILES: O=S(=O)(Nc1cc(Sc2nc3ccccc3s2)c(O)c2ccccc12)c1ccc(Oc2ccccc2)cc1] | C29H20N2O4S3 | 556.6858 | 7.871 |
| F5749-0288 | 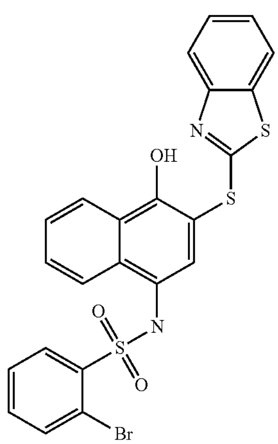 [SMILES: O=S(=O)(Nc1cc(Sc2nc3ccccc3s2)c(O)c2ccccc12)c1ccccc1Br] | C23H15BrN2O3S3 | 543.4836 | 7.057 |

TABLE 10-continued
| IDNUMBER | Structure | Formula structure | MW | LogP |
|---|---|---|---|---|
| F5749-0289 | 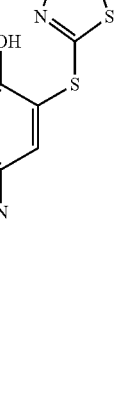 | C23H15BrN2O3S3 | 543.4836 | 7.096 |
| F5749-0290 | 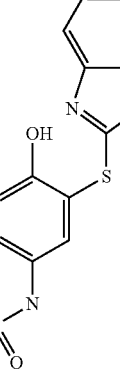 | C23H14BrFN2O3S3 | 561.474 | 7.247 |
| F5749-0291 | 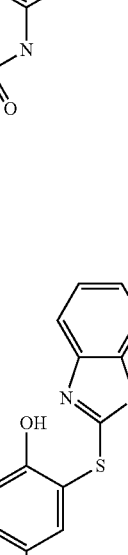 | C24H14BrF3N2O3S3 | 611.482 | 8.02876 |

TABLE 10-continued

| IDNUMBER | Structure | Formula structure | MW | LogP |
| --- | --- | --- | --- | --- |
| F5749-0292 | 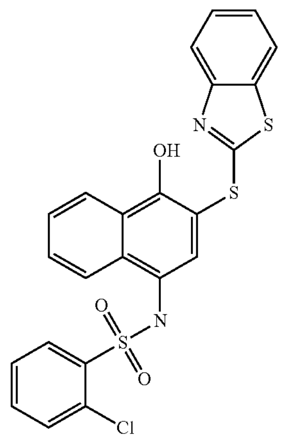 [SMILES: O=S(=O)(Nc1cc(Sc2nc3ccccc3s2)c(O)c2ccccc12)c1ccccc1Cl] | C23H15ClN2O3S3 | 499.0326 | 6.851 |
| F5749-0293 | 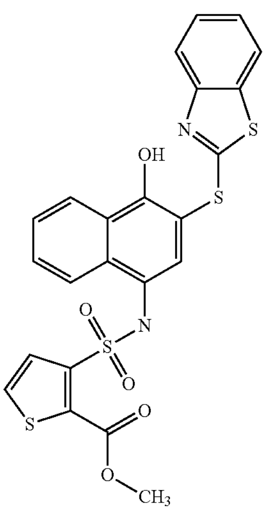 [SMILES: COC(=O)c1sccc1S(=O)(=O)Nc1cc(Sc2nc3ccccc3s2)c(O)c2ccccc12] | C23H16N2O5S4 | 528.6504 | 5.461 |
| F5749-0294 | 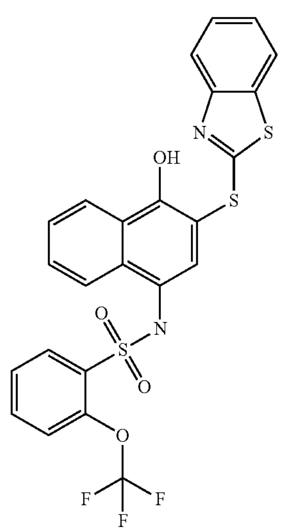 [SMILES: O=S(=O)(Nc1cc(Sc2nc3ccccc3s2)c(O)c2ccccc12)c1ccccc1OC(F)(F)F] | C24H15F3N2O4S3 | 548.5854 | 7.65776 |

TABLE 11

| IDNUMBER | Structure | Formula structure | MW | LogP |
| --- | --- | --- | --- | --- |
| F0433-0038 | 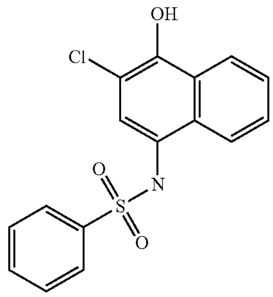 [SMILES: O=S(=O)(Nc1cc(Cl)c(O)c2ccccc12)c1ccccc1] | C16H12ClNO3S | 333.7959 | 4.192 |
| F0433-0041 | 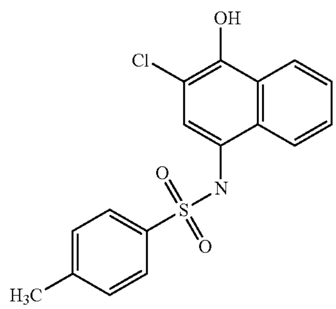 [SMILES: Cc1ccc(S(=O)(=O)Nc2cc(Cl)c(O)c3ccccc23)cc1] | C17H14ClNO3S | 347.823 | 4.49 |
| F0433-0044 | 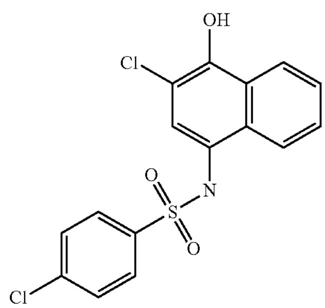 [SMILES: O=S(=O)(Nc1cc(Cl)c(O)c2ccccc12)c1ccc(Cl)cc1] | C16H11Cl2NO3S | 368.241 | 4.784 |
| F0433-0047 | 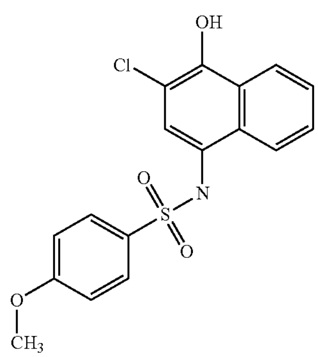 [SMILES: COc1ccc(S(=O)(=O)Nc2cc(Cl)c(O)c3ccccc23)cc1] | C17H14ClNO4S | 363.8224 | 4.148 |
| F0433-0050 | 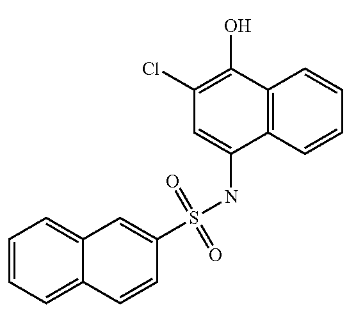 [SMILES: O=S(=O)(Nc1cc(Cl)c(O)c2ccccc12)c1ccc2ccccc2c1] | C20H14ClNO3S | 383.8565 | 5.451 |

TABLE 11-continued

| IDNUMBER | Structure | Formula structure | MW | LogP |
| --- | --- | --- | --- | --- |
| F0808-1895 | 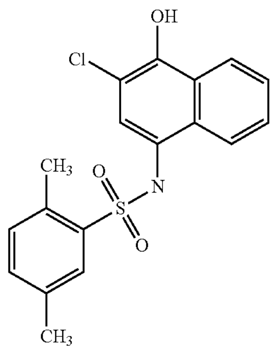 [SMILES: Cc1ccc(C)c(S(=O)(=O)Nc2cc(Cl)c(O)c3ccccc23)c1] | C18H16ClNO3S | 361.8501 | 4.823 |
| F0808-1902 | 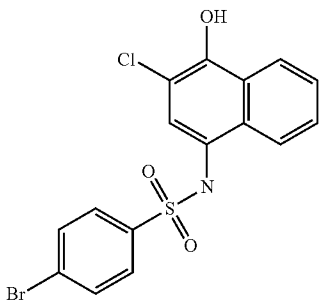 | C16H11BrClNO3S | 412.692 | 4.99 |
| F0808-1909 | 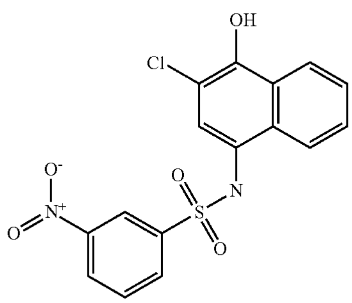 [SMILES: O=[N+]([O-])c1cccc(S(=O)(=O)Nc2cc(Cl)c(O)c3ccccc23)c1] | C16H11ClN2O5S | 378.7935 | 4.164 |
| F0808-1913 | 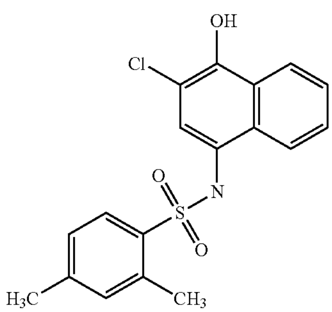 [SMILES: Cc1ccc(S(=O)(=O)Nc2cc(Cl)c(O)c3ccccc23)c(C)c1] | C18H16ClNO3S | 361.8501 | 4.823 |
| F0808-1914 | 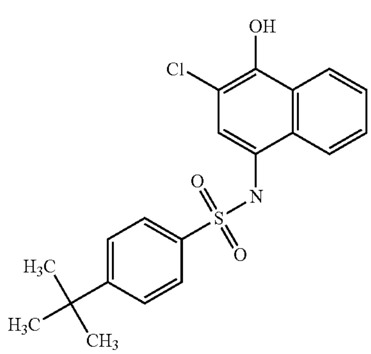 [SMILES: CC(C)(C)c1ccc(S(=O)(=O)Nc2cc(Cl)c(O)c3ccccc23)cc1] | C20H20ClNO3S | 389.9043 | 5.691 |

TABLE 11-continued
| IDNUMBER | Structure | Formula structure | MW | LogP |
|---|---|---|---|---|
| F1269-0272 | 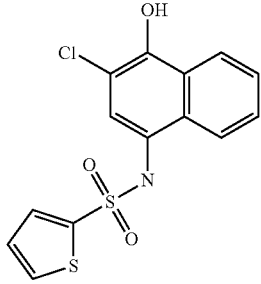 [SMILES: O=S(=O)(Nc1cc(Cl)c(O)c2ccccc12)c1cccs1] | C14H10ClNO3S2 | 339.8217 | 3.705 |
| F1269-1995 | 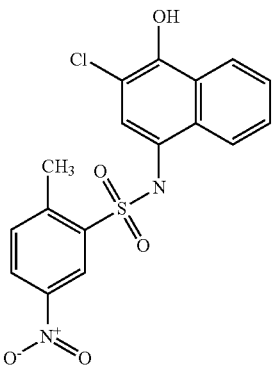 [SMILES: Cc1ccc([N+](=O)[O-])cc1S(=O)(=O)Nc1cc(Cl)c(O)c2ccccc12] | C17H13ClN2O5S | 392.8206 | 4.46 |
| F1566-1223 | 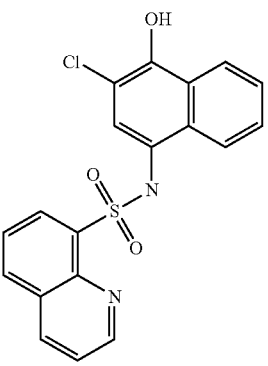 [SMILES: O=S(=O)(Nc1cc(Cl)c(O)c2ccccc12)c1cccc2cccnc12] | C19H13ClN2O3S | 384.8441 | 4.392 |
| F5749-0295 | 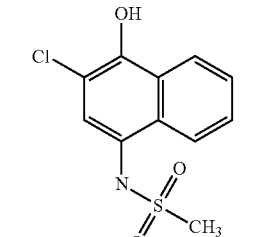 | C11H10ClNO3S | 271.7243 | 2.538 |

TABLE 11-continued
| IDNUMBER | Structure | Formula structure | MW | LogP |
|---|---|---|---|---|
| F5749-0296 | 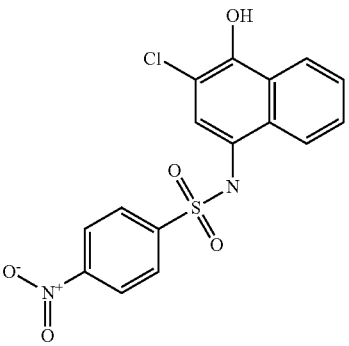 [SMILES: O=[N+]([O-])c1ccc(S(=O)(=O)Nc2cc(Cl)c(O)c3ccccc23)cc1] | C16H11ClN2O5S | 378.7935 | 4.127 |
| F5749-0297 | 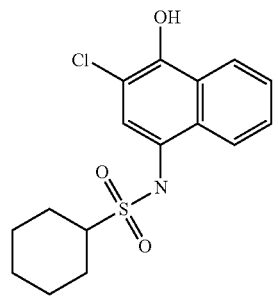 [SMILES: O=S(=O)(Nc1cc(Cl)c(O)c2ccccc12)C1CCCCC1] | C16H18ClNO3S | 339.8438 | 4.517 |
| F5749-0298 | 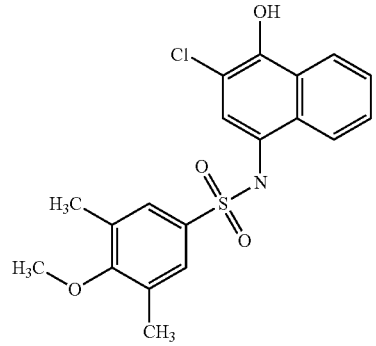 [SMILES: COc1c(C)cc(S(=O)(=O)Nc2cc(Cl)c(O)c3ccccc23)cc1C] | C19H18ClNO4S | 391.8766 | 4.814 |
| F5749-0299 | 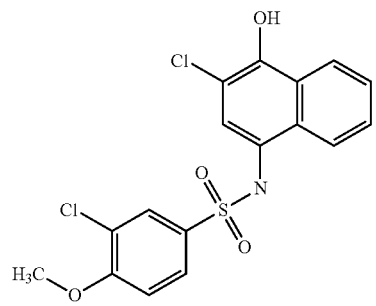 [SMILES: COc1ccc(S(=O)(=O)Nc2cc(Cl)c(O)c3ccccc23)cc1Cl] | C17H13Cl2NO4S | 398.2675 | 4.775 |

TABLE 11-continued

| IDNUMBER | Structure | Formula structure | MW | LogP |
| --- | --- | --- | --- | --- |
| F5749-0300 | 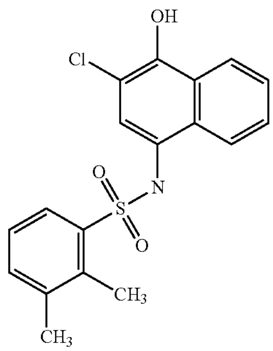 [SMILES: Cc1cccc(S(=O)(=O)Nc2cc(Cl)c(O)c3ccccc23)c1C] | C18H16ClNO3S | 361.8501 | 4.784 |
| F5749-0301 | 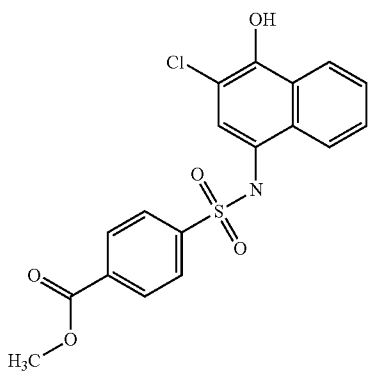 [SMILES: COC(=O)c1ccc(S(=O)(=O)Nc2cc(Cl)c(O)c3ccccc23)cc1] | C18H14ClNO5S | 391.833 | 4.133 |
| F5749-0302 | 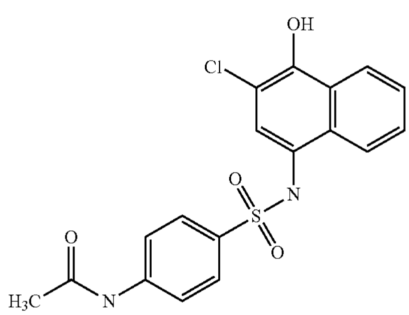 [SMILES: CC(=O)Nc1ccc(S(=O)(=O)Nc2cc(Cl)c(O)c3ccccc23)cc1] | C18H15ClN2O4S | 390.8483 | 3.483 |
| F5749-0303 | 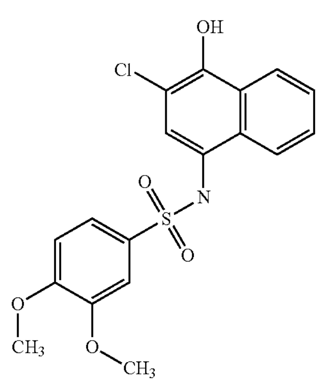 [SMILES: COc1ccc(S(=O)(=O)Nc2cc(Cl)c(O)c3ccccc23)cc1OC] | C18H16ClNO5S | 393.8489 | 3.89074 |

TABLE 11-continued

| IDNUMBER | Structure | Formula structure | MW | LogP |
|---|---|---|---|---|
| F5749-0304 | 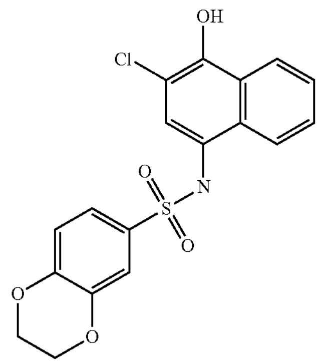 [SMILES: O=S(=O)(Nc1cc(Cl)c(O)c2ccccc12)c1ccc2c(c1)OCCO2] | C18H14ClNO5S | 391.833 | 3.787 |
| F5749-0305 | 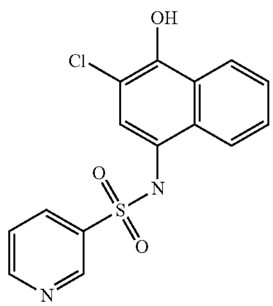 [SMILES: O=S(=O)(Nc1cc(Cl)c(O)c2ccccc12)c1cccnc1] | C15H11ClN2O3S | 334.7835 | 2.959 |
| F5749-0306 | 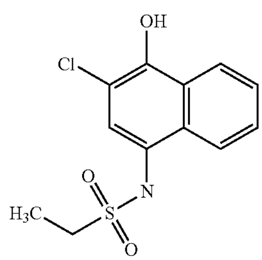 [SMILES: CCS(=O)(=O)Nc1cc(Cl)c(O)c2ccccc12] | C12H12ClNO3S | 285.7513 | 3.051 |
| F5749-0307 | 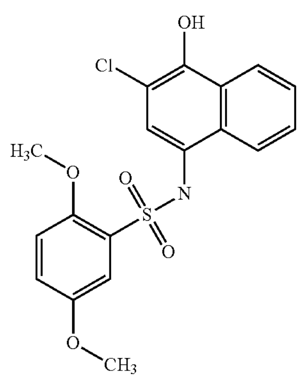 [SMILES: COc1ccc(OC)c(S(=O)(=O)Nc2cc(Cl)c(O)c3ccccc23)c1] | C18H16ClNO5S | 393.8489 | 4.139 |
| F5749-0308 | 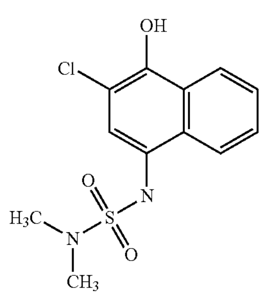 [SMILES: CN(C)S(=O)(=O)Nc1cc(Cl)c(O)c2ccccc12] | C12H13ClN2O3S | 300.766 | 2.086 |

TABLE 11-continued
| IDNUMBER | Structure | Formula structure | MW | LogP |
|---|---|---|---|---|
| F5749-0309 | 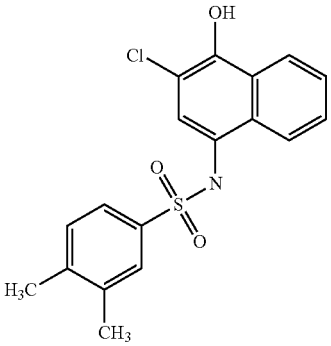 [SMILES: Cc1ccc(S(=O)(=O)Nc2cc(Cl)c(O)c3ccccc23)cc1C] | C18H16ClNO3S | 361.8501 | 4.823 |
| F5749-0310 | 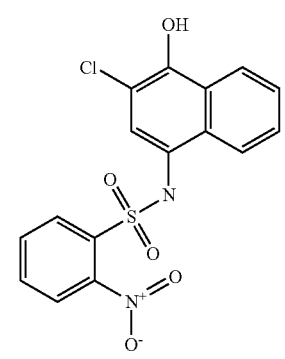 [SMILES: O=[N+]([O-])c1ccccc1S(=O)(=O)Nc1cc(Cl)c(O)c2ccccc12] | C16H11ClN2O5S | 378.7935 | 4.125 |
| F5749-0311 | 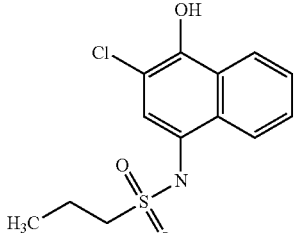 | C13H14ClNO3S | 299.7784 | 3.493 |
| F5749-0312 | 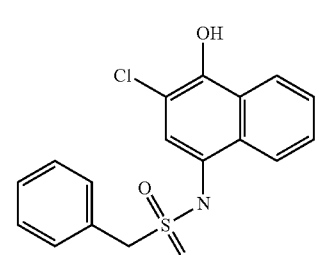 | C17H14ClNO3S | 347.823 | 4.326 |
| F5749-0313 | 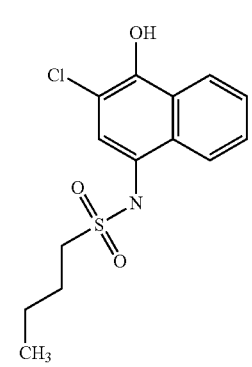 [SMILES: CCCCS(=O)(=O)Nc1cc(Cl)c(O)c2ccccc12] | C14H16ClNO3S | 313.8055 | 3.935 |

TABLE 11-continued

| IDNUMBER | Structure | Formula structure | MW | LogP |
|---|---|---|---|---|
| F5749-0314 | 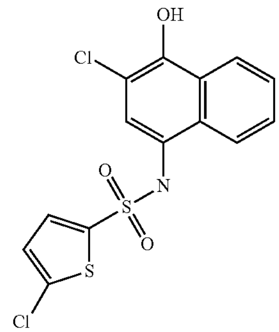 [SMILES: O=S(=O)(Nc1cc(Cl)c(O)c2ccccc12)c1ccc(Cl)s1] | C14H9Cl2NO3S2 | 374.2667 | 4.995 |
| F5749-0315 | 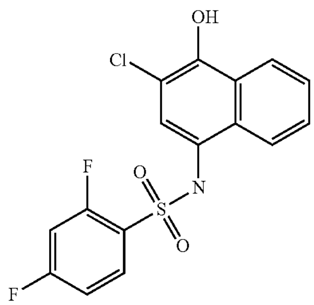 [SMILES: O=S(=O)(Nc1cc(Cl)c(O)c2ccccc12)c1ccc(F)cc1F] | C16H10ClF2NO3S | 369.7768 | 4.533 |
| F5749-0316 | 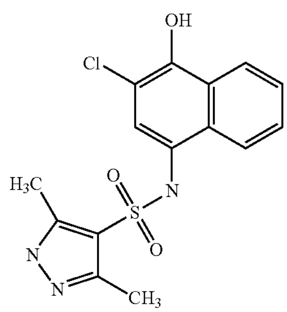 [SMILES: Cc1n[nH]c(C)c1S(=O)(=O)Nc1cc(Cl)c(O)c2ccccc12] | C15H14ClN3O3S | 351.8141 | 3.302 |
| F5749-0317 | 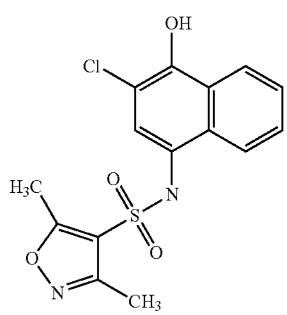 | C15H13ClN2O4S | 352.7989 | 3.336 |
| F5749-0318 | 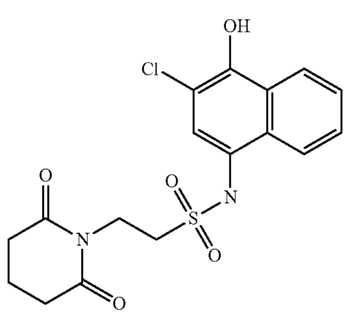 [SMILES: O=C1CCCC(=O)N1CCS(=O)(=O)Nc1cc(Cl)c(O)c2ccccc12] | C17H17ClN2O5S | 396.8524 | 1.979 |

TABLE 11-continued

| IDNUMBER | Structure | Formula structure | MW | LogP |
| --- | --- | --- | --- | --- |
| F5749-0319 | 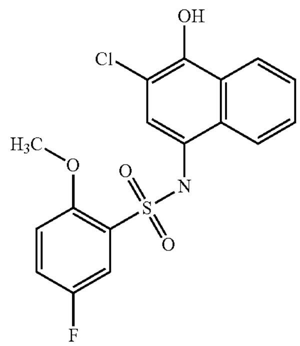 [SMILES: COc1ccc(F)cc1S(=O)(=O)Nc1cc(Cl)c(O)c2ccccc12] | C17H13ClFNO4S | 381.8129 | 4.336 |
| F5749-0320 | 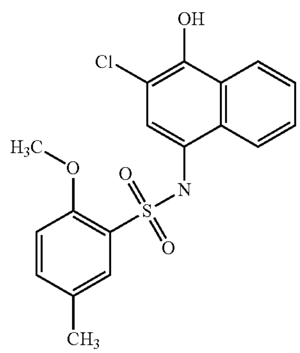 [SMILES: COc1ccc(C)cc1S(=O)(=O)Nc1cc(Cl)c(O)c2ccccc12] | C18H16ClNO4S | 377.8495 | 4.481 |
| F5749-0321 | 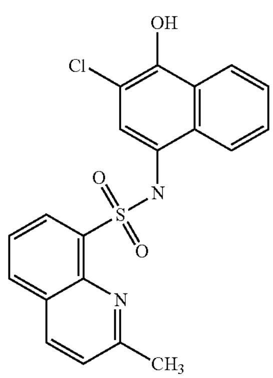 [SMILES: Cc1ccc2cccc(S(=O)(=O)Nc3cc(Cl)c(O)c4ccccc34)c2n1] | C20H15ClN2O3S | 398.8712 | 4.651 |
| F5749-0322 | 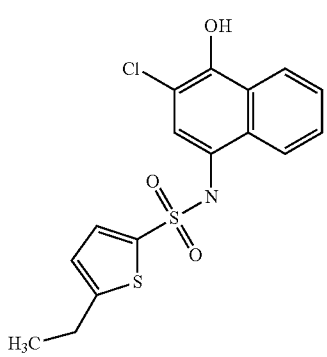 [SMILES: CCc1ccc(S(=O)(=O)Nc2cc(Cl)c(O)c3ccccc23)s1] | C16H14ClNO3S2 | 367.8759 | 4.843 |

TABLE 11-continued

| IDNUMBER | Structure | Formula structure | MW | LogP |
|---|---|---|---|---|
| F5749-0323 | 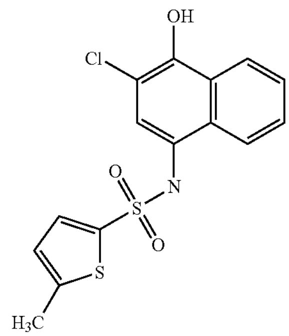 [SMILES: Cc1ccc(S(=O)(=O)Nc2cc(Cl)c(O)c3ccccc23)s1] | C15H12ClNO3S2 | 353.8488 | 4.368 |
| F5749-0324 | 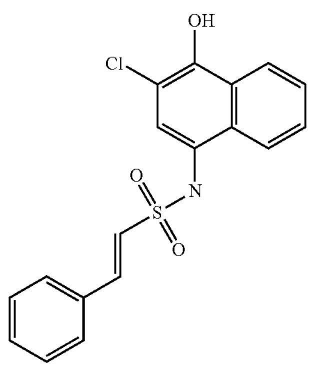 [SMILES: O=S(=O)(/C=C/c1ccccc1)Nc1cc(Cl)c(O)c2ccccc12] | C18H14ClNO3S | 359.8342 | 4.55 |
| F5749-0325 | 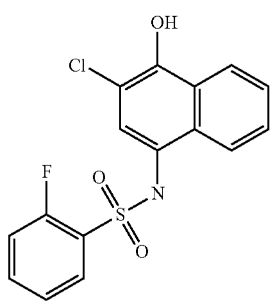 [SMILES: O=S(=O)(Nc1cc(Cl)c(O)c2ccccc12)c1ccccc1F] | C16H11ClFNO3S | 351.7864 | 4.343 |
| F5749-0326 | 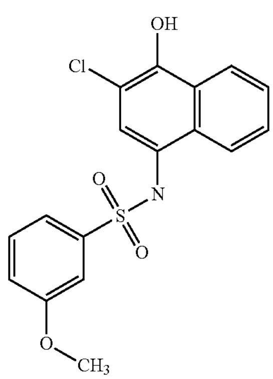 [SMILES: COc1cccc(S(=O)(=O)Nc2cc(Cl)c(O)c3ccccc23)c1] | C17H14ClNO4S | 363.8224 | 4.185 |

TABLE 11-continued
| IDNUMBER | Structure | Formula structure | MW | LogP |
|---|---|---|---|---|
| F5749-0327 | 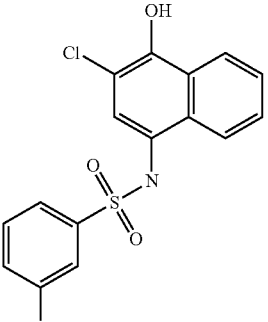 | C16H11ClFNO3S | 351.7864 | 4.382 |
| F5749-0328 | 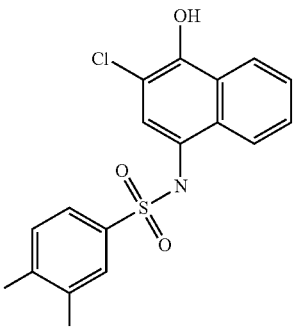 | C16H10Cl2FNO3S | 386.2314 | 4.972 |
| F5749-0329 | 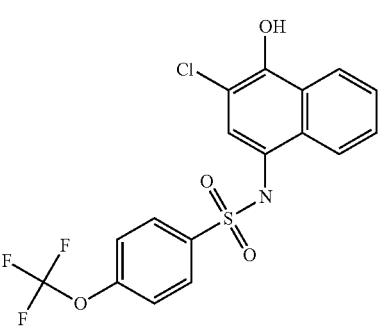 [SMILES: O=S(=O)(Nc1cc(Cl)c(O)c2ccccc12)c1ccc(OC(F)(F)F)cc1] | C17H11ClF3NO4S | 417.7937 | 5.59076 |
| F5749-0330 | 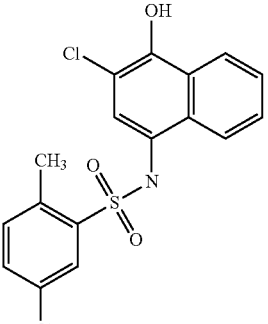 | C17H13Cl2NO3S | 382.2681 | 5.117 |

TABLE 11-continued
| IDNUMBER | Structure | Formula structure | MW | LogP |
| --- | --- | --- | --- | --- |
| F5749-0331 | 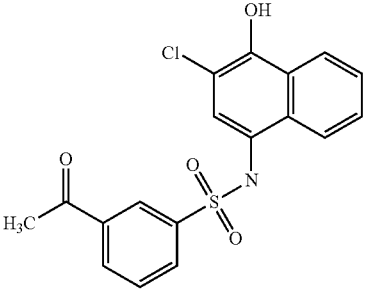 [SMILES: CC(=O)c1cccc(S(=O)(=O)Nc2cc(Cl)c(O)c3ccccc23)c1] | C18H14ClNO4S | 375.8336 | 4.082 |
| F5749-0332 | 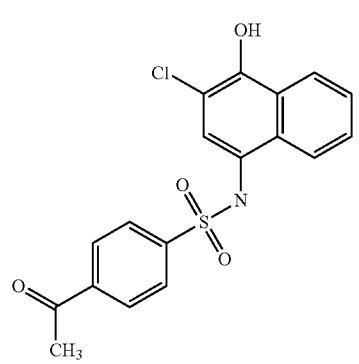 [SMILES: CC(=O)c1ccc(S(=O)(=O)Nc2cc(Cl)c(O)c3ccccc23)cc1] | C18H14ClNO4S | 375.8336 | 4.045 |
| F5749-0333 | 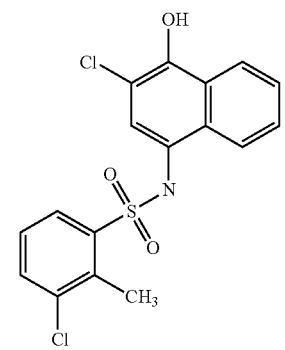 [SMILES: Cc1c(Cl)cccc1S(=O)(=O)Nc1cc(Cl)c(O)c2ccccc12] | C17H13Cl2NO3S | 382.2681 | 5.078 |
| F5749-0334 | 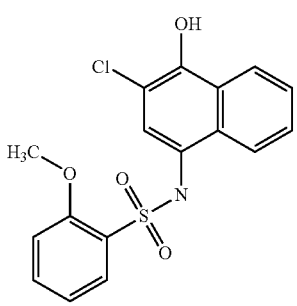 [SMILES: COc1ccccc1S(=O)(=O)Nc1cc(Cl)c(O)c2ccccc12] | C17H14ClNO4S | 363.8224 | 4.146 |
| F5749-0335 | 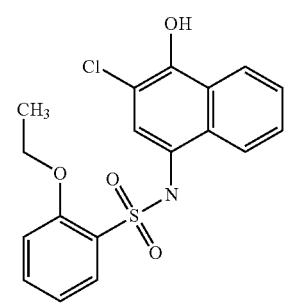 [SMILES: CCOc1ccccc1S(=O)(=O)Nc1cc(Cl)c(O)c2ccccc12] | C18H16ClNO4S | 377.8495 | 4.487 |

TABLE 11-continued

| IDNUMBER | Structure | Formula structure | MW | LogP |
|---|---|---|---|---|
| F5749-0336 | 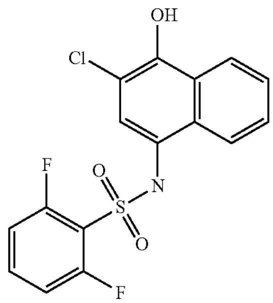 [SMILES: O=S(=O)(Nc1cc(Cl)c(O)c2ccccc12)c1c(F)cccc1F] | C16H10ClF2NO3S | 369.7768 | 4.494 |
| F5749-0337 | 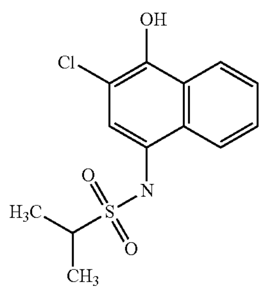 [SMILES: CC(C)S(=O)(=O)Nc1cc(Cl)c(O)c2ccccc12] | C13H14ClNO3S | 299.7784 | 3.685 |
| F5749-0338 | 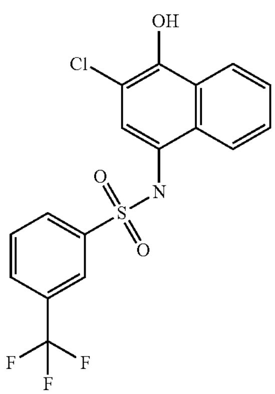 [SMILES: O=S(=O)(Nc1cc(Cl)c(O)c2ccccc12)c1cccc(C(F)(F)F)c1] | C17H11ClF3NO3S | 401.7943 | 5.16376 |
| F5749-0339 | 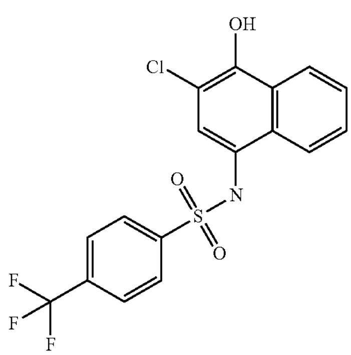 [SMILES: O=S(=O)(Nc1cc(Cl)c(O)c2ccccc12)c1ccc(C(F)(F)F)cc1] | C17H11ClF3NO3S | 401.7943 | 5.12676 |

TABLE 11-continued

| IDNUMBER | Structure | Formula structure | MW | LogP |
|---|---|---|---|---|
| F5749-0340 | 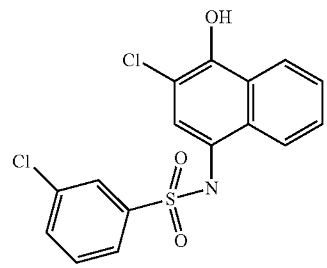 [SMILES: O=S(=O)(Nc1cc(Cl)c(O)c2ccccc12)c1cccc(Cl)c1] | C16H11Cl2NO3S | 368.241 | 4.821 |
| F5749-0341 | 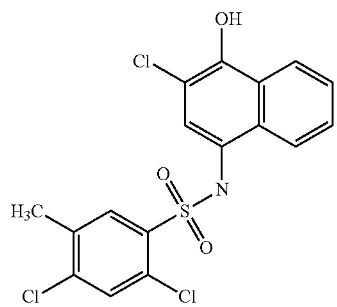 [SMILES: Cc1cc(S(=O)(=O)Nc2cc(Cl)c(O)c3ccccc23)c(Cl)cc1Cl] | C17H12Cl3NO3S | 416.7131 | 5.744 |
| F5749-0342 | 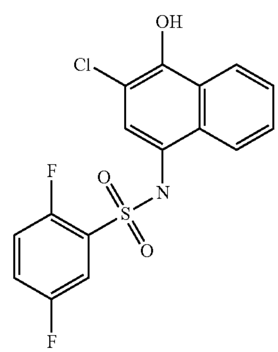 [SMILES: O=S(=O)(Nc1cc(Cl)c(O)c2ccccc12)c1cc(F)ccc1F] | C16H10ClF2NO3S | 369.7768 | 4.533 |
| F5749-0343 | 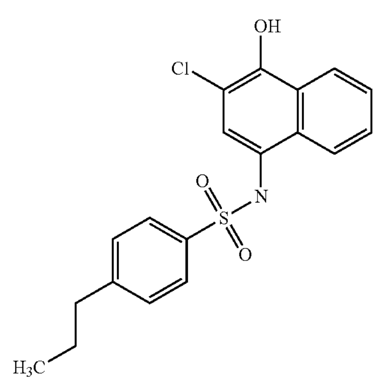 [SMILES: CCCc1ccc(S(=O)(=O)Nc2cc(Cl)c(O)c3ccccc23)cc1] | C19H18ClNO3S | 375.8772 | 5.407 |

TABLE 11-continued
| IDNUMBER | Structure | Formula structure | MW | LogP |
|---|---|---|---|---|
| F5749-0344 | 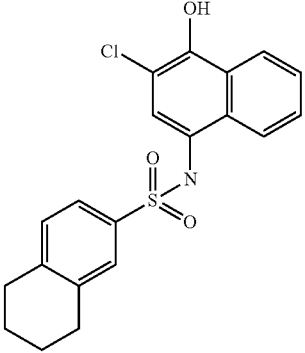 [SMILES: O=S(=O)(Nc1cc(Cl)c(O)c2ccccc12)c1ccc2c(c1)CCCC2] | C20H18ClNO3S | 387.8884 | 5.279 |
| F5749-0345 | 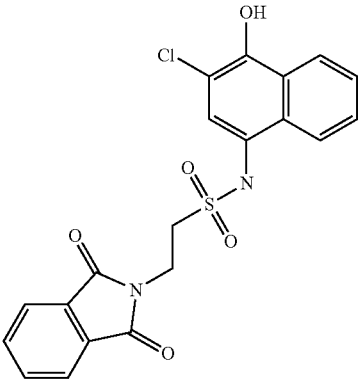 [SMILES: O=C1c2ccccc2C(=O)N1CCS(=O)(=O)Nc1cc(Cl)c(O)c2ccccc12] | C20H15ClN2O5S | 430.87 | 3.319 |
| F5749-0346 | 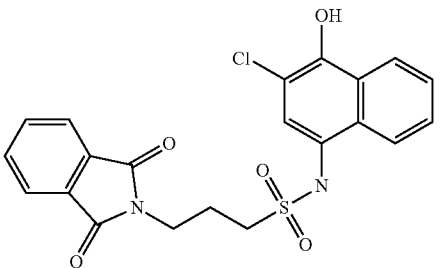 [SMILES: O=C1c2ccccc2C(=O)N1CCCS(=O)(=O)Nc1cc(Cl)c(O)c2ccccc12] | C21H17ClN2O5S | 444.897 | 3.761 |
| F5749-0347 | 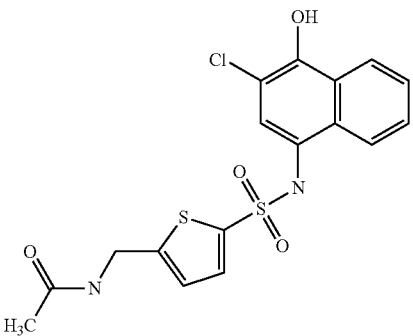 [SMILES: CC(=O)NCc1ccc(S(=O)(=O)Nc2cc(Cl)c(O)c3ccccc23)s1] | C17H15ClN2O4S2 | 410.9011 | 3.495 |

TABLE 11-continued
| IDNUMBER | Structure | Formula structure | MW | LogP |
|---|---|---|---|---|
| F5749-0348 | 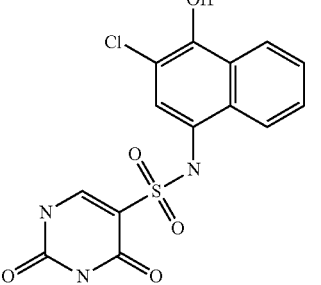 | C14H10ClN3O5S | 367.7699 | 1.237 |
| F5749-0349 | 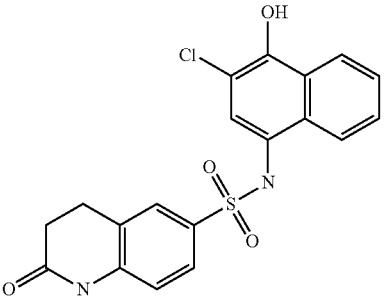 [SMILES: O=C1CCc2cc(S(=O)(=O)Nc3cc(Cl)c(O)c4ccccc34)ccc2N1] | C19H15ClN2O4S | 402.8594 | 3.388 |
| F5749-0350 | 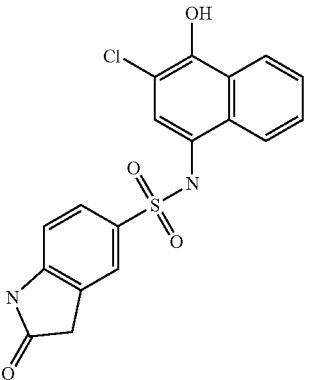 [SMILES: O=C1Cc2cc(S(=O)(=O)Nc3cc(Cl)c(O)c4ccccc34)ccc2N1] | C18H13ClN2O4S | 388.8323 | 3.3 |
| F5749-0351 | 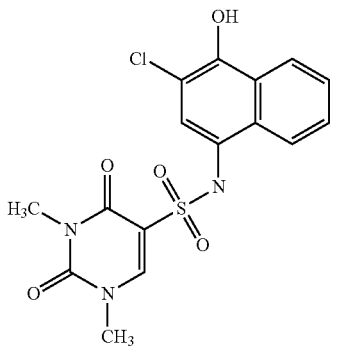 [SMILES: Cn1cc(S(=O)(=O)Nc2cc(Cl)c(O)c3ccccc23)c(=O)n(C)c1=O] | C16H14ClN3O5S | 395.8241 | 1.301 |

TABLE 11-continued

| IDNUMBER | Structure | Formula structure | MW | LogP |
|---|---|---|---|---|
| F5749-0352 | 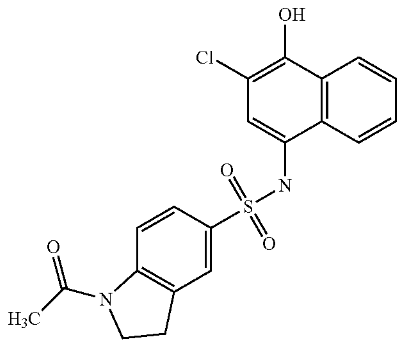 [SMILES: CC(=O)N1CCc2cc(S(=O)(=O)Nc3cc(Cl)c(O)c4ccccc34)ccc21] | C20H17ClN2O4S | 416.8865 | 3.623 |
| F5749-0353 | 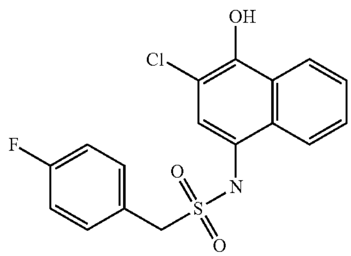 [SMILES: O=S(=O)(Cc1ccc(F)cc1)Nc1cc(Cl)c(O)c2ccccc12] | C17H13ClFNO3S | 365.8135 | 4.479 |
| F5749-0354 | 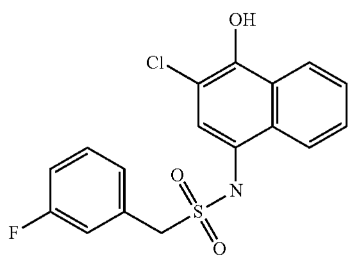 [SMILES: O=S(=O)(Cc1cccc(F)c1)Nc1cc(Cl)c(O)c2ccccc12] | C17H13ClFNO3S | 365.8135 | 4.516 |
| F5749-0355 | 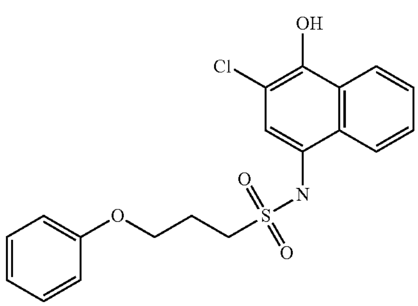 [SMILES: O=S(=O)(CCCOc1ccccc1)Nc1cc(Cl)c(O)c2ccccc12] | C19H18ClNO4S | 391.8766 | 4.552 |
| F5749-0356 | 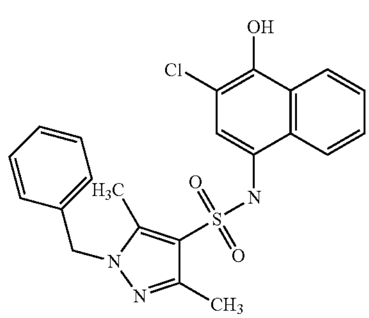 [SMILES: Cc1nn(Cc2ccccc2)c(C)c1S(=O)(=O)Nc1cc(Cl)c(O)c2ccccc12] | C22H20ClN3O3S | 441.94 | 4.471 |

TABLE 11-continued

| IDNUMBER | Structure | Formula structure | MW | LogP |
| --- | --- | --- | --- | --- |
| F5749-0357 | 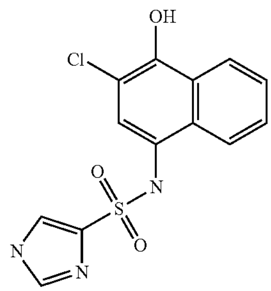 [SMILES: O=S(=O)(Nc1cc(Cl)c(O)c2ccccc12)c1c[nH]cn1] | C13H10ClN3O3S | 323.76 | 2.332 |
| F5749-0358 | 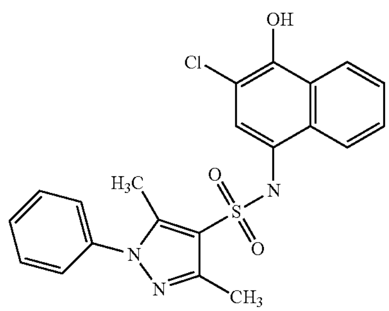 [SMILES: Cc1nn(-c2ccccc2)c(C)c1S(=O)(=O)Nc1cc(Cl)c(O)c2ccccc12] | C21H18ClN3O3S | 427.9129 | 4.337 |
| F5749-0359 | 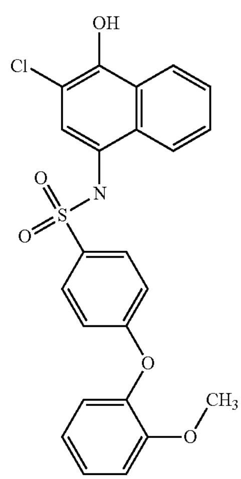 [SMILES: COc1ccccc1Oc1ccc(S(=O)(=O)Nc2cc(Cl)c(O)c3ccccc23)cc1] | C23H18ClNO5S | 455.9206 | 5.50774 |
| F5749-0360 | 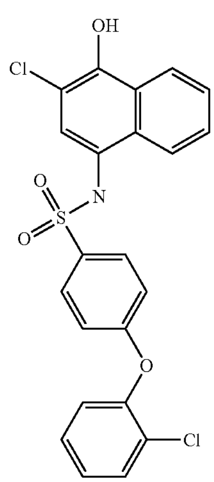 [SMILES: O=S(=O)(Nc1cc(Cl)c(O)c2ccccc12)c1ccc(Oc2ccccc2Cl)cc1] | C22H15Cl2NO4S | 460.3392 | 6.392 |

TABLE 11-continued
| IDNUMBER | Structure | Formula structure | MW | LogP |
|---|---|---|---|---|
| F5749-0361 | 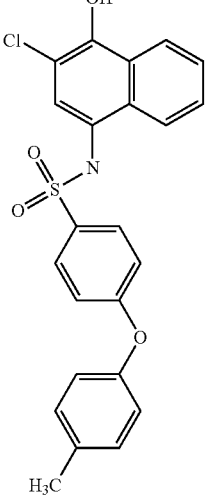 | C23H18ClNO4S | 439.9212 | 6.1 |
| F5749-0362 | 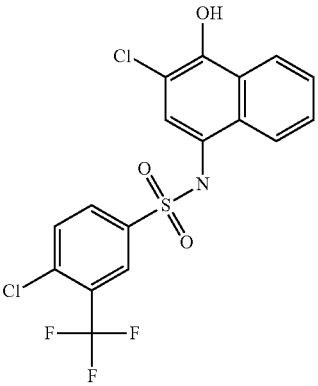 [SMILES: O=S(=O)(Nc1cc(Cl)c(O)c2ccccc12)c1ccc(Cl)c(C(F)(F)F)c1] | C17H10Cl2F3NO3S | 436.2394 | 5.75376 |
| F5749-0363 | 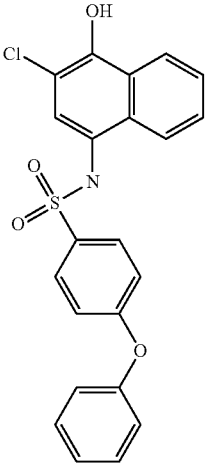 [SMILES: O=S(=O)(Nc1cc(Cl)c(O)c2ccccc12)c1ccc(Oc2ccccc2)cc1] | C22H16ClNO4S | 425.8941 | 5.802 |

TABLE 11-continued

| IDNUMBER | Structure | Formula structure | MW | LogP |
|---|---|---|---|---|
| F5749-0364 | 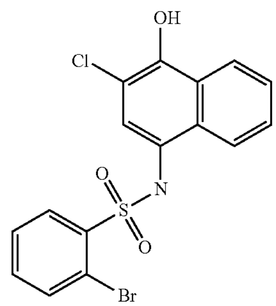 | C16H11BrClNO3S | 412.692 | 4.988 |
| F5749-0365 | 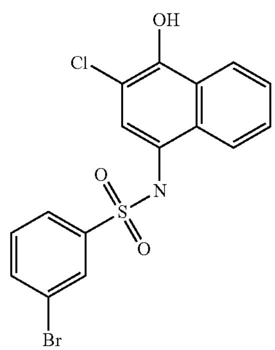 [SMILES: O=S(=O)(Nc1cc(Cl)c(O)c2ccccc12)c1cccc(Br)c1] | C16H11BrClNO3S | 412.692 | 5.027 |
| F5749-0366 | 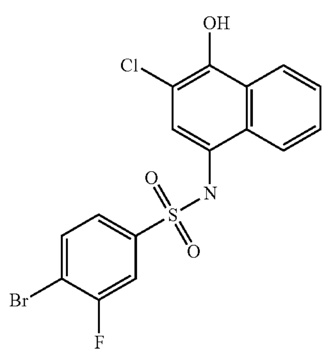 [SMILES: O=S(=O)(Nc1cc(Cl)c(O)c2ccccc12)c1ccc(Br)c(F)c1] | C16H10BrClFNO3S | 430.6824 | 5.178 |
| F5749-0367 | 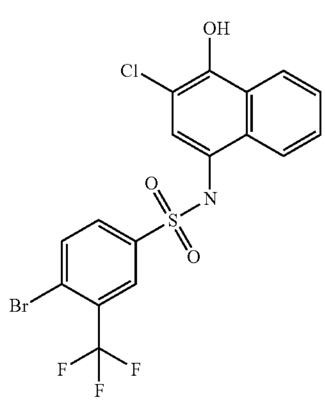 [SMILES: O=S(=O)(Nc1cc(Cl)c(O)c2ccccc12)c1ccc(Br)c(C(F)(F)F)c1] | C17H10BrClF3NO3S | 480.6904 | 5.95976 |

TABLE 11-continued

| IDNUMBER | Structure | Formula structure | MW | LogP |
|---|---|---|---|---|
| F5749-0368 | (structure) | C16H11Cl2NO3S | 368.241 | 4.782 |
| F5749-0369 | (structure) | C16H12ClNO5S2 | 397.8587 | 3.392 |
| F5749-0370 | (structure) | C17H11ClF3NO4S | 417.7937 | 5.58876 |

Example 11

Stat3 Inhibitor as a Treatment for Dermal Fibrosis

Figure 19:
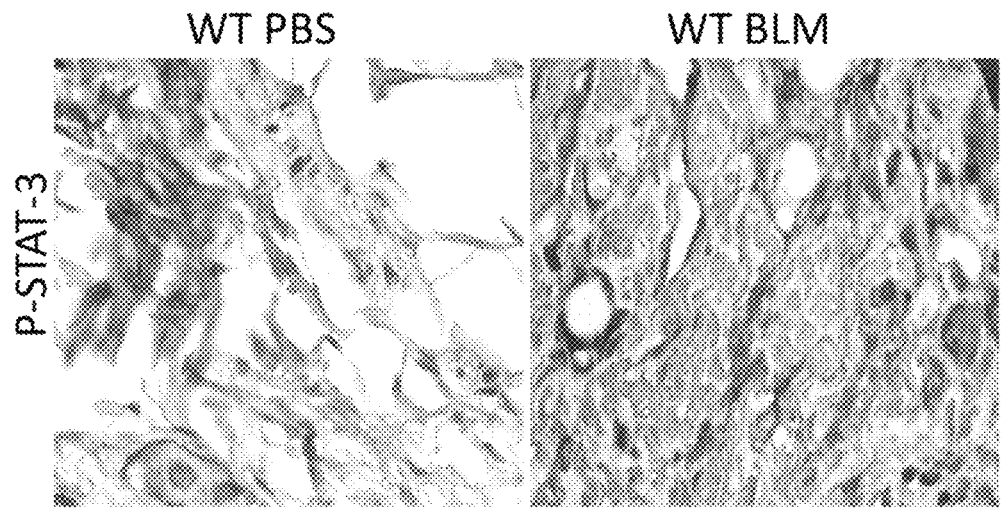
FIG. 19 shows increased STAT-3 activation in a skin fibrosis model.
Figure 19:
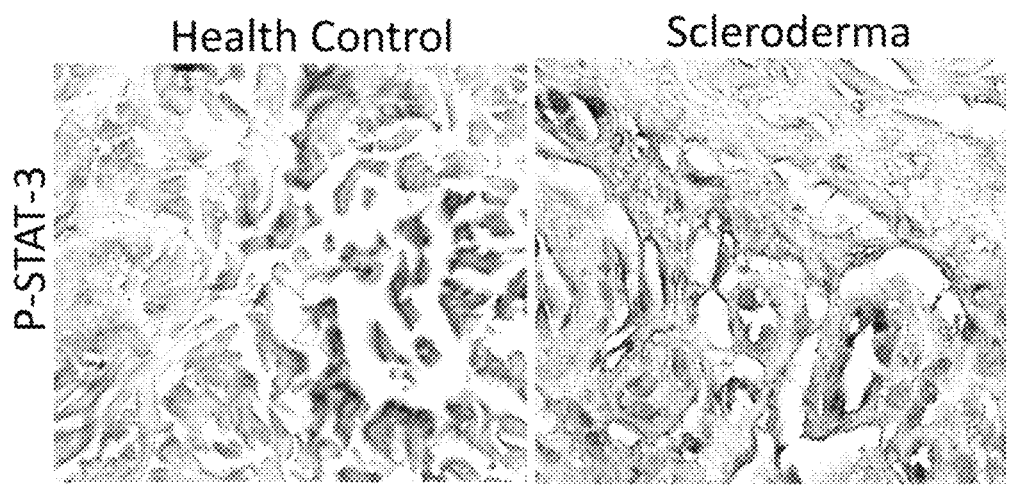

Skin biopsies from the subcutaneous bleomycin skin model in wild type mice and human subjects (healthy control vs. scleroderma) are illustrated in FIG. 19. Scleroderma is an autoimmune disease that manifests as fibrosis in the skin and internal organs. Both bleomycin injected skin with fibrosis and scleroderma skin demonstrate increased staining for phosphorylated (active) Stat3, indicating activation of Stat3 signaling in these fibrotic tissues.

Figure 20:
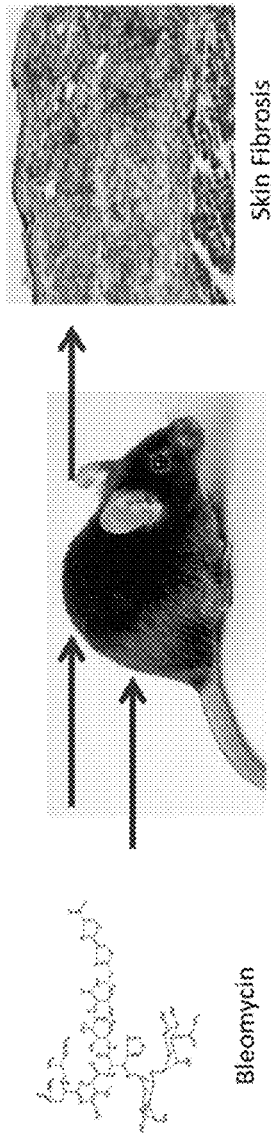
FIG. 20 illustrates generation of an exemplary subcutaneous Bleomycin model for skin fibrosis and exemplary STAT3 inhibitory studies.
Figure 20:
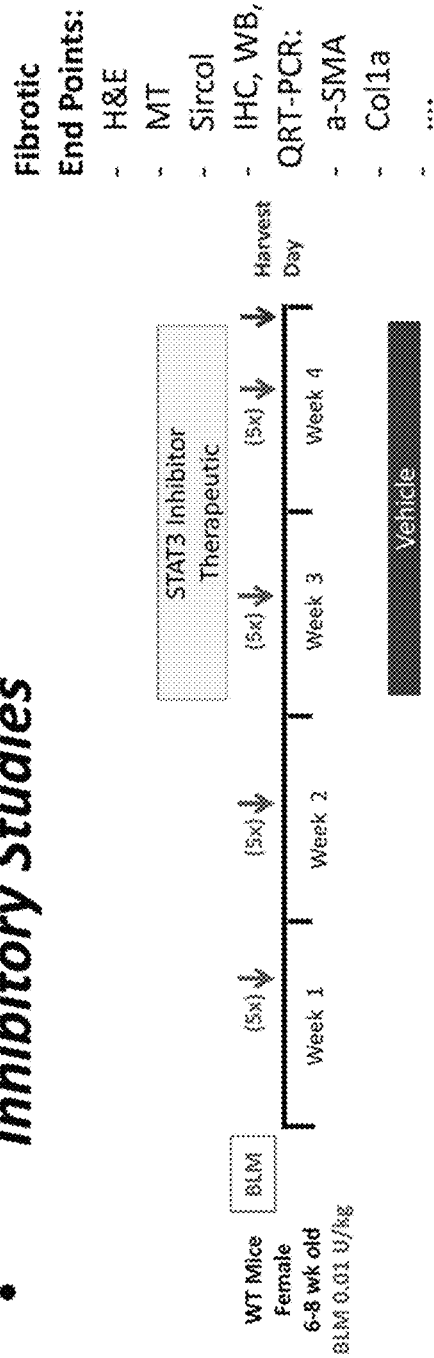

FIG. 20 illustrates an exemplary study design using a subcutaneous (SQ) bleomycin model for skin fibrosis. In a basic model, bleomycin is administered to wild type mice (C57/Bl6) via subcutaneous injection 5 days a week for a total of 4 weeks. PBS is used as a control for the bleomycin. Fibrosis is assessed in the biopsied skin on day 28. Fibrosis is assessed using histology (hematoxylin and eosin stain), where the dermal thickness is quantified as the average linear distance from the dermis-epidermis junction to the subQ muscle layer. Masson's trichrome staining is also performed to stain collagen blue. Immunohistochemistry is performed for alpha-smooth muscle actin, the marker of the myofibroblasts (cell that makes collagen during the process of fibrosis). Future endpoints are assessed including collagen content. To illustrate that STAT3 inhibitor is a useful therapy at least for dermal fibrosis, an example of a STAT3 inhibitor (C188-9) was given via the intraperitoneal route daily, starting in week 3 of the bleomycin model. DMSO was used as a control for the STAT3 inhibitor.

Figure 21:
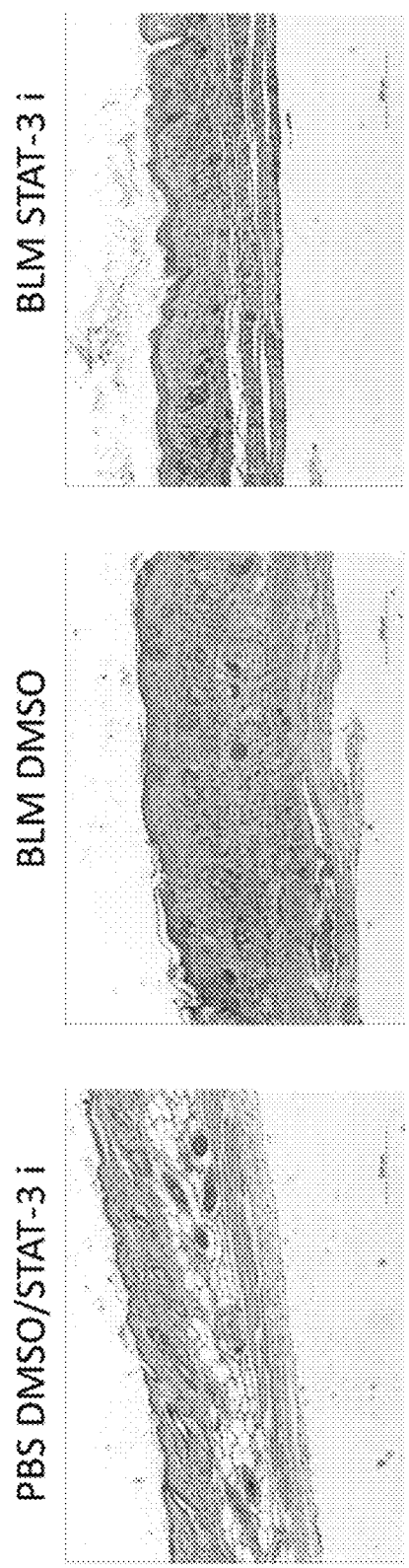
FIG. 21 demonstrates that STAT-3 inhibition is associated with diminished fibrosis (Hematoxylin and eosin stain).

As shown in FIG. 21, wild-type mice given Bleomycin (BLM, middle panel) have increased dermal thickness that is decreased when given the STAT3 inhibitor (right panel). Images are representative images from 1 mouse per group total of 5 mice per group in the study.

Figure 22:
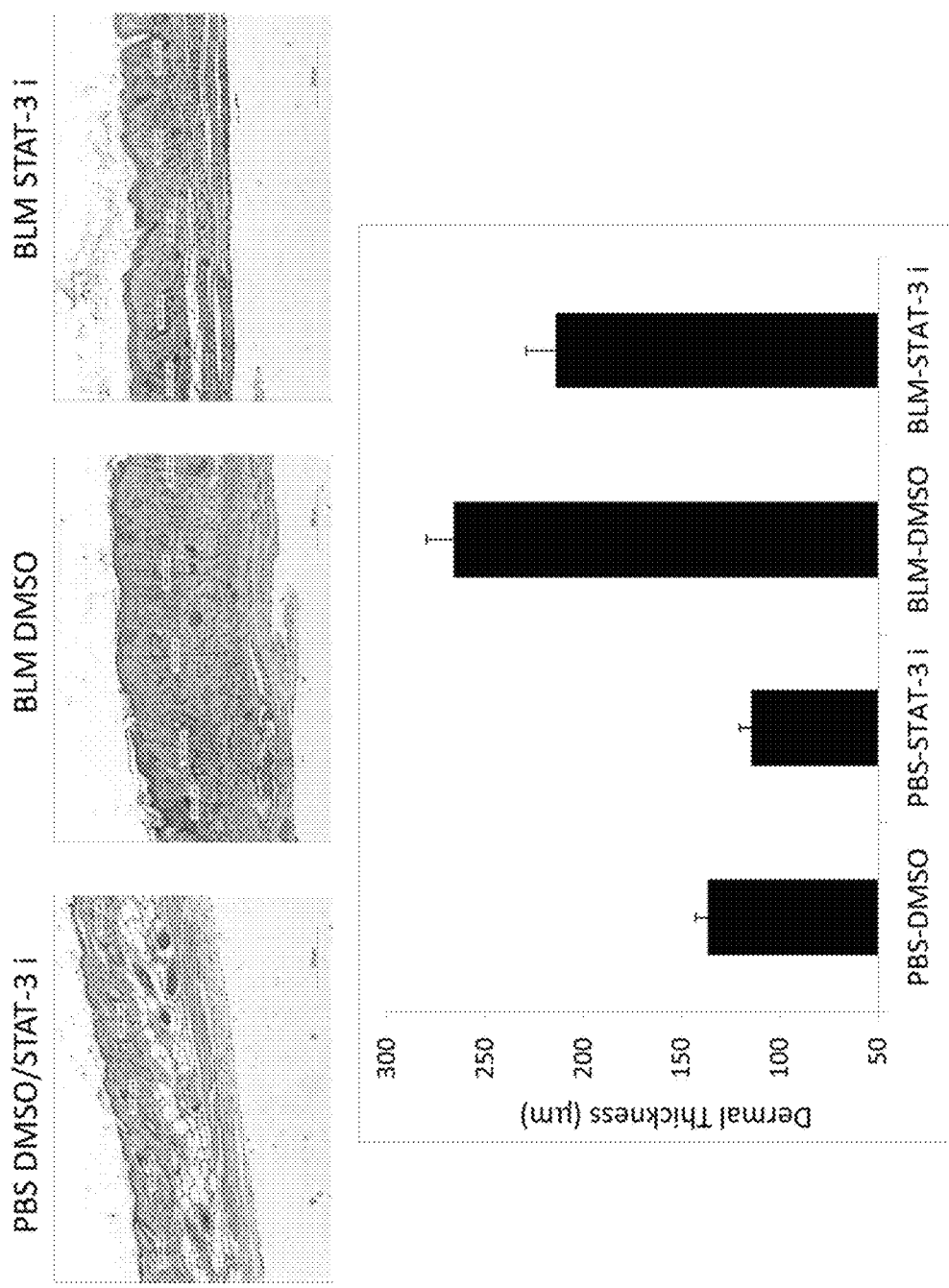
FIG. 22 shows quantification that STAT-3 inhibition leads to diminished fibrosis (dermal thickness).

FIG. 22 provides quantitation of the images in FIG. 22, and all 5 in each group are averaged. There was no difference in dermal thickness between PBS-injected mice with treatment with DMSO or STAT3 inhibitor. However, bleomycin increases the dermal thickness that is reduced in the Bleo/STAT3 inhibitor group.

Figure 23:
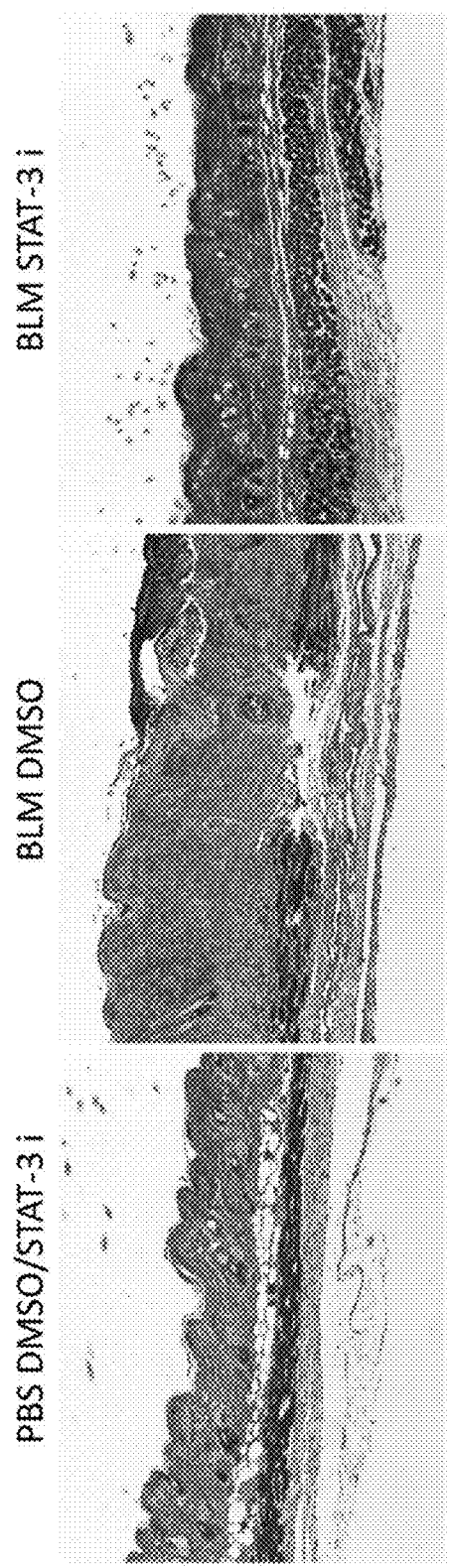
FIG. 23 illustrates that STAT-3 inhibition is associated with diminished fibrosis, using Masson's trichome stain as an indicator.

Wild type mice given Bleomycin (BLM, middle panel) have increased collagen content (blue in Masson's trichrome stain) that is decreased when given the STAT3 inhibitor (right panel) (FIG. 23). Images are representative images from 1 mouse per group total of 5 mice per group in the study.

Figure 24:
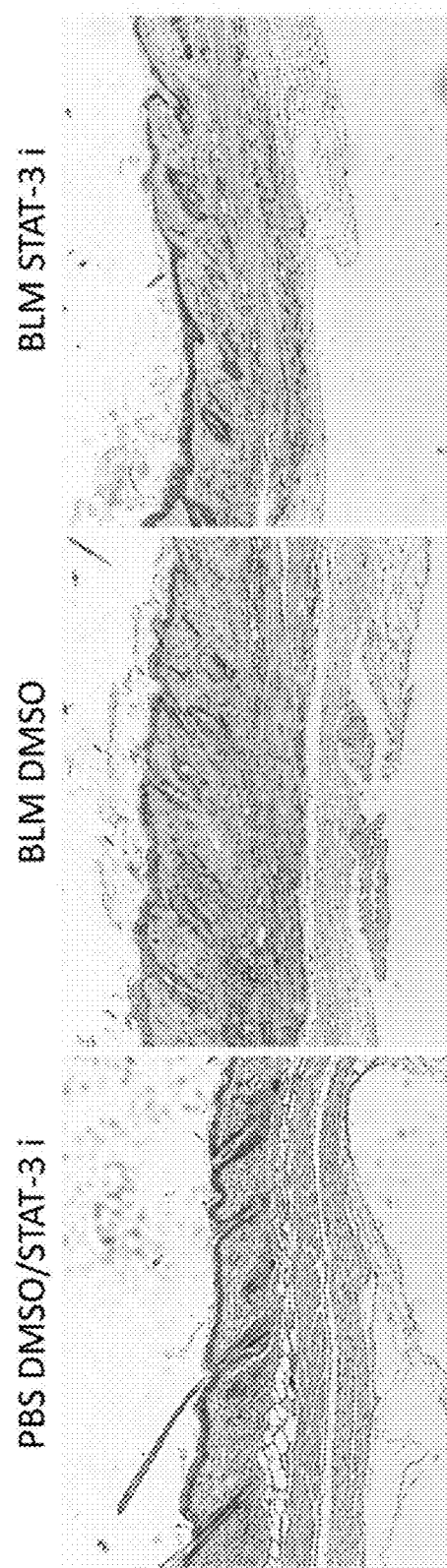
FIG. 24 demonstrates that STAT-3 inhibition is associated with diminished fibrosis, based on alpha smooth muscle actin staining.

In FIG. 24, wild type mice given Bleomycin (BLM, middle panel) have increased alpha Smooth muscle actin staining (bright pink) that is decreased when given the STAT3 inhibitor (right panel). Images are representative images from 1 mouse per group total of 5 mice per group in the experiment. The aSMA stains myofibroblasts; therefore, STAT3 inhibitor decreases fibrosis and the accumulation of myofibroblasts in the subcutaneous bleomycin model.

Figure 25:
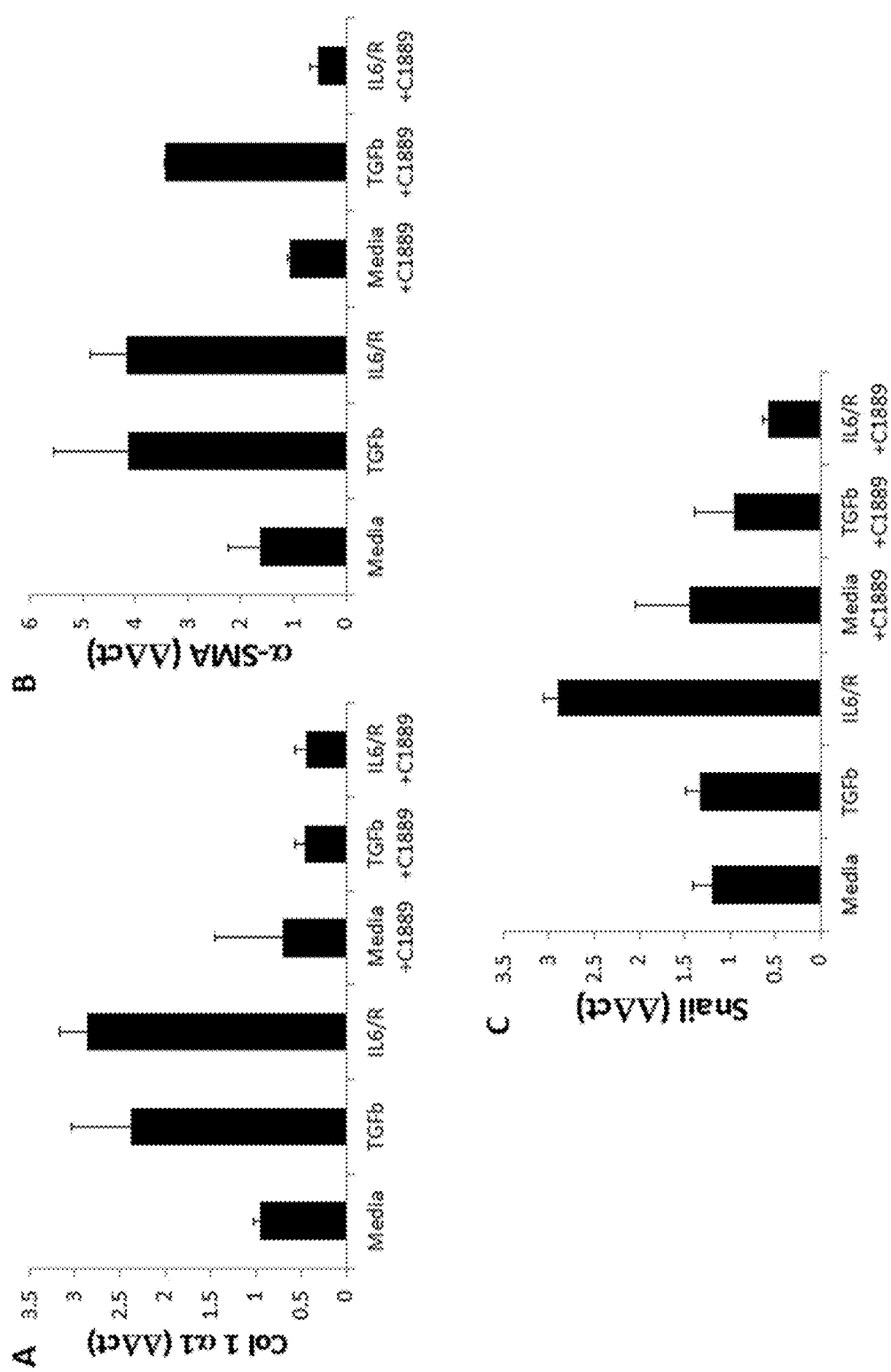
FIGS. 25A-25C shows the effect of C188-9 on dermal fibroblast production of type I collagen (Col1a1), smooth muscle actin (aSMA) and the transcription factor Snail.

FIG. 25 shows the effect of Cpd188-9 on dermal fibroblast production of type I collagen (Col1a1), smooth muscle actin (aSMA) and the transcription factor Snail. Col1a1, aSMA and Snail are important genes involved in the development of fibrosis of the skin and other organs. During fibrosis, TGFbeta and/or IL-6 can increase the expression of these genes in dermal fibroblasts and contribute to the development of tissue fibrosis. As see in FIG. 25, Cpd188-9 blocks the increased expression of Col1a1, aSMA and Snail mRNA induced by TGF-beta or IL6 (plus the IL6 receptor) in mouse dermal fibroblasts. These data demonstrate that Cpd188-9 is antifibrotic in vitro and confirm and extend the in vivo findings in the dermal fibrosis model.

Figure 26:
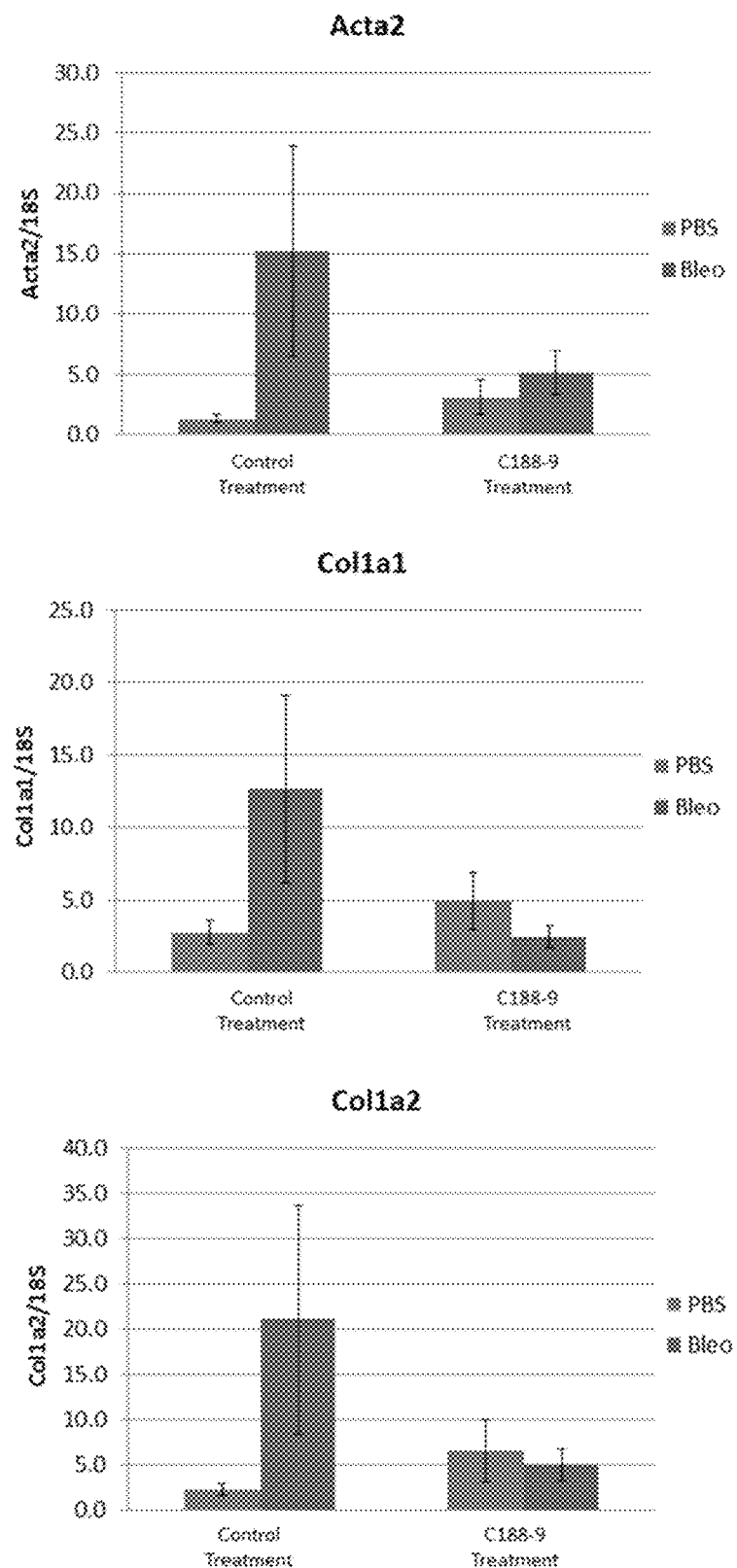
FIG. 26 demonstrates quantification of the antifibrotic effects of C188-9 in a bleomycin skin fibrosis model. RT-PCR was used to assess fibrotic gene expression that was increased with bleomycin but blunted by C188-9 treatment.

FIG. 26 provides quantitative real time PCR assessment of fibrotic gene expression in the skin of wild type mice in the subcutaneous bleomycin model treated with control (DMSO) or Cpd188-9 (exemplary Stat3 inhibitor). As expected, 28 days of subcutaneous bleomycin injection increased the dermal expression of smooth muscle actin (Acta2) and type I collagen (Col1a1 and Col1a2) transcripts. These increases were prevented with intraperitoneal treatment of mice with Cpd188-9 from days 14-28 of the 4 week model. N=5 mice per group.

REFERENCES

All patents and publications cited herein are hereby incorporated by reference in their entirety herein. Full citations for the references cited herein are provided in the following list.

PUBLICATIONS

Akira, S., 2000. Roles of STAT3 defined by tissue-specific gene targeting. Oncogene 19:2607-2611.
Akira, S., 1997, IL-6-regulated transcription factors. Int J Biochem Cell Biol 29:1401-1418.
Akira, S., Isshiki, H., Sugita, T., Tanabe, O., Kinoshita, S., Nishio, Y., Nakajima, T., Hirano, T., and Kishimoto, T. (1990). A nuclear factor for IL-6 expression (NF-IL6) is a member of a C/EBP family. EMBO J. 9, 1897-1906.
Al-Hajj, M., Wicha, M. S., Benito-Hernandez, A., Morrison, S. J., and Clarke, M. F. 2003. Prospective identification of tumorigenic breast cancer cells. Proc Natl Acad Sci USA 100:3983-3988.
Becker, S., Groner B, Muller C W (1998) Three-dimensional structure of the Stat3[beta] homodimer bound to DNA. Nature 394(6689): 145-151.
Bhasin, D., Cisek, K., Pandharkar, T., Regan, N., Li, C., Pandit, B., Lin, J., and Li, P. K. (2008). Design, synthesis, and studies of small molecule STAT3 inhibitors. Bioorg. Med. Chem. Lett. 18, 391-395.
Brinkley, B R, Beall P T, Wible U, Mace M L, Turner D S et al. (1980) Variations in Cell Form and Cytoskeleton in Human Breast Carcinoma Cells in Vitro. Cancer Res 40(9): 3118-3129.
Bromberg, J., 2002. Stat proteins and oncogenesis. J Clin Invest 109:1139-1142.
Bromberg, J., and Darnell, J. E., Jr. 2000. The role of STATs in transcriptional control and their impact on cellular function. Oncogene 19:2468-2473.
Bromberg, J. F., Horvath, C. M., Besser, D., Lathem, W. W., and Darnell, J. E., Jr. 1998. Stat3 activation is required for cellular transformation by v-src. Mol Cell Biol 18:2553-2558.
Bromberg, J. F., Wrzeszczynska, M. H., Devgan, G., Zhao, Y., Pestell, R. G., Albanese, C., and Darnell, J. E., Jr. 1999. Stat3 as an oncogene [published erratum appears in Cell 1999 Oct. 15; 99(2):239]. Cell 98:295-303.
Cailleau R O M, Crueiger Q V J. (1978) Long term human breast carcinoma cell lines of metastatic origin: preliminary characterization. In Vitro 14: 911-915.
Caldenhoven, E., van, D. T. B., Solari, R., Armstrong, J., Raaijmakers, J. A. M., Lammers, J. W. J., Koenderman, L., and de, G. R. P. 1996. STAT3beta, a splice variant of transcription factor STAT3, is a dominant negative regulator of transcription. Journal of Biological Chemistry 271:13221-13227.
Catlett-Falcone, R., Landowski, T. H., Oshiro, M. M., Turkson, J., Levitzki, A., Savino, R., Ciliberto, G., Moscinski, L., Fernandez-Luna, J. L., Nunez, G., et al. 1999. Constitutive activation of Stat3 signaling confers resistance to apoptosis in human U266 myeloma cells. Immunity 10:105-115.
Chakraborty, A., Dyer K F, Cascio M, Mietzner T A, Tweardy D J (1999) Identification of a Novel Stat3 Recruitment and Activation Motif Within the Granulocyte Colony-Stimulating Factor Receptor. Blood 93(1): 15-24.
Chakraborty, A., White, S. M., Schaefer, T. S., Ball, E. D., Dyer, K. F., and Tweardy, D. J. 1996. Granulocyte colony-stimulating factor activation of Stat3 alpha and Stat3 beta in immature normal and leukemic human myeloid cells. Blood 88:2442-2449.
Chapman, R. S., Lourenco, P. C., Tonner, E., Flint, D. J., Seibert, S., Takeda, K., Akira, S., Clarke, A. R., and Watson, C. J. 1999. Suppression of epithelial apoptosis and delayed mammary gland involution in mice with a conditional knockout of Stat3. Genes Dev 13:2604-2616.
Chen, X., Vinkemeier U, Zhao Y, Jeruzalmi D, Darnell J E et al. (1998) Crystal Structure of a Tyrosine Phosphorylated STAT-1 Dimer Bound to DNA. Cell 93(5): 827-839.
Cohen, M. S., Zhang C, Shokat K M, Taunton J (2005) Structural Bioinformatics-Based Design of Selective, Irreversible Kinase Inhibitors. Science 308(5726): 1318-1321.
Coleman, D R, Ren Z, Mandal P K, Cameron A G, Dyer G A et al. (2005) Investigation of the Binding Determinants of Phosphopeptides Targeted to the Src Homology 2 Domain of the Signal Transducer and Activator of Transcription 3. Development of a High-Affinity Peptide Inhibitor. J Med Chem 48(21): 6661-6670.
Costa-Pereira, A. P., Tininini, S., Strobl, B., Alonzi, T., Schlaak, J. F., Is'harc, H., Gesualdo, I., Newman, S. J., Kerr, I. M., and Poli, V. 2002. Mutational switch of an IL-6 response to an interferon-gamma-like response. Proc Natl Acad Sci USA 99:8043-8047.

Daling, J. R., and Malone, K. E. 2003. Incidence of invasive breast cancer by hormone receptor status from 1992 to 1998. J Clin Oncol 21:28-34.

Darnell J E (2005), Validating Stat3 in cancer therapy. Nat Med 11(6): 595-596.

Dave, B., and Chang, J. 2009. Treatment resistance in stem cells and breast cancer. J Mammary Gland Biol Neoplasia 14:79-82.

Diaz, N., Minton, S., Cox, C., Bowman, T., Gritsko, T., Garcia, R., Eweis, I., Wloch, M., Livingston, S., Seijo, E., et al. 2006. Activation of stat3 in primary tumors from high-risk breast cancer patients is associated with elevated levels of activated SRC and survivin expression. Clin Cancer Res 12:20-28.

Dong, S., Chen S-J, Tweardy D J (2003) Cross-talk between Retinoic Acid and Stat3 Signaling Pathways in Acute Promyelocytic Leukemia. Leuk Lymphoma 44: 2023-2029.

Dunn, G P, Bruce A T, Ikeda H, Old L J, Schreiber R D (2002) Cancer immunoediting: from immunosurveillance to tumor escape. Nat Immunol 3(11): 991-998.

Durbin, J. E., Hackenmiller, R., Simon, M. C., and Levy, D. E. 1996. Targeted disruption of the mouse Stat1 gene results in compromised innate immunity to viral disease. Cell 84:443-450.

Eckert, H., Bajorath J (2007) Molecular similarity analysis in virtual screening: foundations, limitations and novel approaches. Drug discovery today 12(5-6): 225-233.

Epling-Burnette, P. K., Liu, J. H., Catlett-Falcone, R., Turkson, J., Oshiro, M., Kothapalli, R., Li, Y., Wang, J. M., Yang-Yen, H. F., Karras, J., et al. 2001. Inhibition of STAT3 signaling leads to apoptosis of leukemic large granular lymphocytes and decreased Mcl-1 expression. J Clin Invest 107:351-362.

Fiala, S., 1968. The cancer cell as a stem cell unable to differentiate. A theory of carcinogenesis. Neoplasma 15:607-622.

Fu, X.-Y., Schindler, C, Improta, T., Aebersold, R., and Darnell, J. E., Jr. 1992. The proteins of ISGF-3, the interferon alpha-induced transcriptional activator, define a gene family involved in signal transduction. Proceedings of the National Academy of Sciences of the United States of America 89:7840-7843.

Garcia, R., and, Jove, R. 1998. Activation of STAT transcription factors in oncogenic tyrosine kinase signaling. Journal of Biomedical Science In press.

Garcia R, Yu C L, Hudnall A, Catlett R, Nelson K L et al. (1997) Constitutive activation of Stat3 in fibroblasts transformed by diverse oncoproteins and in breast carcinoma cells. Cell Growth Differ 8(12): 1267-1276.

Garcia R, Bowman T L, Niu G, Yu H, Minton S et al. (2001) Constitutive activation of Stat3 by the Src and Jak tyrosine kinases participates in growth regulation of human breast carcinoma cells. Oncogene 20: 2499-2513.

Grandis, J. R., Drenning, S. D., Zeng, Q., Watkins, S. C., Melhem, M. F., Endo, S., Johnson, D. E., Huang, L., He, Y., and Kim, J. D. 2000. Constitutive activation of Stat3 signaling abrogates apoptosis in squamous cell carcinogenesis in vivo. Proc Natl Acad Sci USA 97:4227-4232.

Gritsko, T., Williams, A., Turkson, J., Kaneko, S., Bowman, T., Huang, M., Nam, S., Eweis, I., Diaz, N., Sullivan, D., et al. 2006. Persistent activation of stat3 signaling induces survivin gene expression and confers resistance to apoptosis in human breast cancer cells. Clin Cancer Res 12:11-19.

Haan, S., Hemmann, U., Hassiepen, U., Schaper, F., Schneider-Mergener, J., Wollmer, A., Heinrich, P. C., and Grotzinger, J. 1999. Characterization and binding specificity of the monomeric STAT3-SH2 domain. J Biol Chem 274: 1342-1348.

Huang, Y., Qiu J, Dong S, Redell M S, Poli V et al. (2007) Stat3 Isoforms, {alpha} and, Demonstrate Distinct Intracellular Dynamics with Prolonged Nuclear Retention of Stat3 Mapping to Its Unique C-terminal End. J Biol Chem 282(48): 34958-34967.

Jemal, A., Siegel, R., Ward, E., Murray, T., Xu, J., Smigal, C., and Thun, M. J. 2006. Cancer statistics, 2006. CA Cancer J Clin 56:106-130.

Jing, N., Tweardy D J (2005) Targeting Stat3 in cancer therapy. anticancer Drugs 16(6): 601-607.

Jing, N., Zhu Q, Yuan P, Li Y, Mao L et al. (2006) Targeting signal transducer and activator of transcription 3 with G-quartet oligonucleotides: a potential novel therapy for head and neck cancer. Mol Cancer Ther 5(2): 279-286.

Jing, N., Li Y, Xu X, Sha W, Li P et al. (2003) Targeting Stat3 with G-quartet oligodeoxynucleotides in human cancer cells. DNA Cell Biol 22(11): 685-696.

Jing, N., Li, Y., Xiong, W., Sha, W., Jing, L., and Tweardy, D. J. 2004. G-quartet oligonucleotides: a new class of signal transducer and activator of transcription 3 inhibitors that suppresses growth of prostate and breast tumors through induction of apoptosis. Cancer Res 64:6603-6609.

Kaplan, D. H., Shankaran, V., Dighe, A. S., Stockert, E., Aguet, M., Old, L. J., and Schreiber, R. D. 1998. Demonstration of an interferon gamma-dependent tumor surveillance system in immunocompetent mice. Proc Natl Acad Sci USA 95:7556-7561.

Kato, T., Sakamoto E, Kutsuna H, Kimura-Eto A, Hato F et al. (2004) Proteolytic Conversion of STAT3{alpha} to STAT3{gamma} in Human Neutrophils: ROLE OF GRANULE-DERIVED SERINE PROTEASES. J Biol Chem 279(30): 31076-31080.

Kim, J. K., Xu Y, Xu X, Keene D R, Gurusiddappa S et al. (2005) A Novel Binding Site in Collagen Type III for Integrins {alpha}1{beta}1 and {alpha}2{beta}1. J Biol Chem 280(37): 32512-32520.

Kortylewski, M., Kujawski M, Wang T, Wei S, Zhang S et al. (2005) Inhibiting Stat3 signaling in the hematopoietic system elicits multicomponent antitumor immunity. Nat Med 11(12): 1314-1321.

Leong, P. L., Andrews, G. A., Johnson, D. E., Dyer, K. F., Xi, S., Mai, J. C., Robbins, P. D., Gadiparthi, S., Burke, N. A., Watkins, S. F., et al. 2003. Targeted inhibition of Stat3 with a decoy oligonucleotide abrogates head and neck cancer cell growth. Proc Natl Acad Sci USA 100:4138-4143.

Li, C. I., Daling, J. R., and Malone, K. E. 2003. Incidence of invasive breast cancer by hormone receptor status from 1992 to 1998. J Clin Oncol 21:28-34.

Li, L., and Shaw, P. E. 2002. Autocrine-mediated activation of STAT3 correlates with cell proliferation in breast carcinoma lines. J Biol Chem 277:17397-17405.

Li, X., Lewis, M. T., Huang, J., Gutierrez, C., Osborne, C. K., Wu, M. F., Hilsenbeck, S. G., Pavlick, A., Zhang, X., Chamness, G. C., et al. 2008. Intrinsic resistance of tumorigenic breast cancer cells to chemotherapy. J Natl Cancer Inst 100:672-679.

Lin, Q., Lai R, Chirieac L R, Li C, Thomazy V A et al. (2005) Constitutive Activation of JAK3/STAT3 in Colon Carcinoma Tumors and Cell Lines: Inhibition of JAK3/

STAT3 Signaling Induces Apoptosis and Cell Cycle Arrest of Colon Carcinoma Cells. Am J Pathol 167(4): 969-980.

Maritano, D., Sugrue, M. L., Tininini, S., Dewilde, S., Strobl, B., Fu, X., Murray-Tait, V., Chiarle, R., and Poli, V. 2004. The STAT3 isoforms alpha and beta have unique and specific functions. Nat Immunol 5:401-409.

McMurray J S (2006), A New Small-Molecule Stat3 Inhibitor. Chemistry & Biology 13(11): 1123-1124.

Meraz, M. A., White, J. M., Sheehan, K. C., Bach, E. A., Rodig, S. J., Dighe, A. S., Kaplan, D. H., Riley, J. K., Greenlund, A. C., Campbell, D., et al. 1996. Targeted disruption of the Stat1 gene in mice reveals unexpected physiologic specificity in the JAK-STAT signaling pathway. Cell 84:431-442.

Minino, A. M., Heron, M. P., Murphy, S. L., and Kochanek, K. D. 2007. Deaths: final data for 2004. Natl Vital Stat Rep 55:1-119.

Mora, L. B., Buettner, R., Seigne, J., Diaz, J., Ahmad, N., Garcia, R., Bowman, T., Falcone, R., Fairclough, R., Cantor, A., et al. 2002. Constitutive activation of Stat3 in human prostate tumors and cell lines: direct inhibition of Stat3 signaling induces apoptosis of prostate cancer cells. Cancer Res 62:6659-6666.

Neculai, D., Neculai A M, Verrier S, Straub K, Klumpp K et al. (2005) Structure of the Unphosphorylated STAT5a Dimer. J Biol Chem 280(49): 40782-40787.

Nemethy, G., Gibson K D, Palmer K A, Yoon C N, Paterlini G et al. (1992) Energy Parameters in Polypeptides. 10. Improved Geometrical Parameters and Nonbonded Interactions for Use in the ECEPP/3 Algorithm, with Application to Proline-Containing Peptides. J Phys Chem 96: 6472-6484.

Park, O. K., Schaefer, T. S., and Nathans, D. 1996. In vitro activation of Stat3 by epidermal growth factor receptor kinase. Proceedings of the National Academy of Sciences of the United States of America 93:13704-13708.

Park, O. K., Schaefer, L. K., Wang, W., and Schaefer, T. S. 2000. Dimer stability as a determinant of differential DNA binding activity of Stat3 isoforms. J Biol Chem 275:32244-32249.

Qing, Y., and Stark, G. R. 2004. Alternative activation of STAT1 and STAT3 in response to interferon-gamma. J Biol Chem 279:41679-41685.

Ramana, C., Chatterjee-Kishore M, Nguyen H, Stark G (2000) Complex roles of Stat1 in regulating gene expression. Oncogene 19(21): 2619-2627.

Real, P. J., Siena, A., De Juan, A., Segovia, J. C., Lopez-Vega, J. M., and Fernandez-Luna, J. L. 2002. Resistance to chemotherapy via Stat3-dependent overexpression of Bcl-2 in metastatic breast cancer cells. Oncogene 21:7611-7618.

Redell, M S, Tweardy D J (2006) Targeting transcription factors in cancer: Challenges and evolving strategies. Drug Discovery Today: Technologies 3(3): 261-267.

Redell, M. S., and Tweardy, D. J. 2005. Targeting transcription factors for cancer therapy. Curr Pharm Des 11:2873-2887.

Ren, Z., Cabell, L. A., Schaefer, T. S., and McMurray, J. S. 2003. Identification of a high-affinity phosphopeptide inhibitor of stat3. Bioorg Med Chem Lett 13:633-636.

Ryan, J. J., McReynolds, L. J., Huang, H., Nelms, K., and Paul, W. E. 1998. Characterization of a mobile Stat6 activation motif in the human IL-4 receptor. J Immunol 161:1811-1821.

Satya-Prakash K L P S, Hsu T C, Olive M, Cailleau R (1981) Cytogenetic analysis on eight human breast tumor cell lines: high frequencies of 1q, 11q, and HeLa-like marker chromosomes. Cancer GenetCytogenet 3: 61-73.

Schaefer, T. S., Sanders, L. K., and Nathans, D. 1995. Cooperative transcriptional activity of Jun and Stat3 beta, a short form of Stat3. Proceedings of the National Academy of Sciences of the United States of America 92:9097-9101.

Schindler, C., and Darnell, J. E., Jr. 1995. Transcriptional responses to polypeptide ligands: the JAK-STAT pathway. [Review]. Annual Review of Biochemistry 64:621-651.

Schindler, C., Fu, X. Y., Improta, T., Aebersold, R., and Darnell, J. E., Jr. 1992. Proteins of transcription factor ISGF-3: one gene encodes the 91- and 84-kDa ISGF-3 proteins that are activated by interferon alpha. Proceedings of the National Academy of Sciences of the United States of America 89:7836-7839.

Schust, J., Sperl, B., Hollis, A., Mayer, T. U., and Berg, T. (2006). Stattic: a small-molecule inhibitor of STAT3 activation and dimerization. Chem. Biol. 13, 1235-1242.

Shao, H., Cheng H Y, Cook R G, Tweardy D J (2003) Identification and Characterization of Signal Transducer and Activator of Transcription 3 Recruitment Sites within the Epidermal Growth Factor Receptor. Cancer Res 63(14): 3923-3930.

Shao, H., Xu X, Jing N, Tweardy D J (2006) Unique Structural Determinants for Stat3 Recruitment and Activation by the Granulocyte Colony-Stimulating Factor Receptor at Phosphotyrosine Ligands 704 and 744. J Immunol 176(5): 2933-2941.

Shao, H., Xu X, Mastrangelo M-AA, Jing N, Cook R G et al. (2004) Structural Requirements for Signal Transducer and Activator of Transcription 3 Binding to Phosphotyrosine Ligands Containing the YXXQ Motif. J Biol Chem 279(18): 18967-18973.

Sharp, Z. D., Mancini M G, Hinojos C A, Dai F, Berno V et al. (2006) Estrogen-receptor-{alpha} exchange and chromatin dynamics are ligand- and domain-dependent. J Cell Sci 119(19): 4101-4116.

Siddiquee, K., Zhang S, Guida W C, Blaskovich M A, Greedy B et al. (2007)

Selective chemical probe inhibitor of Stat3, identified through structure-based virtual screening, induces antitumor activity. Proceedings of the National Academy of Sciences 104(18): 7391-7396.

Song, H., Wang R, Wang S, Lin J (2005) A low-molecular-weight compound discovered through virtual database screening inhibits Stat3 function in breast cancer cells. Proceedings of the National Academy of Sciences 102 (13): 4700-4705.

Strecker, T. E., Shen, Q., Zhang, Y., Hill, J. L., Li, Y., Wang, C., Kim, H. T., Gilmer, T. M., Sexton, K. R., Hilsenbeck, S. G., et al. 2009. Effect of lapatinib on the development of estrogen receptor-negative mammary tumors in mice. J Natl Cancer Inst 101:107-113.

Takeda, K., Noguchi, K., Shi, W., Tanaka, T., Matsumoto, M., Yoshida, N., Kishimoto, T., and Akira, S. 1997. Targeted disruption of the mouse Stat3 gene leads to early embryonic lethality. Proc Natl Acad Sci USA 94:3801-3804.

Totrov, M., Abagyan R (1997) Proteins 1: 215-220.

Turkson, J., 2004. STAT proteins as novel targets for cancer drug discovery. Expert Opin Ther Targets 8:409-422.

Turkson, J., Bowman, T., Garcia, R., Caldenhoven, E., De Groot, R. P., and Jove, R. 1998. Stat3 activation by Src induces specific gene regulation and is required for cell transformation. Mol Cell Biol 18:2545-2552.

What is claimed is:

1. A method of treating an individual that has fibrosis, comprising the step of providing to the individual an effective amount of one or more compositions selected from the group consisting of N-(1',2-dihydroxy-1,2'-binaphthalen-4'-yl)-4-methoxybenzenesulfonamide, N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-ylsulfanyl)-naphthalen-1-yl]-benzenesulfonamide, and a functional derivative thereof, wherein the fibrosis is not pulmonary fibrosis or myelofibrosis.

2. The method of claim 1, wherein the fibrosis is of the skin, heart, intestine, pancreas, joint, liver, or retroperionteum.

3. The method of claim 1, wherein the individual is provided the composition in multiple doses.

4. The method of claim 3, wherein the multiple doses are separated by hours, days, or weeks.

5. The method of claim 1, wherein the individual is provided with an additional therapy for the fibrosis.

6. The method of claim 1, wherein the composition is selected from the group consisting of N-(1',2-dihydroxy-1,2'-binaphthalen-4'-yl)-4-methoxybenzenesulfonamide, N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-ylsulfanyl)-naphthalen-1-yl]-benzenesulfonamide, a functionally active derivative thereof, and a mixture thereof.

7. The method of claim 1, wherein the composition inhibits Stat3, Stat1, or both.

8. The method of claim 1, further comprising the step of diagnosing the fibrosis.

9. The method of claim 1, wherein the composition is provided intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion, via a catheter, via a lavage, in lipid compositions, in liposome compositions, or as an aerosol.

10. The method of claim 1, wherein the composition is provided by injection.

11. The method of claim 1, wherein the composition is provided topically.

12. The method of claim 1, wherein the composition is provided subcutaneously.

13. The method of claim 1, wherein the composition is provided systemically.

14. The method of claim 1, wherein the composition is provided locally.

15. The method of claim 1, wherein the individual does not have cancer.

16. The method of claim 1, wherein the individual is not suspected of having cancer.

17. The method of claim 1, wherein the fibrosis is scleroderma.

18. The method of claim 1, wherein the composition comprises N-(1',2-dihydroxy-1,2'-binaphthalen-4'-yl)-4-methoxybenzenesulfonamide.

19. A method of treating an individual, comprising the step of providing to the individual an effective amount of one or more compositions selected from the group consisting of N-(1',2-dihydroxy-1,2'-binaphthalen-4'-yl)-4-methoxybenzenesulfonamide, N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-ylsulfanyl)-naphthalen-1-yl]-benzenesulfonamide, and a functional derivative thereof, wherein the fibrosis is not pulmonary fibrosis or myelofibrosis, and wherein the fibrosis is of the heart, pancreas, joint, liver, or retroperionteum.

20. The method of claim 19, wherein the composition is selected from the group consisting of N-(1',2-dihydroxy-1,2'-binaphthalen-4'-yl)-4-methoxybenzenesulfonamide, N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-ylsulfanyl)-naphthalen-1-yl]-benzenesulfonamide, a functionally active derivative thereof, and a mixture thereof.

21. The method of claim 19, wherein the composition is provided intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion, via a catheter, via a lavage, in lipid compositions, in liposome compositions, or as an aerosol.

22. The method of claim 19, wherein the fibrosis is scleroderma.

23. The method of claim 19, wherein the composition comprises N-(1',2-dihydroxy-1,2'-binaphthalen-4'-yl)-4-methoxybenzenesulfonamide.

* * * * *